(12) United States Patent
Stieber et al.

(10) Patent No.: US 8,907,098 B2
(45) Date of Patent: Dec. 9, 2014

(54) INHIBITORS OF SPHINGOSINE KINASE

(75) Inventors: Frank Stieber, Einhausen (DE); Dirk Wienke, Darmstadt (DE)

(73) Assignee: MERCK PATENT GmbH, Darmstadt (DE)

(*) Notice: Subject to any disclaimer, the term of this patent is extended or adjusted under 35 U.S.C. 154(b) by 54 days.

(21) Appl. No.: 13/516,370

(22) PCT Filed: Nov. 18, 2010

(86) PCT No.: PCT/EP2010/007003
§ 371 (c)(1),
(2), (4) Date: Jun. 15, 2012

(87) PCT Pub. No.: WO2011/082732
PCT Pub. Date: Jul. 14, 2011

(65) Prior Publication Data
US 2012/0252815 A1 Oct. 4, 2012

(30) Foreign Application Priority Data
Dec. 17, 2009 (EP) .................................. 09015631

(51) Int. Cl.
| | | |
|---|---|---|
| *C07D 417/04* | (2006.01) | |
| *C07D 417/14* | (2006.01) | |
| *C07D 249/06* | (2006.01) | |
| *C07D 263/32* | (2006.01) | |
| *C07D 277/40* | (2006.01) | |
| *C07D 277/28* | (2006.01) | |

(52) U.S. Cl.
CPC ............ *C07D 249/06* (2013.01); *C07D 263/32* (2013.01); *C07D 277/40* (2013.01); *C07D 417/14* (2013.01); *C07D 277/28* (2013.01); *C07D 417/04* (2013.01)

USPC ............ 546/209; 544/129; 546/16; 546/187; 514/235.5; 514/236.8; 514/278; 514/316; 514/326

(58) Field of Classification Search
USPC ........................................................ 546/209
See application file for complete search history.

(56) References Cited

U.S. PATENT DOCUMENTS

| | | | |
|---|---|---|---|
| 4,612,321 A * | 9/1986 | Terao et al. .................... 514/338 |
| 6,608,087 B1 | 8/2003 | Charifson et al. | |
| 8,436,186 B2 * | 5/2013 | Stieber et al. ................. 546/205 |
| 2009/0143413 A1 | 6/2009 | Adams et al. | |

FOREIGN PATENT DOCUMENTS

DE 102008029734 A1 * 12/2009
WO WO 2007/064553 A2 6/2007

OTHER PUBLICATIONS

Nakai et al., CA 145:145750, 2006.*
International Search Report of PCT/EP2010/007003 (May 12, 2011).
A. J. Tervo et al., "Discovering Inhibitors of Human Sirtuin Type 2: Novel Structural Scaffolds", Journal of Medicinal Chemistry, vol. 49, No. 24 (Feb. 9, 2006) pp. 7239-7241.

* cited by examiner

*Primary Examiner* — Laura L. Stockton
(74) *Attorney, Agent, or Firm* — Millen, White, Zelano & Branigan, P.C.

(57) ABSTRACT

The present invention relates to compounds of the formula (I), in which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $M_1$, $M_2$, $M_3$, $Y_1$, $Y_2$, V, W, n, m and o have the meanings given herein, and physiologically acceptable salts, derivatives, prodrugs, solvates, tautomers and stereoisomers thereof, including mixtures thereof in all ratios, for use in the treatment of diseases which are influenced by inhibition of Sph kinase 1.

8 Claims, No Drawings

INHIBITORS OF SPHINGOSINE KINASE

TECHNICAL AREA

The present invention relates to inhibitors of sphingosine kinase and physiologically acceptable salts, derivatives, prodrugs, solvates, tautomers and stereoisomers thereof, including mixtures thereof in all ratios, for use in the treatment of diseases which are influenced by inhibition of Sph kinase 1.

BACKGROUND OF THE INVENTION

The invention was based on the object of finding novel compounds having valuable properties, in particular those which can be used for the preparation of medicaments.

The present invention relates to compounds and to the use of compounds for the treatment of diseases which are associated with an increase in the sphingosine phosphate level, furthermore to pharmaceutical compositions which comprise these compounds.

In detail, the present invention relates to compounds of the formula (I), which preferably inhibit the enzyme sphingosine kinase 1, which regulates the sphingosine phosphate level by phosphorylation of sphingosine, to compositions which comprise these compounds, and to methods for the use thereof for the treatment of diseases and complaints, such as cancer, tumour formation, growth and spread, arteriosclerosis, eye diseases, choroidal neovascularisation and diabetic retinopathy, inflammatory diseases, arthritis, neurodegeneration, restenosis, heart diseases, wound healing or transplant rejection. In particular, the compounds according to the invention are suitable for the therapy of cancer diseases.

Sphingosine phosphate belongs to the molecule family of the sphingolipids, which, besides their role as structural building blocks of cell membranes, also exert important functions as extra- and intracellular signal molecules. Sphingosine phosphate (S1P) is formed in the cell from sphingomyelin, which initially breaks down to form ceramide and sphingosine, and the latter is phosphorylated by sphingosine kinases. Of the two sphingosine kinases identified to date, sphingosine kinase 1 (SphK1) is ascribed the greater importance in the formation of S1P in the serum (Zemann et al., 2006 Blood Vol 107 page 1454). While ceramide and sphingosine induce cell death and cell growth inhibition (Kolesnick 2002, J Clin Invest Vol 110, page 3; Ogretmen et al. 2004 Nat Rev Cancer Vol 4, page 604), sphingosine phosphate has an opposite effect on the cell and increases the resistance to apoptosis, cell growth and the discharge of messenger substances, which promote perfusion of the tissue and thus also of tumours (Cuvilier et al. 1996, Nature Vol 381, page 800; Perez et al. 1997, Nat Med Vol 3, page 1228). The ratio of ceramide and sphingosine on the one hand and S1P on the other is consequently decisive for cell growth, and inhibition of SphK 1 can thus not only suppress the formation of the growth-promoting sphingosine phosphate, but also increase the cellular concentration of the growth-inhibiting molecules ceramide and sphingosine.

A multiplicity of cellular effects which are triggered by S1P is promoted by secretion of S1P and binding thereof to date 5 different G-protein-coupled receptors (known as $S1P_{1-5}$). Signal propagation in turn takes place via various G-proteins ($G_i$, $G_q$, $G_{12/13}$), meaning that a number of different cellular signalling pathways, such as, for example, ERK or PI3K, which are particularly important in cancer formation and growth, are activated. In addition, an increasing number of publications shows that S1P is an important factor in tumoral angiogenesis. Angiogenesis is an important process in tumour growth, by means of which blood vessels are re-formed starting from already existing ones and the supply of the tumour with nutrients is thus ensured. For this reason, inhibition of angiogenesis is an important starting point for cancer and tumour therapy. (Folkman, 2007, Nature Reviews Drug Discovery Vol. 6, page 273-286). S1P stimulates chemotactic movement of endothelial cells and induces differentiation to give multicellular structures, both early steps in the formation of new blood vessels (Lee et al. 1999 Biochem Biophys Res Commun Vol 264 page 325; Argraves et al. 2004 J Biol Chem Vol 279 page 50580). In addition, S1P promotes the migration of endothelial precursor cells originating from bone marrow to neovascular initiation sites (Annabi et al. 2003 Exp Hematology Vol 31 page 640) and trans-activates the receptor of VEGF, one of the most important proangiogenic factors, in particular in tumour biology (Tanimoto et al. 2002 J Biol Chem Vol 277 page 42997; Endo et al. 2002 J Biol Chem Vol 277 page 23747). Direct evidence of the activity of S1P in tumour angiogenesis has been provided by experiments with an antibody which binds specifically to S1P. The S1P antibody inhibited the migration and vascularisation of endothelial cells in vitro, blocked the S1P-dependent secretion of proangiogenic factors, such as VEGF, IL-8 and IL-6, in vitro and in vivo and significantly reduced the growth of tumour models of the breast, lung and ovaries in mouse xenograft experiments (Visentin 2006 Cancer Cell Vol 9 page 225).

In addition, S1P also has intracellular functions, such as, for example, the activation of the transcription factor NF-κB, which plays a major role in apoptosis resistance of cancer cells (Xia et al. 2002 J Biol Chem Vol 277 page 7996). However, the intracellular interaction partners of S1P have not yet been identified.

It follows from this that, in contrast to a likewise conceivable intervention with the cancer-promoting action of S1P by pharmacological blockade of the extracellular receptors, inhibition of the enzyme SphK1, which is responsible for S1P formation, has the advantage of thus also suppressing the intracellular activities of S1P. This approach is supported by investigations by Xia et al. (2000 Curr Biol Vol 10 page 1527), which show that non-tumorigenic fibroblasts are transformed by ectopic expression of SphK1 and can form tumours in mice. SphK1 can thus be classified as an oncogene. In various expression studies, increased SphK1-mRNA concentrations in tumour tissues of the brain, breast, lung, ovaries, stomach, uterus, kidneys and small and large intestine have been observed compared with healthy tissue (French et al. 2003 Cancer Research Vol. 63 page 5962; Johnson et al. 2005 J Histochem Cytochem Vol 53 page 1159; Van Brocklyn et al. 2005 J Neuropathol Exp Neurol Vol 64 page 695). In addition, increased expression of SphK1 correlates with a worse prognosis in patients with glioblastoma multiforme (Van Brocklyn et al. 2005 J Neuropathol Exp Neurol Vol 64 page 695).

SphK1 has an important role in the modulation of the apoptosis of cancer cells induced by chemotherapeutic agents. Thus, overexpression of SphK1 increases the resistance of breast cancer, prostate cancer and leukaemia cells to chemotherapeutic agents, such as anthracyclines, docetaxel, camptothecin or doxorubicin (Nava et al. 2002 Exp Cell Res Vol 281 page 115; Pchejetski 2005 Cancer Res Vol 65 page 11667; Bonhoure 2006 Leukemia Vol 20 page 95). It has been shown that the increased presence of SphK1 results in a shift in the ceramide/S1P equilibrium towards S1P, which promotes apoptosis resistance. A possible mechanism here is the inhibition of the mitochondrial cytochrome C discharge by SphK1, which normally represents an early event in programmed cell death (Cuvilier et al. 2001 Blood Vol 98 page 2828; Bonhoure 2006 Leukemia Vol 20 page 95).

Conversely, specific blockade of SphK1 expression by means of siRNA in tumour cell models of various indications, such as leukaemia, breast cancer, glioblastoma or prostate cancer, enables apoptosis to be triggered or the effect of chemotherapeutic agents to be increased (Bonhoure 2006

Leukemia Vol 20 page 95; Taha et al. 2004 J Biol Chem Vol 279 page 20546; Taha et al. 2006 FASEB J Vol 20 page 482; Van Brocklyn et al. 2005 J Neuropathol Exp Neurol Vol 64 page 695; Pchejetski 2005 Cancer Res Vol 65 page 11667).

It has been shown in a mouse model that overexpression of SphK1 triggers degenerative changes of cardiomyocytes and myocardial fibrosis, which increased with increasing age of the experimental animals. A function of the S1P signalling pathway in heart diseases is also supported by the fact that the formation of cardiovascular fibroses is strongly inhibited in mice in which the expression of the S1P3 receptor has been specifically suppressed (Takuwa 2008 Biochimica and Biophysica Acta in press). S1P also has a role in the differentiation of fibroblasts to give myofibroblasts and thus in the formation and progression of fibrotic diseases in other organs, such as, for example, the lung (Kono et al. 2007 Am J Respir Cell Mol Biol page 395).

It has been found that the compounds according to the invention cause specific inhibition of sphingosine kinase 1, but not of sphingosine kinase 2. The compounds according to the invention preferably exhibit an advantageous biological activity which can be detected in the tests described herein, for example. In such tests, the compounds according to the invention exhibit and cause an inhibiting effect, which is usually documented by $IC_{50}$ values in a suitable range, preferably in the micromolar range and more preferably in the nanomolar range.

In general, all solid and non-solid tumours can be treated with the compounds of the formula (I), such as, for example, monocytic leukaemia, brain, urogenital, lymph system, stomach, laryngeal, ovarian and lung carcinoma, including lung adenocarcinoma and small-cell lung carcinoma. Further examples include prostate, pancreatic and breast carcinoma.

As discussed herein, effects of the compound according to the invention are relevant for various diseases. Accordingly, the compounds according to the invention are useful in the prophylaxis and/or treatment of diseases which are influenced by inhibition of SphK1.

The present invention therefore relates to compounds according to the invention as medicaments and/or medicament active ingredients in the treatment and/or prophylaxis of the said diseases and to the use of compounds according to the invention for the preparation of a pharmaceutical agent for the treatment and/or prophylaxis of the said diseases, and also to a method for the treatment of the said diseases comprising the administration of one or more compounds according to the invention to a patient in need of such an administration.

The host or patient can belong to any mammalian species, for example a primate species, particularly humans; rodents, including mice, rats and hamsters, rabbits, horses, cows, dogs, cats, etc. Animal models are of interest for experimental investigations, where they represent a model for the treatment of human disease.

The sensitivity of a particular cell to treatment with the compounds according to the invention can be determined by in vitro tests. Typically, a culture of the cell is combined with a compound according to the invention at various concentrations for a period of time which is sufficient to enable the active agents to lower the intracellular S1P concentration and in addition to block the secretion of angiogenesispromoting substances or to induce cell death. For testing in vitro, use can be made of cultivated cells from a biopsy sample or established cancer cell lines in which SphK1 is expressed.

The dose varies depending on the specific compound used, the specific disease, the patient status, etc. A therapeutic dose is typically sufficient to considerably reduce the undesired cell population in the target tissue, while the viability of the patient is maintained. The treatment is generally continued until a considerable reduction has occurred, for example at least about 50% reduction in the cell burden, and can be continued until essentially no undesired cells can be detected in the body.

Use

As described in the introduction, SphK1, S1P and the cell surface receptors $S1P_{1-5}$ thereof are involved in a multiplicity of physiological and pathophysiological processes. For this reason, it can be expected that the inhibition of SphK1 by the substances described here can be utilised for therapeutic purposes in various diseases.

The formation of S1P by SphK1 and the associated shift in the ceramide/S1P equilibrium results, as stated above, in the cells proliferating to a greater extent and becoming more resistant to apoptotic stimuli. A general function of SphK1 can be derived therefrom in hyperproliferative diseases, such as cancer, psoriasis, restenosis and arteriosclerosis. The compounds of the formula I on which this invention is based and which inhibit SphK1 and thus regulate and/or modulate the S1P level, compositions which comprise these compounds, and the methods described can thus be employed for the treatment of these diseases. In general, all solid and non-solid tumours can be treated with the compounds of the formula X, such as, for example, monocytic leukaemia, brain, urogenital, lymph system, stomach, laryngeal ovarian and lung carcinoma, including lung adenocarcinoma and small-cell lung carcinoma. Further examples include bowel, prostate, pancreatic and breast carcinoma.

Besides the function in cell growth, S1P also plays a role in the neoformation of blood vessels (angiogenesis). In many disease processes, angiogenesis is either causally at the centre of the disease or has a worsening effect on the progression of the disease. In cancer events, for example, angiogenesis results in the tumour being enlarging and possibly spreading into other organs. Further diseases in which angiogenesis plays an important role are psoriasis, arthrosis, arteriosclerosis and eye diseases, such as diabetic retinopathy, age-induced macular degeneration, rubeosis iridis or neovascular glaucoma. The compounds of the formula I on which this invention is based and which inhibit SphK1 and thus regulate and/or modulate the S1P level, compositions which comprise these compounds, and the methods described can thus be employed for the treatment of these diseases.

Furthermore, SphK1 and S1P influence the proliferation, differentiation, migration and secretion of immune cells (Rosen and Goetzl 2005 Nat Rev Immunol Vol 5 page 560) and are thus involved in various functions of the immune system and in inflammatory processes. Stimulation of the immune system increases the formation and discharge of S1P in mast cells, blood platelet cells and some mononuclear phagocytes (Stunff et al. 2004 J Cell Biochem Vol 92 page 882; Olivera and Rivera 2005 j Immunol Vol 174 page 1153). The activity of SphK1 is greatly increased, in particular, by factors such as tumour necrosis factor (TNF) and crosslinking of IgG receptors (Stunff et al. 2004 J Cell Biochem Vol 92 page 882; Delon et al. 2004 J Biol Chem Vol 279 page 44763). In addition, it has been shown that SphK1 and S1P are important for the TNF-dependent formation of pro-inflammatory enzymes, such as cyclooxygenase-2 (COX-2) and nitric oxide synthase (NOS) (Pettus et al. 2003 FASEB J Vol 17 page 1411; Kwon et al. 2001 J Biol Chem Vol 276 page 10627-33). The compounds of the formula I on which this invention is based and which inhibit SphK1 and thus regulate and/or modulate the S1P level, compositions which comprise these compounds, and the methods described can thus be employed for the treatment of inflammation-induced diseases, such as arthrosis, arteriosclerosis, psoriasis, multiple sclerosis, chronic inflammatory bowel diseases (Crohn's disease, colitis ulcerosa) asthma and other allergic diseases.

The compounds of the formula (I) can furthermore be used for the isolation and investigation of the activity or expression of Sph kinase. In addition, they are particularly suitable for use in diagnostic methods for diseases in connection with unregulated or disturbed Sph kinase activity.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For the identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

For the identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

For the identification of kinase inhibitors, various assay systems are available. In scintillation proximity assay (Sorg et al., J. of Biomolecular Screening, 2002, 7, 11-19) and flashplate assay, the radioactive phosphorylation of a protein, peptide or, in the case of SphK1, a lipid as substrate using gamma-ATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Another non-radioactive ELISA assay method uses a specific antibody against S1P for the quantification of S1P (assay system from Echelon).

There are many diseases associated with deregulation of cellular proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, peri-anastomatic prosthetic restenosis, restenosis after angioplasty or stent placement, and the like.

PRIOR ART

WO 2005/103022 describes substituted thiazole and pyrimidine derivatives as melanocortin receptor modulators.

WO 2006/73167 describes pyrrolidine derivatives.

WO 2007/100610 describes pyridine, pyrimidine and pyrazine derivatives as CXCR3 receptor modulators.

US 2007/043083 describes thiazolylpiperidine derivatives.

SUMMARY OF THE INVENTION

The invention relates to compounds of the formula (I)

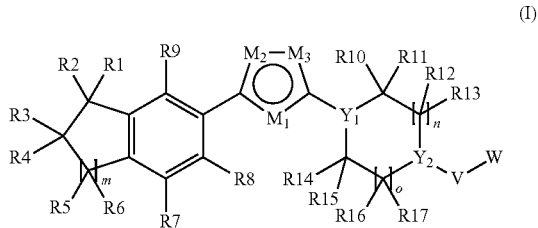

in which, in each case independently of one another:
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ denote H, D (deuterium), A, $OR^{18}$, CN, F, Cl and $NR^{18}R^{18'}$;

where $R^1$ and $R^2$, $R^3$ and $R^4$, $R^5$ and $R^6$, $R^{10}$ and $R^{11}$, $R^{12}$ and $R^{13}$, $R^{14}$ and $R^{15}$, $R^{16}$ and $R^{17}$ together may in each case also form =O (carbonyl oxygen);

where $R^9$ and $R^1$, $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^{10}$ and $R^{11}$, $R^{11}$ and $R^{12}$, $R^{12}$ and $R^{13}$, $R^{14}$ and $R^{15}$, $R^{15}$ and $R^{16}$, $R^{16}$ and $R^{17}$ together may in each case also form cyclic alkyl having 3, 4, 5, 6 or 7 C atoms or Het having 3, 4, 5, 6 or 7 ring atoms;

where $R^{10}$ and $R^{19}$, if $Y_1=CR^{19}$, $R^{11}$ and $R^{12}$, $R^{13}$ and $R^{19}$, if $Y_2=CR^{19}$, $R^{14}$ and $R^{19}$, if $Y_1=CR^{19}$, $R^{15}$ and $R^{16}$, $R^{17}$ and $R^{19}$, if $Y_2=CR^{19}$, together may in each case also form a C=C double bond with the single bond and the C atoms to which they are attached;

$R^{18}$, $R^{18'}$ denote H, D or A;

$R^{19}$, $R^{19'}$ denote H, D, A, $OR^{18}$, $NR^{18}R^{18'}$, $C(O)OR^{18}$, $C(O)NR^{18}R^{18'}$, F, Cl, Br, CN, Het or A-Het;

$M_1$, $M_2$, $M_3$, denote $CR^{19}$, N, S or O;

$Y_1$, $Y_2$ denote $CR^{19}$ or N;

V denotes $C(R^{19})(R^{19'})$, $NR^{19}$ or is absent;

W denotes $C(R^{19})(R^{19'})]_pZ$, $CO—[C(R^{19})(R^{19'})]_pZ$, $[C(R^{19})(R^{19'})]_pN(R^{19})—Z$, $CO—N(R^{19})—[C(R^{19})(R^{19'})]_pZ$, $N(R^{19})—CO—[C(R^{19})(R^{19'})]_pZ$, $CO—O—[C(R^{19})(R^{19'})]_pZ$, $C(O)OR^{19}$, $OR^{19}$, H or D;

where V, W and $Y_2$ together may in each case also form cyclic alkyl having 3, 4, 5, 6 or 7 C atoms, in which 1, 2, 3, 4, 5, 6 or 7 H atoms may preferably be replaced by F, Cl, Br, CN and/or OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$, or Het having 3, 4, 5, 6 or 7 ring atoms, where Het preferably represents a saturated, unsaturated or aromatic heterocycle having 1 to 4 N, O and/or S atoms, which may be unsubstituted or mono-, di- or trisubstituted by Hal, F, Cl, Br, CN, A, $OR^{18}$, W, $SR^{18}$, $NO_2$, $N(R^{19})(R^{19'})$, $NR^{18}COOZ$, $OCONHZ$, $NR^{18}SO_2Z$, $SO_2N(R^{18})Z$, $S(O)_mZ$, COZ, CHO, COZ, =S, =NH, =NA, oxy (—O⁻) and/or =O (carbonyl oxygen);

Z denotes Het, Ar or A;

A denotes unbranched or branched alkyl having 1, 2, 3, 4, 5, 6, 7, 8, 9 or 10 C atoms, in which 1, 2, 3, 4, 5, 6 or 7 H atoms may be replaced by F, Cl, Br, CN and/or OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$;

and/or in which one or two $CH_2$ groups may be replaced by O, S, SO, $SO_2$, CO, COO, $NR^{18}$, $NR^{18}CO$, $CONR^{18}$, cyclic alkyl having 3, 4, 5, 6 or 7 C atoms, CH=CH and/or CH≡CH groups;

or cyclic alkyl having 3, 4, 5, 6 or 7 C atoms, in which 1, 2, 3, 4, 5, 6 or 7 H atoms may be replaced by F, Cl, Br, CN and/or OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$;

Ar denotes phenyl, naphthyl or biphenyl, each of which is mono-, di- or trisubstituted by Hal, F, Cl, Br, CN, A, $OR^{18}$, W, $SR^{18}$, $NO_2$, $N(R^{19})(R^{19'})$, $NR^{18}COOZ$, $OCONHZ$, $NR^{18}SO_2Z$, $SO_2N(R^{18})Z$, $S(O)_mZ$, COZ, CHO, COZ, Het in each case, independently of one another, denotes a mono-, bi- or tricyclic saturated, unsaturated or aromatic heterocycle having 1 to 4 N, O and/or S atoms, which may be unsubstituted or mono-, di- or trisubstituted by Hal, F, Cl, Br, CN, A, $OR^{18}$, W, $SR^{18}$, $NO_2$, $N(R^{19})(R^{19'})$, $NR^{18}COOZ$, $OCONHZ$, $NR^{18}SO_2Z$, $SO_2N(R^{18})Z$, $S(O)_mZ$, COZ, CHO, COZ, =S, =NH, =NA, oxy (—O⁻) and/or =O (carbonyl oxygen), m denotes 1, 2 or 3, n, o denote 0, 1 or 2, p denotes 0, 1, 2, 3 or 4 with the proviso that compounds of the formula (I) in which
(a) $M_1$=N, $M_2$=$CR^{19}$, $M_3$=S, and
(b) $Y_1$=CH and $Y_2$=N, and
(c) n=1 and o=1 are excluded;

and physiologically acceptable salts, derivatives, prodrugs, solvates, tautomers and stereoisomers thereof, including mixtures thereof in all ratios.

The invention furthermore relates to preferred, in each case independent embodiments of compounds of the formula (I), in which in each case, independently of one another:

Preferred embodiment (A): $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ denote H, D, F, $OR^{18}$ or A;

where $R^1$ and $R^2$, $R^3$ and $R^4$, $R^5$ and $R^6$, $R^{10}$ and $R^{11}$, $R^{12}$ and $R^{13}$, $R^{14}$ and $R^{15}$, $R^{16}$ and $R^{17}$ together may in each case also form =O (carbonyl oxygen);

where $R^9$ and $R^1$, $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, $R^{10}$ and $R^{11}$, $R^{11}$ and $R^{12}$, $R^{12}$ and $R^{13}$, $R^{14}$ and $R^{15}$, $R^{15}$ and $R^{16}$, $R^{16}$ and $R^{17}$ together may in each case also form cyclic alkyl having 3, 4, 5, 6 or 7 C atoms or Het having 3, 4, 5, 6 or 7 ring atoms;

Preferred embodiment (B): $R^{19}$, $R^{19'}$ denote H, A, $OR^{18}$, $C(O)OR^{18}$, $C(O)NR^{18}R^{18'}$, A-Het;

Preferred embodiment (C): $M_1$ denotes N, and $M_2$ denotes $CR^{19}$ and $M_3$ denotes S;

Preferred embodiment (D): $M_1$ denotes N, and $M_2$ denotes S and $M_3$ denotes $CR^{19}$;

Preferred embodiment (E): $M_1$ denotes O, and $M_2$ denotes N and $M_3$ denotes $CR^{19}$;

Preferred embodiment (F): $M_1$ denotes N, and $M_2$ denotes O and $M_3$ denotes $CR^{19}$;

Preferred embodiment (G): $M_1$ denotes S, and $M_2$ denotes N and $M_3$ denotes N;

Preferred embodiment (H): $M_1$ denotes S, and $M_2$ denotes N and $M_3$ denotes $CR^{19}$;

Preferred embodiment (I): $M_1$ denotes O, and $M_2$ denotes N and $M_3$ denotes N;

Preferred embodiment (J): $M_1$ denotes N, and $M_2$ denotes N and $M_3$ denotes O;

Preferred embodiment (K): $M_1$ denotes N, and $M_2$ denotes N and $M_3$ denotes S;

Preferred embodiment (L): $M_1$ denotes $CR^{19}$, and $M_2$ denotes N and $M_3$ denotes O;

Preferred embodiment (M): $M_1$ denotes $CR^{19}$, and $M_2$ denotes O and $M_3$ denotes N;

Preferred embodiment (N): $Y_1$ denotes N, and $Y_2$ denotes $CR^{19}$;

Preferred embodiment (O): $Y_1$ denotes N, and $Y_2$ denotes N;

Preferred embodiment (P): $Y_1$ denotes $CR^{19}$, and $Y_2$ denotes N;

Preferred embodiment (Q): $Y_1$ denotes $CR^{19}$, and $Y_2$ denotes $CR^{19}$;

Preferred embodiment (R): V denotes $C(R^{19})(R^{19'})$, $NR^{19}$ or is absent;

Preferred embodiment (S): W denotes $[C(R^{19})(R^{19'})]_pZ$, $CO—[C(R^{19})(R^{19'})]_pZ$, $CO—O—[C(R^{19})(R^{19'})]_pZ$, $CO—N(R^{19})—[C(R^{19})(R^{19'})]_pZ$, $[C(R^{19})(R^{19'})]_pN(R^{19})—Z$, $N(R^{19})—CO—[C(R^{19})(R^{19'})]_pZ$, $C(O)OR^{19}$, $OR^{19}$ or H;

where V, W and $Y_2$ together may in each case also form cyclic alkyl having 3, 4, 5, 6 or 7 C atoms, in which 1, 2, 3, 4, 5, 6 or 7 H atoms may preferably be replaced by F, Cl, Br, CN and/or OH, $OR^{19}$, $OC(O)R^{19}$, $NR^{19}C(O)OZ$, $C(O)OR^{19}$, $C(O)N(R^{19})(R^{19'})$ or $N(R^{19})(R^{19'})$, or Het having 3, 4, 5, 6 or 7 ring atoms, where Het preferably represents a saturated, unsaturated or aromatic heterocycle having 1 to 4 N, O and/or S atoms, which may be unsubstituted or mono-, di- or trisubstituted by Hal, F, Cl, Br, CN, A, OR$^{18}$, W, SR$^{18}$, NO$_2$, N(R$^{19}$)(R$^{19'}$), NR$^{18}$COOZ, OCONHZ, NR$^{18}$SO$_2$Z, SO$_2$N(R$^{18}$)Z, S(O)$_m$Z, COZ, CHO, COZ, =S, =NH, =NA, oxy (—O$^-$) and/or =O (carbonyl oxygen);

Preferred embodiment (T): Z denotes Het or A;
Preferred embodiment (U): m denotes 1 or 2;
Preferred embodiment (V): p denotes 0, 1, 2 or 3;
and in each case physiologically acceptable salts, derivatives, prodrugs, solvates, tautomers and stereoisomers thereof, including mixtures thereof in all ratios.

In a preferred embodiment, the invention furthermore relates to compounds of the formula (I) and preferred embodiments depicted here, in which in each case, independently of one another:

R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$ denote H, D, F, OR$^{18}$ or A;

where R$^1$ and R$^2$, R$^3$ and R$^4$, R$^5$ and R$^6$, R$^{10}$ and R$^{11}$, R$^{12}$ and R$^{13}$, R$^{14}$ and R$^{15}$, R$^{16}$ and R$^{17}$ together may in each case also form =O (carbonyl oxygen);

where R$^9$ and R$^1$, R$^1$ and R$^2$, R$^2$ and R$^3$, R$^3$ and R$^4$, R$^4$ and R$^5$, R$^5$ and R$^6$, R$^6$ and R$^7$, R$^7$ and R$^8$, R$^{10}$ and R$^{11}$, R$^{11}$ and R$^{12}$, R$^{12}$ and R$^{13}$, R$^{14}$ and R$^{15}$, R$^{15}$ and R$^{16}$, R$^{16}$ and R$^{17}$ together may in each case also form cyclic alkyl having 3, 4, 5, 6 or 7 C atoms or Het having 3, 4, 5, 6 or 7 ring atoms;

R$^{19}$, R$^{19'}$ denote H, A, OR$^{18}$, C(O)OR$^{18}$, C(O)NR$^{18}$R$^{18'}$, A-Het;

M$_1$ denotes N, and M$_2$ denotes CR$^{19}$ and M$_3$ denotes S; or
M$_1$ denotes N, and M$_2$ denotes S and M$_3$ denotes CR$^{19}$; or
M$_1$ denotes O, and M$_2$ denotes N and M$_3$ denotes CR$^{19}$; or
M$_1$ denotes N, and M$_2$ denotes O and M$_3$ denotes CR$^{19}$; or
M$_1$ denotes S, and M$_2$ denotes N and M$_3$ denotes N; or
M$_1$ denotes S, and M$_2$ denotes N and M$_3$ denotes CR$^{19}$; or
M$_1$ denotes O, and M$_2$ denotes N and M$_3$ denotes N; or
M$_1$ denotes N, and M$_2$ denotes N and M$_3$ denotes O; or
M$_1$ denotes N, and M$_2$ denotes N and M$_3$ denotes S; or
M$_1$ denotes CR$^{19}$, and M$_2$ denotes N and M$_3$ denotes O; or
M$_1$ denotes CR$^{19}$, and M$_2$ denotes O and M$_3$ denotes N;

Y$_1$ denotes N, and Y$_2$ denotes CR$^{19}$; or
Y$_1$ denotes N, and Y$_2$ denotes N; or
Y$_1$ denotes CR$^{19}$, and Y$_2$ denotes N; or
Y$_1$ denotes CR$^{19}$, and Y$_2$ denotes CR$^{19}$;

V denotes C(R$^{19}$)(R$^{19'}$), NR$^{19}$ or is absent;

W denotes [C(R$^{19}$)(R$^{19'}$)]$_p$Z, CO—[C(R$^{19}$)(R$^{19'}$)]$_p$Z, CO—O—[C(R$^{19}$)(R$^{19'}$)]$_p$Z, CO—N(R$^{19}$)—[C(R$^{19}$)(R$^{19'}$)]$_p$Z, [C(R$^{19}$)(R$^{19'}$)]$_p$N(R$^{19}$)—Z, N(R$^{19}$)—CO—[C(R$^{19}$)—(R$^{19'}$)]$_p$Z, C(O)OR$^{19}$, OR$^{19}$ or H;

where V, W and Y$_2$ together may in each case also form cyclic alkyl having 3, 4, 5, 6 or 7 C atoms, in which 1, 2, 3, 4, 5, 6 or 7 H atoms may preferably be replaced by F, Cl, Br, CN and/or OH, OR$^{19}$, OC(O)R$^{19}$, NR$^{19}$C(O)OZ, C(O)OR$^{19}$, C(O)N(R$^{19}$)(R$^{19'}$) or N(R$^{19}$)(R$^{19'}$), or Het having 3, 4, 5, 6 or 7 ring atoms, where Het preferably represents a saturated, unsaturated or aromatic heterocycle having 1 to 4 N, O and/or S atoms, which may be unsubstituted or mono-, di- or trisubstituted by Hal, F, Cl, Br, CN, A, OR$^{18}$, W, SR$^{18}$, NO$_2$, N(R$^{19}$)(R$^{19'}$), NR$^{18}$COOZ, OCONHZ, NR$^{18}$SO$_2$Z, SO$_2$N(R$^{18}$)Z, S(O)$_m$Z, COZ, CHO, COZ, =S, =NH, =NA, oxy (—O$^-$) and/or =O (carbonyl oxygen);

Z denotes Het or A;
m denotes 1 or 2;
p denotes 0, 1, 2 or 3;

and physiologically acceptable salts, derivatives, prodrugs, solvates, tautomers and stereoisomers thereof, including mixtures thereof in all ratios.

The invention furthermore relates to compounds selected from the group consisting of:

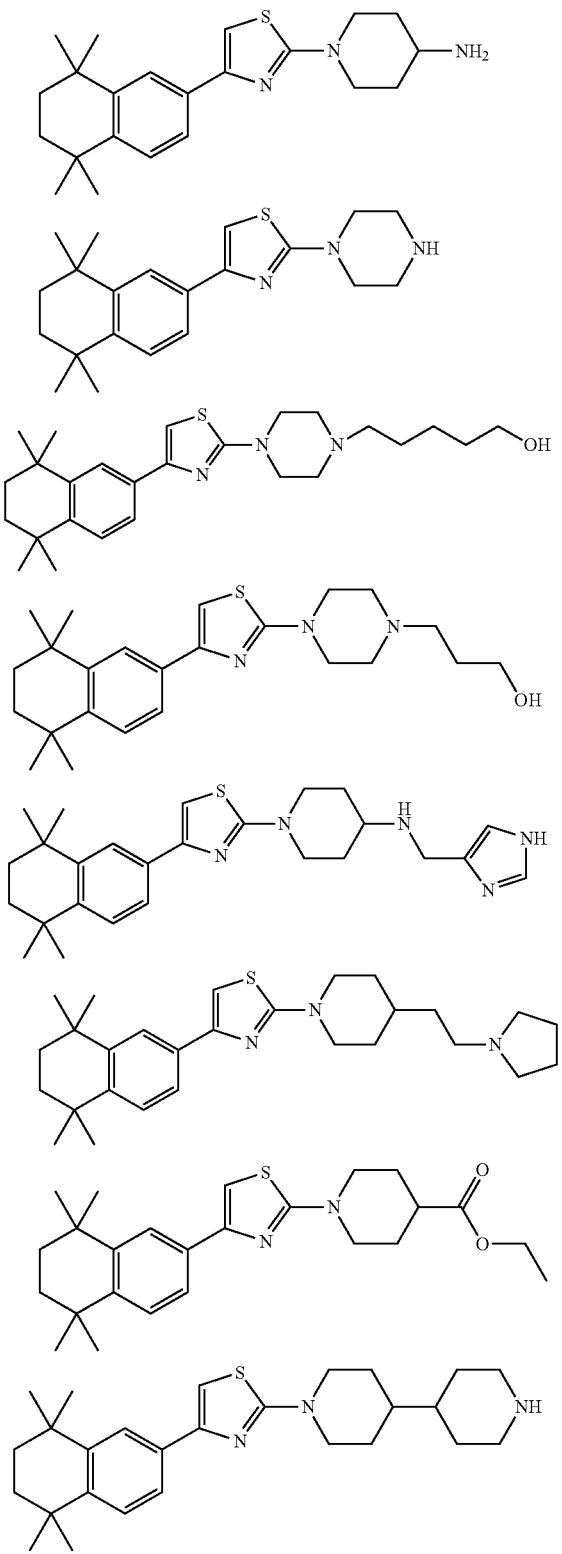

-continued
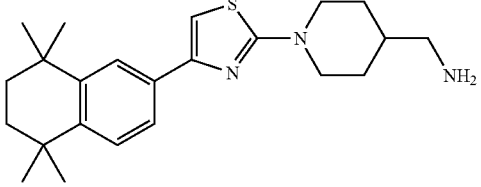
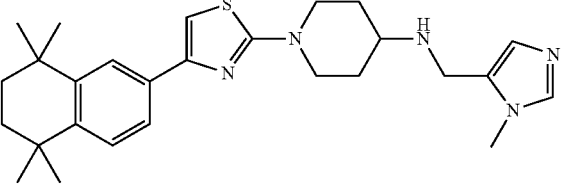
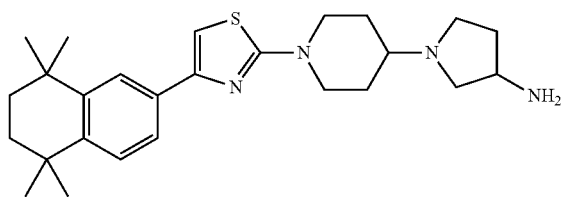
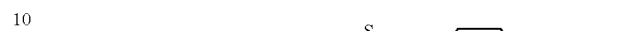
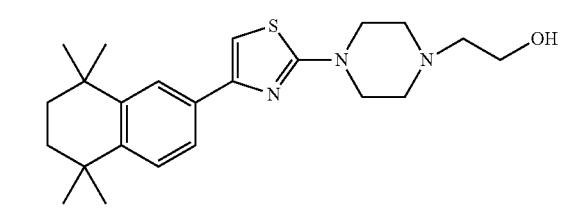
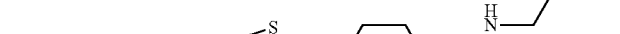
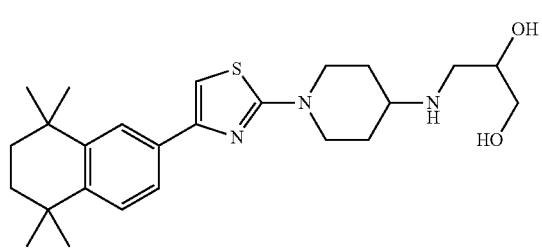
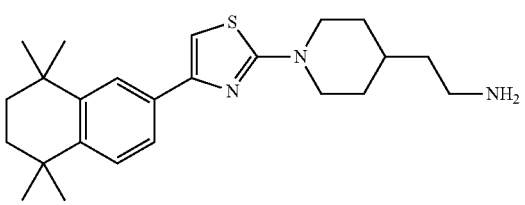
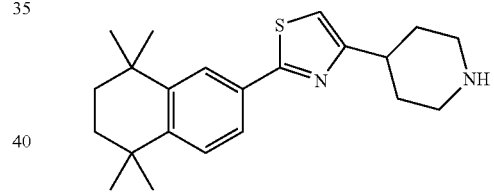
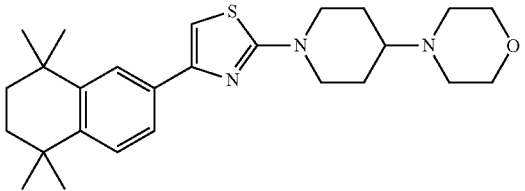
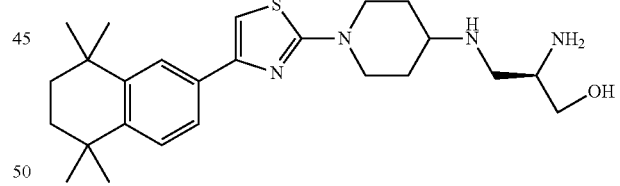
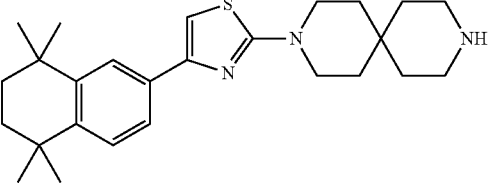
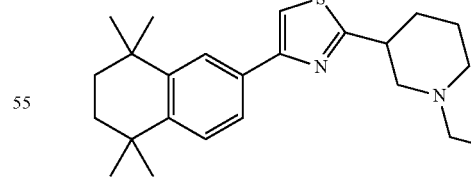
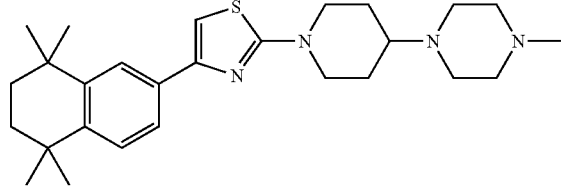
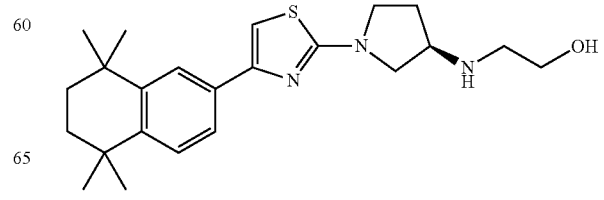

-continued
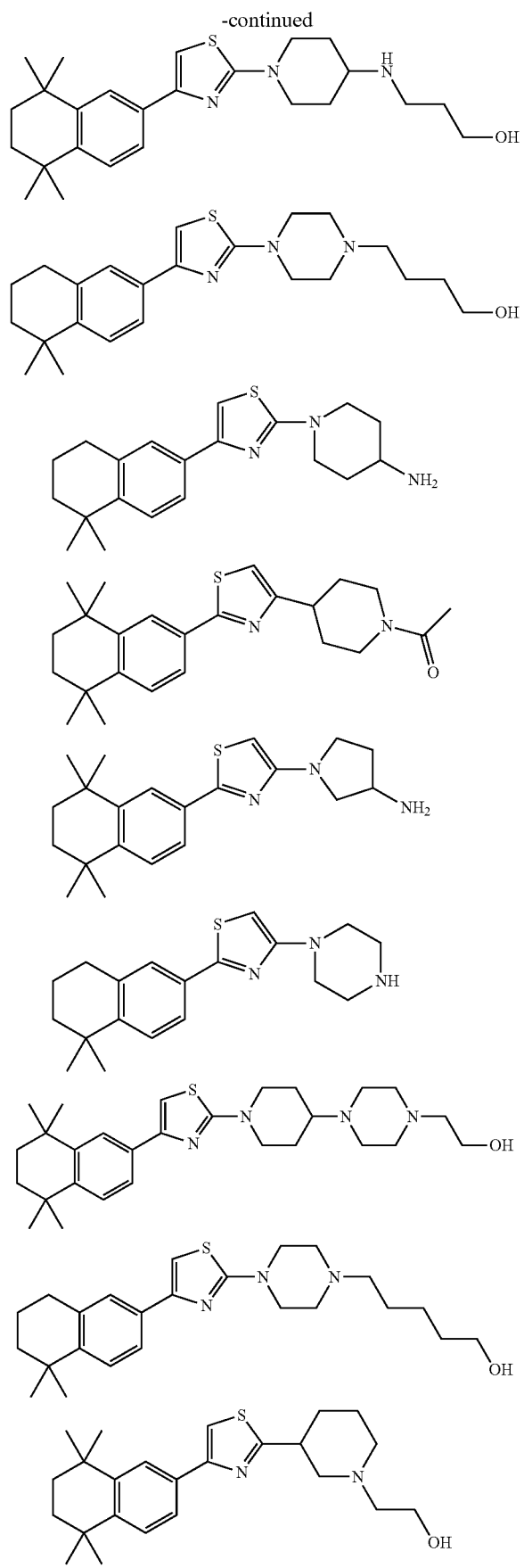
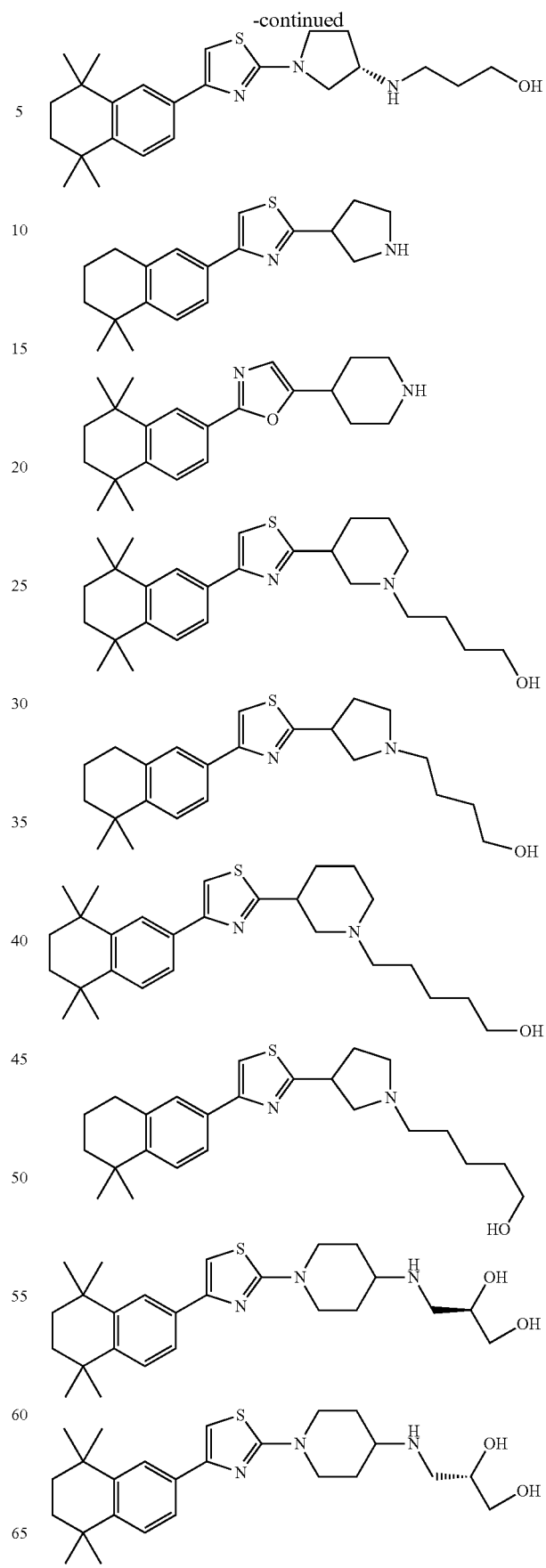

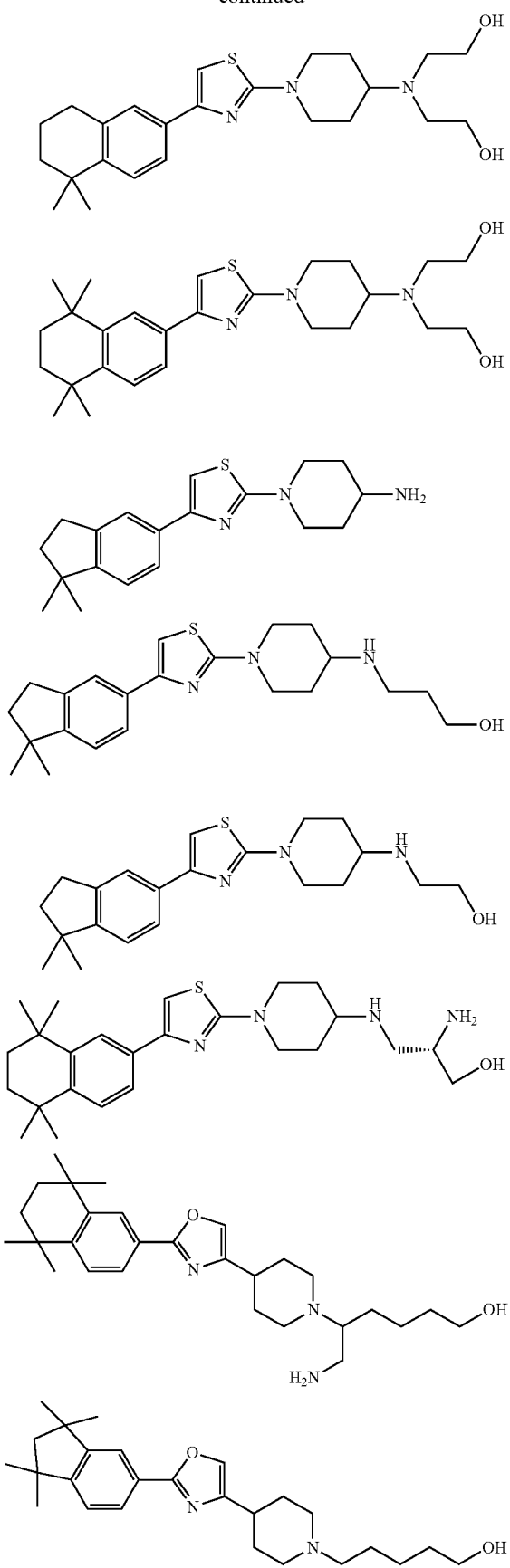
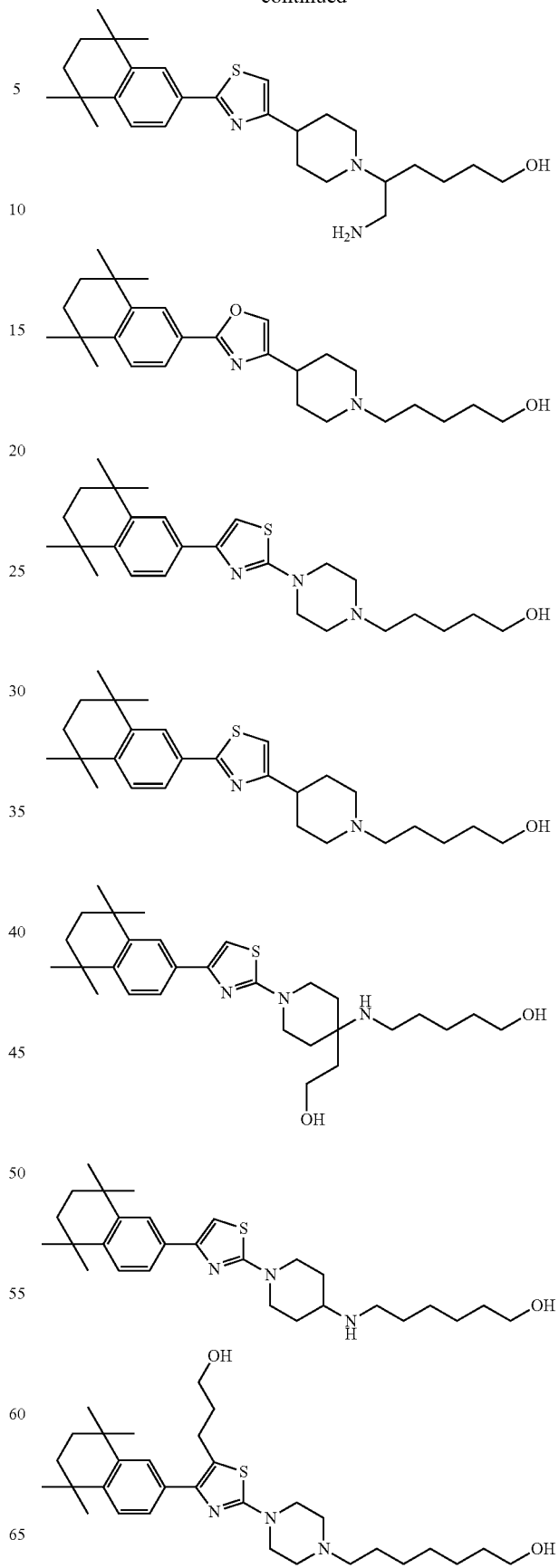

17
-continued
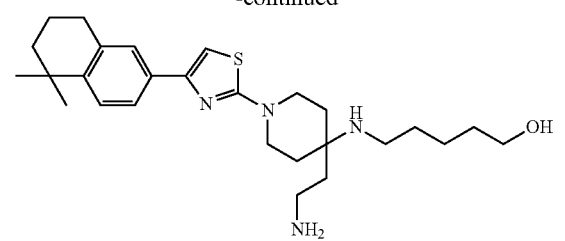
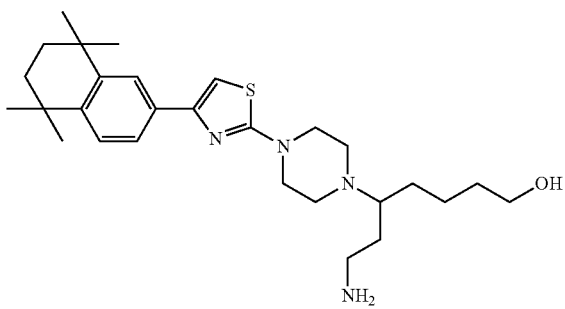
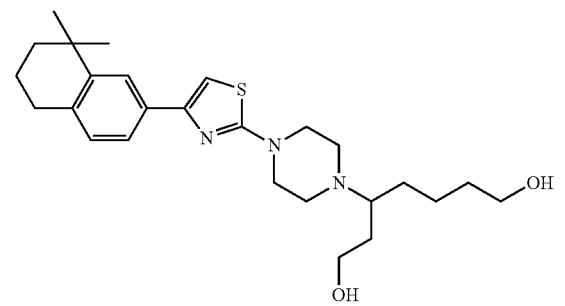
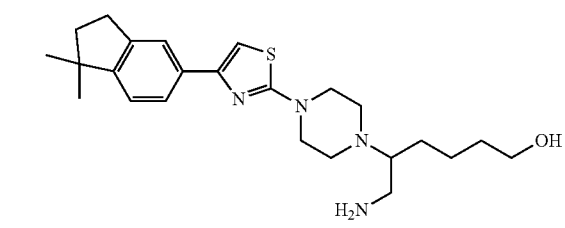
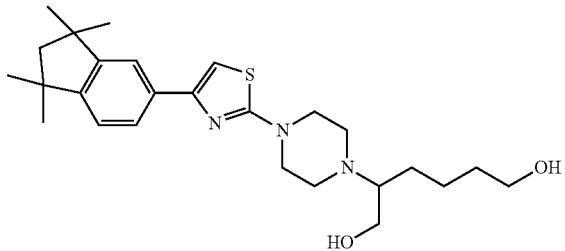
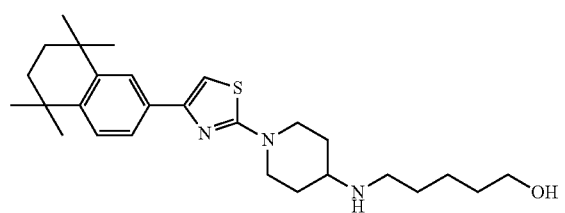
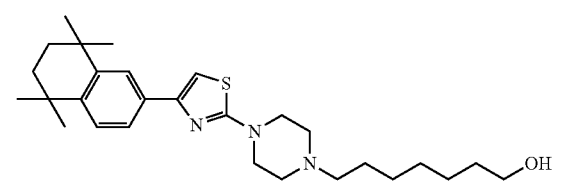
18
-continued
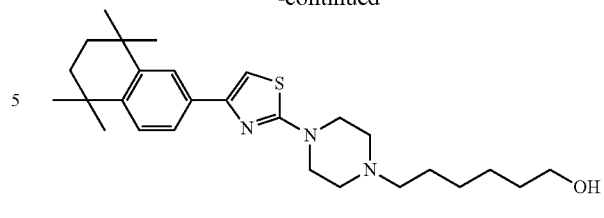
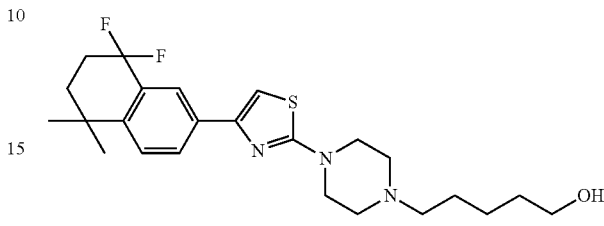
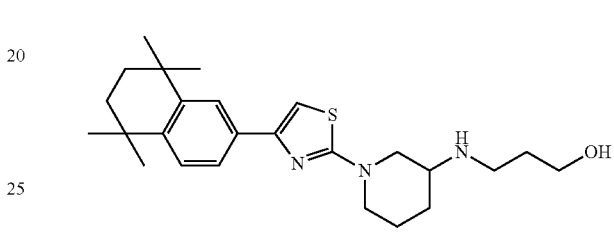
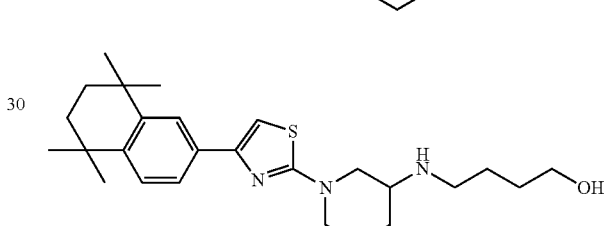
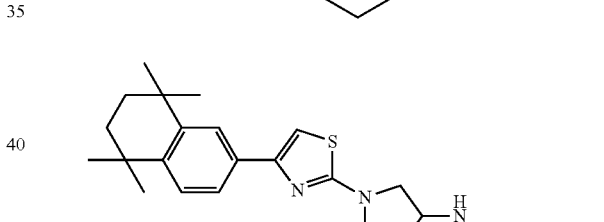
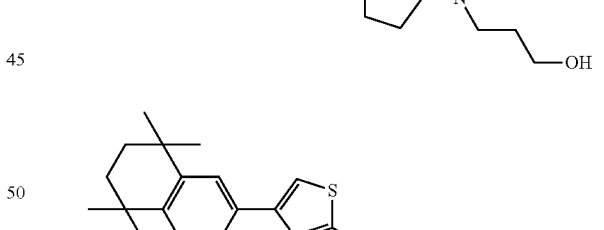
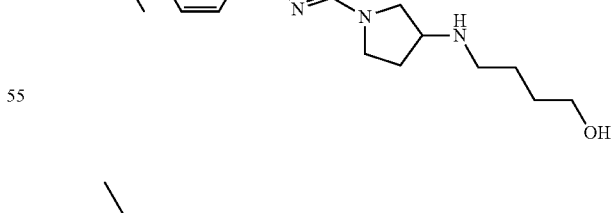
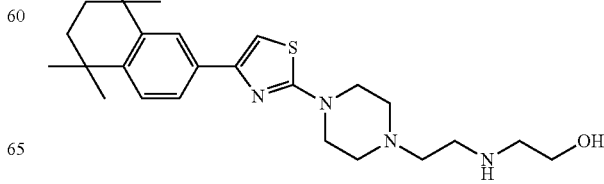

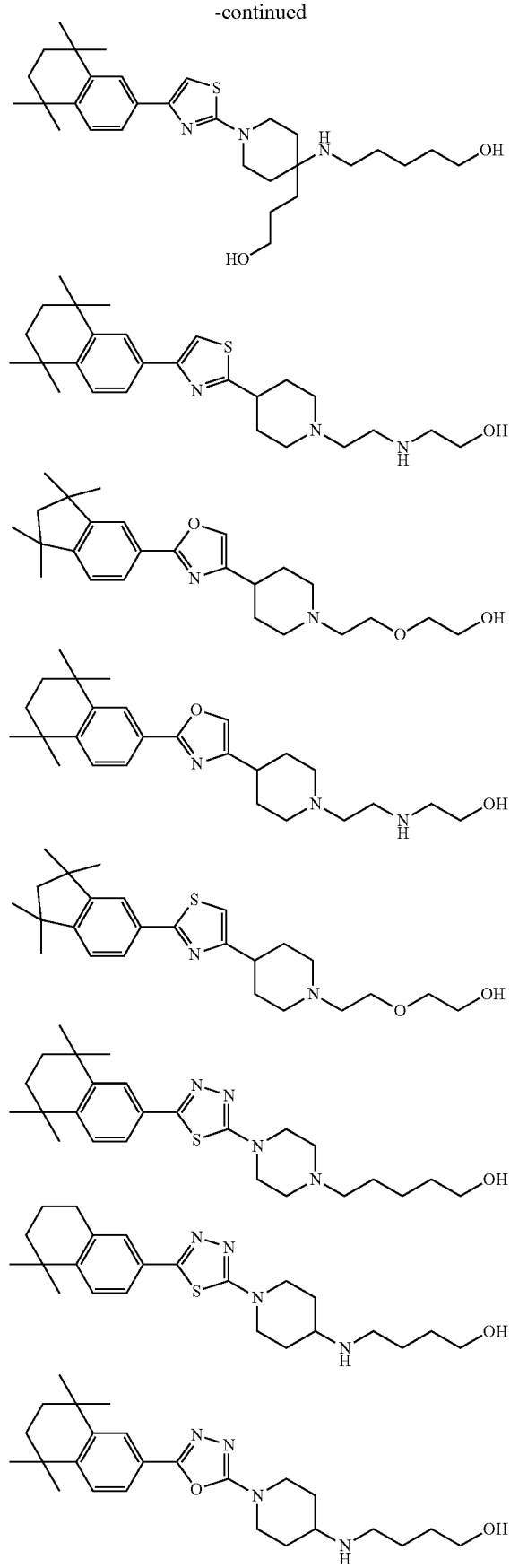
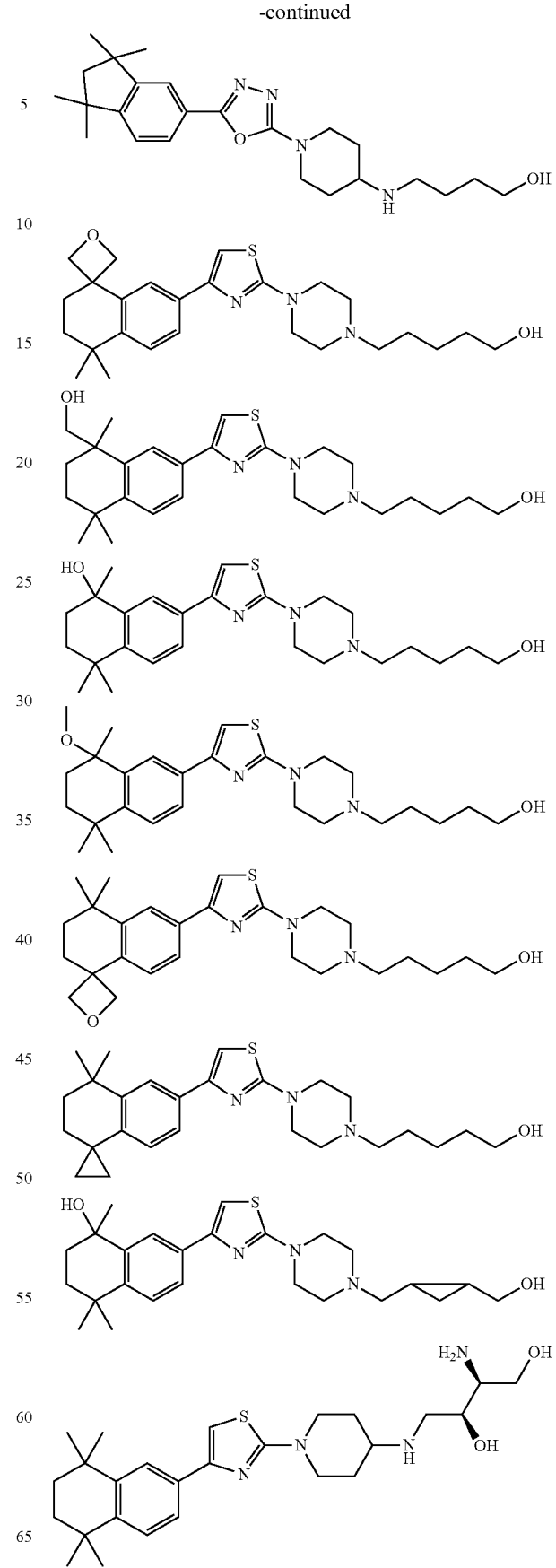

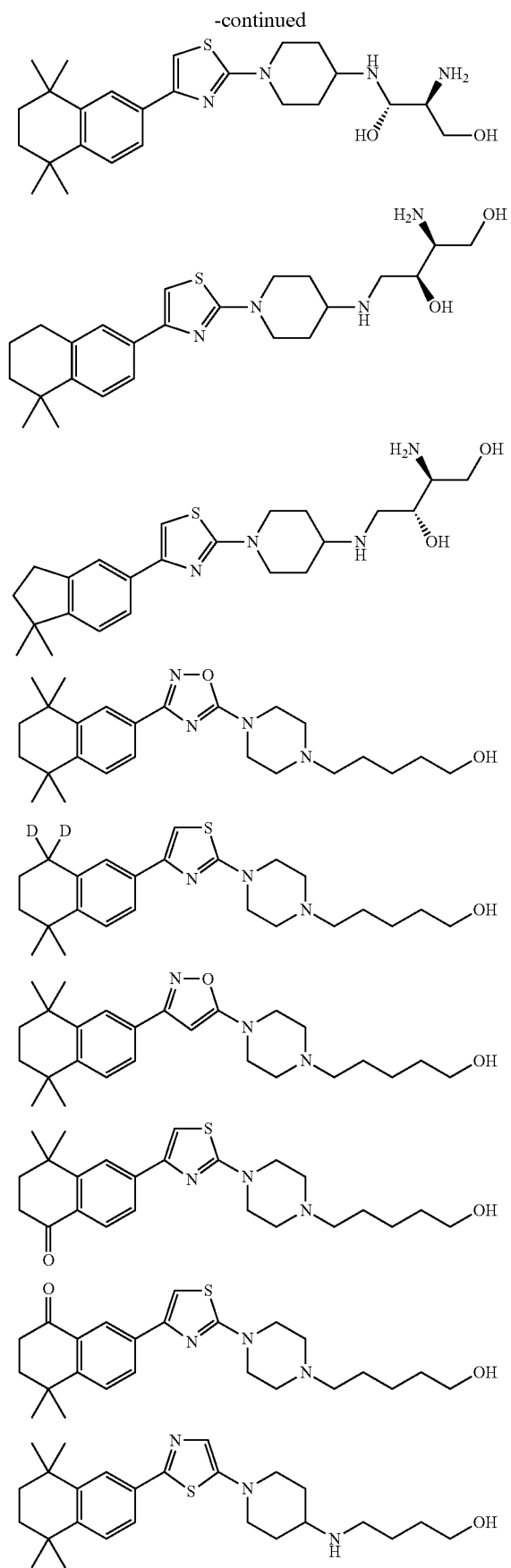
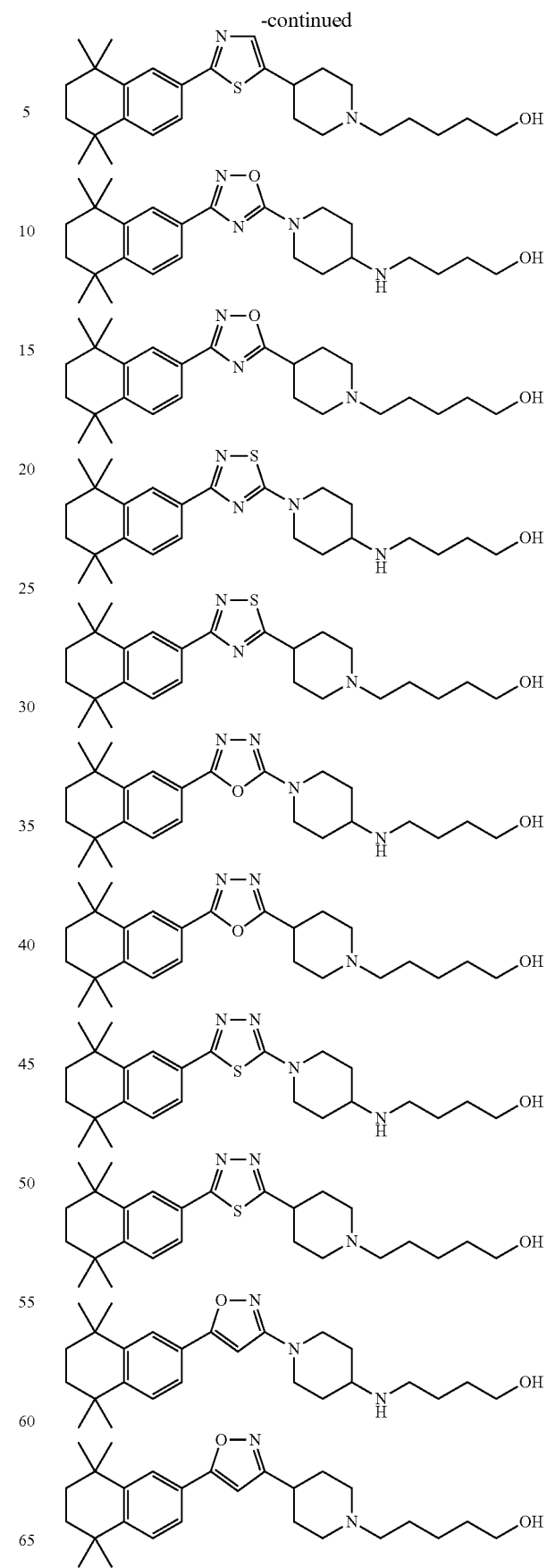

23
-continued
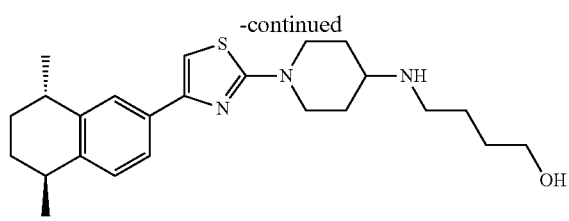
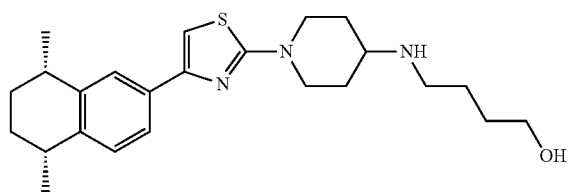
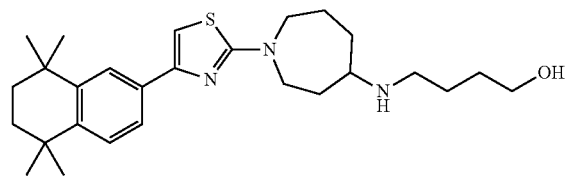
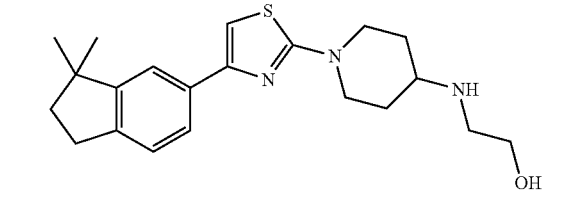
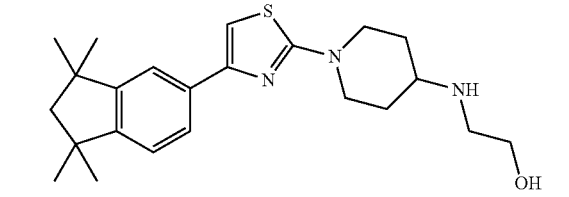
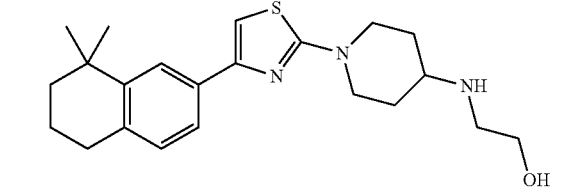
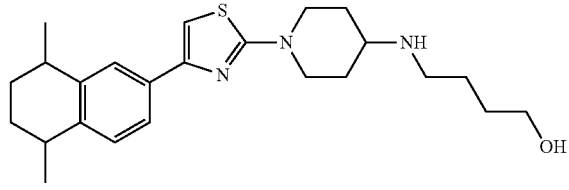
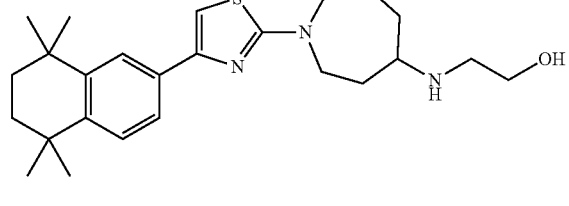
24
-continued
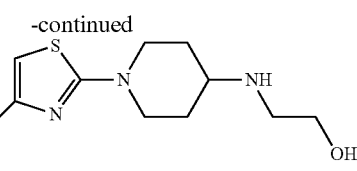
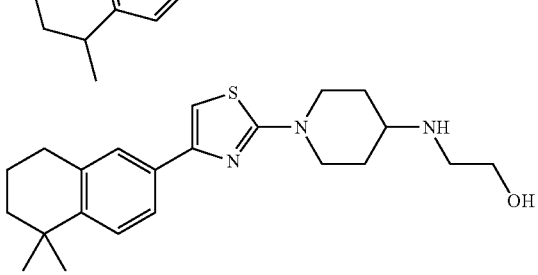
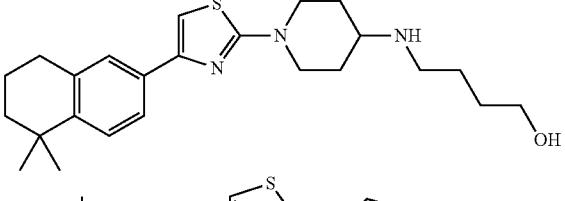
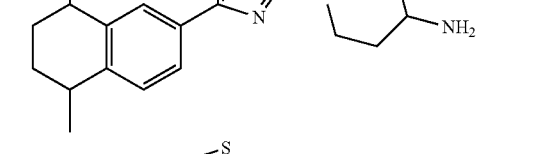
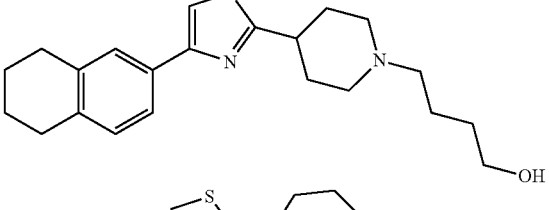
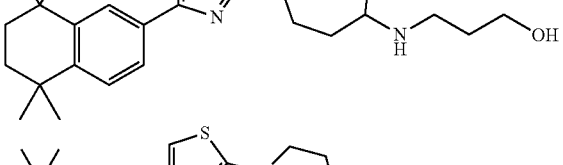
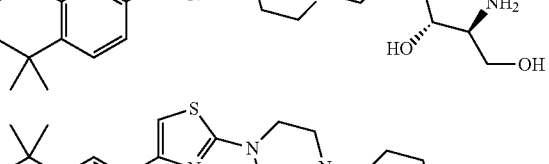
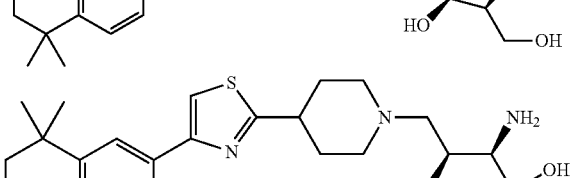

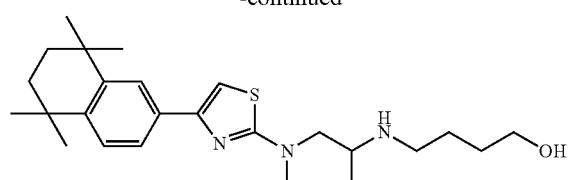
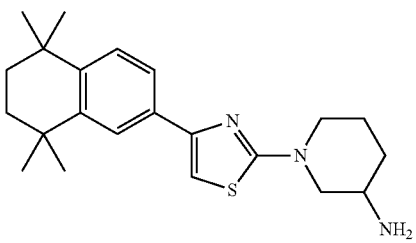
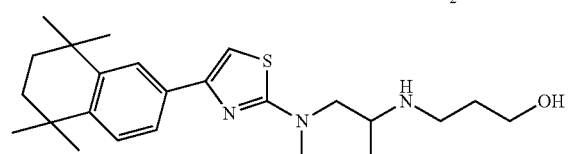
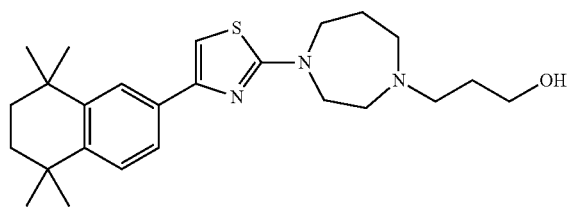
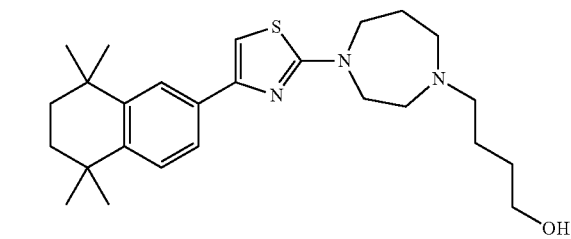
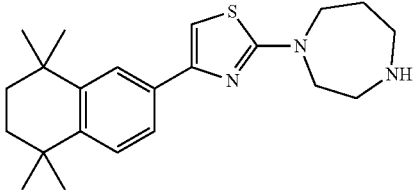
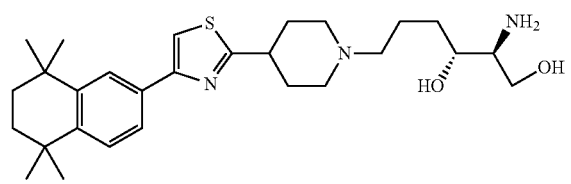
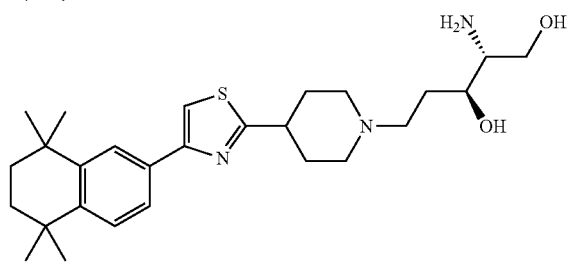
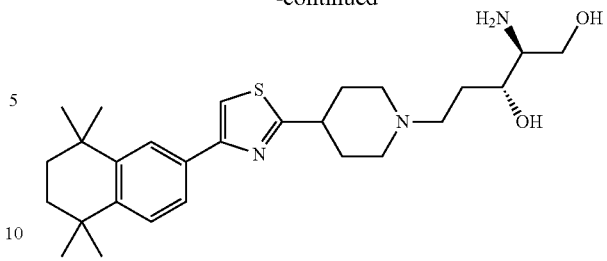
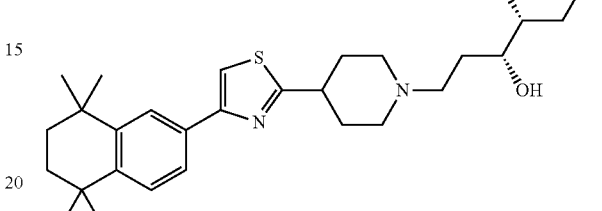
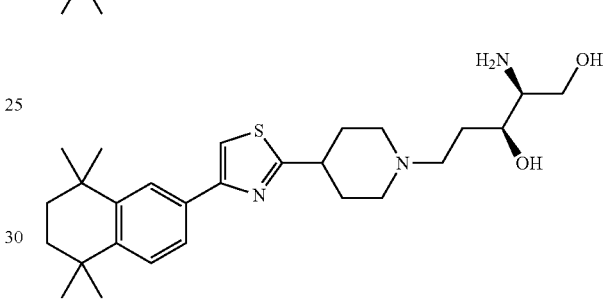
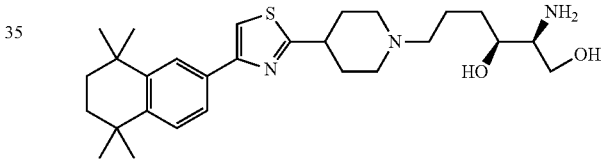
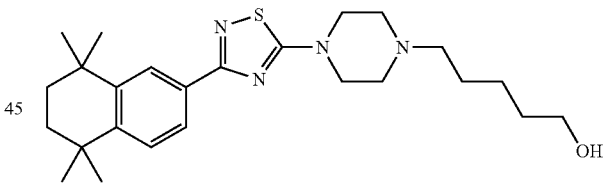
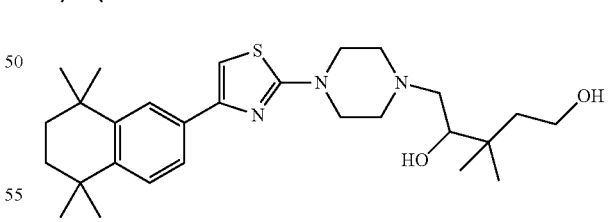
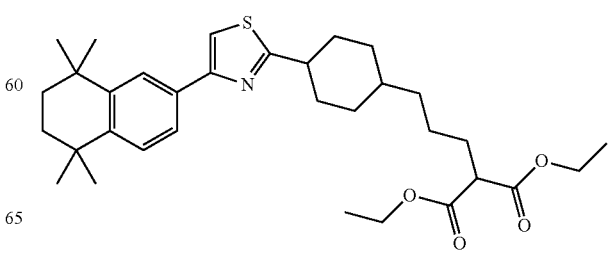

27
-continued
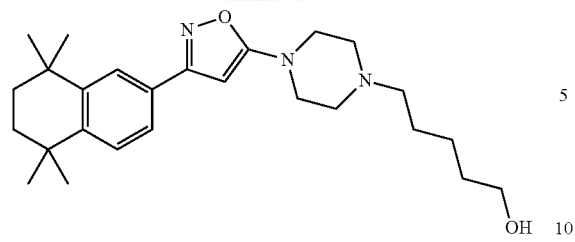
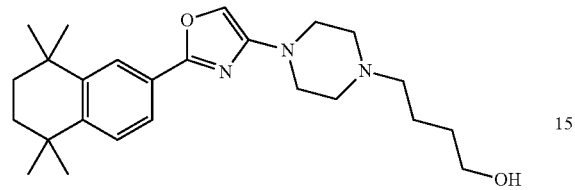
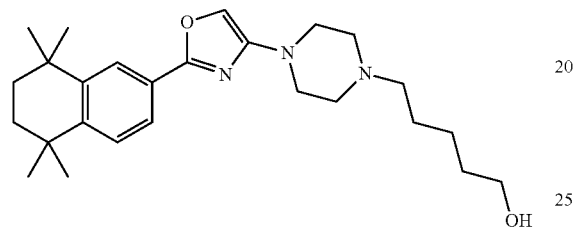
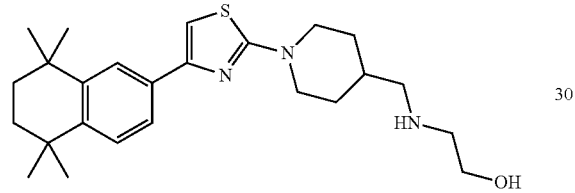
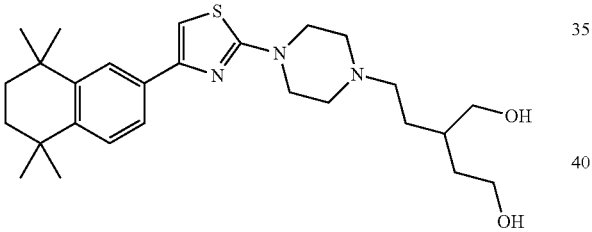
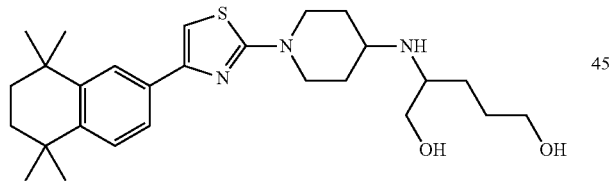
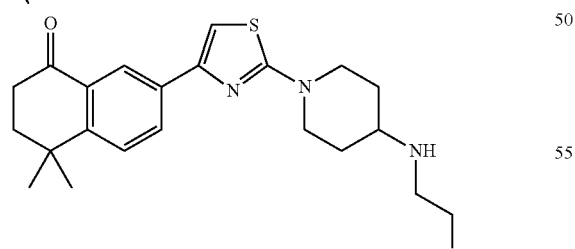
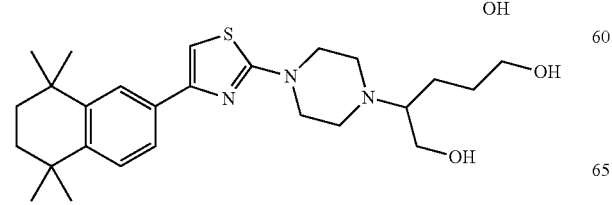
28
-continued
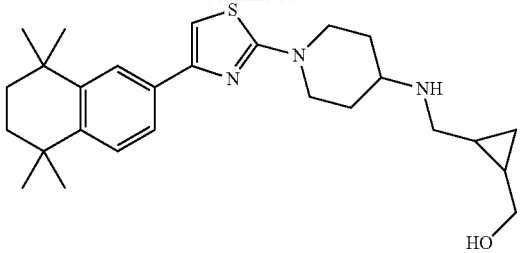
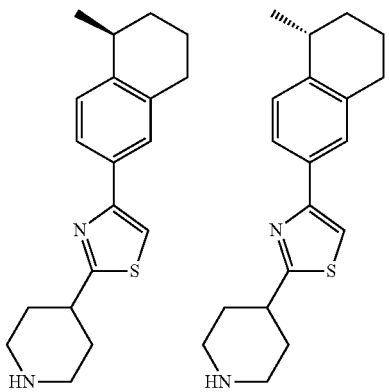
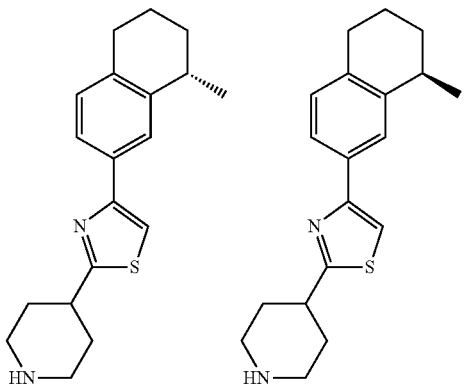
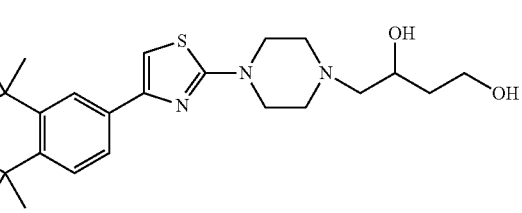
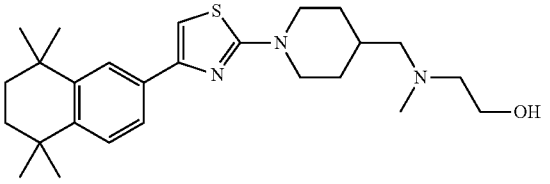
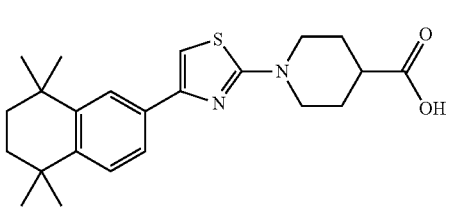

-continued
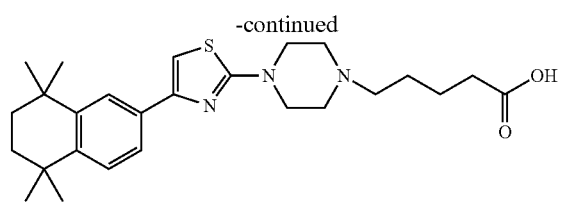
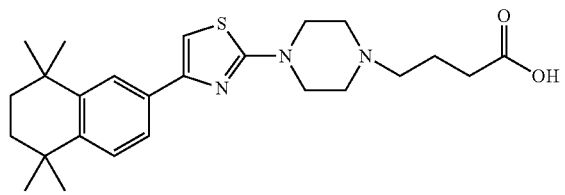
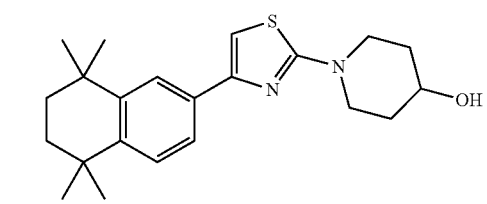
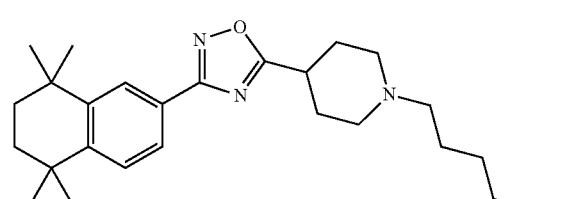
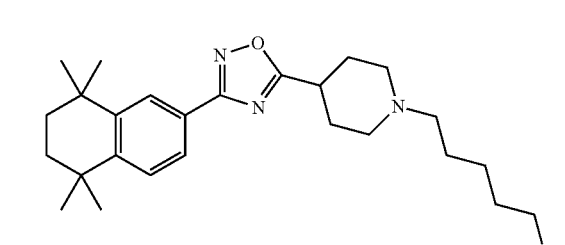
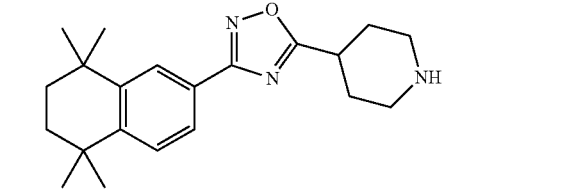
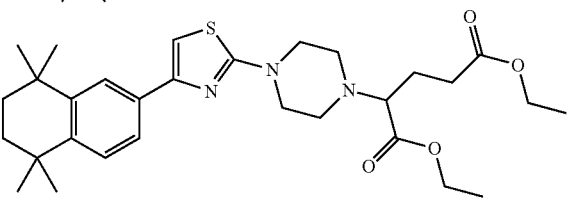
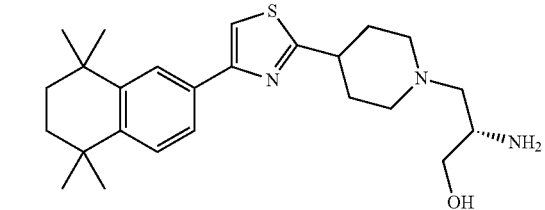
-continued
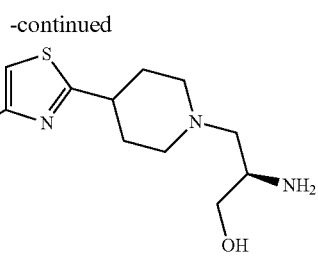
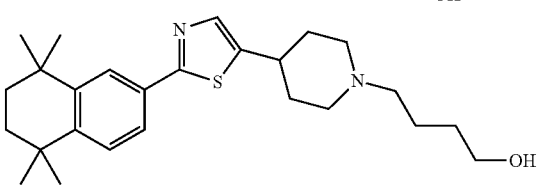
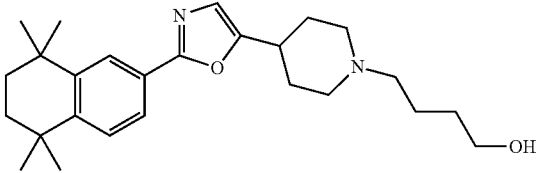
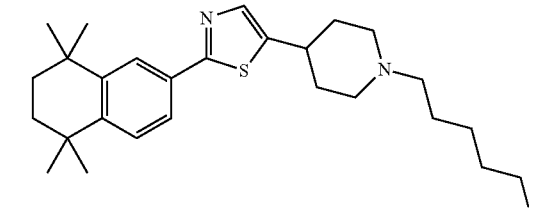
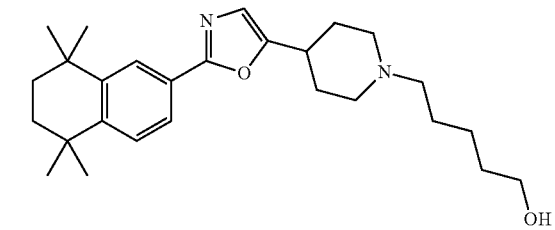
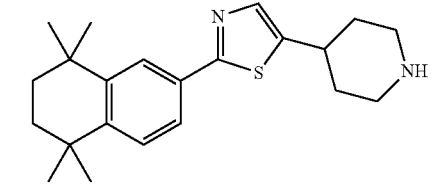
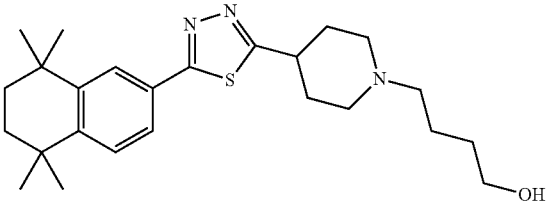
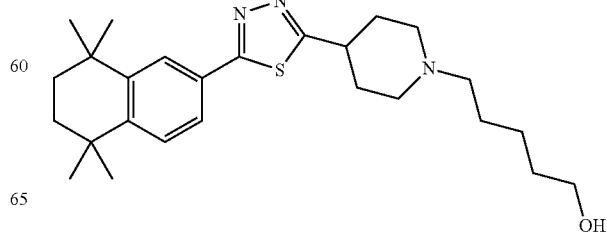

31
-continued
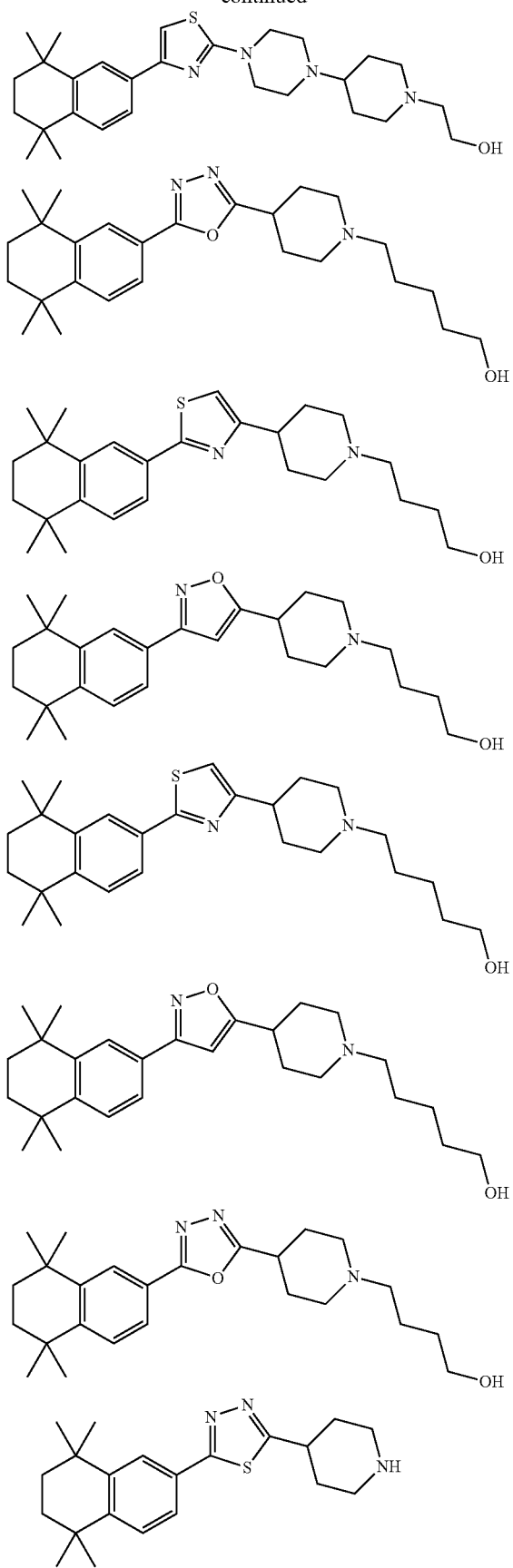
32
-continued
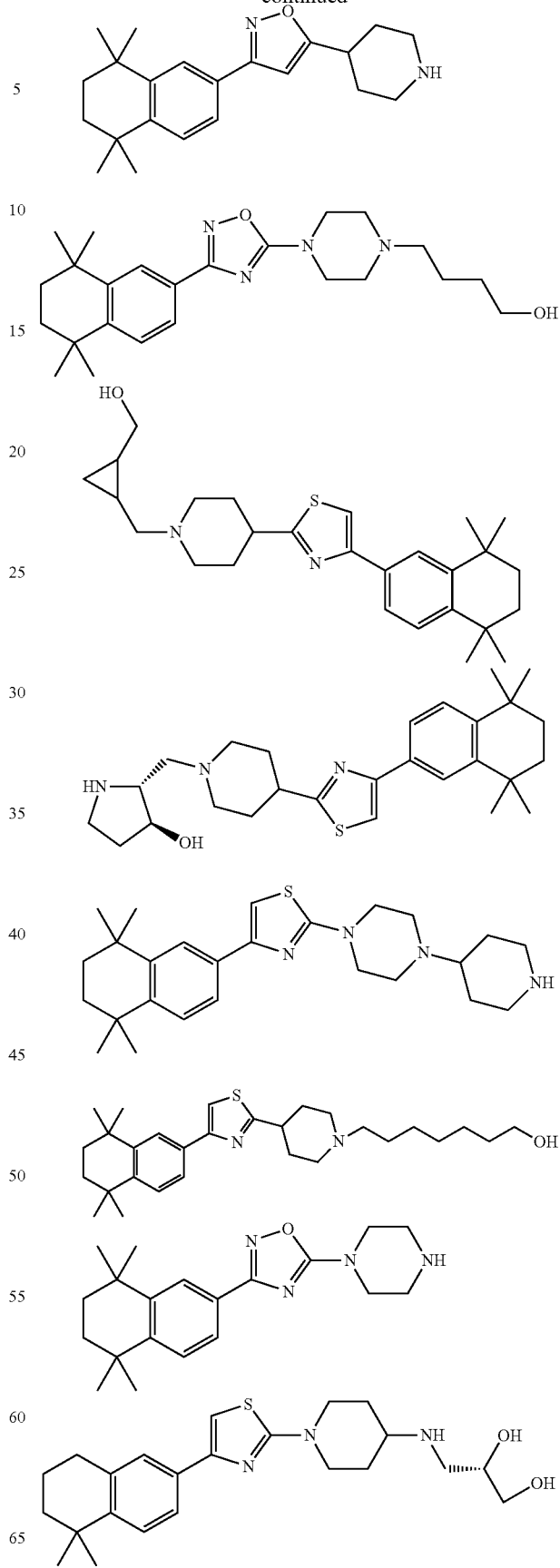

33
-continued
34
-continued
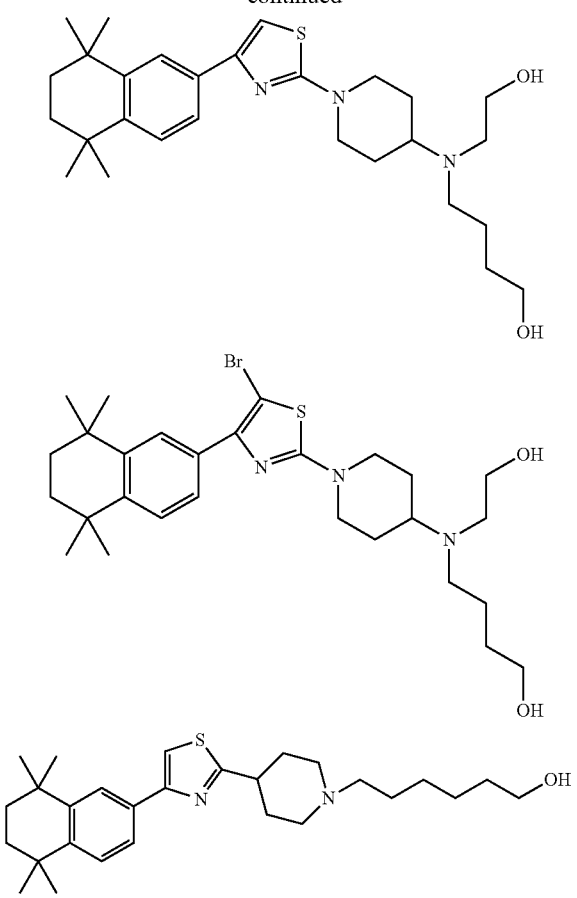
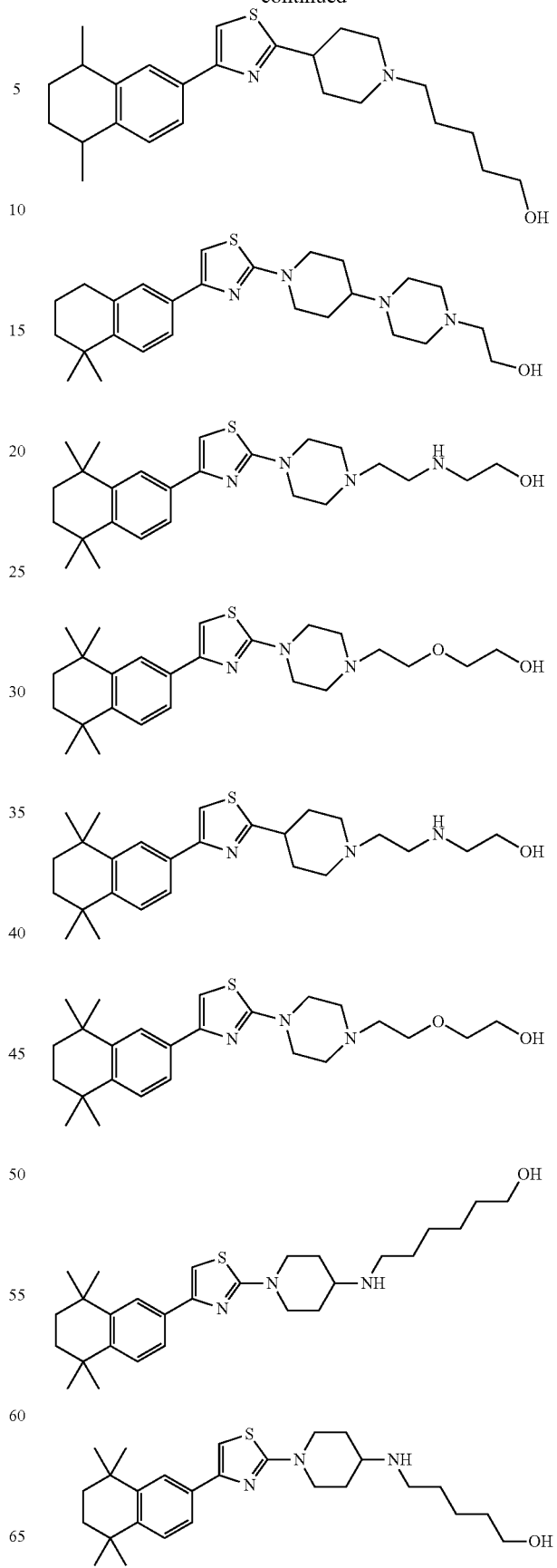

35
-continued
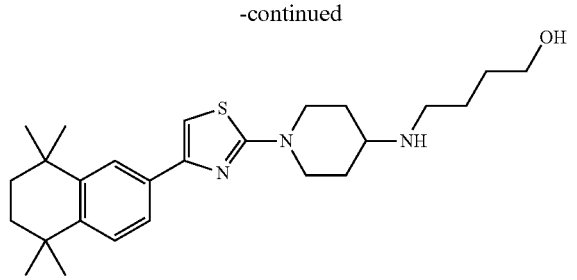
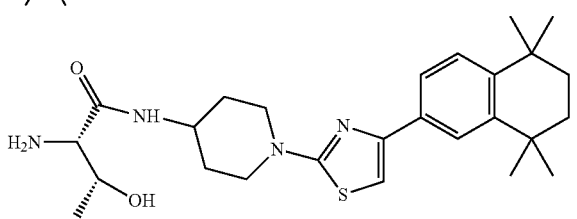
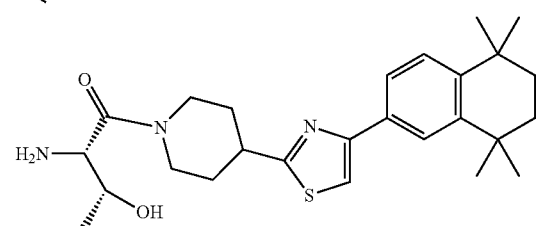
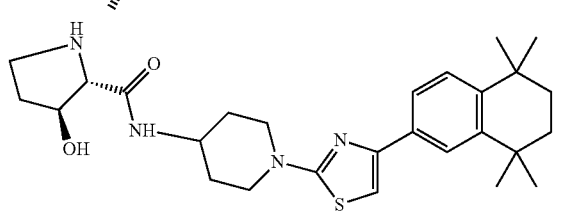
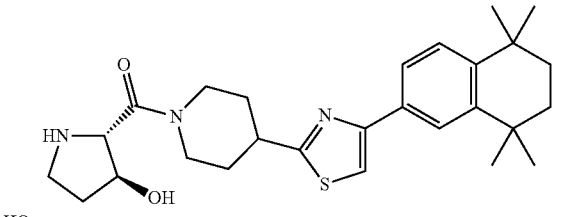
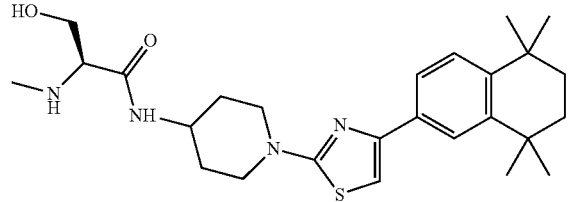
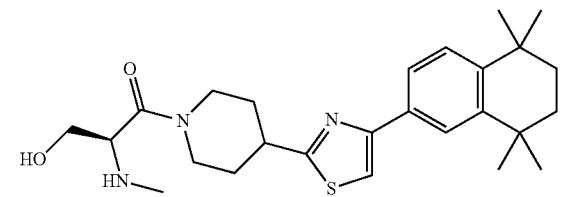
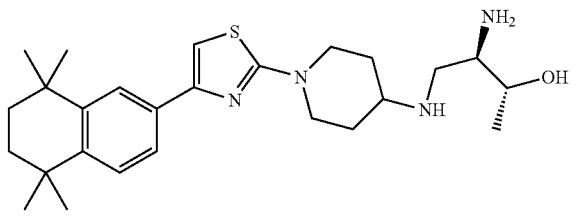
36
-continued
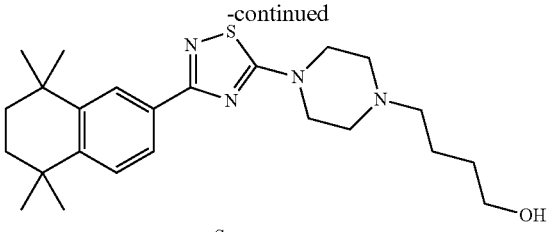
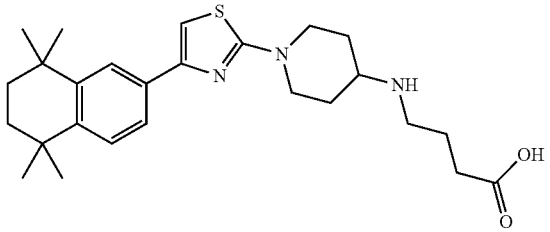
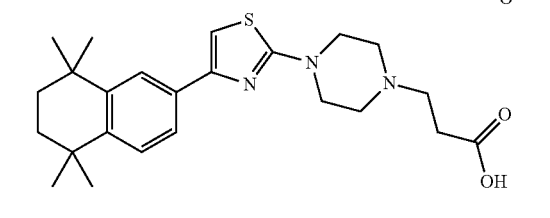
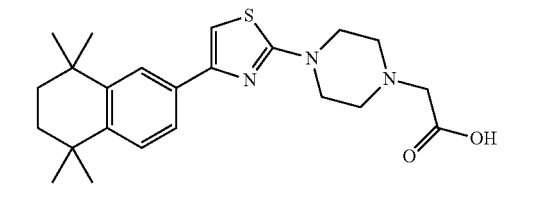
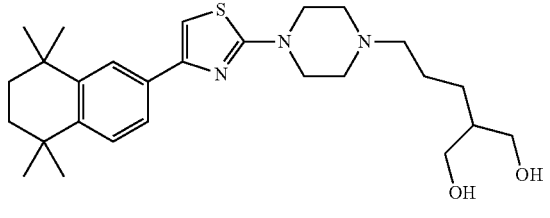
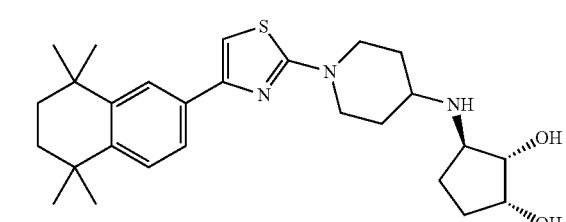
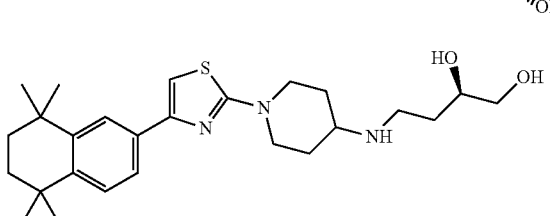
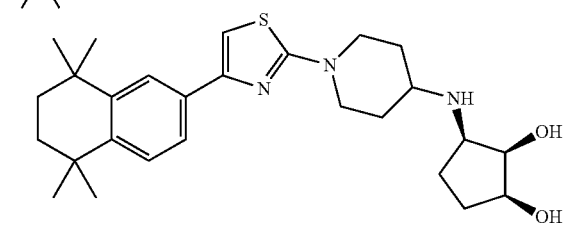

37
-continued
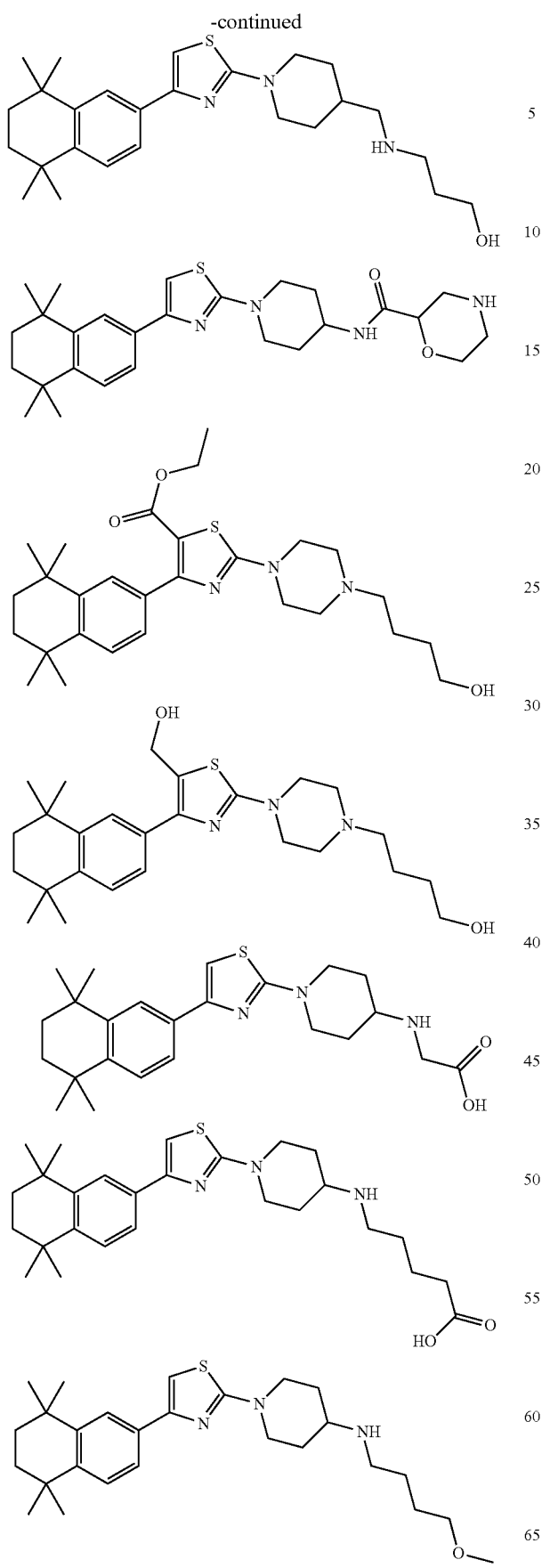
38
-continued
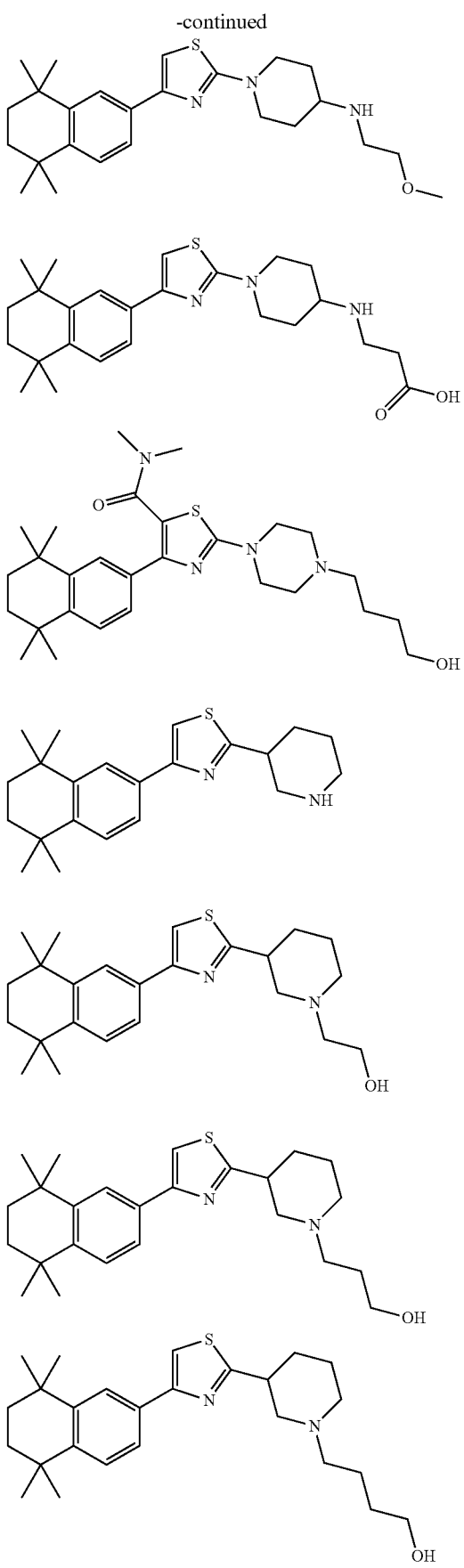

39
-continued
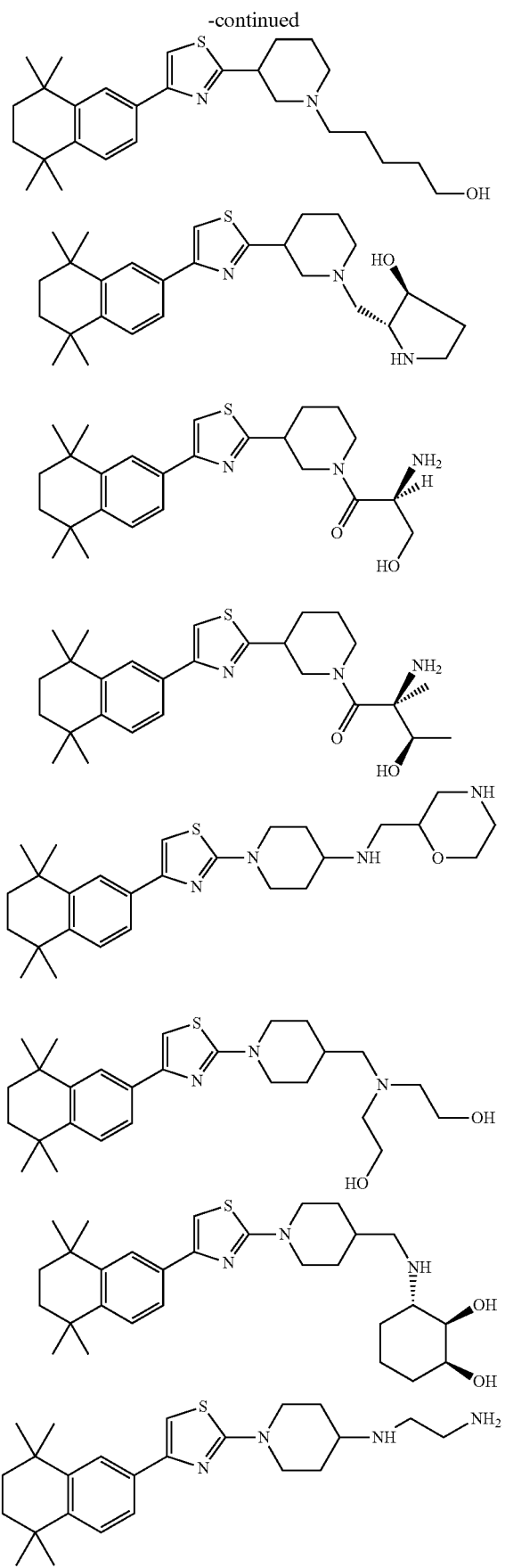
40
-continued
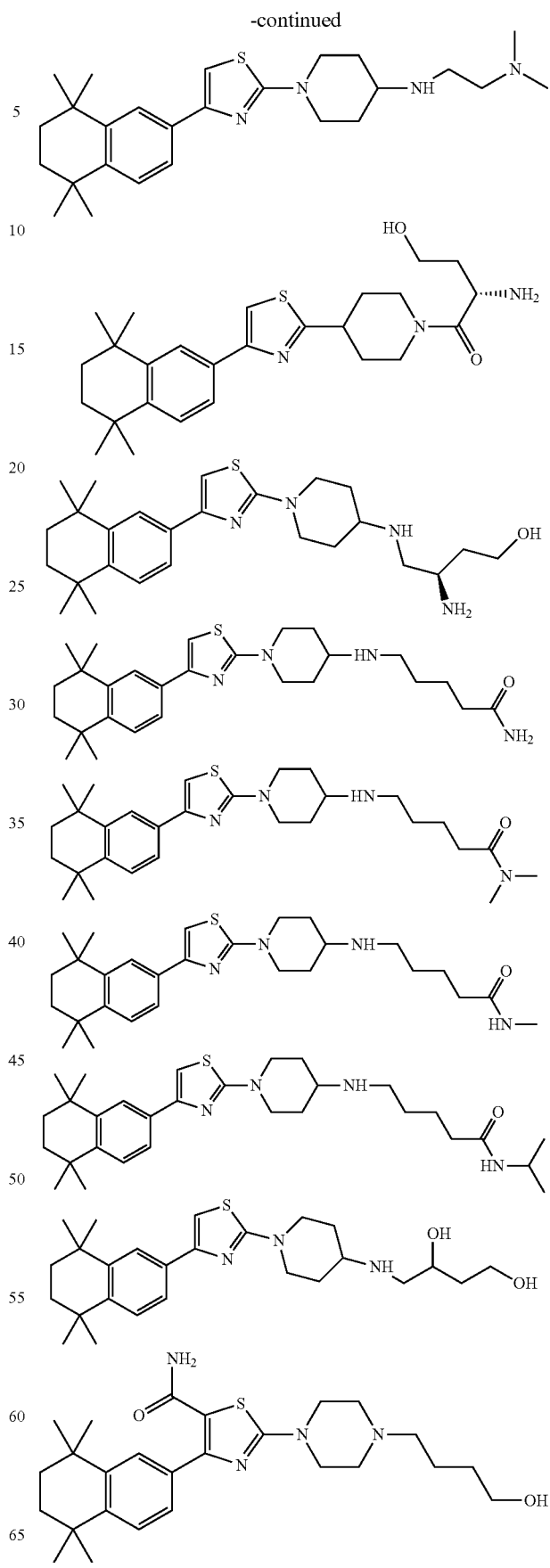

41
-continued
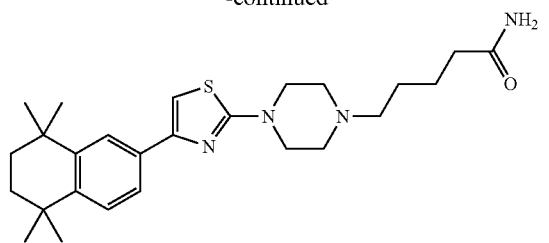
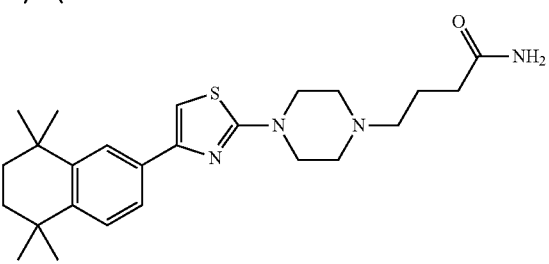
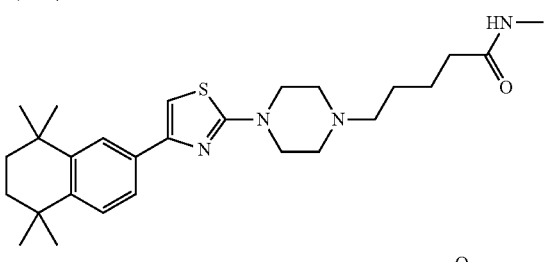
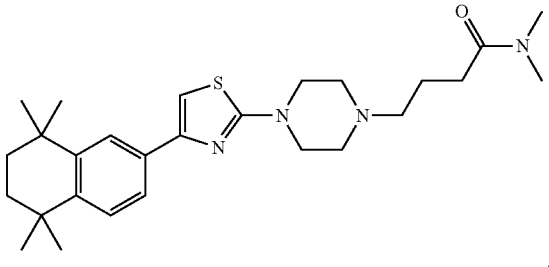
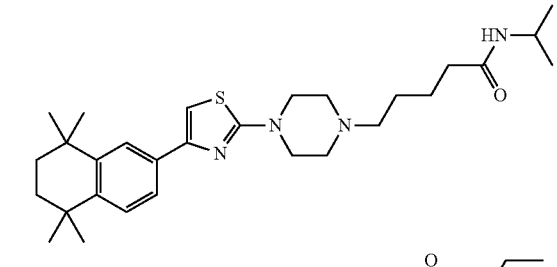
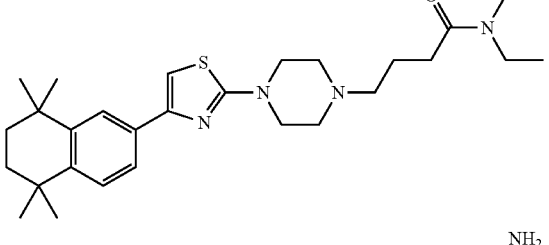
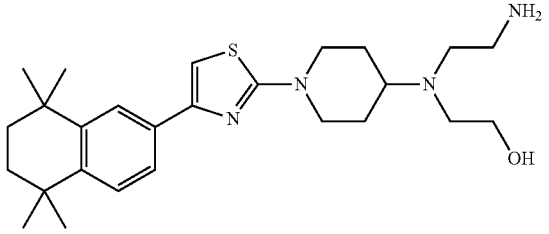
42
-continued
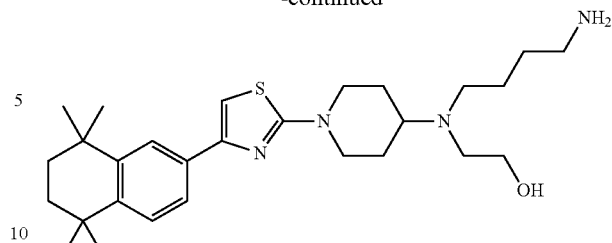
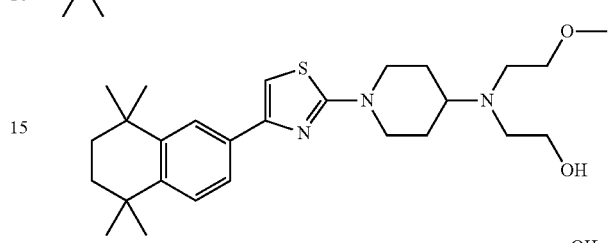
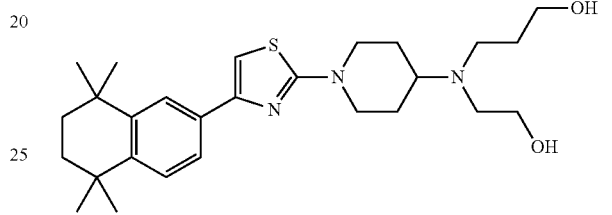
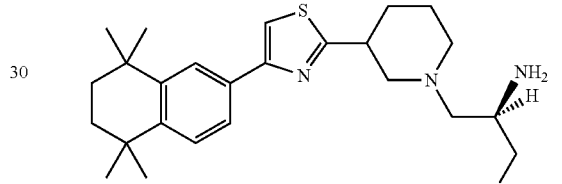
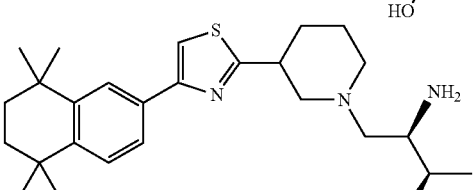
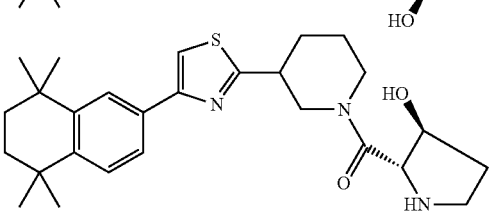
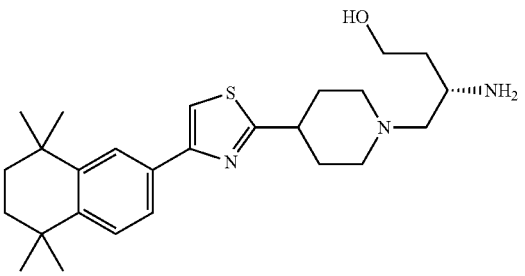
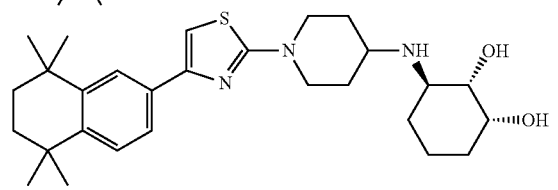

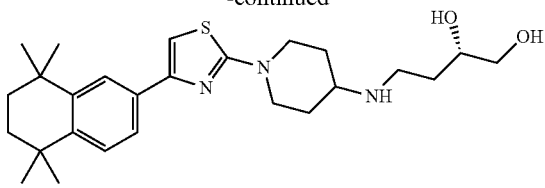

and physiologically acceptable salts, derivatives, prodrugs, solvates, tautomers and stereoisomers thereof, including mixtures thereof in all ratios.

The invention also relates to the precursors of the compounds of the formula (I), to medicaments which comprise these compounds, and to the use thereof for the treatment of diseases as described for the compounds of the formula (I).

Compounds of the formula (I) are also taken to mean the hydrates and solvates of these compounds, furthermore pharmaceutically usable derivatives.

The invention also relates to the optically active forms (stereoisomers), the enantiomers, the racemates, the diastereomers and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Pharmaceutically usable derivatives are taken to mean, for example, so-called prodrug compounds.

Prodrug derivatives are taken to mean compounds of the formula (I) which have been modified by means of, for example, alkyl or acyl groups, amino acids, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side effects or also the reduction in the advance of a disease, complaint or disorder.

The term "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The invention furthermore relates to a process for the preparation of compounds of the formula (I) and preferred embodiments depicted here and disclosed compounds and physiologically acceptable salts, derivatives, prodrugs, solvates, tautomers and stereoisomers thereof, characterised in that (a) a compound of the formula (II)

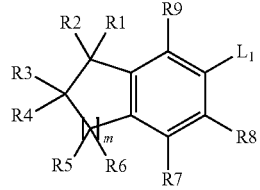

in which $R^1$, $R^2$, $R^3$, $R^4$, $R^5$, $R^6$, $R^7$, $R^8$, $R^9$ and m have the meanings indicated herein and $L_1$ has the meaning indicated below, is reacted with a compound of the formula (III)

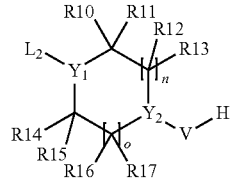

in which $R^{10}$, $R^{11}$, $R^{12}$, $R^{13}$, $R^{14}$, $R^{15}$, $R^{16}$, $R^{17}$, $Y_1$, $Y_2$, V, n, and o have the meanings indicated herein, $L_2$ has the meaning indicated below, "V-H" is optionally provided with a protecting group ("V-protecting group"), and subsequent steps indicated below are optionally also carried out,

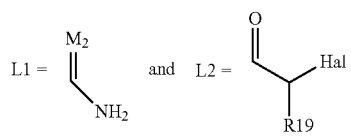

product: $M_1 = N$, $M_2 = S$, O, $M_3 = CR^{19}$

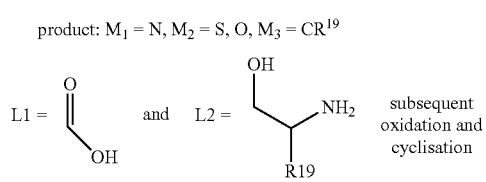

product: $M_1 = O$, S, $M_2 = N$, $M_3 = CR^{19}$

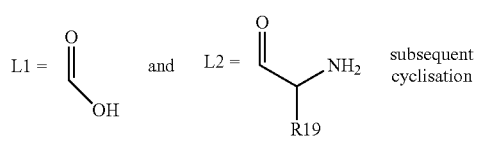

product: $M_1 = O$, S, $M_2 = N$, $M_3 = CR^{19}$

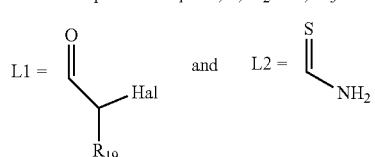

product: $M_1 = N$, $M_2 = CR_{19}$, $M_3 = S$

-continued

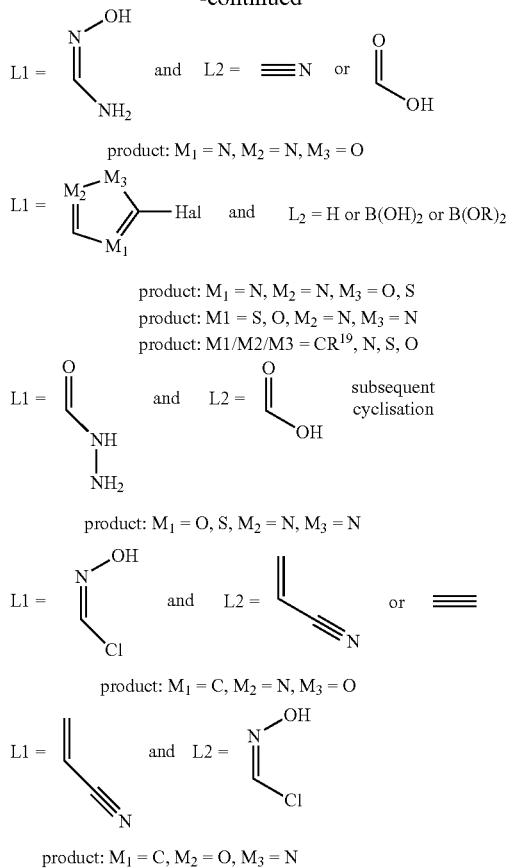

and
(b) the compound of the formula (IV)

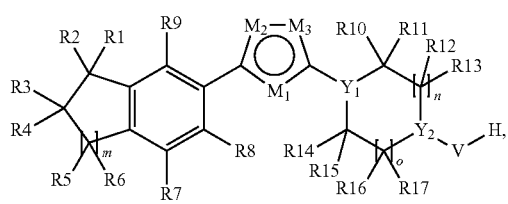

(IV)

in which $R^1, R^2, R^3, R^4, R^5, R^6, R^7, R^8, R^9, R^{10}, R^{11}, R^{12}, R^{13}, R^{14}, R^{15}, R^{16}, R^{17}, M^1, M^2, M^3, Y_1, Y_2, V, m, n,$ and o and m [lacuna] the meanings indicated herein,
resulting from step (a) is optionally freed from the protecting group ("V-protecting group") and reacted with a compound of the formula (V)

L-W  (V)

in which W has the meaning indicated herein and L denotes Cl, Br, I or a free or reactively functionally modified OH group,
or
(c) they are liberated from one of their functional derivatives (for example containing protecting groups) by treatment with an acidic, basic, solvolysing or hydrogenolysing agent,
and/or a base or acid of the formula (I) is converted into one of its salts.

The expression "carbamoyl" means "aminocarbonyl" and vice versa.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyclic alkyl (cycloalkyl) preferably denotes cyclopropyl, cyclobutyl, cylopentyl, cyclohexyl or cycloheptyl.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or phydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)phenyl, o-, m- or p-(N-ethylamino)phenyl, o-, m- or p-(N,N-diethylamino)phenyl, o-, m- or pfluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl)phenyl, o-, m- or p-[2-(morpholin-4-yl)ethoxy]phenyl, o-, m- or p-[3-(N,N-diethylamino)propoxy]phenyl, o-, m- or p-[3-(3-diethylaminopropyl)ureido]phenyl, o-, m- or p-(3-diethylaminopropoxycarbonylamino)phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N, N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl, 2,1,3-benzoxadiazol-5-yl or dibenzofuranyl.

The heterocyclic radicals may also be partially or fully hydrogenated.

Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Hal preferably denotes F, Cl or Br, but also I, particularly preferably F or Cl.

Throughout the invention, all radicals which occur more than once may be identical or different, i.e. are independent of one another.

The compounds of the formula (I) may have one or more chiral centres and can therefore occur in various stereoisomeric forms. The formula (I) encompasses all these forms.

Accordingly, the invention relates, in particular, to the compounds of the formula (I), and the use thereof, in which at least one of the said radicals has one of the preferred meanings indicated above.

The compounds of the formula (I) and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formulae (II), (III), (IV) and (V) are generally known. If they are novel, however, they can be prepared by methods known per se.

The reaction to give the compounds of the formula (I) is generally carried out in the presence of an acid-binding agent, preferably an organic base, such as DIPEA, triethylamine, dimethylaniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

Furthermore, free amino groups can be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The compounds of the formula (I) can furthermore be obtained by liberating them from their functional derivatives (for example containing protecting groups) by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an amino-protecting group instead of an H atom bonded to an N atom, for example those which conform to the formula (I), but contain an NHR' group (in which R' is an amino-protecting group, for example BOC or CBZ) instead of an NH$_2$ group.

Preference is furthermore given to starting materials which carry a hydroxyl-protecting group instead of the H atom of a hydroxyl group, for example those which conform to the formula (I), but contain an R"O-alkyl group (in which R" is a hydroxyl-protecting group) instead of a hydroxyalkyl group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or ethers, such as THF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or THF or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula (I) are for the most part prepared by conventional methods. If the compound of the formula (I) contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula (I) are likewise included. In the case of certain compounds of the formula (I), acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula (I) include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula (I) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising one or more compounds of the formula (I) and preferred embodiments depicted here and disclosed compounds, where compounds of the formula (I) in which (a) $M_1$=N, $M_2$=$CR^{19}$, $M_3$=S, and (b) $Y_1$=CH and $Y_2$=N, and (c) n=1 and o=1, are not excluded, and physiologically acceptable salts, derivatives, prodrugs, solvates, tautomers and stereoisomers thereof, including mixtures thereof in all ratios, for use in the treatment of diseases which are influenced by inhibition of Sph kinase 1 by the compounds of the formula (I) and the embodiments depicted here and disclosed compounds. A corresponding use for the preparation of a medicament for the treatment and/or prophylaxis of the above-mentioned complaints is intended to be included.

In a preferred embodiment, medicaments comprising one or more compounds of the formula (I) and preferred embodiments depicted here and disclosed compounds are furthermore claimed, where compounds of the formula (I) in which (a) $M_1$=N, $M_2$=$CR^{19}$, $M_3$=S, and (b) $Y_1$=CH and $Y_2$=N, and (c) n=1 and o=1, are excluded, and physiologically acceptable salts, derivatives, prodrugs, solvates, tautomers and stereoisomers thereof, including mixtures thereof in all ratios, for use in the treatment of diseases which are influenced by inhibition of Sph kinase 1 by the compounds of the formula (I) and the embodiments depicted here and disclosed compounds. A corresponding use for the preparation of a medicament for the treatment and/or prophylaxis of the above-mentioned complaints is intended to be included.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula (I) depends on a number of factors, including, for example, the age and weight, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to pharmaceutical composition comprising a therapeutically effective amount of at least one compound of the formula (I) and the preferred embodiments depicted here and disclosed compounds.

In a preferred embodiment, a pharmaceutical composition as depicted here is claimed comprising at least one additional compound selected from the group consisting of physiologically acceptable extenders, adjuvants, additives, diluents, excipients and/or additional pharmaceutically active substance, apart from the compounds of the formula (I) and the preferred embodiments depicted here and disclosed compounds.

The invention also relates to a kit comprising a therapeutically effective amount of at least one compound of the formula (I) and the preferred embodiments depicted here and disclosed compounds and/or at least one pharmaceutical composition as depicted here and a therapeutically effective amount of at least one further pharmacologically active substance, apart from the compounds of the formula (I) and the preferred embodiments depicted here and disclosed compounds.

The kit comprises suitable containers, such as boxes, individual bottles, bags or ampoules. The set may, for example, comprise separate ampoules, each containing an effective amount of a compound of the formula (I) and/or pharmaceutically usable derivatives, solvates, tautomers and stereoisomers thereof, including mixtures thereof in all ratios, and an effective amount of a further medicament active ingredient in dissolved or lyophilised form.

Use

The present compounds are suitable as pharmaceutical active ingredients for mammals, especially for humans, in the treatment of sphingosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula (I) and/or physiologically acceptable salts and solvates thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, prostate cancer, intestinal cancer, pancreatic cancer, ovarian carcinoma, renal cancer, liver carcinoma, glioblastomas and breast carcinoma.

Likewise encompassed is the use of the compounds according to the invention and/or physiologically acceptable salts and solvates thereof for the preparation of a medicament for the treatment or prevention of a disease in which angiogenesis is implicated.

Such a disease in which angiogenesis is implicated is an ocular disease, such as retinal vascularisation, diabetic retinopathy, age-induced macular degeneration and the like.

The use of compounds of the formula (I) and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula (I) and/or physiologically acceptable salts and solvates thereof for the preparation of a medicament for the treatment or prevention of a disease or condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use of compounds of the formula (I) and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention. Besides the compounds of the formula (I), precursors thereof can also be used for the treatment of the said diseases.

The compounds of the formula (I) can be administered to patients for the treatment of cancer, in particular fast-growing tumours.

The invention thus relates to the use of compounds of the formula (I), and pharmaceutically usable derivatives, solvates, tautomers and stereoisomers thereof, including mixtures thereof in all ratios, for the preparation of a medicament for the treatment of diseases in which the inhibition, regulation and/or modulation of kinase signal transduction plays a role.

Preference is given here to Sph kinase.

Preference is given to the use of compounds of the formula (I), and pharmaceutically usable derivatives, solvates, tautomers and stereoisomers thereof, including mixtures thereof in all ratios, for the preparation of a medicament for the treatment of diseases which are influenced by inhibition of SphK1 by the compounds of the formula (I) and the preferred embodiments depicted here and disclosed compounds.

The diseases to be treated are preferably selected from the group hyperproliferative disease, inflammatory disease, angiogenic disease.

The hyperproliferative disease is preferably selected from the group
cancer (tumour disease), atherosclerosis, restenosis, proliferative disease of the mesangial cells, psoriasis.

The tumour disease is preferably selected from the group
tumour of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx, the lung, the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma.

The proliferative disease of the mesangial cells is preferably selected from the group
glomerulonephritis, diabetic nephropathy, malignant nephrosclerosis, thrombotic microangiopathy syndrome, transplant rejection, glomerulopathy.

The inflammatory disease is preferably selected from the group
Inflammatory bowel disease, arthritis, atherosclersosis, asthma, allergies, inflammatory kidney diseases, multiple sclerosis, chronic obstructive pulmonary disease, inflammatory skin diseases, pardontal diseases, psoriasis, T-cell-promoted immune disease.

The inflammatory bowel disease is preferably selected from the group
ulcerative colitis, Crohn's disease, non-specific colitis.

The T-cell-promoted immune disease is preferably selected from the group
allergic encephalomyelitis, allergic neuritis, transplant rejection, graft-versus-host reaction, myocarditis, thyroiditis, nephritis, systemic lupus erythematosus, insulin-dependent diabetes mellitus.

The arthritis disease is preferably selected from the group
rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome.

The inflammatory kidney disease is preferably selected from the group
glomerulonephritis, glomerular injury, nephrotic syndrome, interstitial nephritis, lupus nephritis, Goodpasture's syndrome, Wegener's granulomatosis, renal vasculitis, IgA nephropathy, idiopatic glomerular disease.

The inflammatory skin disease is preferably selected from the group
psoriasis, atopic dermatitis, contact sensitivity, acne.

The angiogenic disease is preferably selected from the group
diabetic retinopathy, arthritis, cancer, psoriasis, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome.

The invention furthermore relates to medicaments comprising one or more compounds of the formula (I) and preferred embodiments depicted here and disclosed compounds, and physiologically acceptable salts, derivatives, prodrugs, solvates, tautomers and stereoisomers thereof, including mixtures thereof in all ratios, The invention furthermore relates to medicaments comprising one or more compounds of the formula (I) and preferred embodiments depicted here and disclosed compounds, and physiologically acceptable salts, derivatives, prodrugs, solvates, tautomers and stereoisomers thereof, including mixtures thereof in all ratios, for use in the treatment of diseases which are influenced by inhibition of Sph kinase 1 by the compounds of the formula (I) and the preferred embodiments depicted here and disclosed compounds, where the diseases to be treated are selected from the group consisting of: "hyperproliferative disease, inflammatory disease, angiogenic disease, fibrotic disease of the lung, kidney, liver and the heart, cancer (tumour disease), atherosclerosis, restenosis, proliferative disease of the mesangial cells, psoriasis, tumour of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx, the lung, the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma, glomerulonephritis, diabetic nephropathy, malignant nephrosclerosis, thrombotic microangiopathy syndrome, transplant rejection, glomerulopathy, inflammatory bowel disease, arthritis, asthma, allergies, inflammatory kidney diseases, multiple sclerosis, chronic obstructive pulmonary disease, inflammatory skin diseases, pardontal diseases, T-cell-promoted immune disease, ulcerative colitis, Crohn's disease, non-specific colitis, allergic encephalomyelitis, allergic neuritis, transplant rejection, graft-versus-host reaction, myocarditis, thyroiditis, nephritis, systemic lupus erythematosus, insulin-dependent diabetes mellitus, rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome, glomerulonephritis, glomerular injury, nephrotic syndrome, interstitial nephritis, lupus nephritis, Goodpasture's syndrome, Wegener's granulomatosis, renal vasculitis, IgA nephropathy, idiopatic glomerular disease, atopic dermatitis, contact sensitivity, acne, diabetic retinopathy, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome". A corresponding use for the preparation of a medicament for the treatment and/or prophylaxis of the above-mentioned complaints and also a method for the treatment of the said diseases comprising the administration of one or more compounds according to the invention to a patient in need of such an administration are also intended to be covered here.

In a preferred embodiment, medicaments are furthermore claimed which comprise one or more compounds of the formula (I) and preferred embodiments depicted here and disclosed compounds, and physiologically acceptable salts, derivatives, prodrugs, solvates, tautomers and stereoisomers thereof, including mixtures thereof in all ratios, for use in the treatment of diseases which are influenced by inhibition of Sph kinase 1 by the compounds of the formula (I) and the preferred embodiments depicted here and disclosed compounds, where the diseases to be treated are selected from the group consisting of: "hyperproliferative disease, inflammatory disease, angiogenic disease, fibrotic disease of the lung, kidney, liver and the heart, cancer (tumour disease), atherosclerosis, restenosis, proliferative disease of the mesangial cells, psoriasis, tumour of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx, the lung, the skin, monocytic leukaemia, lung adenocarcinoma, small-cell lung carcinoma, pancreatic cancer, glioblastoma, breast carcinoma, acute myeloid leukaemia, chronic myeloid leukaemia, acute lymphatic leukaemia, chronic lymphatic leukaemia, Hodgkin's lymphoma, non-Hodgkin's lymphoma, glomerulonephritis, diabetic nephropathy, malignant nephrosclerosis, thrombotic microangiopathy syndrome, transplant rejection, glomerulopathy, inflammatory bowel disease, arthritis, asthma, allergies, inflammatory kidney diseases, multiple sclerosis, chronic obstructive pulmonary disease, inflammatory skin diseases, pardontal diseases, T-cell-promoted immune disease, ulcerative colitis, Crohn's disease, non-specific colitis, allergic encephalomyelitis, allergic neuritis, transplant rejection, graft-versus-host reaction, myocarditis, thyroiditis, nephritis, systemic lupus erythematosus, insulin-dependent diabetes mellitus, rheumatoid arthritis, osteoarthritis, Caplan's syndrome, Felty's syndrome, Sjogren's syndrome, spondylitis ankylosans, Still's disease, chondrocalcinosis, metabolic arthritis, rheumatic fever, Reiter's disease, Wissler's syndrome, glomerulonephritis, glomerular injury, nephrotic syndrome, interstitial nephritis, lupus nephritis, Goodpasture's syndrome, Wegener's granulomatosis, renal vasculitis, IgA nephropathy, idiopatic glomerular disease, atopic dermatitis, contact sensitivity, acne, diabetic retinopathy, Kaposi's sarcoma, haemangioma, myocardial angiogenesis, atherosclerotic plaque neovascularisation, angiogenic eye diseases, choroidal neovascularisation, retrolental fibroplasia, macular degeneration, corneal transplant rejection, rubeosis iridis, neuroscular glaucoma, Oster Webber syndrome". A corresponding use for the preparation of a medicament for the treatment and/or prophylaxis of the above-mentioned complaints and also a method for the treatment of the said diseases comprising the administration of one or more compounds according to the invention to a patient in need of such an administration are also intended to be covered here.

In a preferred embodiment, a medicament of this type comprises at least one additional pharmacologically active substance (therapeutic agent, medicament, ingredient).

In a furthermore preferred embodiment, the medicament is used before and/or during and/or after treatment with at least one additional pharmacologically active substance.

The disclosed compounds of the formula I can be administered in combination with other known therapeutic agents (pharmacologically active substances), including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbbI antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine(gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocytemacrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula (I).

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin |
| | Tetraplatin | (Johnson Matthey) |
| | Ormiplatin | BBR-3464 |
| | Iproplatin | (Hoffmann-La Roche) |
| | | SM-11355 (Sumitomo) |
| | | AP-5280 (Access) |

TABLE 1-continued

| | | |
|---|---|---|
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharrna) |
| | Methotrexate | DMDC |
| | Idatrexate | (Hoffmann-La Roche) |
| | | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | | Diflomotecan |
| | Irinotecan (CPT-11) | (Beaufour-Ipsen) |
| | 7-ethyl-10-hydroxycamptothecin | TAS-103 (Taiho) |
| | | Elsamitrucin (Spectrum) |
| | Topotecan | J-107088 (Merck & Co) |
| | Dexrazoxanet (TopoTarget) | BNP-1350 (BioNumerik) |
| | | CKD-602 |
| | Pixantrone (Novuspharrna) | (Chong Kun Dang) |
| | Rebeccamycin analogue (Exelixis) | KW-2170 (Kyowa Hakko) |
| | BBR-3576 (Novuspharrna) | |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 |
| | Cyanomorpholino-doxorubicin | (Gem Pharmaceuticals) |
| | Mitoxantron (Novantron) | |
| Antimitotic agents | Paclitaxel | SB 408075 |
| | Docetaxel | (GlaxoSmithKline) |
| | Colchicine | E7010 (Abbott) |
| | Vinblastine | PG-TXL (Cell Therapeutics) |
| | Vincristine | IDN 5109 (Bayer) |
| | Vinorelbine | A 105972 (Abbott) |
| | Vindesine | A 204197 (Abbott) |
| | Dolastatin 10 (NCI) | LU 223651 (BASF) |
| | Rhizoxin (Fujisawa) | D 24851 (ASTA Medica) |
| | Mivobulin (Warner-Lambert) | ER-86526 (Eisai) |
| | | Combretastatin A4 (BMS) |
| | Cemadotin (BASF) | Isohomohalichondrin-B |
| | RPR 109881A (Aventis) | (PharmaMar) |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB |
| | | (Prescient NeuroPharm) |
| | Vinflunine (Fabre) | Azaepothilon B (BMS) |
| | Auristatin PE (Teikoku Hormone) | BNP-7787 (BioNumerik) |
| | | CA-4-prodrug (OXiGENE) |
| | BMS 247550 (BMS) | Dolastatin-10 (NrH) |
| | BMS 184476 (BMS) | CA-4 (OXiGENE) |
| | BMS 188797 (BMS) | |
| | Taxoprexin (Protarga) | |

TABLE 1-continued

| Category | Agents | | |
|---|---|---|---|
| Aromatase inhibitors | Aminoglutethimide<br>Letrozole<br>Anastrazole<br>Formestan | Exemestan<br>Atamestan (BioMedicines)<br>YM-511 (Yamanouchi) | |
| Thymidylate synthase inhibitors | Pemetrexed (Eli Lilly)<br>ZD-9331 (BTG) | Nolatrexed (Eximias)<br>CoFactor ™ (BioKeys) | |
| DNA antagonists | Trabectedin (PharmaMar)<br>Glufosfamide (Baxter International)<br>Albumin + 32P (Isotope Solutions)<br>Thymectacin (NewBiotics)<br>Edotreotid (Novartis) | Mafosfamide (Baxter International)<br>Apaziquone (Spectrum Pharmaceuticals)<br>O6-benzylguanine (Paligent) | |
| Farnesyl transferase inhibitors | Arglabin (NuOncology Labs)<br>Ionafarnib (Schering-Plough)<br>BAY-43-9006 (Bayer) | Tipifarnib (Johnson & Johnson)<br>Perillyl alcohol (DOR BioPharma) | |
| Pump inhibitors | CBT-1 (CBA Pharma)<br>Tariquidar (Xenova)<br>MS-209 (Schering AG) | Zosuquidar trihydrochloride (Eli Lilly)<br>Biricodar dicitrate (Vertex) | |
| Histone acetyl transferase inhibitors | Tacedinaline (Pfizer)<br>SAHA (Aton Pharma)<br>MS-275 (Schering AG) | Pivaloyloxymethyl butyrate (Titan)<br>Depsipeptide (Fujisawa) | |
| Metalloproteinase inhibitors | Neovastat (Aeterna Laboratories)<br>Marimastat (British Biotech) | CMT-3 (CollaGenex)<br>BMS-275291 (Celltech)<br>Tezacitabine (Aventis) | |
| Ribonucleoside reductase inhibitors | Gallium maltolate (Titan)<br>Triapin (Vion) | Didox (Molecules for Health) | |
| TNF-alpha agonists/ antagonists | Virulizin (Lorus Therapeutics)<br>CDC-394 (Celgene) | Revimid (Celgene) | |
| Endothelin-A receptor antagonists | Atrasentan (Abbot)<br>ZD-4054 (AstraZeneca) | YM-598 (Yamanouchi) | |
| Retinoic acid receptor agonists | Fenretinide (Johnson & Johnson)<br>LGD-1550 (Ligand) | Alitretinoin (Ligand) | |
| Immunomodulators | Interferon<br>Oncophage (Antigenics)<br>GMK (Progenics)<br>Adenocarcinoma vaccine (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine (CTL Immuno)<br>p21-RAS vaccine (GemVax) | Dexosome therapy (Anosys)<br>Pentrix (Australian Cancer Technology)<br>JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) | |
| Hormonal and antihormonal agents | Oestrogens<br>Conjugated oestrogens<br>Ethynyloestradiol chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) | |
| Photodynamic agents | Talaporfin (Light Sciences)<br>Theralux (Theratechnologies)<br>Motexafin-Gadolinium (Pharmacyclics) | Pd-Bacteriopheophorbid (Yeda)<br>Lutetium-Texaphyrin (Pharmacyclics)<br>Hypericin | |
| Tyrosine kinase inhibitors | Imatinib (Novartis)<br>Leflunomide (Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) | |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim)<br>Tiazofurin (IMPDH inhibitor, Ribapharm)<br>Cilengitide (integrin antagonist Merck KGaA)<br>SR-31747 (IL-1 antagonist, Sanofi-Synthelabo)<br>CCI-779 (mTOR kinase inhibitor Wyeth)<br>Exisulind (PDE-V inhibitor, Cell Pathways)<br>CP-461 (PDE-V inhibitor, Cell Pathways)<br>AG-2037 (GART inhibitor, Pfizer)<br>WX-UK1 (plasminogen activator inhibitor, Wilex)<br>PBI-1402 (PMN stimulant, ProMetic LifeSciences)<br>Bortezomib (proteasome inhibitor, Millennium)<br>SRL-172 (T-cell stimulant, SR Pharma)<br>TLK-286 (glutathione-S transferase inhibitor, Telik)<br>PT-100 (growth factor agonist, Point Therapeutics)<br>Midostaurin (PKC inhibitor, Novartis)<br>Bryostatin-1 (PKC stimulant, GPC Biotech)<br>CDA-II (apoptosis promoter, Everlife)<br>SDX-101 (apoptosis | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi)<br>Indisulam (p53 stimulant, Eisai)<br>Aplidin (PPT inhibitor, PharmaMar)<br>Rituximab (CD20 antibody, Genentech)<br>Gemtuzumab (CD33 antibody, Wyeth Ayerst)<br>PG2 (haematopoiesis promoter Pharmagenesis)<br>Immunol ™ (triclosan mouthwash, Endo)<br>Triacetyluridine (uridine prodrug Wellstat)<br>SN-4071 (sarcoma agent, Signature BioScience)<br>TransMID-107 ™ (immunotoxin, KS Biomedix)<br>PCK-3145 (apoptosis promoter, Procyon)<br>Doranidazole (apoptosis promoter, Pola)<br>CHS-828 (cytotoxic agent, Leo)<br>trans-Retinic acid (differentiator, NIH)<br>MX6 (apoptosis promoter, MAXIA)<br>Apomine (apoptosis promoter, ILEX Oncology)<br>Urocidin (apoptosis promoter, Bioniche)<br>Ro-31-7453 (apoptosis promoter, La Roche)<br>Brostallicin (apoptosis promoter, Pharmacia) | |

TABLE 1-continued

| Class | | |
|---|---|---|
| | promoter, Salmedix) | |
| | Ceflatonin (apoptosis promoter, ChemGenex) | |
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharrna) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | | Elsamitrucin (Spectrum) |
| | Topotecan | J-107088 (Merck & Co) |
| | Dexrazoxanet (TopoTarget) | BNP-1350 (BioNumerik) |
| | | CKD-602 (Chong Kun Dang) |
| | Pixantrone (Novuspharrna) | KW-2170 (Kyowa Hakko) |
| | Rebeccamycin analogue (Exelixis) | |
| | BBR-3576 (Novuspharrna) | |
| Antitumour antibiotics | Dactinomycin (Actinomycin D) | Amonafide |
| | | Azonafide |
| | Doxorubicin (Adriamycin) | Anthrapyrazole |
| | Deoxyrubicin | Oxantrazole |
| | Valrubicin | Losoxantrone |
| | Daunorubicin (Daunomycin) | Bleomycin sulfate (Blenoxan) |
| | Epirubicin | Bleomycinic acid |
| | Therarubicin | Bleomycin A |
| | Idarubicin | Bleomycin B |
| | Rubidazon | Mitomycin C |
| | Plicamycinp | MEN-10755 (Menarini) |
| | Porfiromycin | GPX-100 (Gem Pharmaceuticals) |
| | Cyanomorpholino-doxorubicin | |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B (PharmaMar) |
| | RPR 109881A (Aventis) | |
| | TXD 258 (Aventis) | ZD 6126 (AstraZeneca) |
| | Epothilone B (Novartis) | PEG-Paclitaxel (Enzon) |
| | T 900607 (Tularik) | AZ10992 (Asahi) |
| | T 138067 (Tularik) | !DN-5109 (Indena) |
| | Cryptophycin 52 (Eli Lilly) | AVLB (Prescient NeuroPharma) |
| | Vinflunine (Fabre) | Azaepothilon B (BMS) |
| | Auristatin PE (Teikoku Hormone) | BNP-7787 (BioNumerik) |
| | BMS 247550 (BMS) | CA-4-prodrug (OXiGENE) |
| | BMS 184476 (BMS) | Dolastatin-10 (NrH) |
| | BMS 188797 (BMS) | CA-4 (OXiGENE) |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metallo-proteinase inhibitors | Neovastat (Aeterna Laboratories) | CMT-3 (CollaGenex) |
| | | BMS-275291 (Celltech) |
| | Marimastat (British Biotech) | |
| Ribonucleoside reductase inhibitors | | Tezacitabine (Aventis) |
| | Gallium maltolate (Titan) | Didox (Molecules for Health) |
| | Triapin (Vion) | |
| TNF-alpha agonists/antagonists | Virulizin (Lorus Therapeutics) | Revimid (Celgene) |
| | CDC-394 (Celgene) | |
| Endothelin-A receptor antagonists | Atrasentan (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immuno-modulators | Interferon | Dexosome therapy (Anosys) |
| | Oncophage (Antigenics) | Pentrix (Australian Cancer Technology) |
| | GMK (Progenics) | |
| | Adenocarcinoma vaccine (Biomira) | JSF-154 (Tragen) |
| | | Cancer vaccine (Intercell) |
| | CTP-37 (AVI BioPharma) | Norelin (Biostar) |
| | JRX-2 (Immuno-Rx) | BLP-25 (Biomira) |
| | PEP-005 (Peplin Biotech) | MGV (Progenics) |
| | Synchrovax vaccines (CTL Immuno) | !3-Alethin (Dovetail) |
| | | CLL-Thera (Vasogen) |
| | Melanoma vaccine (CTL Immuno) | |
| | p21-RAS vaccine (GemVax) | |
| Hormonal and antihormonal agents | Oestrogens | Prednisone |
| | Conjugated oestrogens | Methylprednisolone |
| | Ethynyloestradiol chlorotrianisene | Prednisolone |
| | | Aminoglutethimide |
| | Idenestrol | Leuprolide |
| | Hydroxyprogesterone caproate | Goserelin |
| | | Leuporelin |
| | Medroxyprogesterone | Bicalutamide |
| | Testosterone | Flutamide |
| | Testosterone propionate | Octreotide |
| | Fluoxymesterone | Nilutamide |
| | Methyltestosterone | Mitotan |
| | Diethylstilbestrol | P-04 (Novogen) |
| | Megestrol | 2-Methoxyoestradiol (EntreMed) |
| | Tamoxifen | |

TABLE 1-continued

| | | | |
|---|---|---|---|
| Photodynamic agents | Toremofin Dexamethasone Talaporfin (Light Sciences) Theralux (Theratechnologies) Motexafin-Gadolinium (Pharmacyclics) | Arzoxifen (Eli Lilly) Pd-Bacteriopheophorbid (Yeda) Lutetium-Texaphyrin (Pharmacyclics) Hypericin | |
| Tyrosine kinase inhibitors | Imatinib (Novartis) Leflunomide (Sugen/Pharmacia) ZDI839 (AstraZeneca) Erlotinib (Oncogene Science) Canertjnib (Pfizer) Squalamine (Genaera) SU5416 (Pharmacia) SU6668 (Pharmacia) ZD4190 (AstraZeneca) ZD6474 (AstraZeneca) Vatalanib (Novartis) PKI166 (Novartis) GW2016 (GlaxoSmithKline) EKB-509 (Wyeth) EKB-569 (Wyeth) | Kahalide F (PharmaMar) CEP-701 (Cephalon) CEP-751 (Cephalon) MLN518 (Millenium) PKC412 (Novartis) Phenoxodiol O Trastuzumab (Genentech) C225 (ImClone) rhu-Mab (Genentech) MDX-H210 (Medarex) 2C4 (Genentech) MDX-447 (Medarex) ABX-EGF (Abgenix) IMC-1C11 (ImClone) | |
| Various agents | SR-27897 (CCK-A inhibitor, Sanofi-Synthelabo) Tocladesine (cyclic AMP agonist, Ribapharm) Alvocidib (CDK inhibitor, Aventis) CV-247 (COX-2 inhibitor, Ivy Medical) P54 (COX-2 inhibitor, Phytopharm) CapCell ™ (CYP450 stimulant Bavarian Nordic) GCS-IOO (gal3 antagonist, GlycoGenesys) G17DT immunogen (gastrin inhibitor, Aphton) Efaproxiral (oxygenator, Allos Therapeutics) PI-88 (heparanase inhibitor, Progen) Tesmilifen (histamine antagonist, YM BioSciences) Histamine (histamine H2 receptor agonist, Maxim) Tiazofurin (IMPDH inhibitor, Ribapharm) Cilengitide (integrin antagonist, Merck KGaA) SR-31747 (IL-1 antagonist, Sanofi-Synthelabo) CCI-779 (mTOR kinase inhibitor, Wyeth) Exisulind (PDE-V inhibitor, Cell Pathways) CP-461 (PDE-V inhibitor, Cell Pathways) AG-2037 (GART inhibitor, Pfizer) WX-UK1 (plasminogen activator inhibitor, Wilex) PBI-1402 (PMN stimulant, ProMetic LifeSciences) Bortezomib (proteasome inhibitor, Millennium) SRL-172 (T-cell stimulant, SR Pharma) TLK-286 (glutathione-S transferase inhibitor, Telik) PT-100 (growth factor agonist, Point Therapeutics) | BCX-1777 (PNP inhibitor, BioCryst) Ranpirnase (ribonuclease stimulant, Alfacell) Galarubicin (RNA synthesis inhibitor, Dong-A) Tirapazamine (reducing agent, SRI International) N-Acetylcysteine (reducing agent, Zambon) R-Flurbiprofen (NF-kappaB inhibitor, Encore) 3CPA (NF-kappaB inhibitor, Active Biotech) Seocalcitol (vitamin D receptor agonist, Leo) 131-I-TM-601 (DNA antagonist, TransMolecular) Eflornithin (ODC inhibitor, ILEX Oncology) Minodronic acid (osteoclast inhibitor, Yamanouchi) Indisulam (p53 stimulant, Eisai) Aplidin (PPT inhibitor, PharmaMar) Rituximab (CD20 antibody, Genentech) Gemtuzumab (CD33 antibody, Wyeth Ayerst) (PG2 (haematopoiesis promoter, Pharmagenesis) Immunol ™ (triclosan mouthwash, Endo) Triacetyluridine (uridine prodrug, Wellstat) (SN-4071 sarcoma agent, Signature BioScience) TransMID-107 ™ (immunotoxin, KS Biomedix) PCK-3145 (apoptosis promoter Procyon) Doranidazole (apoptosis promoter, Pola) CHS-828 (cytotoxic agent, Leo) trans-Retinic acid (differentiator, NIH) MX6 (apoptosis promoter, MAXIA) Apomine (apoptosis promoter, LEX Oncology) Urocidin (apoptosis | |
| | Midostaurin (PKC inhibitor, Novartis) Bryostatin-1 (PKC stimulant, GPC Biotech) CDA-II (apoptosis promoter, Everlife) SDX-101 (apoptosis promoter Salmedix) Ceflatonin (apoptosis promoter, ChemGenex) | promoter, Bioniche) Ro-31-7453 (apoptosis promoter, La Roche) Brostallicin (apoptosis promoter, Pharmacia) | |

A combined treatment of this type can be achieved with the aid of simultaneous, consecutive or separate dispensing of the individual components of the treatment. Combination products of this type employ the compounds according to the invention.

The invention furthermore relates to compounds selected from the group consisting of:

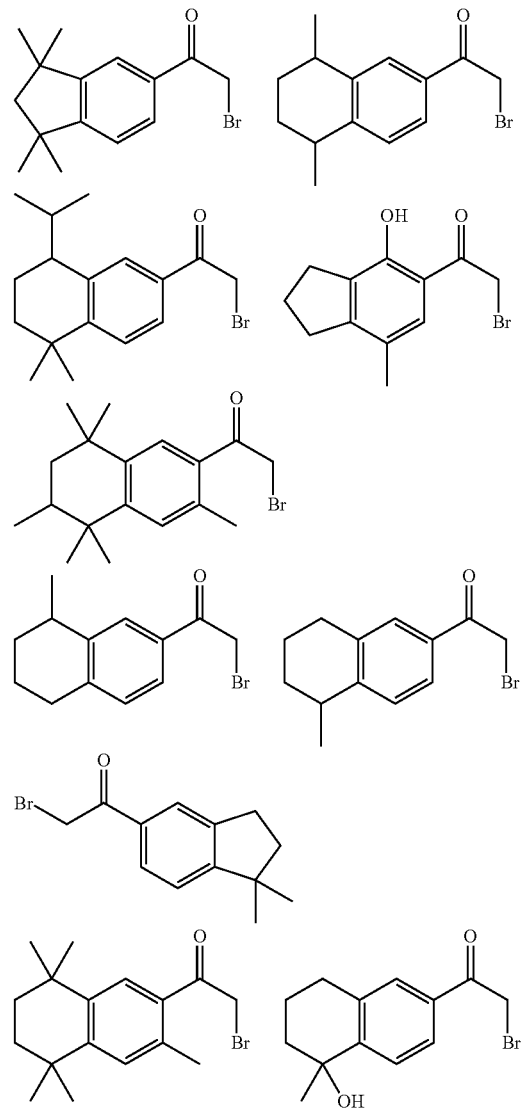

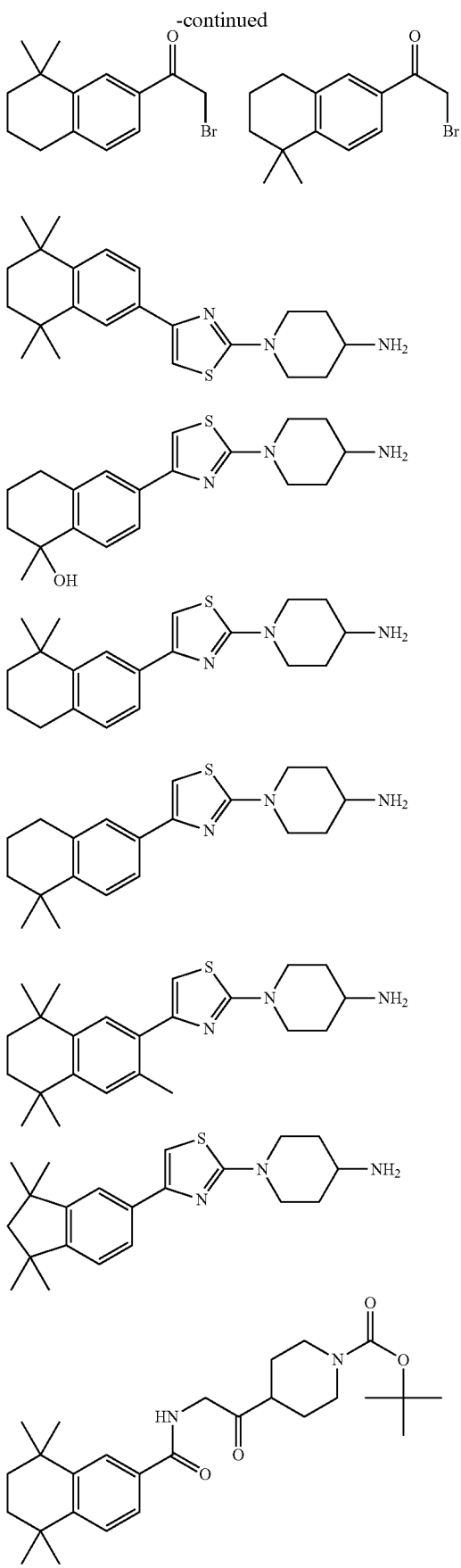
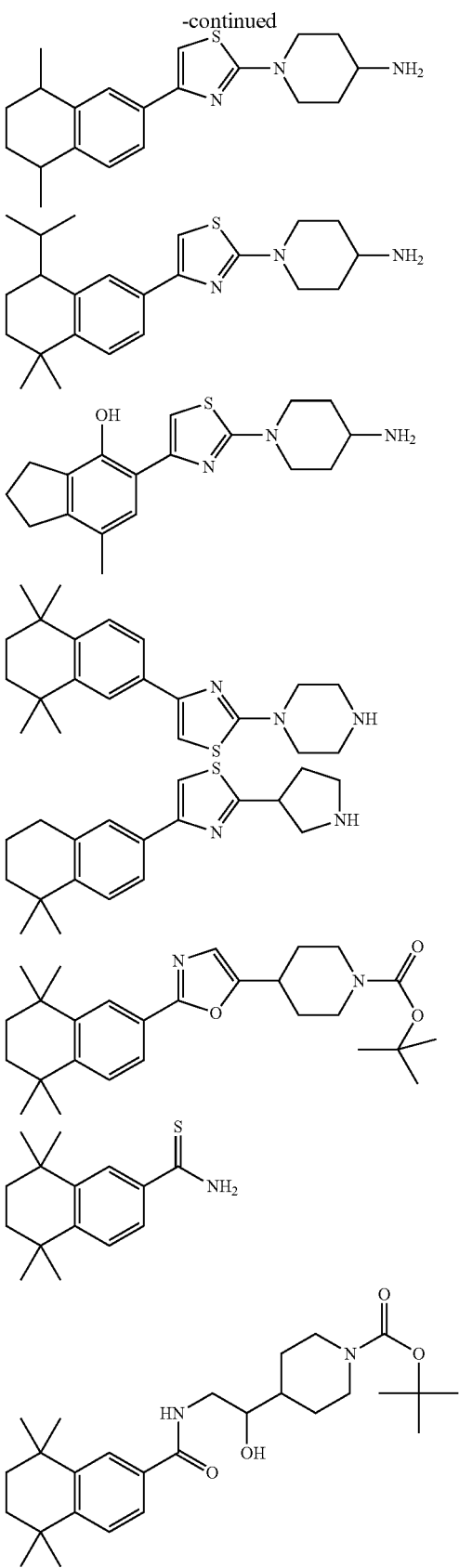
Even without further comments, it is assumed that a person skilled in the art will be able to utilise the above description in the broadest scope. The preferred embodiments should therefore merely be regarded as descriptive disclosure which is absolutely not limiting in any way.

Above and below, all temperatures are indicated in ° C. In the following examples, "conventional work-up" means: if necessary, the solvent is removed, water is added if necessary, the pH is adjusted, if necessary, to values between 2 and 10, depending on the constitution of the end product, the mixture is extracted with ethyl acetate or dichloromethane, the phases are separated, the organic phase is washed with saturated NaHCO$_3$ solution, optionally with water and saturated NaCl solution, the organic phase is dried over sodium sulfate, filtered and evaporated, and the product is purified by chromatography on silica gel, by preparative HPLC and/or by crystallisation. The purified compounds are optionally freeze-dried.

Mass spectrometry (MS): EI (electron impact ionisation) M$^+$
FAB (fast atom bombardment) (M+H)$^+$
ESI (electrospray ionisation) (M+H)$^+$
APCI-MS (atmospheric pressure chemical ionisation-mass spectrometry) (M+H)$^+$
HPLC Methods:
Method A:
Gradient: 4.2 min
Flow rate: 2 ml/min 99:01-0:100 water+0.1% (vol.) of TFA: acetonitrile+0.1% (vol.) of TFA
0.0 to 0.2 min: 99:01
0.2 to 3.8 min: 99:01→0:100
3.8 to 4.2 min: 0:100
Column: Chromolith Performance RP18e; 100 mm long, internal diameter 3 mm
Wavelength: 220 nm
Method B:
Gradient: 5.5 min
Flow rate: 2.75 ml/min 90:10-0:100 water+0.01% (vol.) of TFA:acetonitrile+0.01% (vol.) of TFA
0.0 to 3.5 min: 90:10→0:100
3.5 to 4.3 min: 0:100
Column: Chromolith SpeedRod RP18e; 50 mm long, internal diameter 4.6 mm
Wavelength: 220 nm
Method C:
Gradient: 4.2 min
Flow rate: 2 ml/min 99:01-0:100 water+0.05% (vol.) of formic acid:acetonitrile+0.04% (vol.) of formic acid
0.0 to 0.2 min: 99:01
0.2 to 3.8 min: 99:01→0:100
3.8 to 4.2 min: 0:100
Column: Chromolith Performance RP18e; 100 mm long, internal diameter 3 mm
Wavelength: 220 nm List of Abbreviations and Acronyms:

AcOH acetic acid, anh. anhydrous, atm atmosphere(s), BOC tert-butoxycarbonyl CDI 1,1'-carbonyldiimidazole, conc. concentrated, d day(s), decomp. decomposition, DMAC N,N-dimethylacetamide, DMPU 1,3-dimethyl-3,4,5,6-tetrahydro-2(1H)-pyrimidinone, DMF N,N-dimethylformamide, DMSO dimethyl sulfoxide, DPPA diphenylphosphoryl azide, EDCI 1-(3-dimethylaminopropyl)-3-ethylcarbodiimide, EtOAc ethyl acetate, EtOH ethanol (100%), Et$_2$O diethyl ether, Et$_3$N triethylamine, h hour(s), MeOH methanol, pet. ether petroleum ether (boiling range 30-60° C.), temp. temperature, THF tetrahydrofuran, TFA trifluoroAcOH, Tf trifluoromethanesulfonyl, RT room temperature.

The contents of all cited reference are incorporated in entirety by way of reference here. The invention is explained in greater detail by the following examples, but without being restricted thereto.

EXAMPLES

I. Synthesis of Selected Compounds of the Invention

The following compounds were synthesised and characterised. However, the knowledge of the person skilled in the art includes the preparation and characterisation of these compounds in other ways.

Preparation of the Bromocarbonyl Compounds

Preparation of 2-bromo-1-(5,6,7,8-tetrahydronaphthalen-2-yl)ethanone

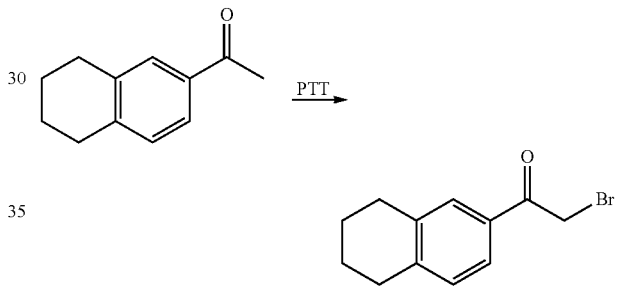

25 g (143 mmol) of 1-(5,6,7,8-tetrahydronaphthalen-2-yl)ethanone were dissolved in 750 ml of THF, 64.7 g (172 mmol) of phenyltrimethylammonium tribromide were added, and the mixture was stirred at room temperature for 15 h. The resultant precipitate was filtered, and the filtrate was evaporated to dryness. The residue was taken up in ethyl acetate, washed with 2× sat. sodium hydrogencarbonate solution and 1× sat. sodium chloride solution, the organic phase was dried over sodium sulfate and evaporated to dryness.

Yield: 62 g, white solid.
HPLC: Rt.=3.06 min.

The following compounds can be prepared analogously to the procedures mentioned above. In some cases, purification by means of column chromatography on silica gel was necessary:

| Starting material | Product | Rt. |
|---|---|---|
| 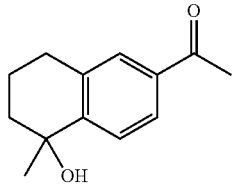 | 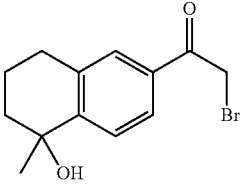 | |

Synthetic Communications 2001, 31(6), 877-892

-continued
| Starting material | Product | Rt. |
|---|---|---|
| 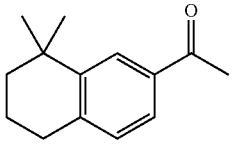<br>Journal of Organic Chemistry 1984, 51(26), 5265-5267 | 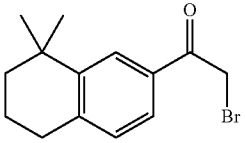 [SMILES: CC1(C)CCCc2ccc(C(=O)CBr)cc21] | 3.42 min (method A) |
| 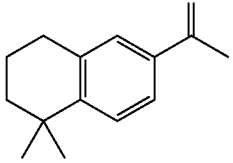<br>US 2005/0148590 | 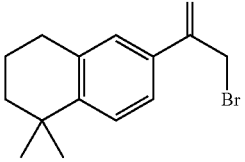 | 3.45 min (method A) |
| 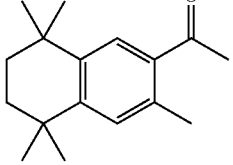<br>US 2005/0148590 | 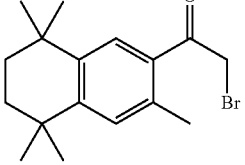 | |
| 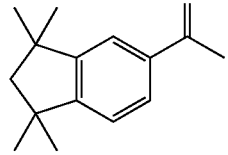<br>US 2005/0148590 | 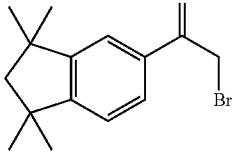 | 3.60 min (method A) |
| 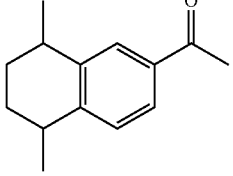<br>Journal of Organic Chemistry 1963, 29(9), 2248-2255 | 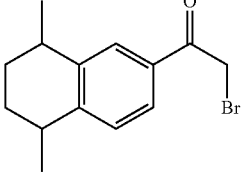 | 3.59 min (method C) |
| 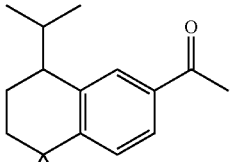<br>Journal of Organic Chemistry 1963, 29(9), 2248-2255 | 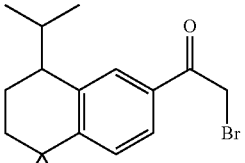 | |

-continued

| Starting material | Product | Rt. |
|---|---|---|
| | | |
| | | 3.99 (method A) |
| | | 3.40 (method C) |

Preparation of
2-bromo-1-(1,1-dimethylindan-5-yl)ethanone

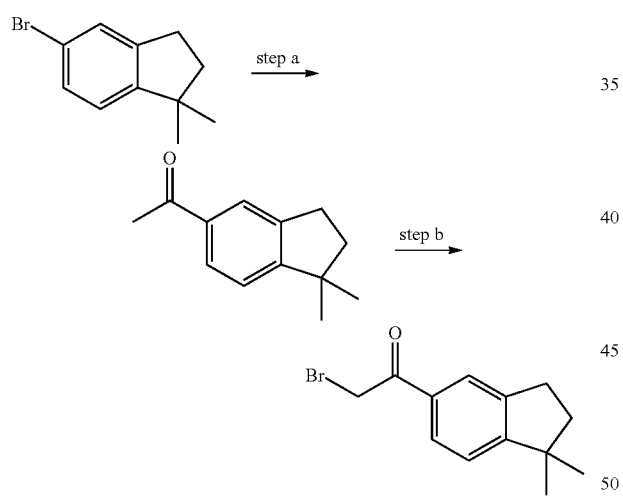

Step a:
3.72 g (16.5 mmol) of 5-bromo-1,1-dimethylindane are dissolved in 100 ml of THF and degassed. 11.2 ml (33.05 mmol) of 1(ethoxyvinyl-)tributyltin and 1.1 g (1.6 mmol) of bis(triphenylphosphine)palladium(II) dichloride were subsequently added. The reaction mixture was refluxed for 15 h under nitrogen atmosphere. After cooling, a Ph of 2 was established using 2 N HCl, and the mixture was stirred at RT for a further 15 h. The reaction mixture was diluted with water and extracted three times with ethyl acetate. The combined organic phases were washed with saturated $NaHCO_3$ solution and saturated NaCl solution, dried over $Na_2SO_4$ and evaporated. The residue was chromatographed by column chromatography on silica gel.
Yield: 2.4 g, oil.
HPLC: Rt.=3.22 min (method A).

Step b:
The α-bromination is carried out as described above using phenyltrimethylammonium tribromide.
Yield: 3.1 g, yellow oil.
HPLC: Rt.=3.41 min (method A).

Preparation of 4-[4-(5,5,8,8-tetramethyl-5,6,7,8-tetrahydronaphthalen-2-yl)thiazol-2-yl]piperidine hydrobromide

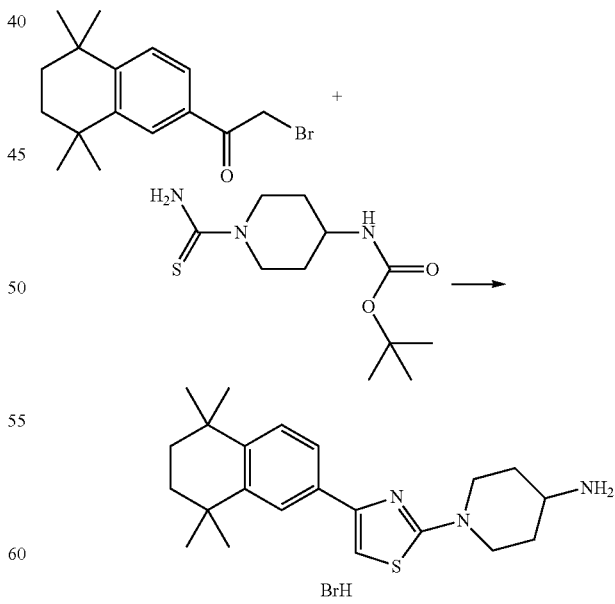

930 mg (3.0 mmol) of 2-bromo-1-(5,5,8,8-tetramethyl-5,6,7,8-tetrahydronaphthalen-2-yl)ethanone and 778 mg (3.0 mmol) of (1-thiocarbamoylpiperidin-4-yl)carbamic acid tert-butyl ester were suspended in 15 ml of ethanol and refluxed for 24 h. The precipitate was filtered off with suction and washed with ethanol and ether. The residue was dried in vacuo.

Yield: 900 mg, solid. The product is in the form of the hydrobromide.

LCMS: 370 (M+H), HPLC: Rt.=2.89 min (method A).

The following compounds can be prepared analogously to the said procedures. In some cases, purification by means of extraction, column chromatography on silica gel or by means of preparative HPLC was necessary:

| Starting material | Product | Rt. |
|---|---|---|
| 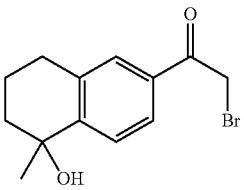 | 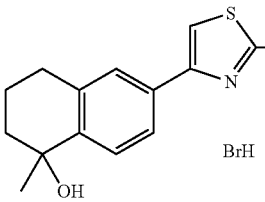 | LCMS: 344 (M + H) |
| 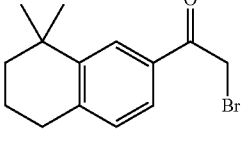 | 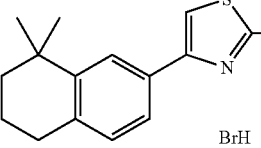 | LCMS: 342 (M + H) |
| 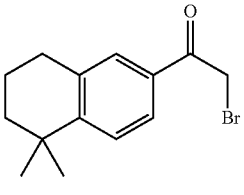 | 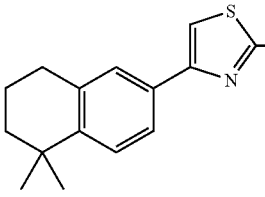 | Rt. = 2.70 min (method A) LCMS: 342 (M + H) ¹H NMR (500 MHz, DMSO/deuterated TFA) δ 7.35 (d, J = 8.2, 1H), 7.29 (d, J = 8.2, 1H), 7.22 (s, 1H), 4.05 (d, J = 13.6, 2H), 3.42-3.29 (m, 3H), 2.69 (t, J = 6.3, 2H), 2.08 (d, J = 9.7, 2H), 1.77-1.65 (m, 4H), 1.60-1.54 (m, 2H), 1.16 (s, 6H). |
| 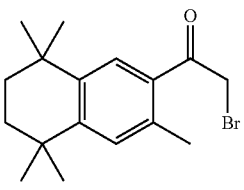 | 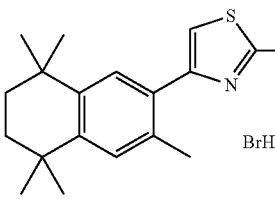 | LCMS: 384 (M + H) |
| 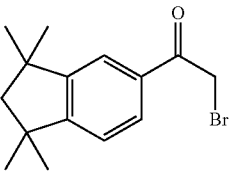 | 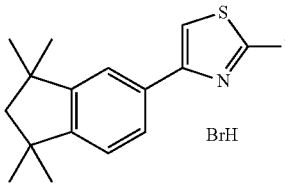 | LCMS: 356 (M + H) |
| 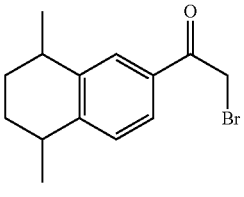 | 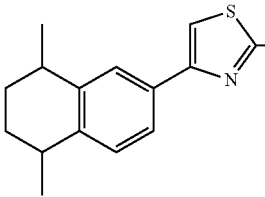 | LCMS: 342 (M + H) |

-continued

| Starting material | Product | Rt. |
|---|---|---|
| 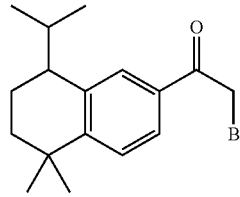 | 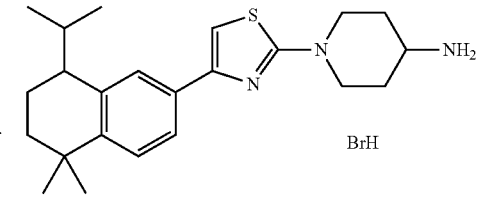 | LCMS: 384 (M + H) |
| 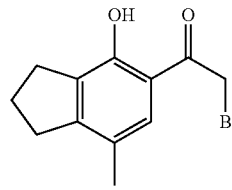 | 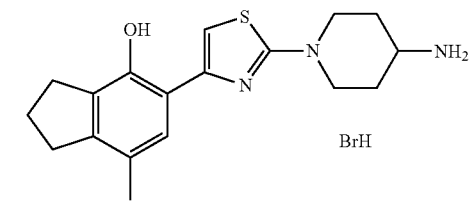 [SMILES: Cc1cc(-c2csc(N3CCC(N)CC3)n2)c(O)c2c1CCC2 ; Br] | LCMS: 330 (M + H) |

The following can be prepared analogously:

1-[4-(5,5,8,8-Tetramethyl-5,6,7,8-tetrahydronaphthalen-2-yl)thiazol-2-yl]-piperazine

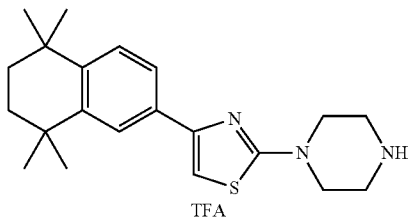 [SMILES: CC1(C)CCC(C)(C)c2cc(-c3csc(N4CCNCC4)n3)ccc21 ; "TFA"]

Yield: 27 mg, oil. The product is in the form of the trifluoroacetate.
Rt.=3.04 min (method A), LCMS: 356 (M+H).
$^1$H NMR (500 MHz, DMSO/deuterated TFA) δ 7.75 (d, J=1.5, 1H), 7.53 (dd, J=8.2, 1.6, 1H), 7.32 (d, J=8.3, 1H), 3.76-3.68 (m, 4H), 3.34-3.26 (m, 4H), 1.64 (s, 4H), 1.25 (d, J=16.7, 12H).

4-(5,5-Dimethyl-5,6,7,8-tetrahydronaphthalen-2-yl)-2-pyrrolidin-3-yl-thiazole

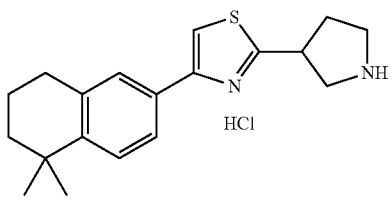 [SMILES: CC1(C)CCCc2cc(-c3csc(C4CCNC4)n3)ccc21 ; Cl]

The preparation is carried out as described above starting from 3-thiocarbamoylpyrrolidine-1-carboxylic acid tert-butyl ester. The Boc protecting group is cleaved off as described using 4 N HCl in dioxane.
Yield: 1.07 g, yellow solid. Product is in the form of the hydrochloride.
Rt.=2.82 min (method A), LCMS: 313 (M+H).
$^1$H NMR (500 MHz, DMSO/deuterated δ 7.78 (d, J=1.3, 1H), 7.72 (d, J=8.2, 1H), 7.65 (s, 1H), 7.42 (d, J=8.2, 1H), 4.06 (p, J=7.2, 1H), 3.74 (dd, J=11.7, 7.9, 1H), 3.65 (dd, J=11.7, 7.0, 1H), 3.54-3.46 (m, 1H), 3.44-3.36 (m, 1H), 2.82 (t, J=6.3, 2H), 2.52 (td, J=13.6, 7.4, 1H), 2.30 (dq, J=14.9, 7.4, 1H), 1.86-1.79 (m, 2H), 1.72-1.66 (m, 2H), 1.29 (s, 6H).

1-[4-(5,5,8,8-Tetramethyl-5,6,7,8-tetrahydronaphthalen-2-yl)thiazol-2-yl]-4,4'-bipiperidinyl

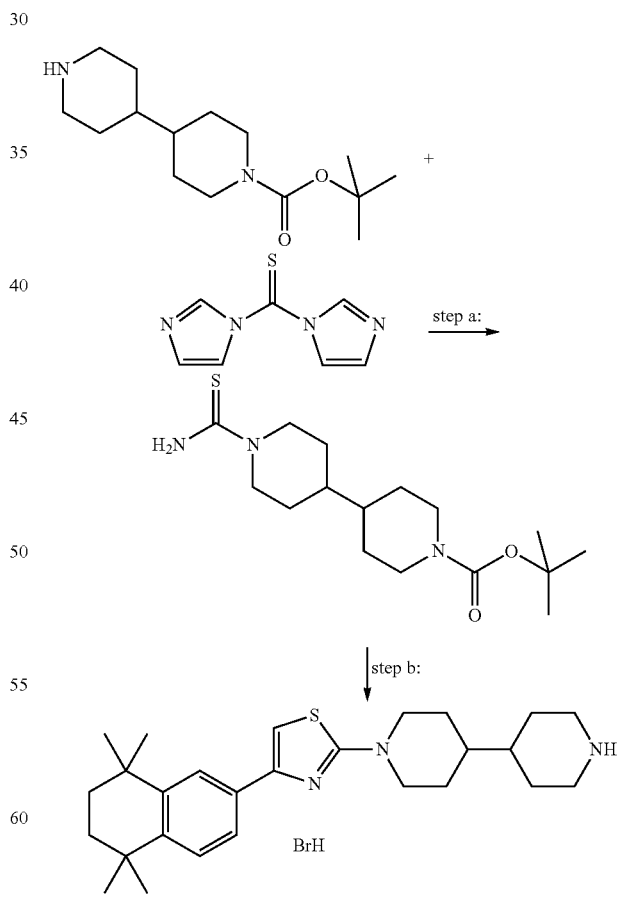

Step a:
403 mg (0.50 mmol) of 4,4'-bipiperidinyl-1-carboxylic acid tert-butyl ester were dissolved in 5 ml of THF, and a solution of 310 mg (1.65 mmol) of thiocarbonylimidazole was added. The reaction mixture is stirred at RT for 2 h, and 5 ml of 25% ammonia solution are subsequently added. The reaction mixture was irradiated in the microwave at 60° C. for 3 h. After cooling, the reaction mixture was evaporated, water was added, the residue was filtered off with suction and washed with a little water.

300 mg, white solid.

Rt.=2.75 min (method A), LCMS: 328 (M+H).

Step b:

The reaction with the bromocarbonyl compound is carried out as described above.

Yield: 76 mg, oil. The product is in the form of the hydrobromide.

Rt.=3.14 min (method A), LCMS: 438 (M+H).

$^1$H NMR (500 MHz, DMSO/deuterated TFA) δ 7.78 (s, 1H), 7.54 (d, J=8.2, 1H), 7.38 (d, J=8.3, 1H), 3.91 (d, J=13.2, 2H), 3.31 (d, J=12.5, 2H), 3.03 (t, J=11.4, 2H), 2.83 (t, J=11.7, 2H), 1.81 (dd, J=31.7, 12.4, 4H), 1.68 (s, 4H), 1.47-1.20 (m, 18H).

4-(2-Pyrrolidin-1-ylethyl)-1-[4-(5,5,8,8-tetramethyl-5,6,7,8-tetrahydronaphthalen-2-yl)thiazol-2-yl]piperidine

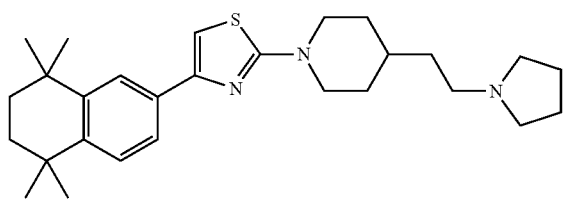 [SMILES: CC1(C)CCC(C)(C)c2cc(-c3csc(N4CCC(CCN5CCCC5)CC4)n3)ccc21]

The preparation is carried out as described above starting from 4-(2-pyrrolidin-1-ylethyl)piperidine.

Yield: 76 mg, oil.

Rt.=3.14 min (method A), LCMS: 452 (M+H).

1-[4-(5,5,8,8-Tetramethyl-5,6,7,8-tetrahydronaphthalen-2-yl)thiazol-2-yl]-piperidine-4-carboxylic acid ethyl ester

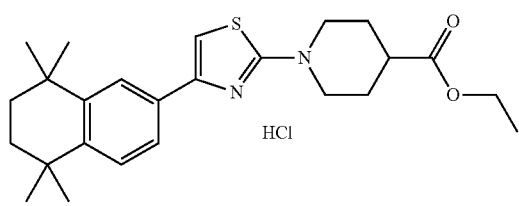 [SMILES: CCOC(=O)C1CCN(c2nc(-c3ccc4c(c3)C(C)(C)CCC4(C)C)cs2)CC1 ; Cl]

The preparation is carried out as described above starting from piperidine-4-carboxylic acid ethyl ester.

Yield: 83 mg, white solid. The product is in the form of the hydrochloride.

Rt.=4.20 min (method A), LCMS: 428 (M+H).

$^1$H NMR (400 MHz, DMSO/deuterated TFA) δ 7.64 (d, J=1.4, 1H), 7.51-7.41 (m, 2H), 4.12 (q, J=7.1, 2H), 4.02 (d, J=13.2, 2H), 3.46 (t, J=10.9, 2H), 2.80-2.69 (m, 1H), 2.06 (dd, J=13.4, 3.1, 2H), 1.88-1.73 (m, 2H), 1.69 (s, 4H), 1.30 (d, J=12.6, 12H), 1.22 (t, J=7.1, 3H).

1-{1-[4-(5,5,8,8-Tetramethyl-5,6,7,8-tetrahydronaphthalen-2-yl)thiazol-2-yl]piperidin-4-yl}pyrrolidin-3-ylamine

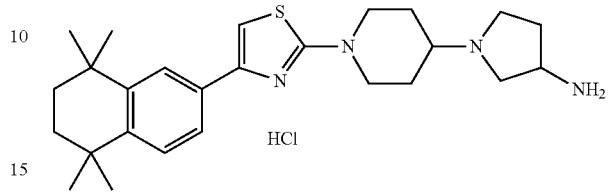

The preparation is carried out as described above starting from (1-piperidin-4-ylpyrrolidin-3-yl)carbamic acid tert-butyl ester. For the cleaving-off of the Boc protecting group, 5 ml of 4 N HCl in dioxane were added to 150 mg (0.28 mmol) of (1-{1-[4-(5,5,8,8-tetramethyl-5,6,7,8-tetrahydronaphthalen-2-yl)thiazol-2-yl]piperidin-4-yl}pyrrolidin-3-yl)carbamic acid tert-butyl ester, and the mixture was stirred at RT for 15 h. The precipitate was filtered off with suction, washed with dioxane and dried in vacuo.

Yield: 119 mg, greenish solid. The product is in the form of the hydrochloride.

Rt.=2.73 min (method A), LCMS: 439 (M+H).

C-{1-[4-(5,5,8,8-Tetramethyl-5,6,7,8-tetrahydronaphthalen-2-yl)thiazol-2-yl]piperidin-4-yl}methylamine

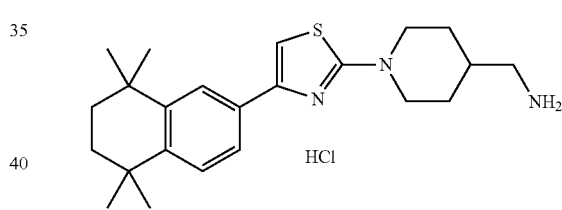

The preparation is carried out as described above starting from piperidin-4-ylmethylcarbamic acid tert-butyl ester. The Boc protecting group is cleaved off as described using 4 N HCl in dioxane.

Yield: 32 mg, beige solid. The product is in the form of the hydrochloride.

Rt.=3.03 min (method A), LCMS: 384 (M+H).

1-[4-(5,5,8,8-Tetramethyl-5,6,7,8-tetrahydronaphthalen-2-yl)thiazol-2-yl]-pyrrolidin-3-ylamine

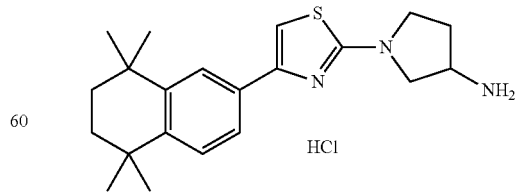

The preparation is carried out as described above starting from pyrrolidin-3-ylcarbamic acid tert-butyl ester. The Boc protecting group is cleaved off as described using 4 N HCl in dioxane.

Yield: 123 mg, pale-green solid. The product is in the form of the hydrochloride.
Rt.=2.69 min (method A), LCMS: 356(M+H).

2-{1-[4-(5,5,8,8-Tetramethyl-5,6,7,8-tetrahydronaphthalen-2-yl)thiazol-2-yl]piperidin-4-yl}ethylamine

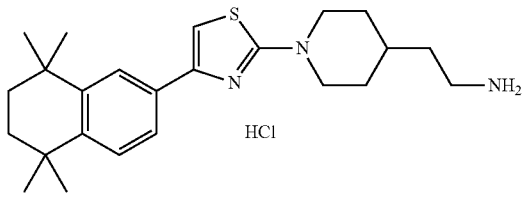 [SMILES: CC1(C)CCC(C)(C)c2cc(-c3csc(N4CCC(CCN)CC4)n3)ccc21 ; Cl]

The preparation is carried out as described above starting from (2-piperidin-4-yl-ethyl)carbamic acid tert-butyl ester. The Boc protecting group is cleaved off as described using 4 N HCl in dioxane.
Yield: 43 mg, pale-green solid. The product is in the form of the hydrochloride.
Rt.=2.93 min (method A), LCMS: 398 (M+H).

4-{1-[4-(5,5,8,8-Tetramethyl-5,6,7,8-tetrahydronaphthalen-2-yl)thiazol-2-yl]piperidin-4-yl}morpholine

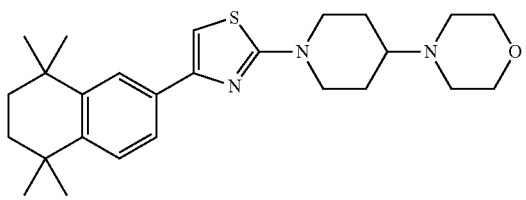 [SMILES: CC1(C)CCC(C)(C)c2cc(-c3csc(N4CCC(N5CCOCC5)CC4)n3)ccc21]

The preparation is carried out as described above starting from 4-piperidin-4-ylmorpholine.
Yield: 495 mg, pale-yellow solid.
Rt.=2.90 min (method A), LCMS: 440 (M+H).
$^1$H NMR (500 MHz, DMSO/deuterated TFA) δ 7.70 (d, J=1.8, 1H), 7.52 (dd, J=8.2, 1.8, 1H), 7.41 (d, J=8.2, 1H), 4.21 (d, J=12.8, 2H), 4.05 (d, J=11.3, 2H), 3.74 (t, J=12.0, 2H), 3.64-3.55 (m, 1H), 3.51 (d, J=11.4, 2H), 3.31 (t, J=12.0, 2H), 3.23-3.16 (m, 2H), 2.27 (d, J=10.1, 2H), 1.91-1.82 (m, 2H), 1.70 (d, J=6.7, 4H), 1.30 (d, J=16.4, 12H).

1-Methyl-4-{1-[4-(5,5,8,8-tetramethyl-5,6,7,8-tetrahydronaphthalen-2-yl)thiazol-2-yl]piperidin-4-yl}piperazine

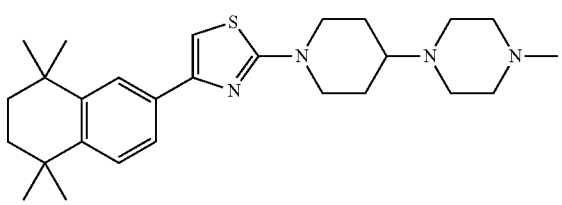

The preparation is carried out as described above starting from 1-methyl-4-piperidin-4-ylpiperazine. Yield: 326 mg, yellow solid.
Rt.=2.86 min (method A), LCMS: 453 (M+H).

3-[4-(5,5,8,8-Tetramethyl-5,6,7,8-tetrahydronaphthalen-2-yl)thiazol-2-yl]-3,9-diazaspiro[5.5]undecane

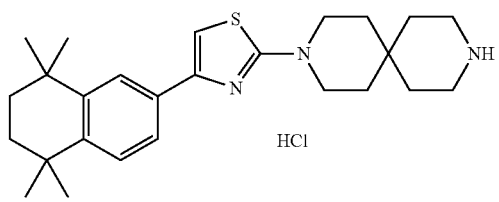 [SMILES: CC1(C)CCC(C)(C)c2cc(-c3csc(N4CCC5(CCNCC5)CC4)n3)ccc21 ; Cl]

The preparation is carried out as described above starting from 3,9-diazaspiro[5.5]undecane-3-carboxylic acid tert-butyl ester. The Boc protecting group is cleaved off as described using 4 N HCl in dioxane.
Yield: 31 mg, green solid. Product is in the form of the hydrochloride.
Rt.=2.94 min (method A), LCMS: 424 (M+H).

3-[4-(5,5,8,8-Tetramethyl-5,6,7,8-tetrahydronaphthalen-2-yl)thiazol-2-yl]-piperidine

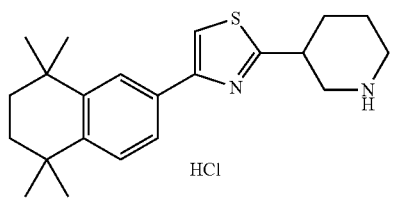 [SMILES: CC1(C)CCC(C)(C)c2cc(-c3csc(C4CCCNC4)n3)ccc21 ; Cl]

The preparation is carried out as described above starting from 3-carbamoylpiperidine-1-carboxylic acid tert-butyl ester. The Boc protecting group is cleaved off as described using 4N HCl in dioxane. Product is in the form of the hydrochloride.
Yield: 3 mg.
Rt.=3.08 min (method A), LCMS: 341 (M+H).

1-[4-(5,5,8,8-Tetramethyl-5,6,7,8-tetrahydronaphthalen-2-yl)thiazol-2-yl]-piperidine-4-carboxylic acid (2-hydroxyethyl)amide

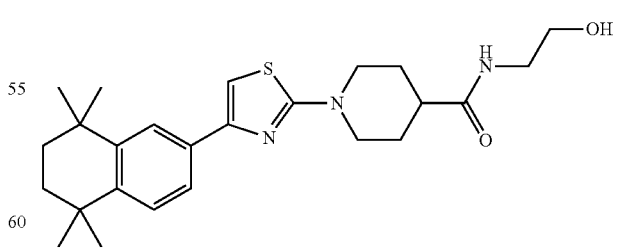

The preparation is carried out as described above starting from piperidine-4-carboxylic acid (2-hydroxyethyl)amide.
Yield: 89 mg, beige solid.
Rt.=2.94 min (method A), LCMS: 442 (M+H).

1'-[4-(5,5,8,8-Tetramethyl-5,6,7,8-tetrahydronaphthalen-2-yl)thiazol-2-yl]-1,4'-bipiperidinyl-3-ol

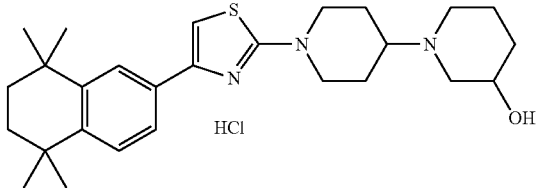 [SMILES: CC1(C)CCC(C)(C)c2cc(-c3csc(N4CCC(N5CCCC(O)C5)CC4)n3)ccc21 ; Cl]

The preparation is carried out as described above starting from 1,4'-bipiperidinyl-3-ol.

Yield: 31 mg, pale-green solid. Product is in the form of the hydrochloride.

Rt.=2.94 min (method A), LCMS: 454 (M+H).

$^1$H NMR (500 MHz, DMSO/deuterated TFA) δ 7.69 (s, 1H), 7.51 (dd, J=8.2, 1.8, 1H), 7.36 (d, J=8.3, 1H), 4.20-4.07 (m, 3H), 3.56 (s, 1H), 3.46-3.35 (m, 1H), 3.30 (d, J=12.0, 1H), 3.23 (d, J=12.6, 2H), 3.10-3.01 (m, 1H), 2.93-2.63 (m, 1H), 2.15 (dt, J=32.0, 17.1, 3H), 2.00-1.67 (m, 5H), 1.66 (s, 4H), 1.26 (d, J=16.1, 12H).

3-{1-[4-(5,5,8,8-Tetramethyl-5,6,7,8-tetrahydronaphthalen-2-yl)thiazol-2-yl]piperidin-4-yl}propan-1-ol

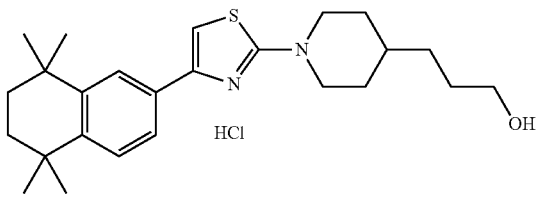 [SMILES: CC1(C)CCC(C)(C)c2cc(-c3csc(N4CCC(CCCO)CC4)n3)ccc21 ; Cl]

The preparation is carried out as described above starting from 3-piperidin-4-ylpropan-1-ol.

Yield: 16 mg, beige solid. Product is in the form of the hydrochloride.

Rt.=3.22 min (method A), LCMS: 413 (M+H).

$^1$H NMR (500 MHz, DMSO/deuterated TFA) δ 7.61 (d, J=1.6, 1H), 7.49-7.42 (m, 2H), 4.07 (d, J=12.6, 2H), 3.45 (t, J=6.5, 2H), 3.38 (dd, J=12.6, 10.4, 2H), 1.89 (d, J=11.0, 2H), 1.70 (s, 4H), 1.68-1.47 (m, 3H), 1.38-1.24 (m, 16H).

2-{1-[4-(5,5,8,8-Tetramethyl-5,6,7,8-tetrahydronaphthalen-2-yl)thiazol-2-yl]-piperidin-3-yl}ethanol

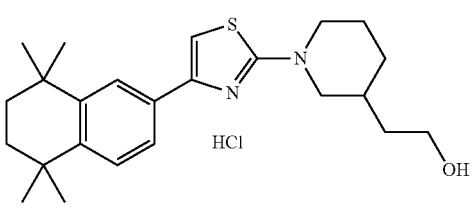 [SMILES: CC1(C)CCC(C)(C)c2cc(-c3csc(N4CCCC(CCO)C4)n3)ccc21 ; Cl]

The preparation is carried out as described above starting from 2-piperidin-3-ylethanol.

Yield: 69 mg, beige solid. Product is in the form of the hydrochloride.

Rt.=3.12 min (method A), LCMS: 399 (M+H).

$^1$H NMR (500 MHz, DMSO/deuterated TFA) δ 7.62 (s, 1H), 7.48-7.43 (m, 2H), 3.97 (d, J=12.8, 2H), 3.56-3.50 (m, 2H), 3.35 (t, J=10.9, 1H), 3.16-3.06 (m, 1H), 1.91-1.81 (m, 4H), 1.69 (s, 4H), 1.68-1.36 (m, 4H), 1.29 (d, J=15.0, 12H).

1-[4-(5,5,8,8-Tetramethyl-5,6,7,8-tetrahydronaphthalen-2-yl)thiazol-2-yl]-piperidine-3-carboxylic acid (2-hydroxyethyl)amide

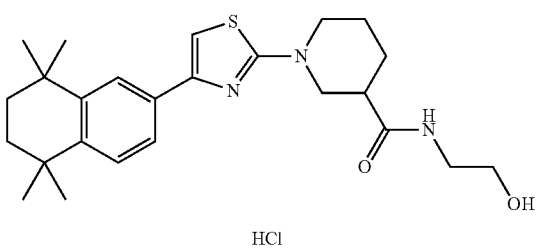 [SMILES: CC1(C)CCC(C)(C)c2cc(-c3csc(N4CCCC(C(=O)NCCO)C4)n3)ccc21 ; Cl]

The preparation is carried out as described above starting from piperidine-3-carboxylic acid (2-hydroxyethyl)amide.

Yield: 20 mg, beige solid. Product is in the form of the hydrochloride.

Rt.=2.96 min (method A), LCMS: 442 (M+H).

1-[4-(5,5,8,8-Tetramethyl-5,6,7,8-tetrahydronaphthalen-2-yl)thiazol-2-yl]-piperidine-3-carboxylic acid (3-hydroxypropyl)amide

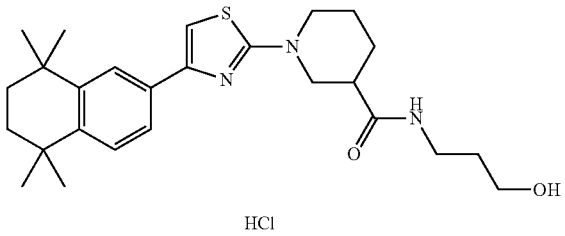 [SMILES: CC1(C)CCC(C)(C)c2cc(-c3csc(N4CCCC(C(=O)NCCCO)C4)n3)ccc21 ; Cl]

The preparation is carried out as described above starting from piperidine-3-carboxylic acid (3-hydroxypropyl)amide.

Yield: 60 mg, yellow solid. Product is in the form of the hydrochloride.

Rt.=3.01 min (method A), LCMS: 456 (M+H).

$^1$H NMR (500 MHz, DMSO/deuterated TFA) δ 7.65 (d, J=1.5, 1H), 7.48 (dd, J=8.2, 1.7, 1H), 7.43 (d, J=8.3, 1H), 4.02 (d, J=9.6, 1H), 3.87 (d, J=13.4, 1H), 3.50-3.34 (m, 5H), 3.20-3.08 (m, 2H), 2.58 (dd, J=9.0, 5.0, 1H), 2.00-1.92 (m, 1H), 1.84 (dd, J=9.4, 4.2, 1H), 1.75-1.62 (m, 6H), 1.62-1.54 (m, 2H), 1.29 (d, J=15.8, 12H).

3-{1-[4-(5,5,8,8-Tetramethyl-5,6,7,8-tetrahydronaphthalen-2-yl)thiazol-2-yl]piperidin-3-yl}propan-1-ol

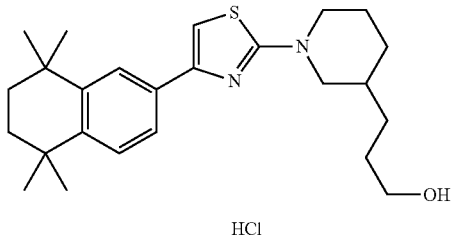 [SMILES: CC1(C)CCC(C)(C)c2cc(-c3csc(N4CCCC(CCCO)C4)n3)ccc21 ; Cl]

HCl

The preparation is carried out as described above starting from 3-piperidin-3-ylpropan-1-ol.

Yield: 18 mg, beige solid. Product is in the form of the hydrochloride.

Rt.=3.19 min (method A), LCMS: 413 (M+H).

$^1$H NMR (500 MHz, DMSO/deuterated TFA) δ 7.65 (d, J=1.5, 1H), 7.48 (dd, J=8.2, 1.7, 1H), 7.43 (d, J=8.3, 1H), 4.02 (d, J=9.6, 1H), 3.87 (d, J=13.4, 1H), 3.50-3.34 (m, 5H), 3.20-3.08 (m, 2H), 2.58 (dd, J=9.0, 5.0, 1H), 2.00-1.92 (m, 1H), 1.84 (dd, J=9.4, 4.2, 1H), 1.75-1.62 (m, 6H), 1.62-1.54 (m, 2H), 1.29 (d, J=15.8, 12H).

(R)-1-[4-(5,5,8,8-Tetramethyl-5,6,7,8-tetrahydronaphthalen-2-yl)thiazol-2-yl]pyrrolidin-3-ylamine

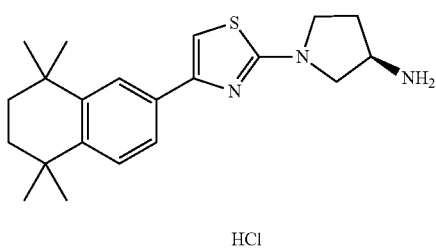 [SMILES: CC1(C)CCC(C)(C)c2cc(-c3csc(N4CC[C@@H](N)C4)n3)ccc21 ; Cl]

HCl

The preparation is carried out as described above starting from (R)-pyrrolidin-3-ylcarbamic acid tert-butyl ester. The Boc protecting group is cleaved off as described using 4 N HCl in dioxane.

Yield: 250 mg, yellow solid. Product is in the form of the hydrochloride.

Rt.=2.72 min (method A), LCMS: 356 (M+H).

(S)-1-[4-(5,5,8,8-Tetramethyl-5,6,7,8-tetrahydronaphthalen-2-yl)thiazol-2-yl]pyrrolidin-3-ylamine

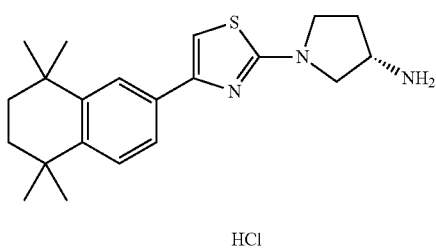 [SMILES: CC1(C)CCC(C)(C)c2cc(-c3csc(N4CC[C@H](N)C4)n3)ccc21 ; Cl]

HCl

The preparation is carried out as described above starting from (S)-pyrrolidin-3-ylcarbamic acid tert-butyl ester. The Boc protecting group is cleaved off as described using 4 N HCl in dioxane.

Yield: 136 mg, yellow solid. Product is in the form of the hydrochloride.

Rt.=2.73 min (method A), LCMS: 356 (M+H).

$^1$H NMR (400 MHz, DMSO/deuterated TFA) δ 7.63 (d, J=1.5, 1H), 7.52-7.44 (m, 2H), 4.16 (d, J=5.4, 1H), 4.01 (dd, J=12.1, 5.9, 1H), 3.92-3.72 (m, 3H), 2.57-2.45 (m, 1H), 2.39-2.26 (m, 1H), 1.71 (s, 4H), 1.31 (d, J=12.2, 12H).

3-{4-[4-(5,5,8,8-Tetramethyl-5,6,7,8-tetrahydronaphthalen-2-yl)thiazol-2-yl]piperazin-1-yl}propane-1,2-diol

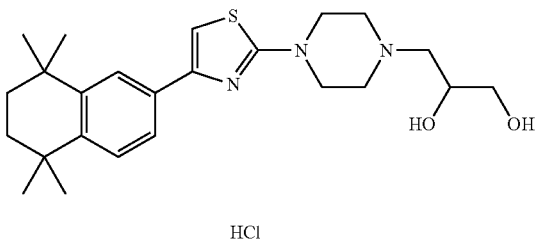 [SMILES: CC1(C)CCC(C)(C)c2cc(-c3csc(N4CCN(CC(O)CO)CC4)n3)ccc21 ; Cl]

HCl

The preparation is carried out as described above starting from 3-piperazin-1-ylpropane-1,2-diol.

Yield: 41 mg, beige solid. Product is in the form of the hydrochloride.

Rt.=3.02 min (method A), LCMS: 430 (M+H).

$^1$H NMR (400 MHz, DMSO/deuterated TFA) δ 7.79 (d, J=1.9, 1H), 7.58 (dd, J=8.2, 1.9, 1H), 7.38 (d, J=8.3, 1H), 4.27-4.10 (m, 2H), 4.07-3.99 (m, 1H), 3.66 (d, J=35.1, 4H), 3.52 (dd, J=11.1, 4.8, 1H), 3.46-3.30 (m, 4H), 3.20 (dd, J=13.1, 10.4, 1H), 1.70 (s, 4H), 1.30 (d, J=14.5, 12H).

Dimethyl-{1-[4-(5,5,8,8-tetramethyl-5,6,7,8-tetrahydronaphthalen-2-yl)thiazol-2-yl]piperidin-4-yl}amine

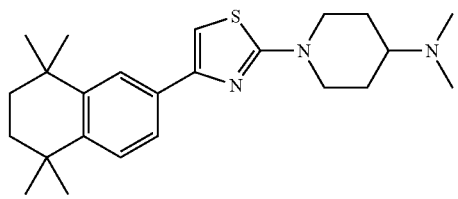

HCl

The preparation is carried out as described above starting from dimethylpiperidin-4-ylamine.

Yield: 53 mg, yellow solid. Product is in the form of the hydrochloride.

Rt.=3.00 min (method A), LCMS: 398 (M+H).

$^1$H NMR (400 MHz, DMSO/deuterated TFA) δ 7.71 (d, J=1.9, 1H), 7.53 (dd, J=8.2, 1.9, 1H), 7.39 (d, J=8.3, 1H), 4.18 (d, J=13.4, 2H), 3.56-3.46 (m, 1H), 3.25 (t, J=11.7, 2H), 2.82 (s, 6H), 2.16 (d, J=10.6, 2H), 1.87-1.74 (m, 2H), 1.68 (s, 4H), 1.28 (d, J=12.8, 12H).

4-[4-(5,5,8,8-Tetramethyl-5,6,7,8-tetrahydronaphthalen-2-yl)thiazol-2-yl]-cyclohexylamine

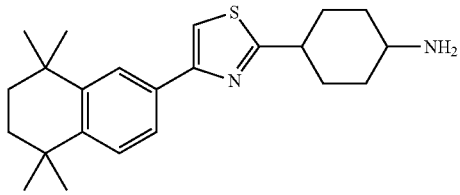

The preparation is carried out as described above starting from (4-carbamoylcyclohexyl)carbamic acid tert-butyl ester. The Boc protecting group is cleaved off as described using 4 N HCl in dioxane.

Yield: 225 mg, yellow solid. Product is in the form of the hydrochloride.

Rt.=3.12 min (method A), LCMS: 369 (M+H).

2-{4-[4-(5,5,8,8-Tetramethyl-5,6,7,8-tetrahydronaphthalen-2-yl)thiazol-2-yl]-piperazin-1-yl}cyclohexanol

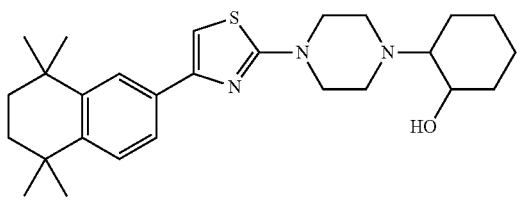

The preparation is carried out as described above starting from 2-piperazin-1-ylcyclohexanol.

Yield: 42 mg, white solid. Product is in the form of the hydrochloride.

Rt.=3.17 min (method A), LCMS: 454 (M+H).

$^1$H NMR (500 MHz, DMSO/deuterated TFA) δ 7.83 (d, J=1.9, 1H), 7.58 (dd, J=8.3, 1.9, 1H), 7.39 (d, J=8.3, 1H), 4.05 (dd, J=26.9, 12.7, 2H), 3.74-3.63 (m, 2H), 3.56-3.35 (m, 5H), 3.22-3.09 (m, 1H), 2.03 (t, J=13.5, 2H), 1.82-1.75 (m, 1H), 1.72-1.63 (m, 5H), 1.51-1.19 (m, 16H).

2-Pyrrolidin-3-yl-4-(5,5,8,8-tetramethyl-5,6,7,8-tetrahydronaphthalen-2-yl)thiazole

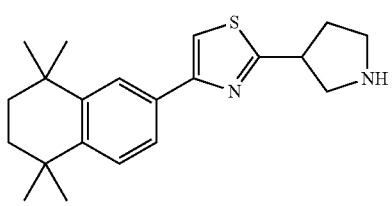

The preparation is carried out as described above starting from 3-carbamoylpyrrolidine-1-carboxylic acid tert-butyl ester. The Boc protecting group is cleaved off as described using 4 N HCl in dioxane.

Yield: 30 mg, pale-yellow solid. Product is in the form of the hydrochloride.

Rt.=2.99 min (method A), LCMS: 341 (M+H).

$^1$H NMR (400 MHz, DMSO/deuterated TFA) δ 7.98 (s, 1H), 7.89 (d, J=1.7, 1H), 7.70 (dd, J=8.2, 1.8, 1H), 7.39 (d, J=8.3, 1H), 4.05 (p, J=7.6, 1H), 3.74 (dd, J=11.6, 8.0, 1H), 3.62-3.51 (m, 1H), 3.51-3.31 (m, 2H), 2.53-2.44 (m, 1H), 2.30-2.17 (m, 1H), 1.69 (s, 4H), 1.30 (d, J=16.8, 12H).

1-[4-(5,5-Dimethyl-5,6,7,8-tetrahydronaphthalen-2-yl)thiazol-2-yl]-piperazine

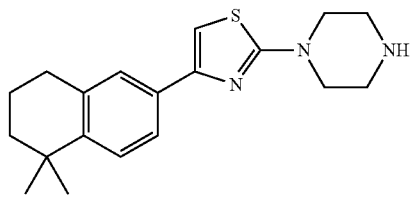

The preparation is carried out as described above starting from piperazine-1-carboxylic acid tert-butyl ester. The Boc protecting group is cleaved off as described using 4 N HCl in dioxane.

Yield: 31 mg, pale-yellow solid. Product is in the form of the hydrochloride.

Rt.=2.89 min (method A), LCMS: 328 (M+H).

$^1$H NMR (500 MHz, DMSO/deuterated TFA) δ 7.59 (dd, J=8.2, 1.7, 1H), 7.51 (d, J=1.2, 1H), 7.38 (d, J=8.2, 1H), 3.78-3.72 (m, 4H), 3.34-3.29 (m, 4H), 2.77 (t, J=6.2, 2H), 1.82-1.74 (m, 2H), 1.68-1.62 (m, 2H), 1.27 (s, 6H).

2-(4-{1-[4-(5,5,8,8-Tetramethyl-5,6,7,8-tetrahydronaphthalen-2-yl)thiazol-2-yl]piperidin-4-yl}piperazin-1-yl)ethanol

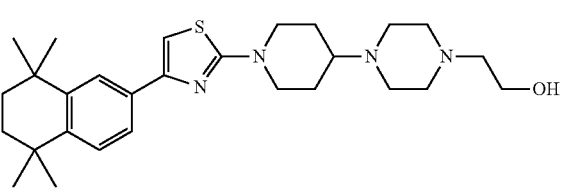

The preparation is carried out as described above starting from 2-(4-piperidin-4-ylpiperazin-1-yl)ethanol.

Yield: 310 mg, pale-yellow solid. Product is in the form of the hydrochloride.

Rt.=2.77 min (method A), LCMS: 483 (M+H).

$^1$H NMR (400 MHz, DMSO/deuterated δ 7.66 (d, J=1.5, 1H), 7.51-7.43 (m, 2H), 4.30 (d, J=13.1, 2H), 3.96-3.36 (m, 15H), 2.33 (d, J=11.2, 2H), 2.00 (dd, J=20.2, 11.7, 2H), 1.72 (s, 4H), 1.31 (d, J=12.9, 12H).

1-[4-(1,1-Dimethylindan-5-yl)thiazol-2-yl]piperidin-4-ylamine

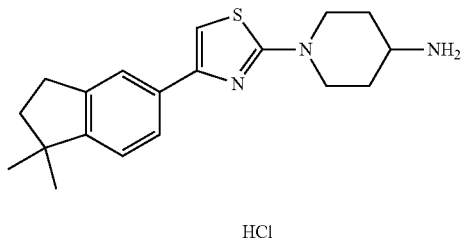 [SMILES: CC1(C)CCc2cc(-c3csc(N4CCC(N)CC4)n3)ccc21 ; Cl]

HCl

The preparation is carried out as described above starting from (1-thiocarbamoylpiperidin-4-yl)carbamic acid tert-butyl ester.

Yield: 1.07 g, pale-green solid. Product is in the form of the hydrochloride.

Rt.=2.59 min (method A), LCMS: 328 (M+H).

$^1$H NMR (400 MHz, DMSO/deuterated δ 7.61-7.53 (m, 2H), 7.27 (d, J=7.8, 1H), 4.15 (d, J=13.8, 2H), 3.44 (t, J=11.6, 3H), 2.94 (t, J=7.1, 2H), 2.14 (d, J=10.2, 2H), 1.95 (dd, J=12.5, 5.2, 2H), 1.85-1.70 (m, 2H), 1.27 (s, 6H).

2-{4-[4-(5,5,8,8-Tetramethyl-5,6,7,8-tetrahydronaphthalen-2-yl)thiazol-2-yl]-piperazin-1-yl}ethanol

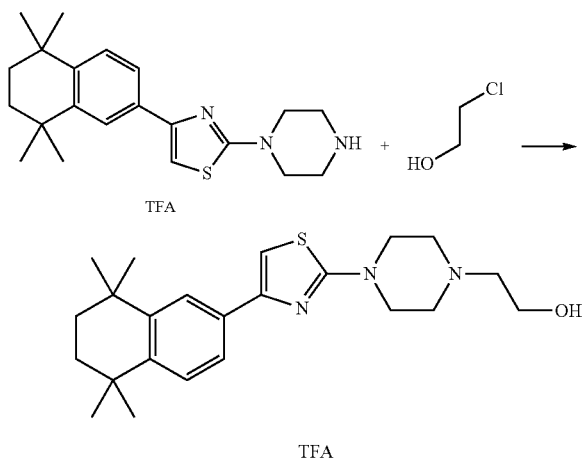

75 mg (0.16 mmol) of 1-[4-(5,5,8,8-tetramethyl-5,6,7,8-tetrahydronaphthalen-2-yl)thiazol-2-yl]piperazine trifluoroacetate were irradiated in the microwave at 160° C. for 2 h with 14 μl (0.19 mmol) of 2-chloroethanol in 6 ml of ethanol and 55 μl (0.39 mmol) of triethylamine. The reaction mixture was evaporated and purified by means of preparative HPLC.

Yield: 16 mg, oil. The product is in the form of the trifluoroacetate.

LCMS: 400 g/mol [M+H], HPLC: Rt.=3.02 min (method A).

$^1$H NMR (500 MHz, DMSO/deuterated TFA) δ 7.79 (d, J=1.9, 1H), 7.58 (dd, J=8.2, 1.9, 1H), 7.35 (d, J=8.3, 1H), 4.12 (b, 2H), 3.86-3.79 (m, 2H), 3.60 (dd, J=32.2, 19.3, 4H), 3.40-3.25 (m, 4H), 1.68 (s, 4H), 1.29 (d, J=17.3, 12H).

The following are prepared analogously:

3-{4-[4-(5,5,8,8-Tetramethyl-5,6,7,8-tetrahydronaphthalen-2-yl)thiazol-2-yl]piperazin-1-yl}propan-1-ol

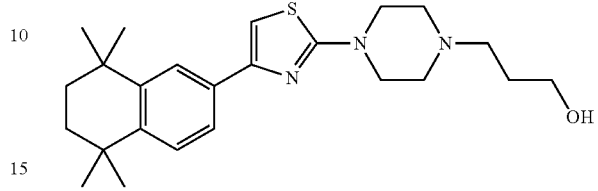

Yield: 34 mg, oil.

LCMS: 414 g/mol [M+H], HPLC: Rt.=3.10 min (method A).

$^1$H NMR (400 MHz, DMSO/deuterated TFA) δ 7.76 (d, J=1.8, 1H), 7.55 (dd, J=8.2, 1.9, 1H), 7.32 (d, J=8.3, 1H), 4.12 (d, J=13.1, 2H), 3.64 (d, J=10.9, 2H), 3.51 (t, J=5.9, 2H), 3.47-3.37 (m, 2H), 3.32-3.16 (m, 4H), 1.90-1.79 (m, 2H), 1.64 (s, 4H), 1.25 (d, J=13.7, 12H).

4-{3-[4-(5,5,8,8-Tetramethyl-5,6,7,8-tetrahydronaphthalen-2-yl)thiazol-2-yl]piperidin-1-yl}propan-1-ol

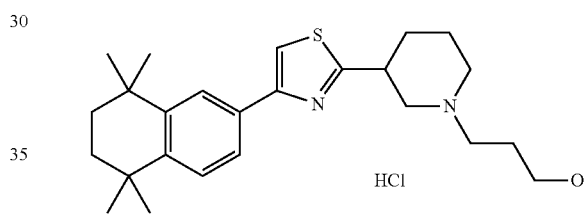

The preparation is carried out starting from 3-[4-(5,5,8,8-tetramethyl-5,6,7,8-tetrahydronaphthalen-2-yl)thiazol-2-yl]piperidine hydrobromide and 3-chloropropan-1-ol. The product is in the form of the hydrochloride.

Yield: 33 mg, solid.

LCMS: 413 [M+H], HPLC: Rt.=3.01 min (method A).

4-{3-[4-(5,5,8,8-Tetramethyl-5,6,7,8-tetrahydronaphthalen-2-yl)thiazol-2-yl]piperidin-1-yl}ethanol

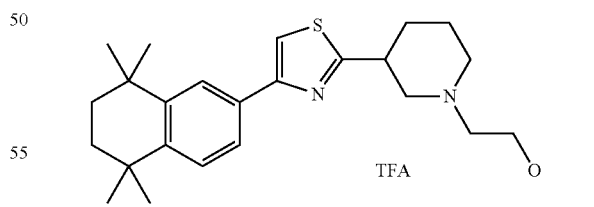

The product is in the form of the TFA salt.

Yield: 26 mg, solid.

LCMS: 399 [M+H], HPLC: Rt.=3.00 min (method A).

$^1$H NMR (500 MHz, DMSO/deuterated TFA) δ 7.98 (d, J=28.1, 1H), 7.90 (dd, J=8.3, 1.8, 1H), 7.74 (ddd, J=45.6, 8.3, 1.8, 1H), 7.39 (d, J=8.3, 1H), 3.97 (d, J=10.6, 1H), 3.93-3.82 (m, 2H), 3.74-3.60 (m, 2H), 3.45-3.25 (m, 3H), 3.12-3.04 (m, 1H), 2.26 (d, J=11.8, 1H), 2.06-1.98 (m, 2H), 1.85-1.75 (m, 1H), 1.70 (s, 4H), 1.30 (d, J=21.1, 12H).

4-{4-[4-(5,5,8,8-Tetramethyl-5,6,7,8-tetrahydronaph-thalen-2-yl)thiazol-2-yl]piperazin-1-yl}butan-1-ol

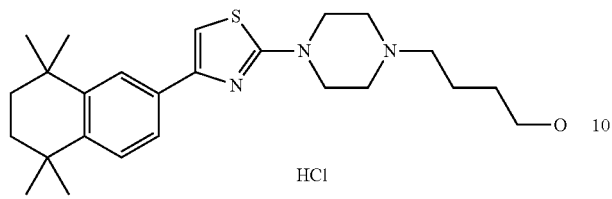

120 mg (0.34 mmol) of 1-[4-(5,5,8,8-tetramethyl-5,6,7,8-tetrahydronaphthalen-2-yl)thiazol-2-yl]piperazine were suspended in 3 ml of DMF with 100 µl (0.68 mmol) of 4-bromobutyl acetate and 56 mg (0.41 mmol) of potassium carbonate and stirred at 60° C. overnight. The reaction mixture was taken up in dichloromethane, washed once each with a concentrated sodium hydrogencarbonate solution and a 1N hydrochloric acid solution. The organic phase was dried over sodium sulfate, filtered and evaporated. The protecting group is cleaved off by means of a 1N NaOH solution in methanol: The reaction mixture was stirred at room temperature and subsequently evaporated. The product was purified by means of preparative HPLC and converted into the hydrochloride by treatment with methanolic HCl.

Yield: 47 mg, yellow solid.
LCMS: 428 [M+H], HPLC: Rt.=3.13 min (method A).

The following compounds were prepared analogously. In some cases, further purification by means of preparative HPLC was not necessary. In some cases, the crude products were purified by means of column chromatography on silica gel, which were then in some cases converted into the hydrochloride using 4 N HCl in dioxane or 1.25 M HCl in methanol:

4-{3-[4-(5,5-Dimethyl-5,6,7,8-tetrahydronaphthalen-2-yl)thiazol-2-yl]-pyrrolidin-1-yl}butan-1-ol

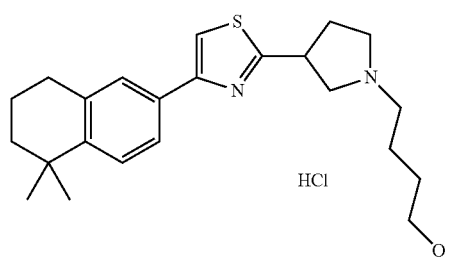 [SMILES: CC1(C)CCCc2cc(-c3csc(C4CCN(CCCCO)C4)n3)ccc21 ; Cl]

The preparation is carried out starting from 4-(5,5-dimethyl-5,6,7,8-tetrahydronaphthalen-2-yl)-2-pyrrolidin-3-ylthiazole hydrobromide and 4-bromobutyl acetate. The protecting group is cleaved off by means of a 1N NaOH solution in methanol. The product was purified by means of preparative HPLC and converted into the hydrochloride by treatment with methanolic HCl.

Yield: 11 mg, solid.
LCMS: 385 [M+H], HPLC: Rt.=2.85 min (method A).
$^1$H NMR (500 MHz, DMSO/deuterated TFA) δ 7.80-7.76 (m, 1H), 7.66-7.62 (m, 1H), 7.57 (d, J=4.9, 1H), 7.34 (d, J=8.2, 1H), 4.20-3.92 (m, 2H), 3.73-3.59 (m, 1H), 3.45 (t, J=6.1, 2H), 3.34-3.18 (m, 3H), 3.15 (s, 1H), 2.74 (t, J=6.3, 2H), 2.49-2.15 (m, 2H), 1.74 (dd, J=12.4, 6.1, 4H), 1.64-1.58 (m, 2H), 1.49 (dq, J=12.2, 6.0, 2H), 1.22 (s, 6H).

5-{3-[4-(5,5,8,8-Tetramethyl-5,6,7,8-tetrahydronaph-thalen-2-yl)thiazol-2-yl]piperidin-1-yl}pentan-1-ol

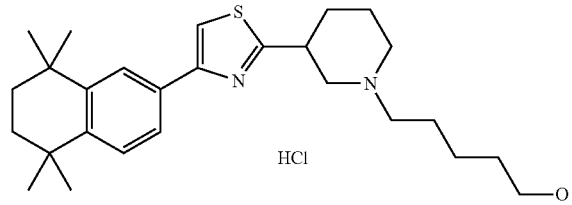 [SMILES: CC1(C)CCC(C)(C)c2cc(-c3csc(C4CCCN(CCCCCO)C4)n3)ccc21 ; Cl]

The preparation is carried out starting from 3-[4-(5,5,8,8-tetramethyl-5,6,7,8-tetrahydronaphthalen-2-yl)thiazol-2-yl]piperidine hydrobromide and 5-chloropentyl acetate. The protecting group is cleaved off by means of a 1N NaOH solution in methanol. The product was purified by means of preparative HPLC and converted into the hydrochloride by treatment with methanolic HCl.

Yield: 16 mg, solid.
LCMS: 441 [M+H], HPLC: Rt.=3.05 min (method A).

4-{3-[4-(5,5,8,8-Tetramethyl-5,6,7,8-tetrahydronaph-thalen-2-yl)thiazol-2-yl]piperidin-1-yl}butan-1-ol

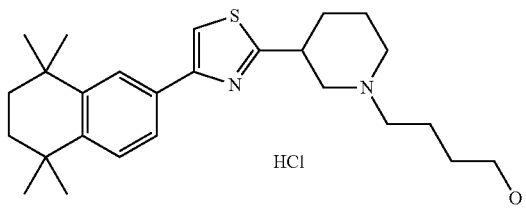 [SMILES: CC1(C)CCC(C)(C)c2cc(-c3csc(C4CCCN(CCCCO)C4)n3)ccc21 ; Cl]

The preparation is carried out starting from 3-[4-(5,5,8,8-tetramethyl-5,6,7,8-tetrahydronaphthalen-2-yl)thiazol-2-yl]piperidine hydrobromide and 4-bromobutyl acetate. The protecting group is cleaved off as described by means of a 1N NaOH solution in methanol. The product was purified by means of preparative HPLC and converted into the hydrochloride by treatment with methanolic HCl.

Yield: 12 mg, solid.
LCMS: 427 [M+H], HPLC: Rt.=3.02 min (method A).

Preparation of tert-butyl(2-{4-[4-(5,5,8,8-tetram-ethyl-5,6,7,8-tetrahydronaphthalen-2-yl)thiazol-2-yl]piperidin-1-yl}ethyl)carbamate

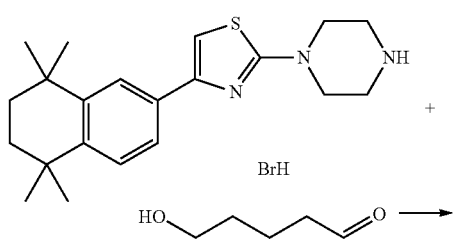

-continued

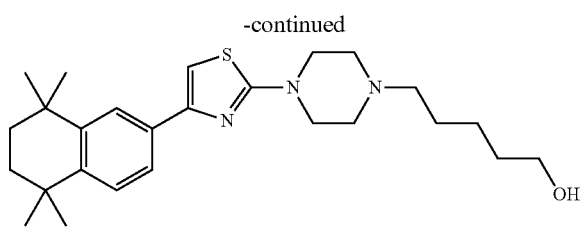

7 ml of THF and 200 µl of glacial acetic acid were added to 100 mg (0.23 mmol) of 1-[4-(5,5,8,8-tetramethyl-5,6,7,8-tetrahydronaphthalen-2-yl)thiazol-2-yl]-piperazine hydrobromide. 47 mg (0.46 mmol) of 5-hydroxypentanal were added, and the mixture was stirred for 30 min. 97 mg (0.46 mmol) of sodium trisacetoxyborohydride were subsequently added, and the reaction mixture was stirred at room temperature for 24 h. The reaction mixture was filtered, the mother liquor was evaporated, and the residue was purified by means of column chromatography on silica gel.

Yield: 56 mg solid.

ESI: 442 (M+H), HPLC: 3.16 min (method A)

$^1$H NMR (500 MHz, DMSO/deuterated TFA) δ 7.79 (d, J=1.8, 1H), 7.58 (dd, J=8.2, 1.8, 1H), 7.34 (d, J=8.3, 1H), 4.14 (d, J=13.5, 2H), 3.64 (d, J=10.7, 2H), 3.50-3.38 (m, 4H), 3.29-3.15 (m, 4H), 1.72 (dt, J=9.5, 6.6, 2H), 1.68 (s, 4H), 1.54-1.46 (m, 2H), 1.40 (tt, J=14.8, 7.2, 2H), 1.32-1.24 (m, 12H).

The following compounds were prepared analogously. In some cases, on use of ketones instead of aldehydes, an increase in the reaction temperature to 40° C. or an extension of the reaction time was necessary:

(1H-Imidazol-4-ylmethyl)-{1-[4-(5,5,8,8-tetramethyl-5,6,7,8-tetrahydronaphthalen-2-yl)thiazol-2-yl]piperidin-4-yl}amine

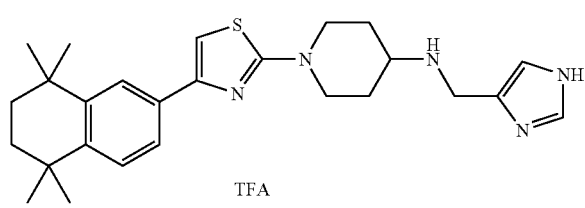 [SMILES: CC1(C)CCC(C)(C)c2cc(-c3csc(N4CCC(NCc5c[nH]cn5)CC4)n3)ccc21 ; "TFA"]

Yield: 20 mg, solid. The product is in the form of the TFA salt.

ESI: 450 (M+H), HPLC: 2.85 min (method A)

$^1$H NMR (500 MHz, DMSO/deuterated TFA) δ 9.19 (d, J=1.2, 1H), 7.82 (s, 1H), 7.73 (d, J=1.7, 1H), 7.54 (dd, J=8.2, 1.7, 1H), 7.39 (d, J=8.3, 1H), 4.44 (s, 2H), 4.15 (d, J=13.5, 2H), 3.55-3.46 (m, 1H), 3.31 (t, J=12.0, 2H), 2.26 (d, J=10.2, 2H), 1.83-1.73 (m, 2H), 1.69 (s, 4H), 1.29 (d, J=16.3, 13H).

(3-Methyl-3H-imidazol-4-ylmethyl)-{1-[4-(5,5,8,8-tetramethyl-5,6,7,8-tetrahydronaphthalen-2-yl)thiazol-2-yl]piperidin-4-yl}amine

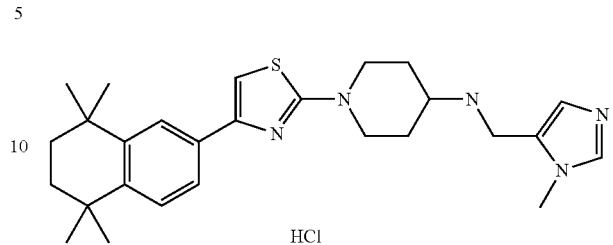

Yield: 38 mg, solid, product is the hydrochloride.

LCMS: 464 [M+H], HPLC: Rt.=2.85 min (method A).

$^1$H NMR (400 MHz, DMSO/deuterated TFA) δ 7.85 (d, J=1.4, 1H), 7.74 (d, J=1.6, 1H), 7.55 (dd, J=8.2, 1.7, 1H), 7.38 (d, J=8.3, 1H), 4.50 (s, 2H), 4.15 (d, J=13.3, 2H), 3.95 (s, 3H), 3.59 (s, 1H), 3.29 (t, J=12.0, 2H), 2.28 (d, J=10.3, 2H), 1.84-1.72 (m, 2H), 1.68 (s, 4H), 1.29 (d, J=13.1, 12H).

Bis-(1H-pyrazol-3-ylmethyl)-{1-[4-(5,5,8,8-tetramethyl-5,6,7,8-tetrahydronaphthalen-2-yl)thiazol-2-yl]piperidin-4-yl}amine

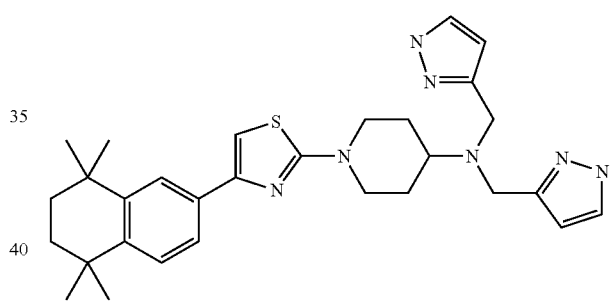

Yield: 52 mg, solid.

LCMS: 530 [M+H], HPLC: Rt.=3.08 min (method A).

$^1$H NMR (500 MHz, DMSO/deuterated TFA) δ 7.82 (d, J=2.2, 2H), 7.68 (d, J=1.8, 1H), 7.50 (dd, J=8.2, 1.8, 1H), 7.43 (d, J=8.3, 1H), 6.53 (d, J=2.2, 2H), 4.49 (s, 4H), 4.22 (d, J=13.2, 2H), 3.62 (t, J=11.8, 1H), 3.33 (t, J=12.1, 2H), 2.39 (d, J=11.6, 2H), 2.12-2.01 (m, 2H), 1.71 (s, 4H), 1.30 (d, J=16.7, 12H).

2-{1-[4-(5,5,8,8-Tetramethyl-5,6,7,8-tetrahydronaphthalen-2-yl)thiazol-2-yl]piperidin-4-ylamino}ethanol

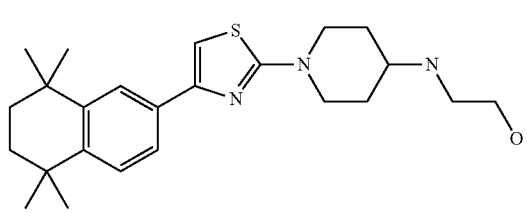 [SMILES: CC1(C)CCC(C)(C)c2cc(-c3csc(N4CCC(NCCO)CC4)n3)ccc21]

The preparation is carried out starting from 1-[4-(5,5,8,8-tetramethyl-5,6,7,8-tetrahydronaphthalen-2-yl)thiazol-2-yl]piperidin-4-ylamine hydrobromide and (tertbutyldimethylsilanyloxy)acetaldehyde. The protecting group is cleaved off in THF using 5 equivalent of a 1M TBAF/THF solution: The reaction mixture was stirred at room temperature for 2 h and evaporated to dryness. The product was purified by means of reversed-phase chromatography. The fractions were extracted under basic conditions, dried, filtered and evaporated.

Yield: 120 mg, white solid.

LCMS: 414 [M+H], HPLC: Rt.=2.75 min (method B).

$^1$H NMR (400 MHz, DMSO/deuterated TFA) δ 7.70 (d, J=1.5, 1H), 7.52 (dd, J=8.2, 1.5, 1H), 7.44 (d, J=8.3, 1H), 4.18 (d, J=13.3, 2H), 3.79-3.71 (m, 2H), 3.55-3.43 (m, 1H), 3.38 (t, J=12.0, 2H), 3.16-3.10 (m, 2H), 2.26 (d, J=10.7, 2H), 1.82 (qd, J=12.4, 4.4, 2H), 1.71 (s, 4H), 1.31 (d, J=13.0, 12H).

3-{1-[4-(5,5,8,8-Tetramethyl-5,6,7,8-tetrahydronaphthalen-2-yl)thiazol-2-yl]piperidin-4-ylamino}propan-1-ol

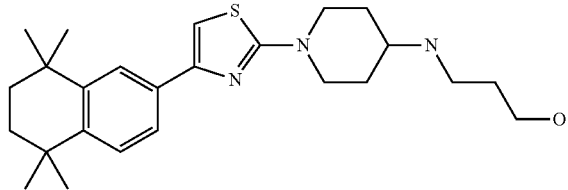

The preparation is carried out starting from 1-[4-(5,5,8,8-tetramethyl-5,6,7,8-tetrahydronaphthalen-2-yl)thiazol-2-yl]piperidin-4-ylamine hydrobromide and 3-(tert-butyldimethylsilanyloxy)propionaldehyde. The protecting group is cleaved off as already described by means of a 1M TBAF/THF solution. The product was purified by means of reversed-phase chromatography. The fractions were extracted under basic conditions, dried, filtered and evaporated.

Yield: 19 mg, white solid.

LCMS: 428 [M+H], HPLC: Rt.=2.70 min (method B).

$^1$H NMR (500 MHz, DMSO/deuterated TFA) δ 7.73 (d, J=1.8, 1H), 7.55 (dd, J=8.2, 1.8, 1H), 7.42 (d, J=8.3, 1H), 4.15 (d, J=13.3, 2H), 3.57 (t, J=5.9, 2H), 3.51-3.40 (m, 1H), 3.32 (t, J=11.8, 2H), 3.14-3.07 (m, 2H), 2.21 (d, J=10.4, 2H), 1.87-1.72 (m, 4H), 1.71 (s, 4H), 1.31 (d, J=16.2, 12H).

(R)-2-Amino-3-{1-[4-(5,5,8,8-tetramethyl-5,6,7,8-tetrahydronaphthalen-2-yl)thiazol-2-yl]piperidin-4-ylamino}propan-1-ol

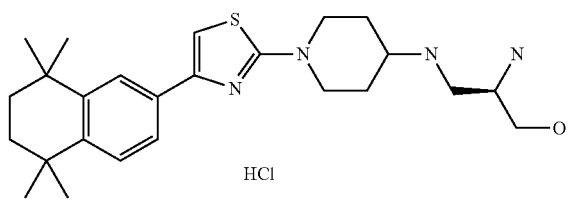 [SMILES: CC1(C)CCC(C)(C)c2cc(-c3csc(N4CCC(NC[C@@H](N)CO)CC4)n3)ccc21 ; Cl]

The preparation is carried out starting from 1-[4-(5,5,8,8-tetramethyl-5,6,7,8-tetrahydronaphthalen-2-yl)thiazol-2-yl]piperidin-4-ylamine hydrobromide and (S)-4-formyl-2,2-dimethyloxazolidine-3-carboxylic acid tert-butyl ester. The protecting group is cleaved off by means of a 4N HCl/dioxane solution: The reaction mixture was stirred at room temperature for 2 h and evaporated to dryness. The product is converted into the hydrochloride by treatment with methanolic HCl.

Yield: 9 mg, white solid.

LCMS: 443 [M+H], HPLC: Rt.=2.74 min (method A).

$^1$H NMR (500 MHz, DMSO/deuterated TFA) δ 7.67 (s, 1H), 7.51-7.43 (m, 2H), 4.22 (d, J=13.8, 2H), 3.76 (ddd, J=17.0, 11.7, 4.9, 2H), 3.65-3.54 (m, 2H), 3.49-3.35 (m, 3H), 3.28 (dd, J=13.5, 6.7, 1H), 2.34-2.23 (m, 2H), 1.94-1.82 (m, 2H), 1.72 (s, 4H), 1.31 (d, J=15.9, 12H).

3-{1-[4-(1,1-Dimethylindan-5-yl)thiazol-2-yl]piperidin-4-ylamino}propan-1-ol

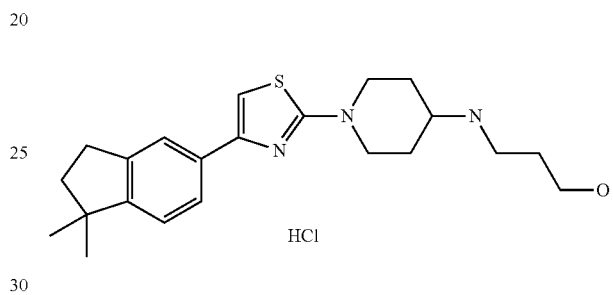

The preparation is carried out starting from 1-[4-(1,1-dimethylindan-5-yl)thiazol-2-yl]piperidin-4-ylamine hydrochloride and 3-(tert-butyldimethylsilanyloxy)propionaldehyde. The protecting group is cleaved off by means of a 1M tetramethylammonium/THF solution: The reaction mixture was stirred at room temperature overnight and subsequently evaporated to dryness. The product was purified by means of preparative HPLC and converted into the hydrochloride by treatment with methanolic HCl.

Yield: 18 mg, solid.

LCMS: 386 [M+H], HPLC: Rt.=2.63 min (method A).

2-{1-[4-(1,1-Dimethylindan-5-yl)thiazol-2-yl]piperidin-4-ylamino}ethanol

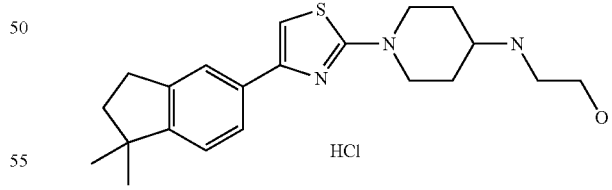

The preparation is carried out starting from 1-[4-(1,1-dimethylindan-5-yl)thiazol-2-yl]piperidin-4-ylamine hydrochloride and (tert-butyldimethylsilanyloxy)acetaldehyde. The protecting group is cleaved off as already described by means of a 1M tetramethylammonium/THF solution. The product was purified by means of preparative HPLC and converted into the hydrochloride.

Yield: 6 mg, solid.

LCMS: 372 [M+H], HPLC: Rt.=2.61 min (method A).

2-((2-Hydroxyethyl)-{1-[4-(5,5,8,8-tetramethyl-5,6,7,8-tetrahydronaphthalen-2-yl)thiazol-2-yl]piperidin-4-yl}amino)ethanol

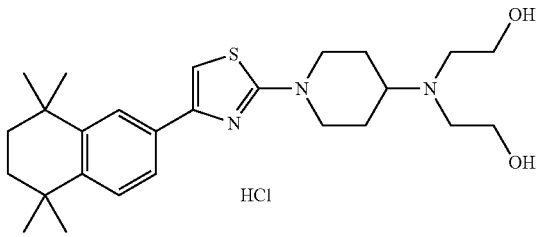 [SMILES: CC1(C)CCC(C)(C)c2cc(-c3csc(N4CCC(N(CCO)CCO)CC4)n3)ccc21 ; Cl]

The preparation is carried out starting from 1-[4-(5,5,8,8-tetramethyl-5,6,7,8-tetrahydronaphthalen-2-yl)thiazol-2-yl]piperidin-4-ylamine hydrobromide and (tertbutyldimethylsilanyloxy)acetaldehyde. The protecting group is cleaved off as already described by means of a 1M TBAF/THF solution. The product was purified by means of reversed-phase chromatography and converted into the hydrochloride.

Yield: 23 mg, white solid.

LCMS: 458 [M+H], HPLC: Rt.=2.69 min (method B).

$^1$H NMR (500 MHz, DMSO/deuterated TFA) δ 7.65 (d, J=1.6, 1H), 7.50-7.43 (m, 2H), 4.26 (d, J=13.0, 2H), 3.96-3.83 (m, 5H), 3.52-3.28 (m, 6H), 2.29 (d, J=11.6, 2H), 2.08-1.96 (m, 2H), 1.72 (s, 4H), 1.31 (d, J=16.3, 12H).

2-[{1-[4-(5,5-Dimethyl-5,6,7,8-tetrahydronaphthalen-2-yl)thiazol-2-yl]-piperidin-4-yl}-(2-hydroxyethyl)amino]ethanol

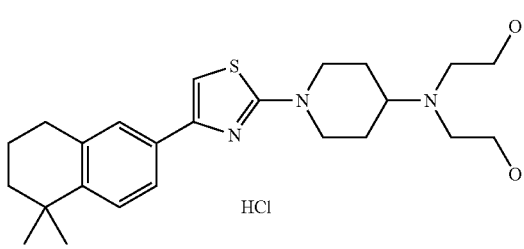 [SMILES: CC1(C)CCCc2cc(-c3csc(N4CCC(N(CCO)CCO)CC4)n3)ccc21 ; Cl]

The preparation is carried out starting from 1-[4-(5,5-dimethyl-5,6,7,8-tetrahydronaphthalen-2-yl)thiazol-2-yl]piperidin-4-ylamine and (tert-butyldimethylsilanyloxy)acetaldehyde. The protecting group is cleaved off as already described by means of a 1M tetramethylammonium/THF solution. The product was purified by means of preparative HPLC and converted into the hydrochloride.

Yield: 4 mg, brown oil.

LCMS: 430 [M+H], HPLC: Rt.=2.72 min (method A).

$^1$H NMR (500 MHz, DMSO/deuterated TFA) δ 7.41 (q, J=8.2, 2H), 7.34 (s, 1H), 4.18 (d, J=12.9, 2H), 3.78 (t, J=5.1, 3H), 3.44-3.20 (m, 6H), 3.15 (s, 2H), 2.74 (t, J=6.2, 2H), 2.20 (d, J=10.7, 2H), 1.99-1.88 (m, 2H), 1.76-1.72 (m, 2H), 1.64-1.59 (m, 2H), 1.21 (s, 6H).

(R)-3-{1-[4-(5,5,8,8-Tetramethyl-5,6,7,8-tetrahydronaphthalen-2-yl)thiazol-2-yl]piperidin-4-ylamino}propane-1,2-diol

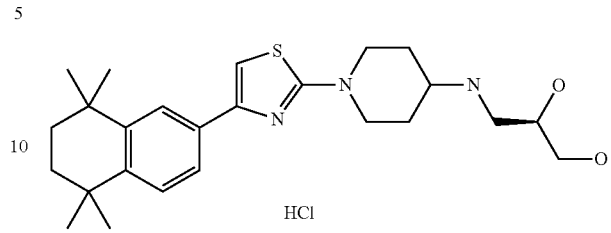

The preparation is carried out starting from 1-[4-(5,5,8,8-tetramethyl-5,6,7,8-tetrahydronaphthalen-2-yl)thiazol-2-yl]piperidin-4-ylamine hydrobromide and (S)-2,2-dimethyl-1,3-dioxolane-4-carbaldehyde. The protecting group is cleaved off by means of a 1.25 N HCl/methanol solution: The reaction mixture was stirred at room temperature for 5 h, evaporated to dryness and dried under a high vacuum. The product was converted into the hydrochloride by treatment with methanolic HCl.

Yield: 33 mg, green solid.

LCMS: 444 [M+H], HPLC: Rt.=2.69 min (method B).

(S)-3-{1-[4-(5,5,8,8-Tetramethyl-5,6,7,8-tetrahydronaphthalen-2-yl)thiazol-2-yl]piperidin-4-ylamino}propane-1,2-diol

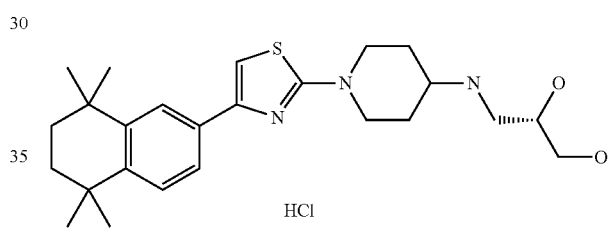

The preparation is carried out starting from 1-[4-(5,5,8,8-tetramethyl-5,6,7,8-tetrahydronaphthalen-2-yl)thiazol-2-yl]piperidin-4-ylamine hydrobromide and (R)-2,2-dimethyl-1,3-dioxolane-4-carbaldehyde. The protecting group is cleaved off as described by means of a 1.25 N HCl/methanol solution. The product was converted into the hydrochloride.

Yield: 30 mg, brown solid.

LCMS: 444 [M+H], HPLC: Rt.=2.64 min (method B).

5-{3-[4-(5,5-Dimethyl-5,6,7,8-tetrahydronaphthalen-2-yl)thiazol-2-yl]pyrrolidin-1-yl}pentan-1-ol

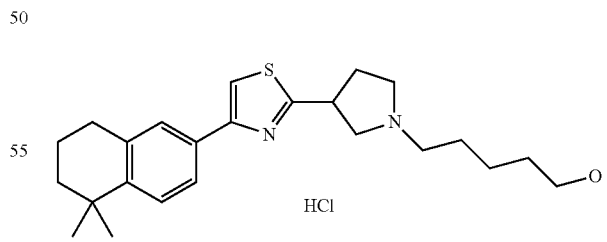

Yield: 21 mg, brown oil, product is the hydrochloride.

LCMS: 399 [M+H], HPLC: Rt.=2.88 min (method A).

$^1$H NMR (500 MHz, DMSO/deuterated TFA) δ 7.91 (s, 1H), 7.71 (d, J=7.9, 1H), 7.65-7.62 (m, 1H), 7.42 (d, J=8.2, 1H), 4.27-3.95 (m, 2H), 3.85-3.50 (m, 2H), 3.47 (t, J=6.3, 2H), 3.39-3.22 (m, 3H), 3.21 (s, 1H), 2.80 (t, J=6.3, 2H), 2.41-2.25 (m, 1H), 1.83-1.77 (m, 2H), 1.76-1.70 (m, 2H), 1.67 (dd, J=7.4, 4.1, 2H), 1.55-1.48 (m, 2H), 1.45-1.38 (m, 2H), 1.28 (s, 6H).

5-{4-[4-(5,5-Dimethyl-5,6,7,8-tetrahydronaphthalen-2-yl)thiazol-2-yl]-piperazin-1-yl}pentan-1-ol

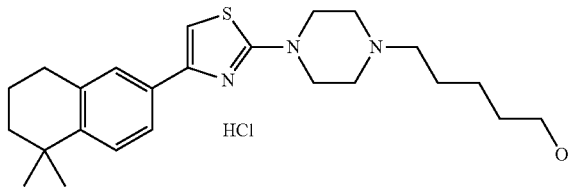 [SMILES: CC1(C)CCCc2cc(-c3csc(N4CCN(CCCCCO)CC4)n3)ccc21 ; Cl]

Yield: 17 mg, solid. Product is the hydrochloride.
LCMS: 414 [M+H], HPLC: Rt.=2.92 min (method A).
$^1$H NMR (500 MHz, DMSO/deuterated TFA) δ 7.58 (dd, J=8.2, 1.7, 1H), 7.50 (d, J=1.4, 1H), 7.35 (d, J=8.2, 1H), 7.26 (s, 1H), 4.06 (d, J=13.8, 2H), 3.58 (d, J=11.9, 2H), 3.53-3.45 (m, 2H), 3.41 (t, J=6.4, 2H), 3.20-3.08 (m, 4H), 2.74 (t, J=6.3, 2H), 1.79-1.68 (m, 4H), 1.65-1.61 (m, 2H), 1.50-1.43 (m, 2H), 1.38-1.30 (m, 2H), 1.25 (s, 6H).

5-{4-[4-(5,5-Dimethyl-5,6,7,8-tetrahydronaphthalen-2-yl)thiazol-2-yl]-piperazin-1-yl}butan-1-ol

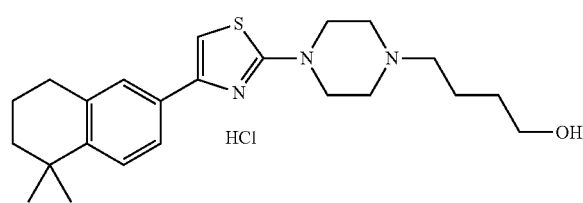 [SMILES: CC1(C)CCCc2cc(-c3csc(N4CCN(CCCCO)CC4)n3)ccc21 ; Cl]

The preparation is carried out starting from 1-[4-(5,5-dimethyl-5,6,7,8-tetrahydronaphthalen-2-yl)thiazol-2-yl]piperazine hydrobromide and 4-bromobutyl acetate. The protecting group is cleaved off as described by means of a 1N NaOH solution in methanol. The product was purified by means of preparative HPLC and converted into the hydrochloride by treatment with methanolic HCl.
Yield: 12 mg, solid.
LCMS: 400 [M+H], HPLC: Rt.=2.86 min (method A).

3-{(S)-1-[4-(5,5,8,8-Tetramethyl-5,6,7,8-tetrahydronaphthalen-2-yl)thiazol-2-yl]pyrrolidin-3-ylamino}propan-1-ol

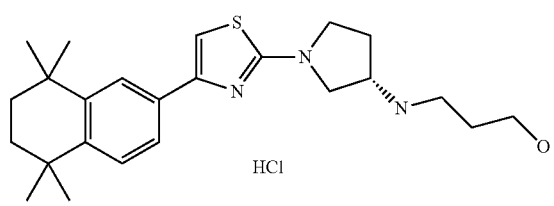 [SMILES: CC1(C)CCC(C)(C)c2cc(-c3csc(N4CC[C@H](NCCCO)C4)n3)ccc21 ; Cl]

The preparation is carried out starting from (S)-1-[4-(5,5,8,8-tetramethyl-5,6,7,8-tetrahydronaphthalen-2-yl)thiazol-2-yl]pyrrolidin-3-ylamine and 3-(tertbutyldimethylsilanyloxy)propionaldehyde. The protecting group is cleaved off as already described by means of a 1M TBAF/THF solution. The product was purified by means of preparative HPLC and converted into the hydrochloride by treatment with methanolic HCl.
Yield: 5 mg, colourless oil.
LCMS: 414 [M+H], HPLC: Rt.=2.71 min (method A).
$^1$H NMR (500 MHz, DMSO/deuterated TFA) δ 7.62-7.58 (m, 1H), 7.47-7.39 (m, 2H), 7.18 (s, 1H), 4.10 (s, 1H), 3.98 (dd, J=12.0, 6.4, 1H), 3.94-3.85 (m, 1H), 3.84-3.74 (m, 1H), 3.74-3.64 (m, 1H), 3.52 (t, J=5.9, 2H), 3.18-2.98 (m, 2H), 2.41-2.34 (m, 1H), 1.83-1.75 (m, 2H), 1.65 (s, 4H), 1.62-1.50 (m, 1H), 1.25 (d, J=15.9, 12H).

3-{(R)-1-[4-(5,5,8,8-Tetramethyl-5,6,7,8-tetrahydronaphthalen-2-yl)thiazol-2-yl]pyrrolidin-3-ylamino}ethan-1-ol

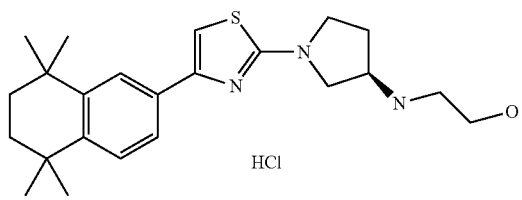 [SMILES: CC1(C)CCC(C)(C)c2cc(-c3csc(N4CC[C@@H](NCCO)C4)n3)ccc21 ; Cl]

The preparation is carried out starting from (R)-1-[4-(5,5,8,8-tetramethyl-5,6,7,8-tetrahydronaphthalen-2-yl)thiazol-2-yl]pyrrolidin-3-ylamine and (tert-butyldimethylsilanyloxy)acetaldehyde. The protecting group is cleaved off as already described by means of a 1M TBAF/THF solution. The product is purified by means of preparative HPLC and converted into the hydrochloride by treatment with methanolic HCl.
Yield: 11 mg, colourless oil.
LCMS: 400 [M+H], HPLC: Rt.=2.70 min (method A).
$^1$H NMR (400 MHz, DMSO/deuterated TFA) δ 7.67 (s, 1H), 7.53-7.39 (m, 2H), 7.23 (s, 1H), 4.13 (d, J=4.8, 1H), 4.01 (dd, J=11.9, 6.5, 1H), 3.93-3.76 (m, 2H), 3.76-3.63 (m, 3H), 3.23-3.10 (m, 2H), 2.48-2.35 (m, 1H), 1.69 (s, 4H), 1.68-1.50 (m, 1H), 1.30 (d, J=12.3, 12H).

(S)-2-Amino-3-{1-[4-(5,5,8,8-tetramethyl-5,6,7,8-tetrahydronaphthalen-2-yl)thiazol-2-yl]piperidin-4-ylamino}propan-1-ol

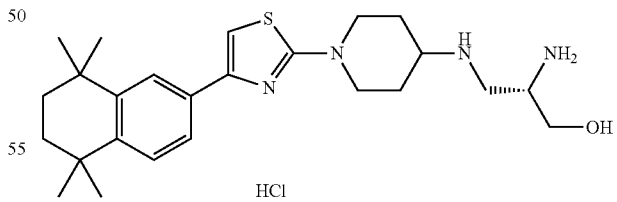

The preparation is carried out starting from 1-[4-(5,5,8,8-tetramethyl-5,6,7,8-tetrahydronaphthalen-2-yl)thiazol-2-yl]piperidin-4-ylamine hydrobromide and (R)-4-formyl-2,2-dimethyloxazolidine-3-carboxylic acid tert-butyl ester. The protecting group is cleaved off by means of a 4N HCl/dioxane solution: The reaction mixture was stirred at room temperature for 2 h and evaporated to dryness. The product was converted into the hydrochloride by treatment with methanolic HCl.

Yield: 6 mg, beige solid.
LCMS: 443 [M+H], HPLC: Rt.=2.76 min (method A).
¹H NMR (500 MHz, DMSO/deuterated TFA)¹H NMR (500 MHz, DMSO) δ 7.66 (s, 1H), 7.51-7.44 (m, 2H), 4.24 (d, J=13.2, 2H), 3.77 (ddd, J=28.3, 11.7, 4.9, 2H), 3.62 (dt, J=23.3, 8.5, 2H), 3.53-3.36 (m, 3H), 3.31 (dd, J=13.4, 6.9, 1H), 2.36-2.26 (m, 2H), 1.97-1.85 (m, 2H), 1.73 (s, 4H), 1.32 (d, J=15.6, 12H).

Preparation of N-(1-{1-[4-(5,5,8,8-tetramethyl-5,6,7,8-tetrahydronaphthalen-2-yl)thiazol-2-yl]piperidin-4-yl}pyrrolidin-3-yl)acetamide

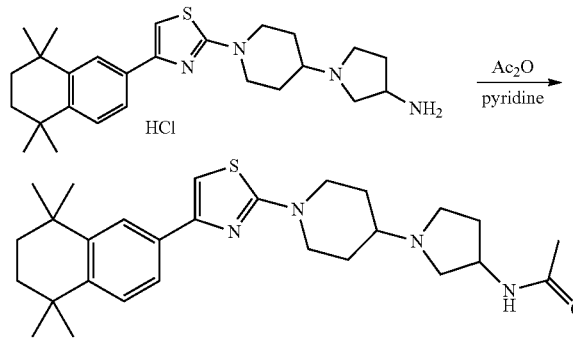

150 mg (0.32 mmol) of 1-{1-[4-(5,5,8,8-tetramethyl-5,6,7,8-tetrahydronaphthalen-2-yl)thiazol-2-yl]piperidin-4-yl}pyrrolidin-3-ylamine were dissolved in 1 ml of pyridine, and 90 μl of acetic anhydride were added. The reaction mixture was stirred at RT for 15 h and subsequently evaporated. The residue was taken up in ethyl acetate, washed with sat. NaHCO₃ solution, dried over Na₂SO₄ and evaporated. The oil obtained in this way was stirred with ether, and the precipitate formed was filtered off with suction, washed with ether and dried.
Yield: 21 mg, white solid.
LCMS: 481 g/mol [M+H], HPLC: Rt.=2.99 min (method A).
¹H NMR (500 MHz, DMSO/deuterated TFA) δ 7.71 (s, 1H), 7.53 (d, J=8.3, 1H), 7.40 (d, J=8.3, 1H), 4.34 (d, J=6.9, 1H), 4.15 (d, J=12.8, 2H), 3.90-3.02 (m, 7H), 2.42-1.70 (m, 6H), 1.87 (d, J=2.4, 3H), 1.69 (s, 4H), 1.29 (d, J=16.2, 12H).

3-{1-[4-(5,5,8,8-Tetramethyl-5,6,7,8-tetrahydronaphthalen-2-yl)thiazol-2-yl]piperidin-4-ylamino}propane-1,2-diol

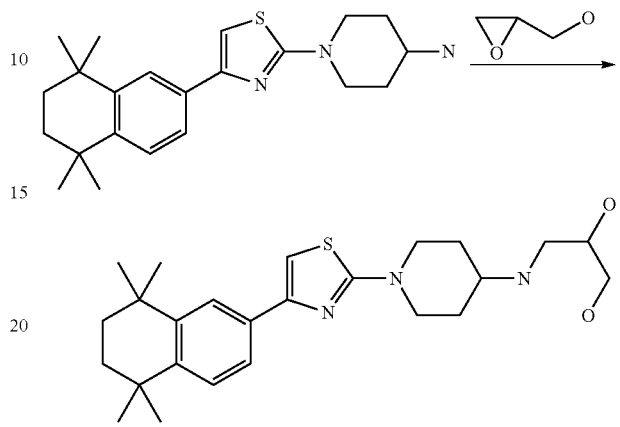

150 mg (0.41 mmol) of 1-[4-(5,5,8,8-tetramethyl-5,6,7,8-tetrahydronaphthalen-2-yl)thiazol-2-yl]piperidin-4-ylamine were dissolved in 2 ml of DMF, and 27.4 μl (0.41 mmol) of 2,3-epoxy-1-propanol were added. The reaction mixture was irradiated in the microwave at 120° C. for 3 h and subsequently stripped off to dryness. The residue was purified by means of flash chromatography on silica gel.
5.7 mg solid, LCMS: 444 [M+H], HPLC: Rt.=2.92 min (method A).
¹H NMR (500 MHz, DMSO) δ 7.71 (d, J=1.8, 1H), 7.52 (dd, J=8.2, 1.9, 1H), 7.39 (d, J=8.3, 1H), 4.13 (d, J=12.8, 2H), 3.87-3.79 (m, 1H), 3.56-3.22 (m, 5H), 3.16 (dd, J=12.6, 2.9, 1H), 2.93 (dd, J=12.6, 9.5, 1H), 2.30-2.13 (m, 2H), 1.86-1.72 (m, 2H), 1.69 (s, 4H), 1.29 (d, J=16.3, 12H).

4-[2-(5,5,8,8-Tetramethyl-5,6,7,8-tetrahydronaphthalen-2-yl)thiazol-4-yl]-piperidine

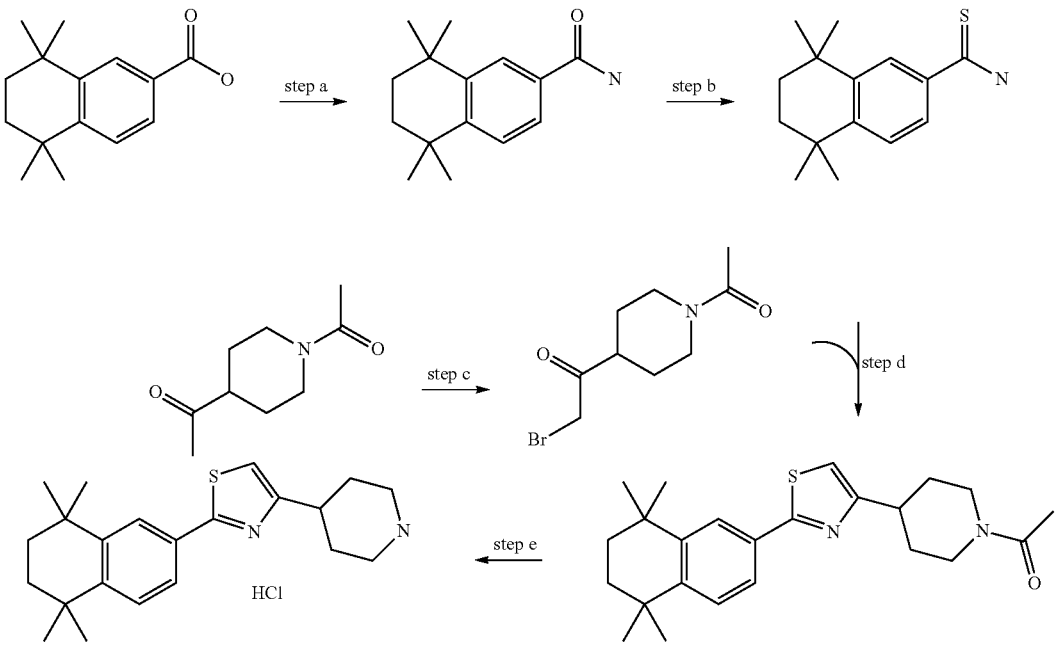

Step a:

1 g (4.18 mmol) of 5,5,8,8-tetramethyl-5,6,7,8-tetrahydro-2-naphthalenecarboxylic acid was dissolved in 10 ml of dioxane, and 1.62 g (8.35 mmol) of EDCI, 582 mg (4.18 mmol) of HOBt and 936 µl (8.35 mmol) of methylmorpholine were added. The reaction mixture was stirred at room temperature for 30 min. 8.35 ml of a 0.5 M ammonia solution in dioxane were subsequently added. The mixture is stirred at room temperature overnight, and water is then added. The resultant residue was filtered off with suction, rinsed with water and purified by means of flash chromatography on silica gel.

277 mg, Rt.=3.08 min (method A), LCMS: 232 (M+H).

Step b:

The product from step a (270 mg, 1.17 mmol) was dissolved in 8 ml of DCM and 25 ml of DME, and 354 mg (0.87 mmol) of 2,4-bis(4-methoxyphenyl)-2,4-dithioxo-1,3,2,4-dithiadiphosphethane were subsequently added. The suspension was stirred at room temperature overnight, stripped off to dryness and purified by means of flash chromatography on silica gel.

259 mg, Rt.=3.30 min (method A), LCMS: 248 (M+H).

Step c:

1 g (5.73 mmol) of 1-(4-acetylpiperidino)ethan-1-one was dissolved in 20 ml of methanol, and 308 µl (6.02 mmol) of bromine were slowly added at room temperature. The reaction mixture was stirred further for 6 h and subsequently stripped off to dryness. The residue is taken up in ethyl acetate and extracted against saturated sodium hydrogencarbonate solution. The organic phase was washed with a saturated sodium chloride solution, dried over sodium sulfate and evaporated to dryness.

980 mg, Rt.=1.88 min (method A), LCMS: 249 (M+H).

Step d:

A mixture of the product from step b (100 mg, 0.40 mmol) and the product from step c (125 mg, 0.40 mmol) 1-(1-acetylpiperidin-4-yl)-2-bromoethanone in 2 ml of ethanol was stirred at 90° C. overnight, then stripped off to dryness. The residue was purified by means of flash chromatography on silica gel.

123 mg, Rt.=3.77 min (method A), LCMS: 397 (M+H).

$^1$H NMR (500 MHz, DMSO/deuterated TFA) δ 7.87 (d, J=1.9, 1H), 7.67 (dd, J=8.2, 1.9, 1H), 7.46 (d, J=8.3, 1H), 7.36 (s, 1H), 4.54 (d, J=12.8, 1H), 3.99-3.91 (m, 1H), 3.27-3.18 (m, 1H), 3.13-3.06 (m, 1H), 2.77-2.68 (m, 1H), 2.14-2.02 (m, 5H), 1.74-1.64 (m, 5H), 1.62-1.51 (m, 1H), 1.31 (d, J=16.0, 12H).

Step e:

The product from step d (100 mg, 0.25 mmol) was dissolved in 8 ml of ethanol, and 212 mg (3.78 mmol) of KOH and 1 ml of water were added. The reaction mixture was stirred at 60° C. overnight, then water and ethyl acetate were added, and the mixture was extracted by shaking. The organic phase was washed with water, dried over sodium sulfate and evaporated. The residue was purified by means of preparative HPLC. The product is in the form of the hydrochloride.

58 mg, Rt.=3.06 min (method A), LCMS: 355 (M+H).

$^1$H NMR (500 MHz, DMSO/deuterated TFA) δ 7.90 (d, J=1.8, 1H), 7.67 (dd, J=8.2, 1.7, 1H), 7.46 (d, J=8.3, 1H), 7.37 (s, 1H), 3.43 (d, J=12.7, 2H), 3.21-3.06 (m, 3H), 2.24 (d, J=12.1, 2H), 2.02-1.91 (m, 2H), 1.72 (s, 4H), 1.31 (d, J=16.0, 12H).

4-[2-(5,5,8,8-Tetramethyl-5,6,7,8-tetrahydronaphthalen-2-yl)oxazol-5-yl]-piperidine

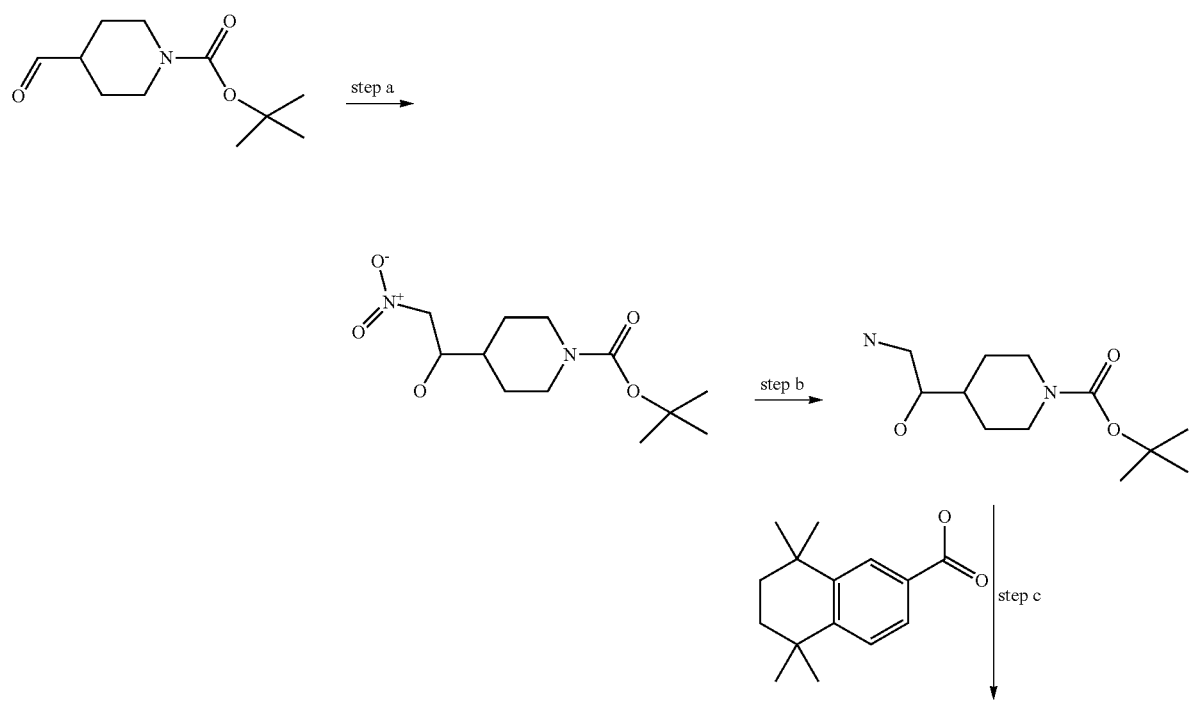

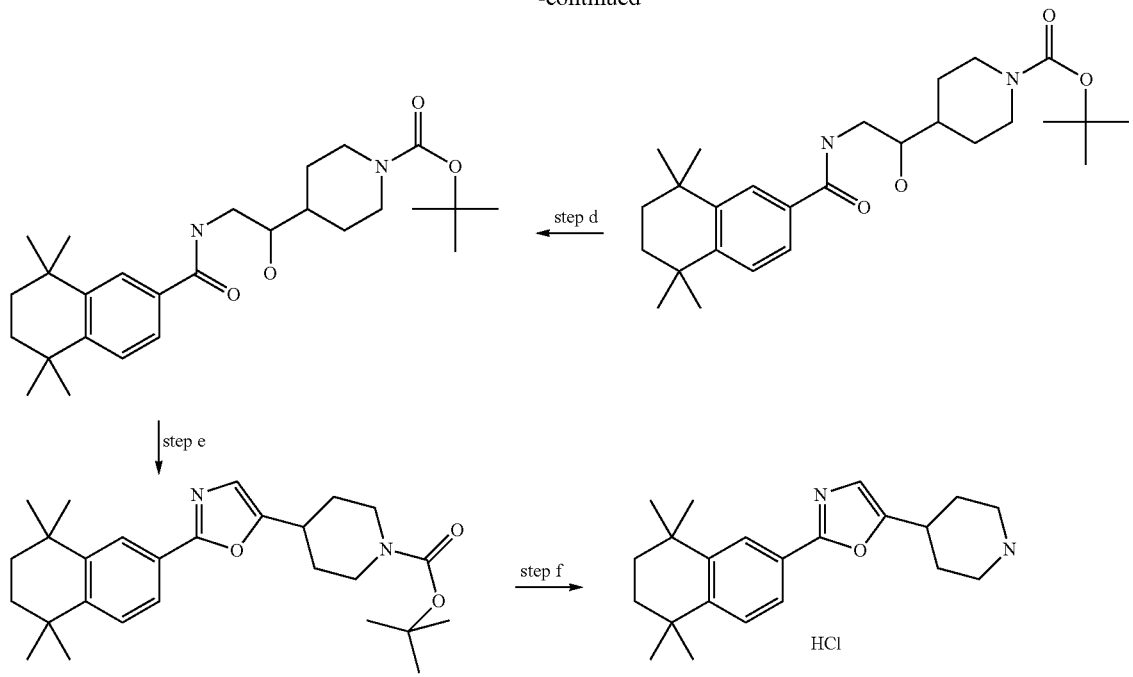

Step a:

5 g (23.44 mmol) of 4-formylpiperidine-1-carboxylic acid tert-butyl ester were dissolved in 40 ml of THF and 40 ml of tert-butanol. 2.63 g (23.44 mmol) of potassium tert-butoxide and 2.51 ml (46.89 mmol) of nitromethane were added, and the reaction mixture was stirred at room temperature for 2 h. 1.6 ml of acetic acid was added, and the reaction mixture was diluted with ethyl acetate, washed 4 times with a saturated sodium chloride solution, dried over sodium sulfate, filtered and evaporated to dryness.

7.2 g yellow oil, Rt.=2.91 min (method A), LCMS: 275 (M+H).

Step b:

The product from step a (6.4 mg, 23.33 mmol) was dissolved in 65 ml of methanol. 6.4 g of 5% Pd/C catalyst (50.5% of water) were added. The mixture was hydrogenated with 1.57 l of hydrogen 3.0 for 17.5 h at room temperature and under atmospheric pressure. The reaction mixture was filtered off and evaporated.

5.89 g oil, LCMS: 245 (M+H).

Step c:

A mixture of the product from step b (612 mg, 2.50 mmol) and 300 mg (1.25 mmol) of 5,5,8,8-tetramethyl-5,6,7,8-tetrahydronaphthalene-2-carboxylic acid with 576 mg (3.76 mmol) of HOBt and 720 mg (3.76 mmol) of EDCI in 5 ml of DMF was stirred at room temperature overnight. Ethyl acetate was added to the reaction mixture, which was then washed by shaking with 15 ml of each of a 1N hydrochloric acid solution and a concentrated sodium hydrogencarbonate solution. The organic phase was dried over sodium sulfate, filtered and evaporated. 738 mg oil, Rt.=3.40 min (method A), LCMS: 359 (M+H-Boc).

Step d:

The product from step c (738 mg, 1.29 mmol) was dissolved in 10 ml of dichloromethane. 8.02 ml (3.86 mmol) of Dess-Martin periodinane were added. The reaction mixture was stirred at room temperature for 1 h, 15 ml of a saturated sodium hydrogencarbonate solution and 5 ml of a saturated sodium thiosulfate solution were subsequently added, and the mixture was stirred vigorously for 1 h. The organic phase was separated off. The water phase was extracted again with dichloromethane. The combined organic phase was washed once each with water and a 0.1 N hydrochloric acid solution, dried over sodium sulfate, filtered and evaporated to dryness. The residue was purified by means of flash chromatography on silica gel.

153 mg, Rt.=3.68 min (method A), LCMS: 457 (M+H).

Step e:

The product from step d (75 mg, 0.16 mmol) was mixed with 78 mg (0.33 mmol) of Burgess reagent, suspended in 5 ml of THF and stirred at 60° C. for several days.

The reaction mixture was taken up in dichloromethane and washed once each with a saturated sodium hydrogencarbonate solution and a 1 N hydrochloric acid solution. The organic phase was dried over sodium sulfate and evaporated.

84 mg, Rt.=4.25 (method A), LCMS: 439 (M+H).

Step f:

6 ml of a 4N hydrochloric acid/dioxane solution were added to the product from step e (84 mg, 0.19 mmol), and the mixture was stirred at room temperature. The reaction mixture was evaporated and purified by means of preparative HPLC. The product is in the form of the hydrochloride.

11 mg yellow solid, Rt.=2.84 min (method A), LCMS: 339 (M+H).

$^1$H NMR (500 MHz, DMSO/deuterated TFA) δ 7.94 (d, J=1.8, 1H), 7.73 (dd, J=8.3, 1.8, 1H), 7.49 (d, J=8.3, 1H), 7.15 (d, J=0.8, 1H), 3.44-3.37 (m, 2H), 3.24-3.17 (m, 1H), 3.10 (dt, J=12.5, 2.7, 2H), 2.23 (dd, J=14.1, 3.2, 2H), 1.96-1.85 (m, 2H), 1.72 (s, 4H), 1.31 (d, J=13.3, 12H).

Preparation of 4,4-dimethyl-7-(4,4,5,5-tetramethyl-1,3,2-dioxaborolan-2-yl)-3,4-dihydro-2H-naphthalen-1-one

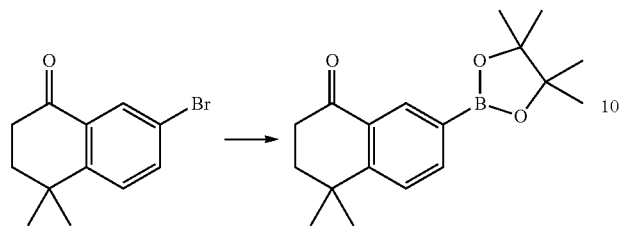

The preparation was carried out as already described above starting from 570 mg (1.98 mmol) of 7-bromo-4,4-dimethyl-3,4-dihydro-2H-naphthalen-1-one (preparation see Journal of Medicinal Chemistry, 1995, vol. 38, #24 p. 4764-4767) and 654 mg (2.58 mmol) of bis(pinacolato)diboron.

338 mg, yellow solid, Rt.=3.41 min (method A), LCMS: 301 (M+H).

Preparation of 7-{2-[4-(2-hydroxyethylamino)piperidin-1-yl]thiazol-4-yl}-4,4-dimethyl-3,4-dihydro-2H-naphthalen-1-one

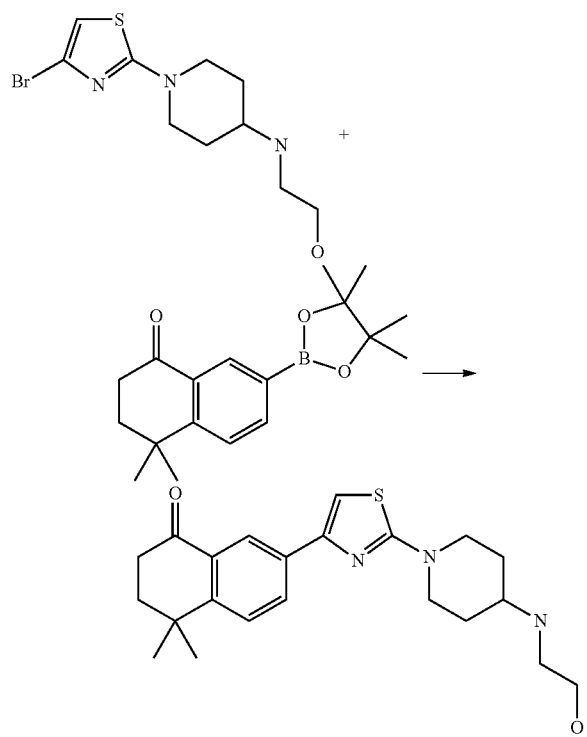

The preparation is carried out as already described above starting from 100 mg (0.27 mmol) of 2-[1-(4-bromothiazol-2-yl)piperidin-4-ylamino]ethanol (preparation already described above) and 88 mg (0.29 mmol) of 4,4-dimethyl-7-(4,4,5,5-tetramethyl-1,3,2-dioxaborolan-2-yl)-3,4-dihydro-2H-naphthalen-1-one. The product was purified by means of flash chromatography on silica gel.

55 mg, yellow oil, LCMS: 400 (M+H), Rt.=2.40 min (method A).

$^1$H NMR (500 MHz, DMSO/deuterated TFA) δ=8.32 (d, J=2.1, 1H), 8.02 (dd, J=8.3, 2.1, 1H), 7.62 (d, J=8.3, 1H), 4.19 (d, J=13.4, 2H), 3.79-3.72 (m, 2H), 3.52-3.42 (m, 1H), 3.33 (t, J=11.9, 2H), 3.16-3.05 (m, 2H), 2.78-2.70 (m, 2H), 2.25 (d, J=10.4, 2H), 2.03 (t, J=6.8, 2H), 1.83 (qd, J=12.4, 4.3, 2H), 1.41 (s, 6H).

Preparation of 4-{1-[4-(5,5,8,8-tetramethyl-5,6,7,8-tetrahydronaphthalen-2-yl)thiazol-2-yl]piperidin-4-ylamino}butan-1-ol

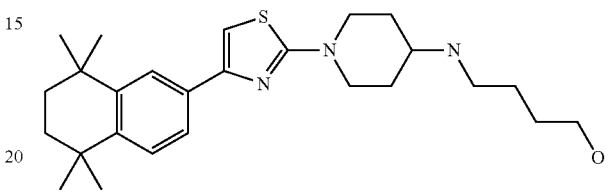

The preparation was carried out as already described starting from 120 mg (0.19 mmol) of 1-[4-(5,5,8,8-tetramethyl-5,6,7,8-tetrahydronaphthalen-2-yl)thiazol-2-yl]piperidin-4-ylamine hydrochloride (preparation described above) and 57 µl (0.38 mmol) of 4-bromobutyl acetate. The protecting group was cleaved off by means of a 1N NaOH solution in methanol. The product was purified by means of preparative HPLC and is in the form of the hydrochloride.

9 mg, solid, LCMS: 442 [M+H], HPLC: Rt.=2.92 min (method A).

$^1$H NMR (500 MHz, DMSO/deuterated TFA) δ=7.69 (d, J=1.8, 1H), 7.50 (dd, J=8.2, 1.9, 1H), 7.43 (d, J=8.3, 1H), 4.17 (d, J=13.6, 2H), 3.53-3.34 (m, 5H), 3.07-3.00 (m, 2H), 2.23 (d, J=10.7, 2H), 1.84-1.69 (m, 8H), 1.60-1.52 (m, 2H), 1.30 (d, J=16.6, 12H).

Preparation of 5-{1-[4-(5,5,8,8-tetramethyl-5,6,7,8-tetrahydronaphthalen-2-yl)thiazol-2-yl]piperidin-4-ylamino}pentan-1-ol

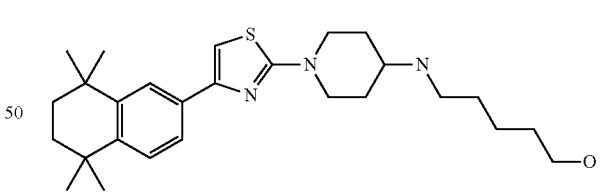

The preparation was carried out as already described via a reductive amination starting from 50 mg (0.08 mmol) of 1-[4-(5,5,8,8-tetramethyl-5,6,7,8-tetrahydronaphthalen-2-yl)thiazol-2-yl]piperidin-4-ylamine hydrochloride and 8 mg (0.08 mmol) of 5-hydroxypentanal.

5 mg, solid, LCMS: 456 [M+H], HPLC: Rt.=2.94 min (method A).

$^1$H NMR (400 MHz, DMSO/deuterated TFA) δ=7.72 (s, 1H), 7.53 (d, J=8.2, 1H), 7.38 (d, J=8.3, 1H), 4.12 (d, J=13.4, 2H), 3.47-3.34 (m, 3H), 3.26 (t, J=12.1, 2H), 3.03-2.93 (m, 2H), 2.18 (d, J=10.6, 2H), 1.78-1.58 (m, 9H), 1.52-1.35 (m, 5H), 1.28 (d, J=13.1, 13H).

Preparation of 6-{1-[4-(5,5,8,8-tetramethyl-5,6,7,8-tetrahydronaphthalen-2-yl)thiazol-2-yl]piperidin-4-ylamino}hexan-1-ol

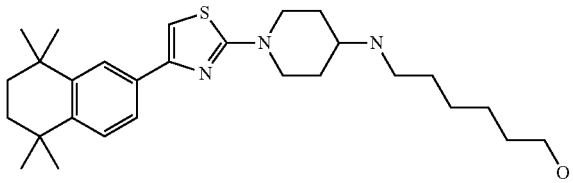 [SMILES: CC1(C)CCC(C)(C)c2cc(-c3csc(N4CCC(NCCCCCCO)CC4)n3)ccc21]

The preparation was carried out as already described starting from 100 mg (0.16 mmol) of 1-[4-(5,5,8,8-tetramethyl-5,6,7,8-tetrahydronaphthalen-2-yl)thiazol-2-yl]piperidin-4-ylamine hydrochloride and 90 µl (0.32 mmol) of (6-bromohexyloxy)tert-butyldimethylsilane. The protecting group was cleaved off in THF using 7 equivalent of TMAF. The product was purified by means of preparative HPLC. The product is in the form of the hydrochloride.

4 mg, solid, LCMS: 470 [M+H], HPLC: Rt.=2.97 min (method A).

$^1$H NMR (500 MHz, DMSO/deuterated TFA) δ=7.52 (d, J=1.7, 1H), 7.36-7.29 (m, 2H), 4.05 (d, J=13.2, 2H), 3.37-3.26 (m, 6H), 2.89-2.83 (m, 2H), 2.11 (d, J=10.8, 2H), 1.73-1.50 (m, 11H), 1.40-1.32 (m, 3H), 1.29-1.22 (m, 5H), 1.21-1.14 (m, 15H).

Preparation of 6-{4-[4-(5,5,8,8-tetramethyl-5,6,7,8-tetrahydronaphthalen-2-yl)thiazol-2-yl]piperidin-1-yl}hexan-1-ol

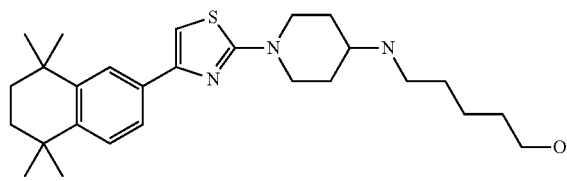 [SMILES: CC1(C)CCC(C)(C)c2cc(-c3csc(N4CCC(NCCCCCO)CC4)n3)ccc21]

The preparation was carried out as already described starting from 100 mg (0.26 mmol) of 4-[4-(5,5,8,8-tetramethyl-5,6,7,8-tetrahydronaphthalen-2-yl)thiazol-2-yl]piperidine hydrochloride and 92 mg (0.31 mmol) of (6-bromohexyloxy)-tert-butyldimethylsilane. The product was purified by means of flash chromatography on silica gel. The protecting group was cleaved off as already described using an HCl solution in dioxane. The product is in the form of the hydrochloride.

43 mg, white solid, LCMS: 455 [M+H], HPLC: Rt.=3.07 min (method A).

$^1$H NMR (500 MHz, DMSO/deuterated TFA) δ=7.79 (d, J=1.7, 1H), 7.72 (d, J=23.8, 1H), 7.61-7.53 (m, 1H), 7.27 (d, J=8.3, 1H), 3.54 (d, J=12.6, 2H), 3.41-3.28 (m, 3H), 3.07-2.96 (m, 4H), 2.26 (d, J=14.4, 2H), 2.02 (dd, J=23.4, 12.4, 2H), 1.67-1.55 (m, 6H), 1.43-1.34 (m, 2H), 1.33-1.23 (m, 4H), 1.18 (d, J=19.9, 12H).

Preparation of 7-{4-[4-(5,5,8,8-tetramethyl-5,6,7,8-tetrahydronaphthalen-2-yl)thiazol-2-yl]piperidin-1-yl}heptan-1-ol

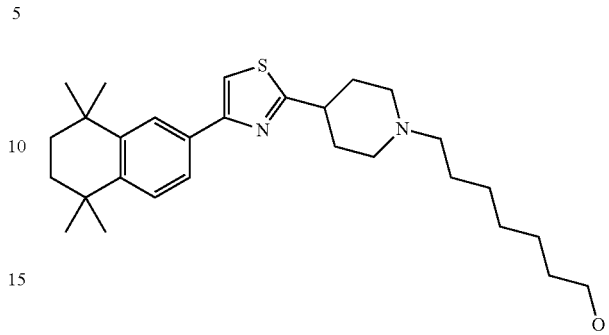

100 mg (0.26 mmol) of 4-[4-(5,5,8,8-tetramethyl-5,6,7,8-tetrahydronaphthalen-2-yl)thiazol-2-yl]piperidine hydrochloride were dissolved in 4 ml of ethanol, and 50 µl (0.31 mmol) of 7-bromoheptan-1-ol and 107 µl (0.77 mmol) of triethylamine were added. The reaction mixture was heated at 150° C. overnight, evaporated, and the product was isolated from the crude mixture by means of preparative HPLC. The product is in the form of the hydrochloride.

15 mg, white solid, LCMS: 469 [M+H], HPLC: Rt.=3.12 min (method A).

$^1$H NMR (500 MHz, DMSO/deuterated TFA) δ=7.97-7.87 (m, 2H), 7.74-7.65 (m, 1H), 7.39 (d, J=8.3, 1H), 3.66 (d, J=12.4, 2H), 3.50-3.40 (m, 3H), 3.19-3.08 (m, 4H), 2.40-2.30 (m, 2H), 2.16-2.04 (m, 2H), 1.77-1.66 (m, 6H), 1.52-1.42 (m, 2H), 1.34 (d, J=19.8, 12H), 1.28 (s, 6H).

Preparation of (S)-3-{1-[4-(5,5-dimethyl-5,6,7,8-tetrahydronaphthalen-2-yl)thiazol-2-yl]piperidin-4-ylamino}propane-1,2-diol

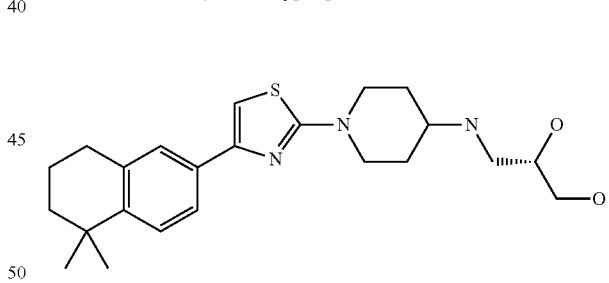

The preparation was carried out as already described above starting from 100 mg (0.27 mmol) of 1-[4-(5,5-dimethyl-5,6,7,8-tetrahydronaphthalen-2-yl)thiazol-2-yl]piperidin-4-ylamine hydrochloride and 34 mg (0.27 mmol) of (R)-2,2-dimethyl-1,3-dioxolane-4-carbaldehyde. The protecting group was cleaved off as described by means of a 1.25 N HCl/methanol solution. The product was converted into the hydrochloride.

21 mg, solid, LCMS: 416 [M+H], HPLC: Rt.=2.66 min (method A).

$^1$H NMR (500 MHz, DMSO/deuterated TFA) δ=7.54-7.38 (m, 3H), 4.19 (d, J=12.7, 2H), 3.92-3.84 (m, 1H), 3.58-3.35 (m, 5H), 3.25-3.13 (m, 1H), 2.97 (dd, J=12.6, 9.5, 1H), 2.81 (t, J=6.3, 2H), 2.33-2.22 (m, 2H), 1.94-1.78 (m, 4H), 1.73-1.64 (m, 2H), 1.29 (s, 6H).

Preparation of (S)-2-amino-4-hydroxy-N-{1-[4-(5,5,8,8-tetramethyl-5,6,7,8-tetrahydronaphthalen-2-yl)thiazol-2-yl]piperidin-4-yl}butyramide

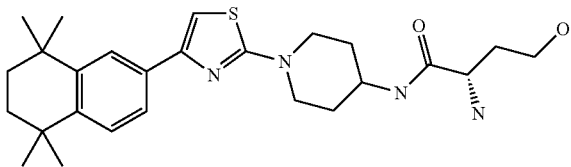 [SMILES: CC1(C)CCC(C)(C)c2cc(-c3csc(N4CCC(NC(=O)[C@@H](N)CCO)CC4)n3)ccc21]

50 mg (0.12 mmol) of 1-[4-(5,5,8,8-tetramethyl-5,6,7,8-tetrahydronaphthalen-2-yl)thiazol-2-yl]piperidin-4-ylamine hydrochloride and 44 mg (0.13 mmol) of (S)-2-tert-butoxycarbonylamino-4-(tert-butyldimethylsilanyloxy)butyric acid (preparation analogous to Tetrahedron, 2005, vol. 61, #43 p. 10277-10284) were dissolved in 1 ml of DCM together with 50 μl (0.29 mmol) of N-ethyldiisopropylamine and stirred at 0° C. for 5 min. 73 mg (0.14 mmol) of benzotriazol-1-yloxytripyrrolidinophosphonium hexafluorophosphate and 50 μl (0.29 mmol) of ethyldiisopropylamine were then added. The mixture was stirred further at 0° C. for 1 h, diluted with EA and washed by shaking with water and a saturated sodium hydrogencarbonate solution and a saturated sodium chloride solution. The organic phase was dried over sodium sulfate, filtered and evaporated. A 1.25 M HCl solution in methanol was then added to the residue, and the mixture was stirred for 1 h. The methanolic solution was evaporated, and the product was purified by means of preparative HPLC. The product is in the form of the hydrochloride.

4 mg, solid, LCMS: 471 [M+H], HPLC: Rt.=2.86 min (method A).

Preparation of (2S,3R)-2-amino-3-hydroxy-N-{1-[4-(5,5,8,8-tetramethyl-5,6,7,8-tetrahydronaphthalen-2-yl)thiazol-2-yl]piperidin-4-yl}butyramide

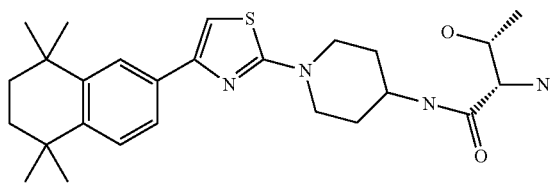 [SMILES: C[C@@H](O)[C@H](N)C(=O)NC1CCN(c2nc(-c3ccc4c(c3)C(C)(C)CCC4(C)C)cs2)CC1]

190 mg (0.47 mmol) of 1-[4-(5,5,8,8-tetramethyl-5,6,7,8-tetrahydronaphthalen-2-yl)thiazol-2-yl]piperidin-4-ylamine were dissolved in 5 ml of THF, and 86 mg (0.56 mmol) of 1-hydroxybenzotriazole hydrate, 239 μl (1.40 mmol) of N-ethyldiisopropylamine, 108 mg (0.56 mmol) of N-(3-dimethylaminopropyl)-N'-ethylcarbodiimide hydrochloride and 113 mg (0.56 mmol) of N-(tert-butoxycarbonyl)-L-threonine were added. The mixture was stirred at room temperature overnight, dissolved in EA and 1 N NaOH and shaken. The organic phase was washed with water, dried over sodium sulfate, filtered and evaporated. The protecting group was cleaved off as already described using HCl in dioxane. The product was purified by means of preparative HPLC and is in the form of the hydrochloride.

16 mg, solid, LCMS: 471 [M+H], HPLC: Rt.=2.74 min (method A).

$^1$H NMR (500 MHz, DMSO/deuterated TFA) δ=7.62 (s, 1H), 7.46 (q, J=8.2, 2H), 4.13-4.04 (m, 3H), 4.01-3.94 (m, 3H), 3.67-3.56 (m, 3H), 3.25 (s, 3H), 2.07 (d, J=12.8, 2H), 1.82-1.68 (m, 6H), 1.32 (d, J=15.6, 12H), 1.24 (d, J=6.4, 3H).

Preparation of (2S,3R)-2-amino-3-hydroxy-1-{4-[4-(5,5,8,8-tetramethyl-5,6,7,8-tetrahydronaphthalen-2-yl)thiazol-2-yl]piperidin-1-yl}butan-1-one

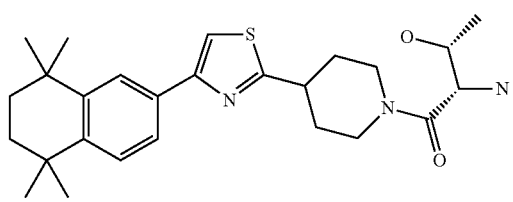 [SMILES: C[C@@H](O)[C@H](N)C(=O)N1CCC(c2nc(-c3ccc4c(c3)C(C)(C)CCC4(C)C)cs2)CC1]

The preparation was carried out analogously starting from 200 mg (0.47 mmol) of 4-[4-(5,5,8,8-tetramethyl-5,6,7,8-tetrahydronaphthalen-2-yl)thiazol-2-yl]piperidine hydrochloride and 113 mg (0.52 mmol) of N-(tert-butoxycarbonyl)-L-threonine. The protecting group was cleaved off as already described using HCl in dioxane. The product was purified by means of preparative HPLC and is in the form of the hydrochloride.

8 mg, solid, LCMS: 456 [M+H], HPLC: Rt.=2.97 min (method A).

$^1$H NMR (500 MHz, DMSO/deuterated TFA) δ=7.91 (dd, J=6.1, 1.7, 1H), 7.87-7.80 (m, 1H), 7.68 (d, J=8.1, 1H), 7.40 (d, J=8.2, 1H), 4.66-4.54 (m, 1H), 4.35 (dd, J=25.3, 4.5, 1H), 4.15 (t, J=11.3, 1H), 4.09-3.96 (m, 1H), 3.54-3.43 (m, 1H), 3.35 (t, J=13.1, 1H), 3.24 (s, 1H), 3.03-2.90 (m, 1H), 2.35-2.20 (m, 2H), 1.95-1.82 (m, 1H), 1.81-1.67 (m, 5H), 1.38-1.29 (m, 12H), 1.28-1.24 (m, 3H).

Preparation of (2S,3S)-3-hydroxypyrrolidine-2-carboxylic acid {1-[4-(5,5,8,8-tetramethyl-5,6,7,8-tetrahydronaphthalen-2-yl)thiazol-2-yl]piperidin-4-yl}amide

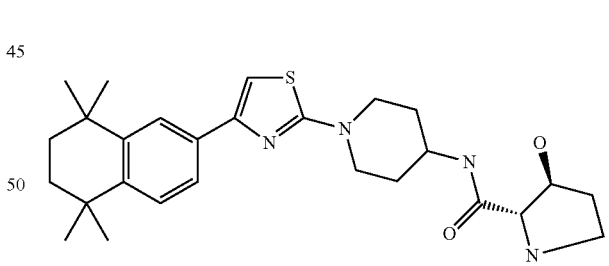

The preparation was carried out analogously starting from 244 mg (0.50 mmol) of 1-[4-(5,5,8,8-tetramethyl-5,6,7,8-tetrahydronaphthalen-2-yl)thiazol-2-yl]piperidin-4-ylamine and 116 mg (0.50 mmol) of (2S,3S)-3-hydroxypyrrolidine-1,2-dicarboxylic acid 1-tert-butyl ester. The protecting group was cleaved off analogously using HCl in dioxane. The product was purified by means of flash chromatography on silica gel.

158 mg, yellow oil, LCMS: 483 [M+H], HPLC: Rt.=2.70 min (method A).

$^1$H NMR (500 MHz, DMSO/deuterated TFA) δ=7.66 (s, 1H), 7.51-7.42 (m, 2H), 5.72-5.65 (m, 1H), 4.43 (dd, J=5.6, 3.5, 1H), 4.09 (d, J=2.0, 1H), 4.07-3.97 (m, 3H), 3.58-3.50

(m, 2H), 3.49-3.34 (m, 3H), 2.06-1.92 (m, 5H), 1.77-1.65 (m, 7H), 1.29 (dd, J=17.7, 8.9, 14H), 1.23-1.16 (m, 2H).

Preparation of ((2S,3S)-3-hydroxypyrrolidin-2-yl)-{4-[4-(5,5,8,8-tetramethyl-5,6,7,8-tetrahydronaphthalen-2-yl)thiazol-2-yl]piperidin-1-yl}methanone

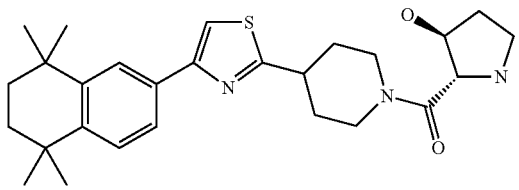 [SMILES: CC1(C)CCC(C)(C)c2cc(-c3csc(C4CCN(C(=O)[C@H]5NCC[C@@H]5O)CC4)n3)ccc21]

The preparation was carried out analogously starting from 150 mg (0.36 mmol) of 4-[4-(5,5,8,8-tetramethyl-5,6,7,8-tetrahydronaphthalen-2-yl)thiazol-2-yl]piperidine hydrochloride and 94 mg (0.40 mmol) of (2S,3S)-3-hydroxypyrrolidine-1,2-dicarboxylic acid 1-tert-butyl ester in DMSO. The product was purified by means of flash chromatography on silica gel. The protecting group was cleaved off analogously using HCl in methanol. The product is in the form of the hydrochloride.

145 mg, solid, LCMS: 468 [M+H], HPLC: Rt.=3.05 min (method A).

$^1$H NMR (400 MHz, DMSO/deuterated TFA) δ=7.93-7.87 (m, 2H), 7.69 (ddd, J=8.2, 3.4, 1.9, 1H), 7.39 (dd, J=8.3, 1.7, 1H), 4.64-4.40 (m, 3H), 4.14 (d, J=13.5, 1H), 3.54-3.33 (m, 5H), 3.06-2.94 (m, 1H), 2.33-2.17 (m, 3H), 1.91 (dd, J=34.3, 9.9, 3H), 1.78-1.65 (m, 5H), 1.30 (d, J=15.9, 12H).

Preparation of (2R,3S)-2-{4-[4-(5,5,8,8-tetramethyl-5,6,7,8-tetrahydronaphthalen-2-yl)thiazol-2-yl]piperidin-1-ylmethyl}pyrrolidin-3-ol

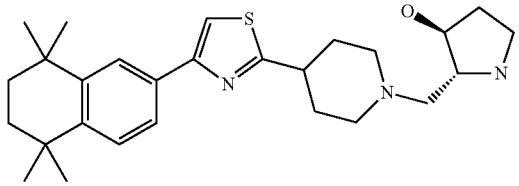 [SMILES: CC1(C)CCC(C)(C)c2cc(-c3csc(C4CCN(C[C@H]5NCC[C@@H]5O)CC4)n3)ccc21]

The preparation was carried out as already described using a 2N lithium aluminium hydride solution in THF starting from 30 mg (0.06 mmol) of ((2S,3S)-3-hydroxypyrrolidin-2-yl)-{4-[4-(5,5,8,8-tetramethyl-5,6,7,8-tetrahydronaphthalen-2-yl)thiazol-2-yl]piperidin-1-yl}methanone. The product was purified by means of preparative HPLC and is in the form of the hydrochloride.

7 mg, solid, LCMS: 454 [M+H], HPLC: Rt.=2.79 min (method A).

$^1$H NMR (400 MHz, DMSO/deuterated TFA) δ=7.96 (s, 1H), 7.89 (d, J=1.8, 1H), 7.68 (d, J=8.4, 1H), 7.38 (d, J=8.3, 1H), 4.26-4.19 (m, 1H), 3.86-3.74 (m, 2H), 3.71-3.62 (m, 1H), 3.56-3.47 (m, 3H), 3.44-3.35 (m, 3H), 2.40 (d, J=11.9, 2H), 2.23-2.05 (m, 3H), 1.94-1.84 (m, 1H), 1.69 (s, 4H), 1.29 (d, J=14.6, 13H).

Preparation of (S)-3-hydroxy-2-methylamino-N-{1-[4-(5,5,8,8-tetramethyl-5,6,7,8-tetrahydronaphthalen-2-yl)thiazol-2-yl]piperidin-4-yl}propionamide

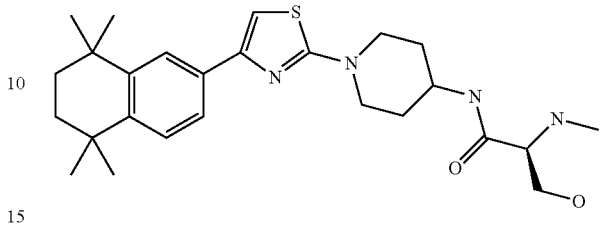

The preparation was carried out analogously starting from 50 mg (0.12 mmol) of 1-[4-(5,5,8,8-tetramethyl-5,6,7,8-tetrahydronaphthalen-2-yl)thiazol-2-yl]piperidin-4-ylamine hydrochloride and 33 mg (0.13 mmol) of (S)-2-(tert-butoxycarbonylmethylamino)-3-hydroxypropionic acid. The product was purified by means of flash chromatography on silica gel. The protecting group was cleaved off analogously using HCl in methanol.

27 mg, solid, LCMS: 471 [M+H], HPLC: Rt.=2.81 min (method A).

$^1$H NMR (400 MHz, DMSO/deuterated TFA) δ=7.65 (d, J=1.6, 1H), 7.51-7.42 (m, 2H), 4.09-3.98 (m, 3H), 3.93-3.86 (m, 1H), 3.85-3.79 (m, 2H), 3.60-3.44 (m, 6H), 2.09-1.97 (m, 2H), 1.75-1.64 (m, 6H), 1.30 (d, J=12.7, 13H).

Preparation of (S)-3-hydroxy-2-methylamino-1-{4-[4-(5,5,8,8-tetramethyl-5,6,7,8-tetrahydronaphthalen-2-yl)thiazol-2-yl]piperidin-1-yl}propan-1-one

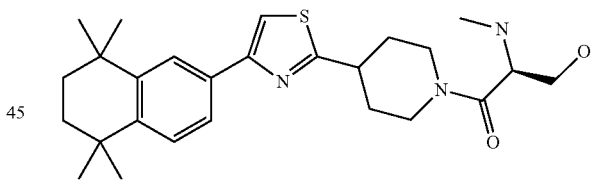

The preparation was carried out analogously starting from 50 mg (0.12 mmol) of 4-[4-(5,5,8,8-tetramethyl-5,6,7,8-tetrahydronaphthalen-2-yl)thiazol-2-yl]piperidine hydrochloride and 30 mg (0.13 mmol) of (S)-2-(tert-butoxycarbonylmethylamino)-3-hydroxypropionic acid. The product was purified by means of flash chromatography on silica gel. The protecting group was cleaved off analogously using HCl in methanol. The product is in the form of the hydrochloride.

35 mg, solid, LCMS: 456 [M+H], HPLC: Rt.=3.04 min (method A).

$^1$H NMR (500 MHz, DMSO/deuterated TFA) δ=7.82 (d, J=1.8, 1H), 7.75 (d, J=5.8, 1H), 7.59 (d, J=8.0, 1H), 7.31 (d, J=8.2, 1H), 4.55-4.36 (m, 2H), 3.94 (d, J=10.8, 1H), 3.81 (dd, J=12.3, 3.9, 1H), 3.74-3.65 (m, 1H), 3.44-3.34 (m, 1H), 3.27 (t, J=12.2, 1H), 2.95-2.81 (m, 1H), 2.63-2.54 (m, 2H), 2.25-2.10 (m, 2H), 1.85-1.58 (m, 6H), 1.22 (d, J=20.4, 12H).

Preparation of 4-{4-[2-(5,5,8,8-tetramethyl-5,6,7,8-tetrahydronaphthalen-2-yl)thiazol-4-yl]piperidin-1-yl}butan-1-ol

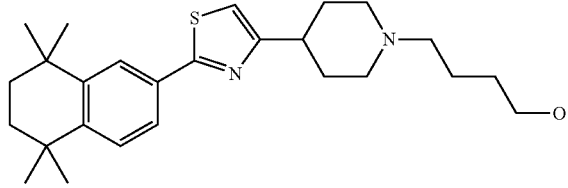

The preparation was carried out as already described starting from 100 mg (0.28 mmol) of 4-[2-(5,5,8,8-tetramethyl-5,6,7,8-tetrahydronaphthalen-2-yl)thiazol-4-yl]piperidine hydrochloride (preparation already described above) and 61 µl (0.42 mmol) of 4-bromobutyl acetate. The protecting group was cleaved off by means of a 1N NaOH solution in methanol. The product was purified by means of preparative HPLC and is in the form of the hydrochloride.

33 mg, solid, LCMS: 427 [M+H], HPLC: Rt.=3.03 min (method A).

$^1$H NMR (400 MHz, DMSO/deuterated TFA) δ=7.83 (d, J=1.9, 1H), 7.65-7.58 (m, 1H), 7.43-7.27 (m, 2H), 3.58 (d, J=12.3, 2H), 3.49-3.41 (m, 2H), 3.16-3.00 (m, 5H), 2.24 (d, J=13.9, 2H), 2.05-1.91 (m, 2H), 1.80-1.69 (m, 2H), 1.64 (s, 4H), 1.53-1.44 (m, 2H), 1.24 (d, J=13.1, 12H).

Preparation of 5-{4-[2-(5,5,8,8-tetramethyl-5,6,7,8-tetrahydronaphthalen-2-yl)thiazol-4-yl]piperidin-1-yl}pentan-1-ol

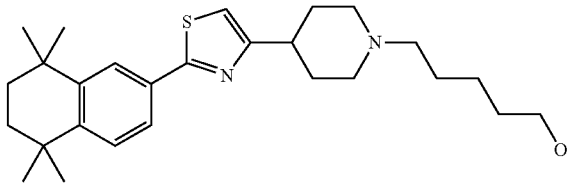 [SMILES: CC1(C)CCC(C)(C)c2cc(-c3nc(C4CCN(CCCCCO)CC4)cs3)ccc21]

The preparation was carried out as already described via a reductive amination starting from 100 mg (0.28 mmol) of 4-[2-(5,5,8,8-tetramethyl-5,6,7,8-tetrahydronaphthalen-2-yl)thiazol-4-yl]piperidine hydrochloride (preparation already described above) and 58 mg (0.56 mmol) of 5-hydroxypentanal. The product was purified by means of preparative HPLC and is in the form of the hydrochloride.

77 mg, solid, LCMS: 441 [M+H], HPLC: Rt.=3.07 min (method A).

$^1$H NMR (400 MHz, DMSO/deuterated TFA) δ=7.83 (d, J=1.9, 1H), 7.65-7.55 (m, 1H), 7.43-7.25 (m, 2H), 3.57 (d, J=12.3, 2H), 3.47-3.31 (m, 2H), 3.28-2.98 (m, 5H), 2.23 (d, J=13.7, 2H), 2.07-1.91 (m, 2H), 1.77-1.59 (m, 6H), 1.52-1.41 (m, 2H), 1.40-1.30 (m, 2H), 1.23 (d, J=13.6, 12H).

Preparation of (S)-2-amino-3-{4-[4-(5,5,8,8-tetramethyl-5,6,7,8-tetrahydronaphthalen-2-yl)thiazol-2-yl]piperidin-1-yl}propan-1-ol

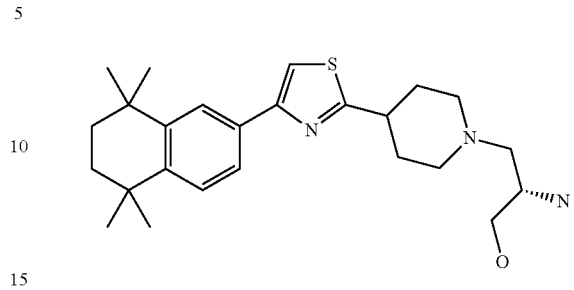

The preparation was carried out analogously via a reductive amination starting from 100 mg (0.26 mmol) of 4-[2-(5,5,8,8-tetramethyl-5,6,7,8-tetrahydronaphthalen-2-yl)thiazol-4-yl]piperidine hydrochloride and 55 µl (0.26 mmol) of (R)-4-formyl-2,2-dimethyloxazolidine-3-carboxylic acid tert-butyl ester. The product was purified by means of flash chromatography on silica gel. The protecting group was cleaved off analogously using HCl in methanol. The product is in the form of the hydrochloride.

16 mg, solid, LCMS: 428 [M+H], HPLC: Rt.=2.75 min (method A).

$^1$H NMR (500 MHz, DMSO/deuterated TFA) δ=7.93 (d, J=1.5, 1H), 7.84 (s, 1H), 7.69 (d, J=7.5, 1H), 7.41 (d, J=8.3, 1H), 3.96-3.85 (m, 2H), 3.81-3.67 (m, 4H), 3.63-3.58 (m, 3H), 3.56-3.47 (m, 2H), 3.47-3.39 (m, 1H), 3.38-3.21 (m, 2H), 2.43 (d, J=11.5, 2H), 2.35-2.19 (m, 2H), 1.72 (s, 4H), 1.32 (d, J=20.6, 12H).

Preparation of (R)-2-amino-3-{4-[4-(5,5,8,8-tetramethyl-5,6,7,8-tetrahydronaphthalen-2-yl)thiazol-2-yl]piperidin-1-yl}propan-1-ol

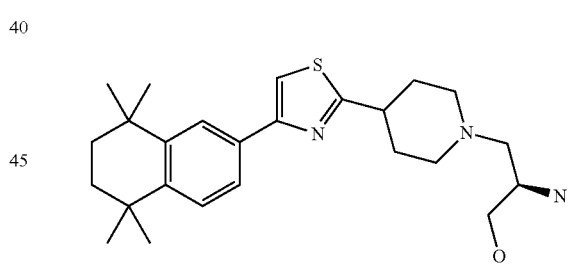

The preparation was carried out analogously via a reductive amination starting from 100 mg (0.26 mmol) of 4-[2-(5,5,8,8-tetramethyl-5,6,7,8-tetrahydronaphthalen-2-yl)thiazol-4-yl]piperidine hydrochloride and 55 µl (0.26 mmol) of (S)-4-formyl-2,2-dimethyloxazolidine-3-carboxylic acid tert-butyl ester. The product was purified by means of flash chromatography on silica gel. The protecting group was cleaved off analogously using HCl in methanol. The product is in the form of the hydrochloride.

39 mg, solid, LCMS: 428 [M+H], HPLC: Rt.=2.74 min (method A).

$^1$H NMR (400 MHz, DMSO/deuterated TFA) δ=7.88-7.79 (m, 2H), 7.63 (d, J=7.6, 1H), 7.33 (d, J=8.3, 1H), 3.79 (s, 2H), 3.72-3.63 (m, 3H), 3.61-3.47 (m, 3H), 3.47-3.39 (m, 2H), 3.38-3.27 (m, 2H), 3.26-3.18 (m, 1H), 3.13-3.05 (m, 1H), 2.38-2.30 (m, 2H), 2.25-2.07 (m, 2H), 1.64 (s, 4H), 1.24 (d, J=15.9, 12H).

Preparation of 2-{1-[4-(5,5,8,8-tetramethyl-5,6,7,8-tetrahydronaphthalen-2-yl)thiazol-2-yl]piperidin-4-ylamino}pentane-1,5-diol

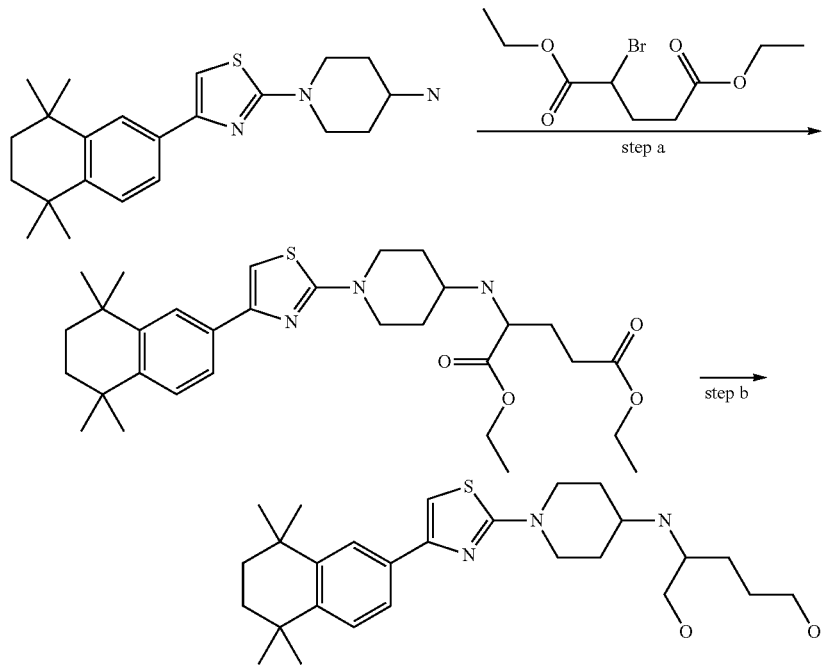

Step a:

100 mg (0.25 mmol) of 1-[4-(5,5,8,8-tetramethyl-5,6,7,8-tetrahydronaphthalen-2-yl)thiazol-2-yl]piperidin-4-ylamine (preparation described above) were dissolved in 6 ml of DMF together with 79 mg (0.30 mmol) of 2-bromopentanedioic acid diethyl ester (preparation analogous to Synthesis, 1999, #2 p. 270-274), and 137 µl (0.99 mmol) of triethylamine were added. The reaction mixture was stirred at room temperature for 3 days, stirred into 12 ml of water and extracted twice with EA. The organic phase was dried over sodium sulfate, filtered, stripped off to dryness and purified by means of flash chromatography on silica gel.

21 mg, residue, Rt.=3.19 min (method A), LCMS: 556 (M+H).

Step b:

4.3 mg (0.11 mmol) of lithium aluminium hydride were initially introduced in 2 ml of THF, and 21 mg (0.04 mmol) of 2-{1-[4-(5,5,8,8-tetramethyl-5,6,7,8-tetrahydronaphthalen-2-yl)thiazol-2-yl]piperidin-4-ylamino}pentanedioic acid diethyl ester from step a, pre-dissolved in 2 ml of THF, were slowly added. The reaction mixture was stirred at room temperature overnight, 20 ml of water were added, and the mixture was extracted twice with EA. The organic phase was dried over sodium sulfate, filtered, stripped off to dryness and purified by means of preparative HPLC. The product is in the form of the TFA salt.

12 mg, solid, Rt.=2.81 min (method A), LCMS: 472 (M+H).

$^1$H NMR (400 MHz, DMSO/deuterated TFA) δ=7.68 (d, J=1.9, 1H), 7.50 (dd, J=8.2, 1.9, 1H), 7.43 (d, J=8.3, 1H), 4.17 (d, J=12.9, 2H), 3.80 (dd, J=12.2, 3.1, 1H), 3.67-3.57 (m, 2H), 3.55-3.47 (m, 2H), 3.47-3.29 (m, 3H), 2.25 (s, 2H), 1.91-1.69 (m, 8H), 1.68-1.48 (m, 2H), 1.31 (d, J=13.0, 12H).

2-(3-{4-[4-(5,5,8,8-Tetramethyl-5,6,7,8-tetrahydronaphthalen-2-yl)thiazol-2-yl]piperazin-1-yl}propyl)propane-1,3-diol

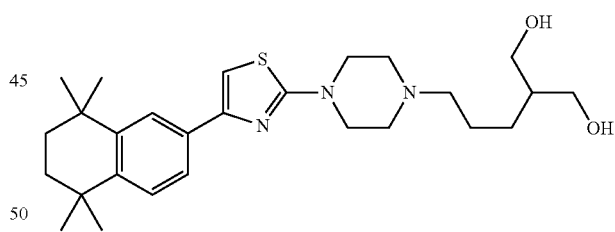

The preparation was carried out analogously as described above starting from 200 mg (0.53 mmol) of 1-[4-(5,5,8,8-tetramethyl-5,6,7,8-tetrahydronaphthalen-2-yl)thiazol-2-yl]piperazine and 234 µl (0.1.06 mmol) of 2-(3-chloropropyl)malonic acid diethyl ester and subsequent reduction using lithium aluminium hydride prepared. The product is in the form of the hydrochloride.

16 mg, solid, LCMS: 472 [M+H], HPLC: Rt.=2.84 min (method A).

$^1$H NMR (400 MHz, DMSO/deuterated TFA) δ 7.75 (d, J=1.8 Hz, 1H), 7.54 (dd, J=8.2, 1.9 Hz, 1H), 7.33 (d, J=8.3 Hz, 1H), 7.22 (s, 1H), 4.14 (b, 2H), 3.72-3.56 (m, 2H), 3.56-3.37 (m, 6H), 3.30-3.11 (m, 4H), 1.83-1.71 (m, 2H), 1.66 (s, 4H), 1.61-1.51 (m, 1H), 1.33 (dt, J=12.1, 6.1 Hz, 2H), 1.26 (d, J=13.8 Hz, 12H).

121
Preparation of [2-({1-[4-(5,5,8,8-tetramethyl-5,6,7,8-tetrahydronaphthalen-2-yl)thiazol-2-yl]piperidin-4-ylamino}methyl)cyclopropyl]methanol

122
Preparation of (2-{4-[4-(5,5,8,8-tetramethyl-5,6,7,8-tetrahydronaphthalen-2-yl)thiazol-2-yl]piperidin-1-ylmethyl}cyclopropyl)methanol

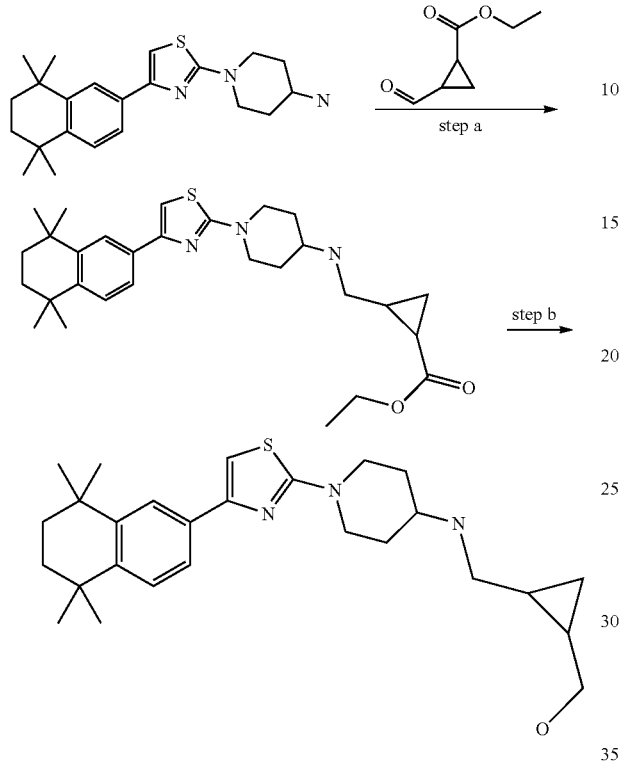
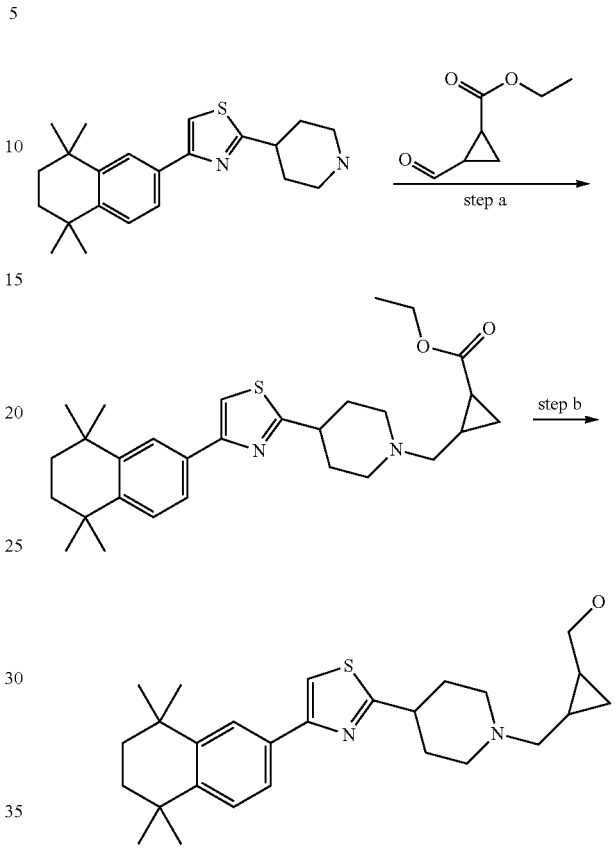

Step a:

The preparation was carried out as already described via a reductive amination starting from 150 mg (0.37 mmol) of 1-[4-(5,5,8,8-tetramethyl-5,6,7,8-tetrahydronaphthalen-2-yl)thiazol-2-yl]piperidin-4-ylamine and 56 μl (0.41 mmol) of 2-formylcyclopropanecarboxylic acid ethyl ester. The product was purified by means of flash chromatography on silica gel.

49 mg, Yellow oil, Rt.=3.10 min (method A), LCMS: 496 (M+H).

Step b:

49 mg (0.10 mmol) of 2-({1-[4-(5,5,8,8-tetramethyl-5,6,7,8-tetrahydro-naphthalen-2-yl)thiazol-2-yl]piperidin-4-ylamino}methyl)cyclopropanecarboxylic acid ethyl ester from step a were dissolved in 2 ml of THF under nitrogen. 475 μl of a 1M diisobutylaluminium hydride solution in THF were added dropwise. The mixture was stirred at 60° C. overnight, water and EA were added, the mixture was filtered through Cellite, evaporated and purified by means of flash chromatography on silica gel.

20 mg, yellow solid, Rt.=2.88 min (method A), LCMS: 454 (M+H).

$^1$H NMR (500 MHz, DMSO/deuterated TFA) δ=7.66 (d, J=1.7, 1H), 7.52-7.41 (m, 2H), 4.23-4.05 (m, 2H), 3.60-3.37 (m, 4H), 3.32-3.25 (m, 1H), 3.10-2.87 (m, 2H), 2.26 (d, J=10.2, 2H), 1.88-1.76 (m, 2H), 1.72 (s, 4H), 1.35-1.26 (m, 13H), 1.16-1.08 (m, 1H), 1.06-0.97 (m, 1H), 0.65-0.54 (m, 2H).

Step a:

The preparation was carried out analogously via a reductive amination starting from 100 mg (0.23 mmol) of 4-[2-(5,5,8,8-tetramethyl-5,6,7,8-tetrahydronaphthalen-2-yl)thiazol-4-yl]piperidine hydrobromide and 63 μl (0.46 mmol) of ethyl 2-formyl-1-cyclopropanecarboxylate. The product was purified by means of preparative HPLC.

110 mg, lyophilisate, LCMS: 481 [M+H], HPLC: Rt.=3.15 min (method A).

Step b:

The reduction was carried out analogously starting from the product from step a and a 1M diisobutylaluminium hydride solution in THF. The product was purified and by means of flash chromatography on silica gel and is in the form of the hydrochloride.

22 mg, solid, Rt.=3.01 min (method A), LCMS: 439 (M+H).

$^1$H NMR (500 MHz, DMSO/deuterated TFA) δ=7.97 (d, J=25.6, 1H), 7.89 (d, J=1.8, 1H), 7.72-7.65 (m, 1H), 7.38 (d, J=8.3, 1H), 3.78 (d, J=12.5, 1H), 3.69 (d, J=12.2, 1H), 3.56-3.50 (m, 1H), 3.45-3.36 (m, 1H), 3.25-3.10 (m, 4H), 3.02-2.94 (m, 1H), 2.39-2.28 (m, 2H), 2.13-2.02 (m, 2H), 1.68 (s, 4H), 1.33-1.23 (m, 13H), 1.15-1.06 (m, 1H), 1.04-0.96 (m, 1H), 0.65-0.50 (m, 2H).

Preparation of 1-[3-(5,5,8,8-tetramethyl-5,6,7,8-tetrahydronaphthalen-2-yl)-1,2,4-thiadiazol-5-yl]piperazine

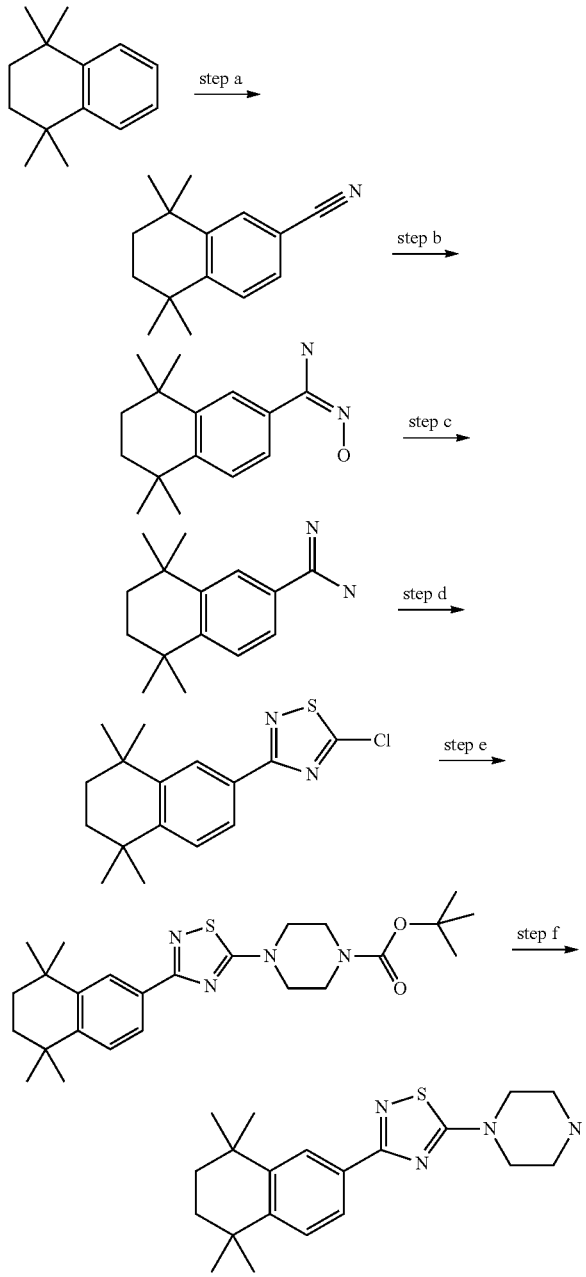

Step a:

10 g (35.55 mmol) of 6-bromo-1,1,4,4-tetramethyl-1,2,3,4-tetrahydronaphthalene were weighed out together with 8.92 g (99.55 mmol) of copper(I) cyanide, and NMP was added. The reaction mixture was stirred overnight at 140° C. and stirred into 400 ml of water. The resultant precipitate was filtered off with suction, washed a number of times with water, suspended in EA, filtered off with suction and washed well with EA. The filtrate was washed with a saturated sodium hydrogencarbonate solution. The organic phase was dried over sodium sulfate, filtered, evaporated to dryness and purified by means of flash chromatography on silica gel.

4.50 g, yellow crystals, Rt.=3.57 min (method A), LCMS: 241 (M+H).

Step b:

894 mg (4.19 mmol) of 5,5,8,8-tetramethyl-5,6,7,8-tetrahydronaphthalene-2-carbonitrile from step a was weighed out together with hydroxylammonium chloride (1.46 g, 20.96 mmol), and 20 ml of ethanol and triethylamine (2.9 ml, 20.96 mmol) were added. The reaction mixture was stirred at room temperature overnight and was stripped off to dryness. The residue was suspended in water and extracted twice with EA. The organic phase was dried over sodium sulfate, filtered and evaporated to dryness.

989 mg brown residue, Rt.=2.48 min (method A), LCMS: 247 (M+H).

Step c:

989 mg (4.02 mmol) of N-hydroxy-5,5,8,8-tetramethyl-5,6,7,8-tetrahydronaphthalene-2-carboxamidine from step b were dissolved in methanol and hydrogenated in the presence of glacial acetic acid and Raney nickel under atmospheric pressure and at room temperature. The reaction mixture was filtered, evaporated and purified by means of flash chromatography on silica gel.

433 mg brown residue, Rt.=2.50 min (method A), LCMS: 231 (M+H).

Step d:

A solution of 290 mg (7.25 mmol) of NaOH in 3 ml of water was slowly added dropwise at −5° C. to a solution of 433 mg (1.45 mmol) of 5,5,8,8-tetramethyl-5,6,7,8-tetrahydronaphthalene-2-carboxamidine from step c and 166 µl (1.45 mmol) of perchloromethyl mercaptan in 3 ml of DCM. The reaction mixture was stirred at −5° C. for a further 30 min, then warmed to room temperature, diluted with 60 ml of water and extracted 3 times with DCM. The organic phase was washed with a saturated sodium chloride solution, dried over sodium sulfate, filtered, evaporated to dryness and purified by means of flash chromatography on silica gel.

181 mg brown oil, Rt.=4.13 min (method A), LCMS: 307 (M+H).

Step e:

181 mg (0.53 mmol) of 5-chloro-3-(5,5,8,8-tetramethyl-5,6,7,8-tetrahydronaphthalen-2-yl)-1,2,4-thiadiazole from step d were weighed out together with 109 mg (0.58 mmol) of tert-butyl 1-piperazinecarboxylate, 13.5 mg (0.03 mmol) of 1,3-bis(2,6-di-isopropylphenyl)imidazolium chloride and 102 mg (1.06 mmol) of sodium tert-butoxide, and 10 ml of toluene were added. The reaction mixture was degassed, 14.6 mg (0.02 mmol) of tris(dibenzylideneacetone)dipalladium (0) were subsequently added, the mixture was stirred at 85° C. overnight, filtered, stripped off to dryness and purified by means of flash chromatography on silica gel.

169 mg pale residue, Rt.=4.09 min (method A), LCMS: 457 (M+H).

Step f:

The protecting group was cleaved off as already described. The product is in the form of the hydrochloride.

137 mg pale solid, Rt.=2.89 min (method A), LCMS: 357 (M+H).

Preparation of 5-{4-[3-(5,5,8,8-tetramethyl-5,6,7,8-tetrahydronaphthalen-2-yl)-1,2,4-thiadiazol-5-yl]piperazin-1-yl}pentan-1-ol

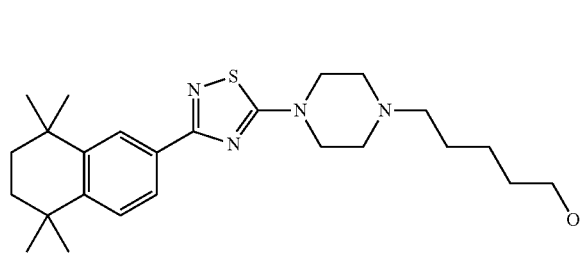

The preparation was carried out as already described starting from 65 mg (0.17 mmol) of 1-[3-(5,5,8,8-tetramethyl-5,6,7,8-tetrahydronaphthalen-2-yl)-1,2,4-thiadiazol-5-yl]piperazine hydrochloride and 17 mg (0.165 mmol) of 5-hydroxypentanal.

37 mg pale oil, Rt.=2.93 min (method A), LCMS: 443 (M+H).

$^1$H NMR (400 MHz, DMSO/deuterated TFA) δ=8.14 (d, J=1.8, 1H), 7.90 (dd, J=8.3, 1.8, 1H), 7.42 (d, J=8.3, 1H), 4.23-4.09 (m, 2H), 3.74-3.61 (m, 4H), 3.51 (t, J=6.3, 2H), 3.31 (s, 2H), 3.26-3.18 (m, 2H), 1.85-1.74 (m, 2H), 1.72 (s, 4H), 1.60-1.50 (m, 2H), 1.49-1.38 (m, 2H), 1.31 (d, J=10.5, 12H).

4-{4-[3-(5,5,8,8-Tetramethyl-5,6,7,8-tetrahydronaphthalen-2-yl)-1,2,4-thiadiazol-5-yl]piperazin-1-yl}butan-1-ol

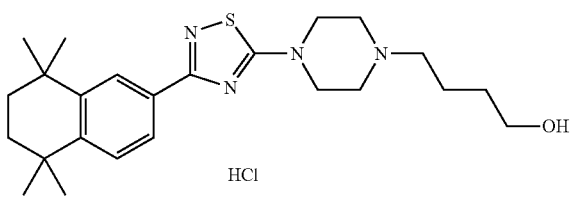 [SMILES: CC1(C)CCC(C)(C)c2cc(-c3nsc(N4CCN(CCCCO)CC4)n3)ccc21 ; Cl]

The preparation was carried out as already described starting from 65 mg (0.16 mmol) of 1-[3-(5,5,8,8-tetramethyl-5,6,7,8-tetrahydronaphthalen-2-yl)-1,2,4-thiadiazol-5-yl]piperazine and 36 μl (0.25 mmol) of 4-bromobutyl acetate. The protecting group was cleaved off by means of a 1N NaOH solution in methanol. The product was purified by means of preparative HPLC and is in the form of the hydrochloride.

21 mg, solid, LCMS: 429 [M+H], HPLC: Rt.=2.83 min (method A).

$^1$H NMR (400 MHz, DMSO/deuterated TFA) δ 8.06 (d, J=1.8 Hz, 1H), 7.82 (dd, J=8.3, 1.8 Hz, 1H), 7.33 (d, J=8.3 Hz, 1H), 4.07 (d, J=12.9 Hz, 2H), 3.61 (t, J=13.8 Hz, 4H), 3.47 (t, J=6.0 Hz, 2H), 3.31-3.11 (m, 4H), 1.77 (dt, J=15.4, 7.6 Hz, 2H), 1.64 (s, 4H), 1.54-1.45 (m, 2H), 1.22 (d, J=11.1 Hz, 12H).

Preparation of 1-[3-(5,5,8,8-tetramethyl-5,6,7,8-tetrahydronaphthalen-2-yl)-1,2,4-oxadiazol-5-yl]piperazine

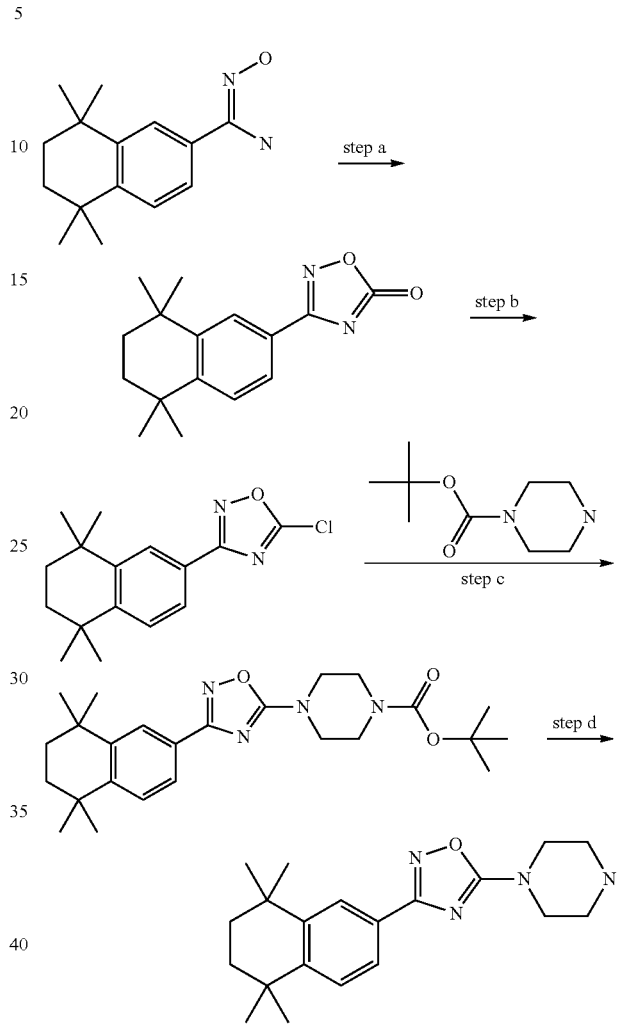

Step a:
1.24 g (4.79 mmol) of N-hydroxy-5,5,8,8-tetramethyl-5,6,7,8-tetrahydronaphthalene-2-carboxamidine (preparation already described) were dissolved in 15 ml of NMP, and 1.16 ml (14.38 mmol) of pyridine were added. Ethyl chloroformate (502 μl, 5.27 mmol) was added to the reaction mixture. The mixture was stirred at 80° C. overnight, stirred into 200 ml of water and extracted twice with EA. The combined organic phases were washed with 100 ml of water, dried over sodium sulfate, stripped off to dryness and purified by means of flash chromatography on silica gel.

980 mg brown residue, Rt.=3.25 min (method A), LCMS: 273 (M+H).

Step b:
248 mg (0.63 mmol) of 3-(5,5,8,8-tetramethyl-5,6,7,8-tetrahydronaphthalen-2-yl)-4H-1,2,4-oxadiazol-5-one from step a were dissolved in 5 ml of DCM, and pyridine (101 μl, 1.25 mmol) and phosphoryl chloride (115 μl, 1.25 mmol) were added. The reaction mixture was stirred at room temperature for 2 days, diluted with DCM and extracted against water. The organic phase was dried over sodium sulfate and stripped off to dryness.

201 mg brown oil, Rt.=4.03 min (method A).

Step c:

67 mg (0.22 mmol) of 5-chloro-3-(5,5,8,8-tetramethyl-5,6,7,8-tetrahydronaphthalen-2-yl)-1,2,4-oxadiazole from step b were dissolved in 3 ml of THF, and 61 mg (0.33 mmol) of tert-butyl 1-piperazinecarboxylate and 36 μl (0.26 mmol) of triethylamine were added. The reaction mixture was stirred at room temperature overnight, 40 ml of water were added, and the mixture was extracted twice with EA. The organic phase was dried over sodium sulfate and stripped off to dryness.

133 mg, residue, Rt.=4.02 min (method A), LCMS: 441 (M+H).

Step d:

The protecting group was cleaved off as already described using HCl in methanol.

The product was purified by means of flash chromatography on silica gel.

31 mg, pale solid, Rt.=2.83 min (method A), LCMS: 341 (M+H).

$^1$H NMR (500 MHz, DMSO/deuterated TFA) δ=7.84 (d, J=1.7, 1H), 7.65 (dd, J=8.2, 1.7, 1H), 7.46 (d, J=8.3, 1H), 3.90-3.80 (m, 4H), 3.35-3.26 (m, 4H), 1.69 (s, 4H), 1.28 (d, J=2.6, 12H).

Preparation of 4-{4-[3-(5,5,8,8-tetramethyl-5,6,7,8-tetrahydronaphthalen-2-yl)-1,2,4-oxadiazol-5-yl]piperazin-1-yl}butan-1-ol

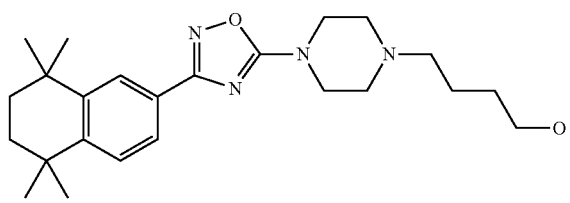 [SMILES: CC1(C)CCC(C)(C)c2cc(-c3noc(N4CCN(CCCCO)CC4)n3)ccc21]

The preparation was carried out as already described starting from 20 mg (0.06 mmol) of 1-[3-(5,5,8,8-tetramethyl-5,6,7,8-tetrahydronaphthalen-2-yl)-1,2,4-oxadiazol-5-yl]piperazine and 13 μl (0.09 mmol) of 4-bromobutyl acetate. The protecting group was cleaved off by means of a 1N NaOH solution in methanol. The product was purified by means of preparative HPLC and is in the form of the hydrochloride.

2 mg, solid, LCMS: 413 [M+H], HPLC: Rt.=2.85 min (method A).

$^1$H NMR (400 MHz, DMSO/deuterated TFA) δ=7.92 (d, J=1.7, 1H), 7.70 (dd, J=8.2, 1.7, 1H), 7.46 (d, J=8.3, 1H), 4.30 (d, J=15.0, 2H), 3.65 (t, J=11.9, 4H), 3.54 (t, J=6.0, 2H), 3.38-3.19 (m, 5H), 1.88-1.78 (m, 2H), 1.72 (s, 4H), 1.61-1.52 (m, 2H), 1.30 (d, J=5.4, 13H).

Preparation of 3,3-dimethyl-5-{4-[4-(5,5,8,8-tetramethyl-5,6,7,8-tetrahydronaphthalen-2-yl)thiazol-2-yl]piperazin-1-yl}pentane-1,4-diol

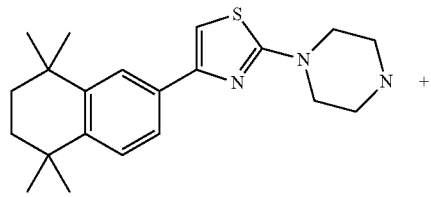

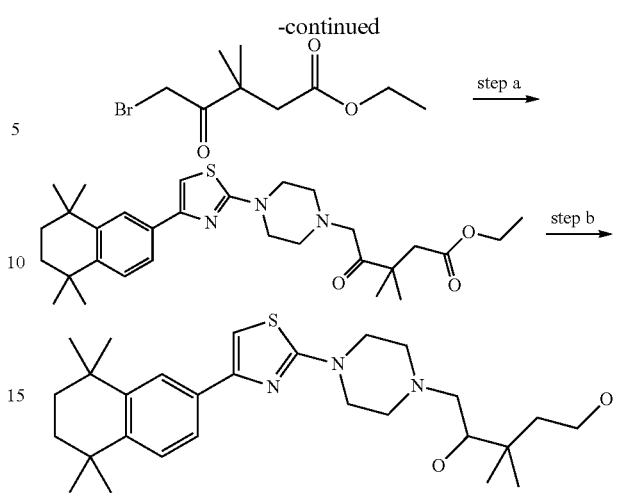

Step a:

200 mg (0.53 mmol) of 1-[4-(5,5,8,8-tetramethyl-5,6,7,8-tetrahydronaphthalen-2-yl)thiazol-2-yl]piperazine were dissolved in DCM, 277 mg (1.06 mmol) of 5-bromo-3,3-dimethyl-4-oxopentanoic acid ethyl ester and 220 μl (1.59 mmol) of triethylamine were added, the mixture was stirred at room temperature overnight. The reaction mixture was evaporated to dryness and purified by means of flash chromatography on silica gel.

90 mg, yellow oil, Rt.=3.29 min (method A), LCMS: 526 (M+H).

Step b:

90 mg (0.171 mmol) of 3,3-dimethyl-4-oxo-5-{4-[4-(5,5,8,8-tetramethyl-5,6,7,8-tetrahydronaphthalen-2-yl)thiazol-2-yl]piperazin-1-yl}pentanoic acid ethyl ester from step a was dissolved in 8 ml of THF. 1.71 ml (1.71 mmol) of a 1M lithium aluminium hydride solution in THF was added dropwise with ice-cooling. The mixture was stirred for a further 1 h with cooling, then stirred at room temperature and subsequently at 40° C. overnight, decomposed using a saturated sodium sulfate solution with cooling and extracted twice with EA. The organic phase was washed with a saturated sodium chloride solution, dried over sodium sulfate, filtered, evaporated to dryness and purified by means of preparative HPLC. The product is in the form of the hydrochloride.

31 mg pale solid, Rt.=3.03 min (method A), LCMS: 486 (M+H).

$^1$H NMR (400 MHz, DMSO/deuterated TFA) δ=7.79 (d, J=1.9, 1H), 7.58 (dd, J=8.2, 1.9, 1H), 7.37 (d, J=8.3, 1H), 4.25-4.04 (m, 2H), 3.79-3.52 (m, 7H), 3.45-3.15 (m, 5H), 1.70 (s, 4H), 1.62-1.52 (m, 1H), 1.50-1.40 (m, 1H), 1.34-1.25 (m, 13H), 0.93 (d, J=4.9, 6H).

Preparation of 2-(2-{4-[4-(5,5,8,8-tetramethyl-5,6,7,8-tetrahydronaphthalen-2-yl)thiazol-2-yl]piperazin-1-yl}ethyl)butane-1,4-diol

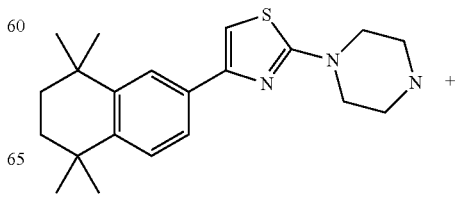

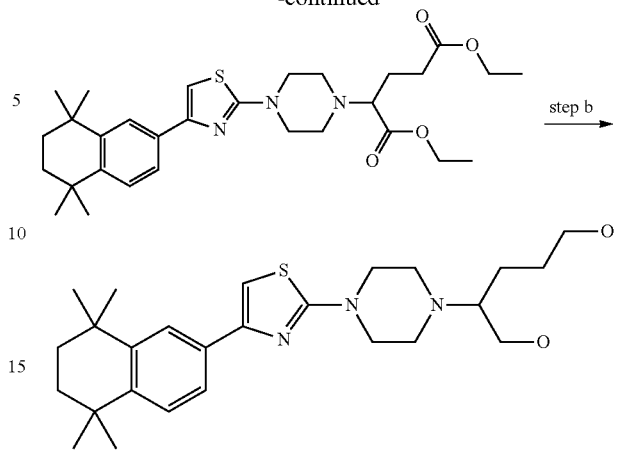

Step a:

The preparation was carried out analogously starting from 250 mg (0.66 mmol) of 1-[4-(5,5,8,8-tetramethyl-5,6,7,8-tetrahydronaphthalen-2-yl)thiazol-2-yl]piperazine and 255 mg (1.32 mmol) of 3-(2-bromoethyl)dihydrofuran-2-one. 77 mg, beige solid, Rt.=3.07 min (method A), LCMS: 468 (M+H).

Step b:

The reduction was carried out analogously starting from 77 mg of 3-(2-{4-[4-(5,5,8,8-tetramethyl-5,6,7,8-tetrahydronaphthalen-2-yl)thiazol-2-yl]piperazin-1-yl}-ethyl)dihydrofuran-2-one from step a. The product is in the form of the trifluoroacetate salt.

21 mg brown oil, Rt.=2.77 min (method A), LCMS: 472 (M+H).

$^1$H NMR (500 MHz, DMSO/deuterated TFA) δ=7.77 (s, 1H), 7.56 (d, J=8.2, 1H), 7.38 (d, J=8.3, 1H), 4.27-4.14 (m, 2H), 3.76-3.63 (m, 2H), 3.59-3.48 (m, 4H), 3.41-3.24 (m, 5H), 1.91-1.81 (m, 1H), 1.80-1.66 (m, 6H), 1.60-1.52 (m, 1H), 1.51-1.42 (m, 1H), 1.30 (d, J=17.1, 13H).

Preparation of 2-{4-[4-(5,5,8,8-tetramethyl-5,6,7,8-tetrahydronaphthalen-2-yl)thiazol-2-yl]piperazin-1-yl}pentanedioic acid diethyl ester and 2-(2-{4-[4-(5,5,8,8-tetramethyl-5,6,7,8-tetrahydronaphthalen-2-yl)thiazol-2-yl]piperazin-1-yl}ethyl)butane-1,4-diol

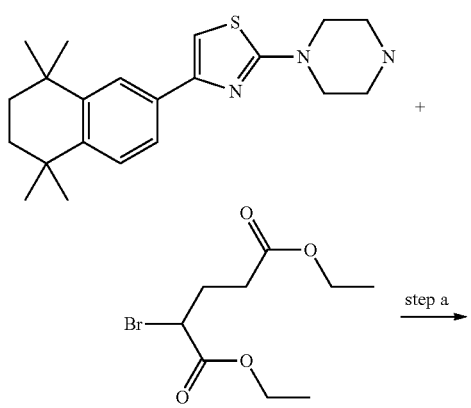

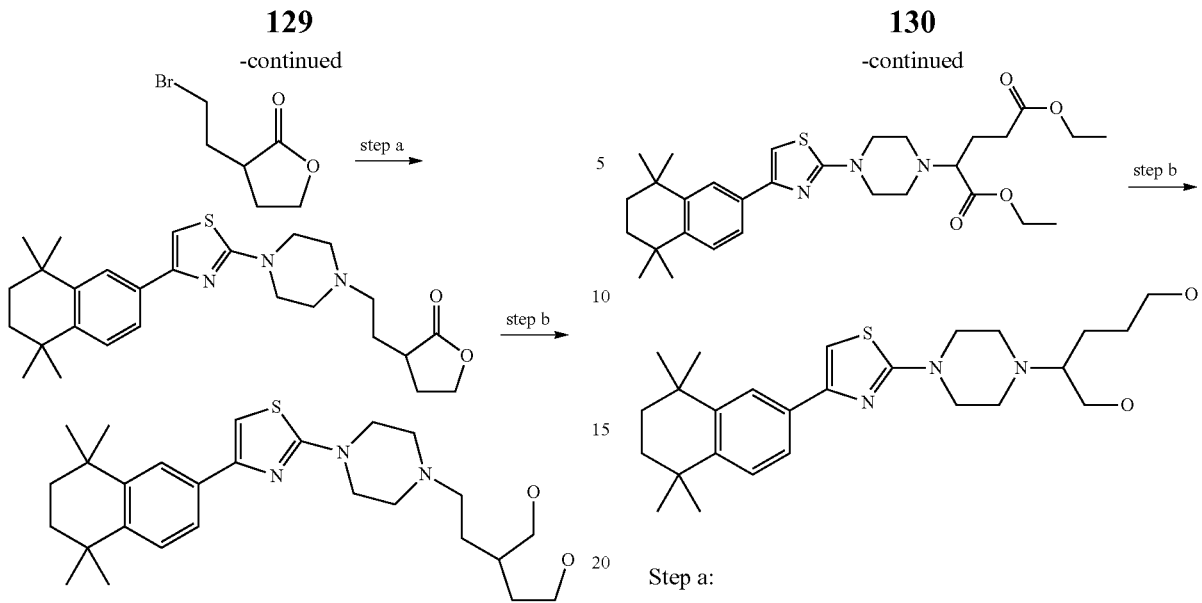

Step a:

The preparation was carried out analogously starting from 200 mg (0.56 mmol) of 1-[4-(5,5,8,8-tetramethyl-5,6,7,8-tetrahydronaphthalen-2-yl)thiazol-2-yl]piperazine and 180 mg (0.68 mmol) of 2-bromopentanedioic acid diethyl ester.

172 mg, brown oil, Rt.=3.51 min (method A), LCMS: 542 (M+H).

$^1$H NMR (500 MHz, DMSO/deuterated TFA) δ=7.79 (d, J=1.8, 1H), 7.57 (dd, J=8.2, 1.8, 1H), 7.38 (t, J=7.3, 1H), 4.37-4.28 (m, 3H), 4.17-4.09 (m, 2H), 3.89 (s, 4H), 3.68-3.57 (m, 2H), 3.55-3.43 (m, 2H), 2.61-2.52 (m, 4H), 2.52-2.44 (m, 1H), 2.43-2.34 (m, 1H), 2.23-2.12 (m, 1H), 1.69 (s, 4H), 1.36-1.18 (m, 21H).

Step b:

The reduction was carried out analogously starting from 172 mg of 2-{4-[4-(5,5,8,8-tetramethyl-5,6,7,8-tetrahydronaphthalen-2-yl)thiazol-2-yl]piperazin-1-yl}-pentanedioic acid diethyl ester from step a.

50 mg brown oil, Rt.=2.92 min (method A), LCMS: 458 (M+H).

$^1$H NMR (500 MHz, DMSO/deuterated TFA) δ=7.64 (s, 1H), 7.44 (dd, J=8.2, 1.3, 1H), 7.32 (d, J=8.3, 1H), 4.27-3.98 (m, 2H), 3.89-3.82 (m, 1H), 3.71-3.40 (m, 8H), 3.36-3.28 (m, 1H), 1.85-1.77 (m, 1H), 1.76-1.66 (m, 1H), 1.65-1.52 (m, 5H), 1.52-1.40 (m, 1H), 1.21 (d, J=16.4, 13H).

Preparation of 4-{4-[4-(5,5,8,8-tetramethyl-5,6,7,8-tetrahydronaphthalen-2-yl)thiazol-2-yl]piperazin-1-yl}butane-1,3-diol

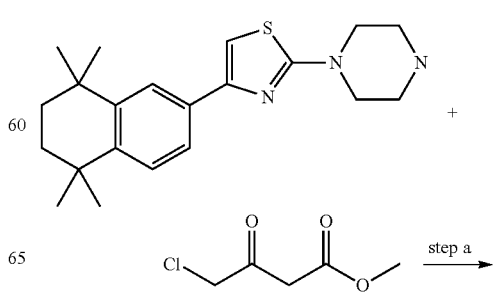

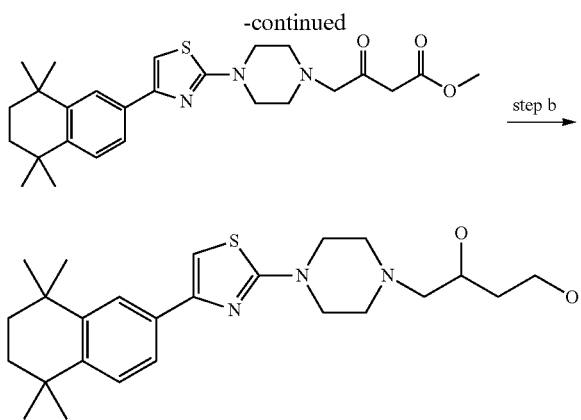

Step a:

The preparation was carried out analogously starting from 250 mg (0.66 mmol) of 1-[4-(5,5,8,8-tetramethyl-5,6,7,8-tetrahydronaphthalen-2-yl)thiazol-2-yl]piperazine and 156 µl (1.32 mmol) of 4-chloro-3-oxobutyric acid methyl ester. 90 mg, yellow oil, Rt.=3.10 min (method A), LCMS: 470 (M+H).

Step b:

The reduction was carried out analogously starting from 90 mg of 3-oxo-4-{-4-[4-(5,5,8,8-tetramethyl-5,6,7,8-tetrahydronaphthalen-2-yl)thiazol-2-yl]piperazin-1-yl}-butyric acid methyl ester from step a.

20 mg brown oil, Rt.=2.91 min (method A), LCMS: 444 (M+H).

$^1$H NMR (500 MHz, DMSO/deuterated TFA) δ=7.73 (d, J=1.9, 1H), 7.53 (dd, J=8.2, 1.8, 1H), 7.42 (d, J=8.3, 1H), 4.29-4.16 (m, 3H), 3.80-3.64 (m, 5H), 3.49-3.28 (m, 3H), 3.19 (dd, J=13.0, 10.8, 1H), 1.72 (s, 4H), 1.67 (dd, J=12.1, 6.0, 2H), 1.31 (d, J=15.8, 13H).

Preparation of 5-{4-[4-(5,5,8,8-tetramethyl-5,6,7,8-tetrahydronaphthalen-2-yl)thiazol-2-yl]piperazin-1-yl}pentanoic acid Step a:

100 mg (0.17 mmol) of 1-[4-(5,5,8,8-tetramethyl-5,6,7,8-tetrahydronaphthalen-2-yl)thiazol-2-yl]piperazine hydrobromide were dissolved in 1.5 ml of NMP, 56 µl (0.35 mmol) of 5-bromopentanoic acid ethyl ester, 340 mg (1.04 mmol) of caesium carbonate and 26 mg (0.17 mmol) of sodium iodide were added, the mixture was stirred at 110° C. overnight. Water was added to the reaction mixture, which was then extracted with EA. The organic phase was dried over sodium sulfate, filtered, evaporated to dryness and purified by means of flash chromatography on silica gel.

60 mg, yellow oil, Rt.=3.23 min (method A), LCMS: 484 (M+H).

Step b:

60 mg of 5-{4-[4-(5,5,8,8-tetramethyl-5,6,7,8-tetrahydronaphthalen-2-yl)thiazol-2-yl]piperazin-1-yl}pentanoic acid ethyl ester from step a was dissolved in 2.5 ml of THF, 250 µl of water and 11 mg (0.43 mmol) of lithium hydroxide were added, and the mixture was stirred at room temperature overnight. The reaction mixture was neutralised using a 1N hydrochloric acid solution, evaporated to dryness and purified by means of preparative HPLC. The product is in the form of the trifluoroacetate salt.

9 mg pale solid, Rt.=3.04 min (method A), LCMS: 456 (M+H).

$^1$H NMR (400 MHz, DMSO/deuterated TFA) δ=7.68 (s, 1H), 7.47 (d, J=8.3, 1H), 7.29 (d, J=8.3, 1H), 4.10 (s, 2H), 3.53 (d, J=39.8, 4H), 3.28-3.12 (m, 4H), 2.26 (t, J=7.1, 2H), 1.74-1.65 (m, 2H), 1.61 (s, 4H), 1.59-1.49 (m, 2H), 1.21 (d, J=13.6, 12H).

Preparation of 4-{4-[4-(5,5,8,8-tetramethyl-5,6,7,8-tetrahydronaphthalen-2-yl)thiazol-2-yl]piperazin-1-yl}butyric acid

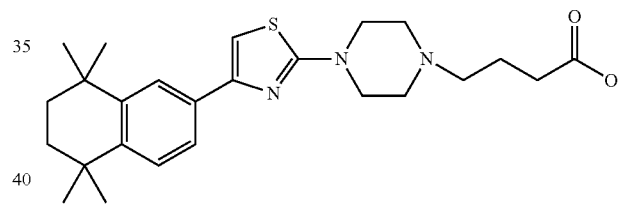

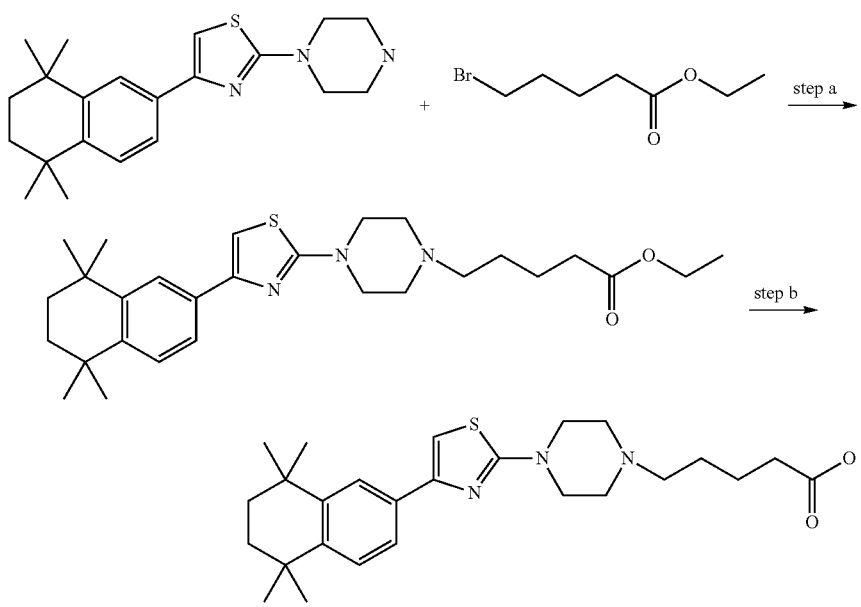

The preparation was carried out analogously starting from 100 mg (0.17 mmol) of 1-[4-(5,5,8,8-tetramethyl-5,6,7,8-tetrahydronaphthalen-2-yl)thiazol-2-yl]piperazine hydrobromide and 63 mg (0.35 mmol) of 4-bromobutyric acid ethyl ester. The product is in the form of the TFA salt.

18 mg pale solid, Rt.=3.00 min (method A), LCMS: 442 (M+H).

$^1$H NMR (500 MHz, DMSO/deuterated TFA) δ=7.75 (d, J=1.8, 1H), 7.54 (dd, J=8.2, 1.8, 1H), 7.32 (d, J=8.3, 1H), 4.12 (d, J=12.7, 2H), 3.64 (d, J=10.6, 2H), 3.50-3.34 (m, 2H), 3.33-3.15 (m, 4H), 2.36 (t, J=7.1, 2H), 1.97-1.87 (m, 2H), 1.64 (s, 4H), 1.25 (d, J=17.3, 12H).

Preparation of 2-(3-{4-[4-(5,5,8,8-tetramethyl-5,6,7,8-tetrahydronaphthalen-2-yl)thiazol-2-yl]piperazin-1-yl}propyl)malonic acid diethyl ester

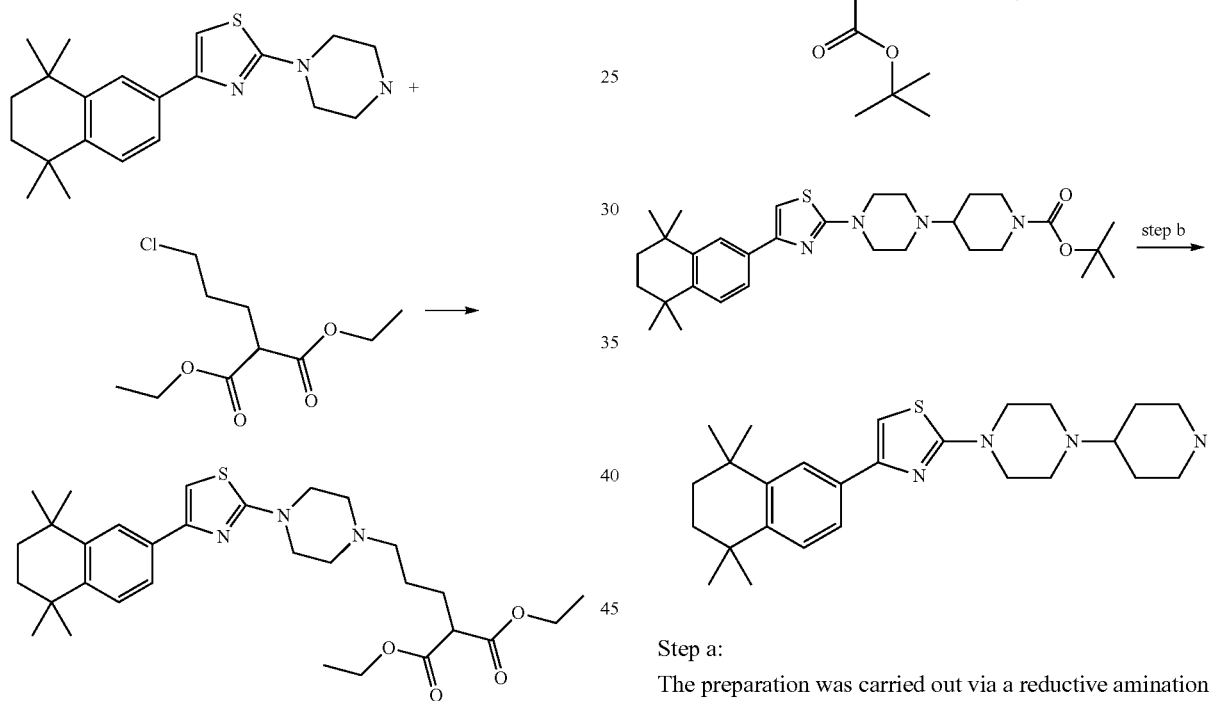

200 mg (0.53 mmol) of 1-[4-(5,5,8,8-tetramethyl-5,6,7,8-tetrahydronaphthalen-2-yl)thiazol-2-yl]piperazine were dissolved in 5 ml of NMP, 235 µl (1.06 mmol) of 2-(3-chloropropyl)malonic acid diethyl ester and 220 µl (1.59 mmol) of triethylamine were added, and the mixture was stirred at 100° C. overnight. The reaction mixture was evaporated to dryness and purified by means of preparative HPLC. The product is in the form of the TFA salt.

89 mg pale solid, Rt.=3.27 min (method A), LCMS: 556 (M+H).

$^1$H NMR (400 MHz, DMSO/deuterated TFA) δ=7.79 (d, J=1.9, 1H), 7.58 (dd, J=8.2, 1.9, 1H), 7.35 (d, J=8.3, 1H), 4.24-4.08 (m, 6H), 3.69-3.56 (m, 3H), 3.54-3.39 (m, 2H), 3.30-3.21 (m, 3H), 1.92-1.82 (m, 2H), 1.82-1.72 (m, 2H), 1.69 (s, 4H), 1.33-1.20 (m, 19H).

Preparation of 1-piperidin-4-yl-4-[4-(5,5,8,8-tetramethyl-5,6,7,8-tetrahydronaphthalen-2-yl)thiazol-2-yl]piperazine

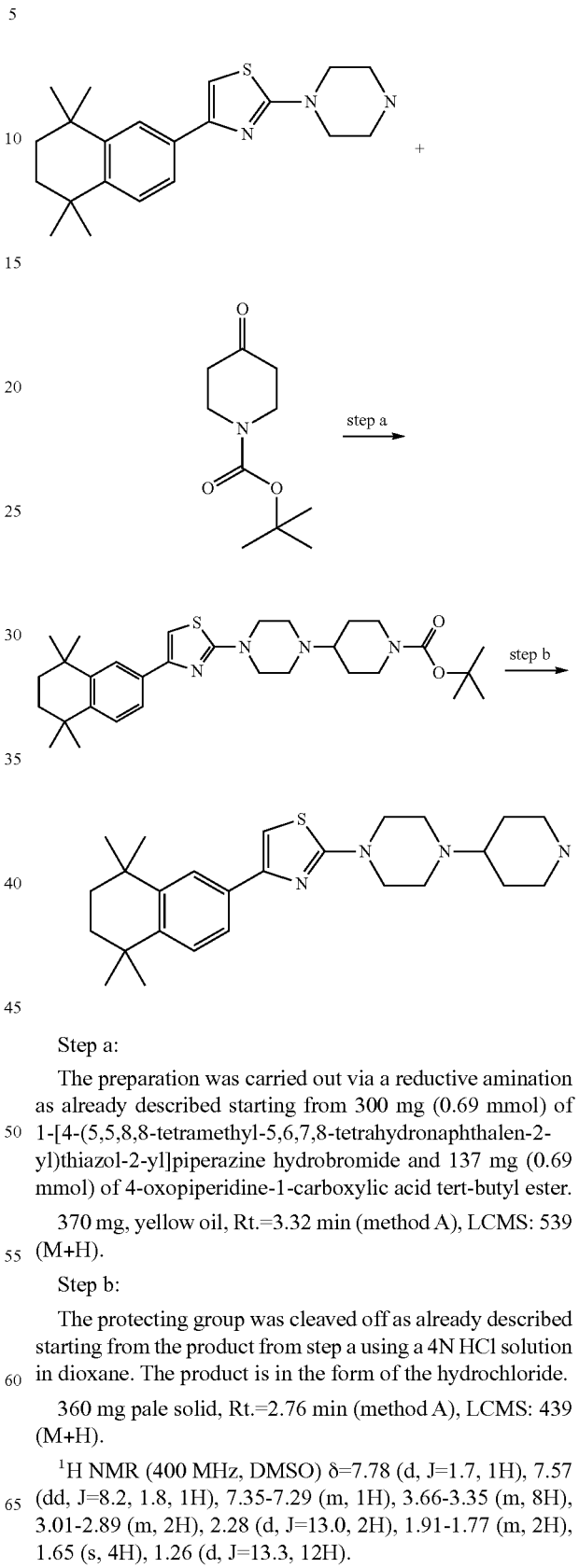

Step a:

The preparation was carried out via a reductive amination as already described starting from 300 mg (0.69 mmol) of 1-[4-(5,5,8,8-tetramethyl-5,6,7,8-tetrahydronaphthalen-2-yl)thiazol-2-yl]piperazine hydrobromide and 137 mg (0.69 mmol) of 4-oxopiperidine-1-carboxylic acid tert-butyl ester.

370 mg, yellow oil, Rt.=3.32 min (method A), LCMS: 539 (M+H).

Step b:

The protecting group was cleaved off as already described starting from the product from step a using a 4N HCl solution in dioxane. The product is in the form of the hydrochloride.

360 mg pale solid, Rt.=2.76 min (method A), LCMS: 439 (M+H).

$^1$H NMR (400 MHz, DMSO) δ=7.78 (d, J=1.7, 1H), 7.57 (dd, J=8.2, 1.8, 1H), 7.35-7.29 (m, 1H), 3.66-3.35 (m, 8H), 3.01-2.89 (m, 2H), 2.28 (d, J=13.0, 2H), 1.91-1.77 (m, 2H), 1.65 (s, 4H), 1.26 (d, J=13.3, 12H).

Preparation of 2-(4-{4-[4-(5,5,8,8-tetramethyl-5,6,7,8-tetrahydronaphthalen-2-yl)thiazol-2-yl]piperazin-1-yl}piperidin-1-yl)ethanol

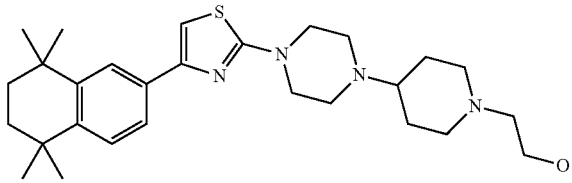 [SMILES: CC1(C)CCC(C)(C)c2cc(-c3csc(N4CCN(C5CCN(CCO)CC5)CC4)n3)ccc21]

The preparation was carried out as already described via a reductive amination starting from 50 mg (0.11 mmol) of 1-piperidin-4-yl-4-[4-(5,5,8,8-tetramethyl-5,6,7,8-tetrahydronaphthalen-2-yl)thiazol-2-yl]piperazine and 24 mg (0.13 mmol) of (tertbutyldimethylsilanyloxy)acetaldehyde. The protecting group was cleaved off as already described using a 4N HCl solution in dioxane. The product is in the form of the hydrochloride.

10 mg, solid, Rt.=2.77 min (method A), LCMS: 483 (M+H).

$^1$H NMR (400 MHz, DMSO/deuterated TFA) δ=7.79 (d, J=1.7, 1H), 7.57 (dd, J=8.2, 1.8, 1H), 7.38 (d, J=8.3, 1H), 3.83-3.72 (m, 5H), 3.60-3.50 (m, 4H), 3.23 (s, 5H), 3.16-3.06 (m, 2H), 2.43-2.35 (m, 2H), 2.23-2.08 (m, 2H), 1.70 (s, 4H), 1.33-1.27 (m, 14H).

Preparation of 2-(2-{4-[4-(5,5,8,8-tetramethyl-5,6,7,8-tetrahydronaphthalen-2-yl)thiazol-2-yl]piperazin-1-yl}ethoxy)ethanol

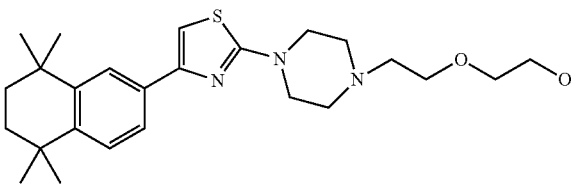 [SMILES: CC1(C)CCC(C)(C)c2cc(-c3csc(N4CCN(CCOCCO)CC4)n3)ccc21]

The preparation was carried out as already described starting from 100 mg (0.28 mmol) of 1-[4-(5,5,8,8-tetramethyl-5,6,7,8-tetrahydronaphthalen-2-yl)thiazol-2-yl]piperazine and 36 μl (0.33 mmol) of 2-(2-chloroethoxy)ethanol. The product is in the form of the hydrochloride.

21 mg, solid, Rt.=2.99 min (method A), LCMS: 444 (M+H).

$^1$H NMR (500 MHz, DMSO/deuterated TFA) δ=7.64 (d, J=1.7, 1H), 7.42 (dd, J=8.2, 1.7, 1H), 7.26 (d, J=8.3, 1H), 4.07 (s, 1H), 3.76-3.71 (m, 2H), 3.66-3.54 (m, 3H), 3.54-3.49 (m, 3H), 3.49-3.43 (m, 3H), 3.37-3.31 (m, 3H), 1.58 (s, 4H), 1.20-1.15 (m, 13H).

Preparation of 2-(2-{4-[4-(5,5,8,8-tetramethyl-5,6,7,8-tetrahydronaphthalen-2-yl)thiazol-2-yl]piperidin-1-yl}ethoxy)ethanol

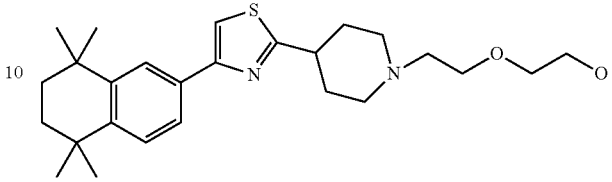

The preparation was carried out as already described starting from 100 mg (0.26 mmol) of 4-[4-(5,5,8,8-tetramethyl-5,6,7,8-tetrahydronaphthalen-2-yl)thiazol-2-yl]piperidine hydrochloride and 34 μl (0.31 mmol) of 2-(2-chloroethoxy)ethanol. The product is in the form of the hydrochloride.

18 mg, solid, Rt.=3.00 min (method A), LCMS: 443 (M+H).

$^1$H NMR (500 MHz, DMSO/deuterated TFA) δ=7.83 (d, J=1.8, 1H), 7.75 (d, J=21.8, 1H), 7.64-7.55 (m, 1H), 7.30 (d, J=8.3, 1H), 3.80-3.70 (m, 2H), 3.65 (d, J=12.7, 2H), 3.57-3.45 (m, 4H), 3.41-3.25 (m, 3H), 3.20-3.06 (m, 2H), 2.29 (d, J=12.7, 2H), 2.17-2.04 (m, 2H), 1.62 (s, 4H), 1.22 (d, J=20.4, 12H).

Preparation of 2-(2-{4-[4-(5,5,8,8-tetramethyl-5,6,7,8-tetrahydronaphthalen-2-yl)thiazol-2-yl]piperazin-1-yl}ethylamino)ethanol

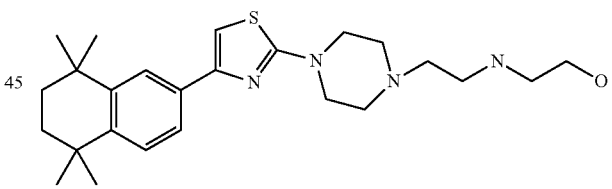

The preparation was carried out as already described starting from 100 mg (0.28 mmol) of 1-[4-(5,5,8,8-tetramethyl-5,6,7,8-tetrahydronaphthalen-2-yl)thiazol-2-yl]piperazine and 50 mg (0.34 mmol) of 3-(2-chloroethyl)oxazolidin-2-one. The protecting group was cleaved off using a 1N sodium hydroxide solution. The product is in the form of the hydrochloride.

19 mg, solid, Rt.=2.79 min (method A), LCMS: 443 (M+H).

$^1$H NMR (500 MHz, DMSO/deuterated TFA) δ=7.66 (d, J=1.7, 1H), 7.45 (dd, J=8.2, 1.6, 1H), 7.30 (d, J=8.3, 1H), 3.95-3.84 (m, 4H), 3.72-3.65 (m, 2H), 3.57-3.48 (m, 6H), 3.45 (t, J=6.1, 2H), 3.10-3.04 (m, 2H), 1.63 (d, J=12.4, 4H), 1.24-1.16 (m, 14H).

Preparation of 2-(2-{4-[4-(5,5,8,8-tetramethyl-5,6,7,8-tetrahydronaphthalen-2-yl)thiazol-2-yl]piperidin-1-yl}ethylamino)ethanol

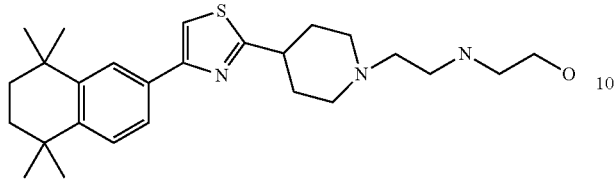

The preparation was carried out as already described starting from 100 mg (0.26 mmol) of 4-[4-(5,5,8,8-tetramethyl-5,6,7,8-tetrahydronaphthalen-2-yl)thiazol-2-yl]piperidine hydrochloride and 46 mg (0.31 mmol) of 3-(2-chloroethyl) oxazolidin-2-one. The protecting group was cleaved off using a 1N sodium hydroxide solution. The product is in the form of the hydrochloride.

41 mg, solid, Rt.=2.76 min (method A), LCMS: 442 (M+H).

$^1$H NMR (500 MHz, DMSO/deuterated TFA) δ=7.78 (d, J=1.6, 1H), 7.70 (s, 1H), 7.54 (d, J=8.0, 1H), 7.25 (d, J=8.3, 1H), 3.69-3.60 (m, 3H), 3.45-3.29 (m, 5H), 3.20-3.08 (m, 2H), 3.02 (s, 2H), 2.29 (d, J=13.5, 2H), 2.12-1.98 (m, 2H), 1.57 (s, 4H), 1.23-1.11 (m, 12H).

Preparation of 4-[3-(5,5,8,8-tetramethyl-5,6,7,8-tetrahydronaphthalen-2-yl)isoxazol-5-yl]piperidine

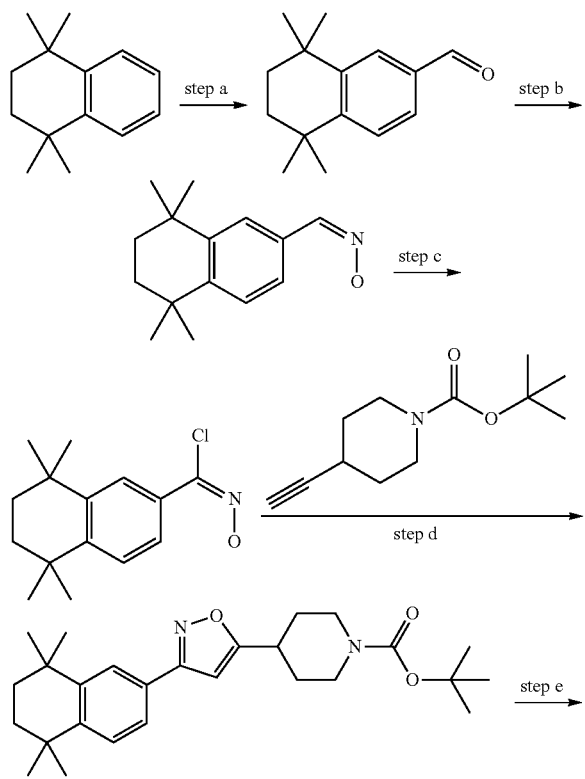

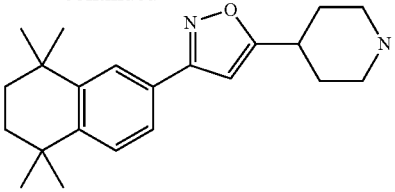

Step a:

1 g (5.31 mmol) of 1,1,4,4-tetramethyl-1,2,3,4-tetrahydronaphthalene was dissolved in DCM and cooled to 0° C. 1.12 ml (9.56 mmol) of tin(IV) chloride was added dropwise with vigorous stirring. 0.47 ml (5.31 mmol) of dichloromethyl methyl ether was subsequently added dropwise over the course of 10 minutes. The reaction mixture was stirred at 0° C. for a further 10 min and then at room temperature for a further 45 min, 30 ml of ice-water were added with cooling. The water phase was separated off. The organic phase was washed with a 2N HCl solution and with a saturated NaCl solution. The organic phase was dried and stripped off to dryness.

1.01 g, Rt.=3.51 min (method A), LCMS: 217 (M+H).

Step b:

20 ml of ethanol were added to the product from step a (1.01 g, 3.94 mmol) together with 0.82 g (11.81 mmol) of hydroxylammonium chloride and 1.25 g (11.81 mmol) of sodium carbonate. The reaction mixture was stirred at 80° C. overnight and filtered off with suction. The filtrate was stripped off to dryness. The residue was purified by flash chromatography on silica gel.

672 mg, Rt.=3.33 min (method A), LCMS: 232 (M+H).

Step c:

The product from step b (672 mg, 2.91 mmol) was dissolved in 5 ml of DMF, and 1 ml of a saturated HCl solution in diethyl ether was added. 1.08 g (3 mmol) of 45% potassium monopersulfate was added to the solution. The reaction mixture was stirred at room temperature for 4 h and stripped off to dryness. The residue was dissolved in EA and washed with a 0.5N HCl solution, a saturated sodium hydrogencarbonate solution and a saturated NaCl solution. The organic phase was dried and stripped off to dryness.

665 mg, Rt.=3.57 min (method A), LCMS: 266 (M+H).

Step d:

A solution of L-sodium ascorbate (13 mg, 0.07 mmol), potassium carbinate (91 mg, 0.66 mmol) and copper(II) sulfate 5-hydrate (5.25 mg, 0.03 mmol) in 2 ml of tert-butanol and 2 ml of water was added to 69 mg (0.33 mmol) of 4-ethynylpiperidine-1-carboxylic acid tert-butyl ester (preparation analogous to Journal of the American Chemical Society, 2003, vol. 125, #13, p. 3714-3715). The product from step c (100 mg, 0.33 mmol) was added to the mixture. The reaction mixture was stirred at room temperature for 3 h, diluted with water and extracted 3 times with EA. The organic phase was dried and stripped off to dryness. The residue was purified by flash chromatography on silica gel.

50 mg, Rt.=4.10 min (method A), LCMS: 383 (M+H-t-butyl).

Step e:

The protecting group was cleaved off as already described using an HCl solution in methanol. The product was purified by means of preparative HPLC and is in the form of the hydrochloride.

11 mg solid, Rt.=2.94 min (method A), LCMS: 339 (M+H).

¹H NMR (400 MHz, DMSO/deuterated TFA) δ=7.79 (d, J=1.8, 1H), 7.61 (dd, J=8.2, 1.8, 1H), 7.45 (d, J=8.3, 1H), 6.87 (d, J=0.6, 1H), 3.46-3.37 (m, 2H), 3.31-3.21 (m, 1H), 3.12 (td, J=12.6, 2.8, 2H), 2.30-2.21 (m, 2H), 2.00-1.87 (m, 2H), 1.71 (s, 4H), 1.31 (d, J=13.0, 12H).

Preparation of 4-{4-[3-(5,5,8,8-tetramethyl-5,6,7,8-tetrahydronaphthalen-2-yl)isoxazol-5-yl]piperidin-1-yl}butan-1-ol

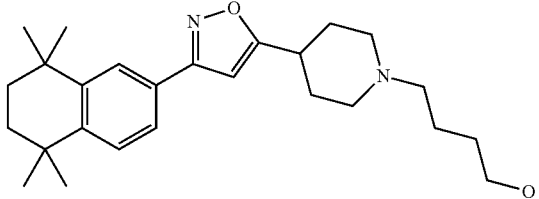 [SMILES: CC1(C)CCC(C)(C)c2cc(-c3cc(C4CCN(CCCCO)CC4)on3)ccc21]

The preparation was carried out as already described starting from 130 mg of 4-[3-(5,5,8,8-tetramethyl-5,6,7,8-tetrahydronaphthalen-2-yl)isoxazol-5-yl]piperidine and 83 μl of 4-bromobutyl acetate. The protecting group was cleaved off by means of a 1N NaOH solution in methanol. The product was purified by means of preparative HPLC and converted into the hydrochloride by treatment with methanolic HCl.

37 mg, solid, LCMS: 411 [M+H], HPLC: Rt.=2.93 min (method A).

¹H NMR (400 MHz, DMSO/deuterated TFA) δ=7.82-7.76 (m, 1H), 7.64-7.55 (m, 1H), 7.48-7.42 (m, 1H), 6.75 (s, 1H), 3.67 (d, J=12.5, 2H), 3.59-3.50 (m, 2H), 3.30-3.09 (m, 7H), 2.39-2.27 (m, 2H), 2.12-1.97 (m, 2H), 1.90-1.76 (m, 2H), 1.72 (s, 4H), 1.62-1.51 (m, 2H), 1.31 (d, J=11.7, 12H).

Preparation of 5-{4-[3-(5,5,8,8-tetramethyl-5,6,7,8-tetrahydronaphthalen-2-yl)isoxazol-5-yl]piperidin-1-yl}pentan-1-ol

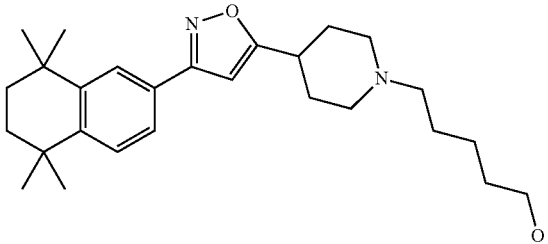 [SMILES: CC1(C)CCC(C)(C)c2cc(-c3cc(C4CCN(CCCCCO)CC4)on3)ccc21]

The preparation was carried out as already described starting from 130 mg of 4-[3-(5,5,8,8-tetramethyl-5,6,7,8-tetrahydronaphthalen-2-yl)isoxazol-5-yl]piperidine and 79 mg of 5-hydroxypentanal. The product was purified by means of preparative HPLC and converted into the hydrochloride by treatment with methanolic HCl.

55 mg, solid, LCMS: 425 [M+H], HPLC: Rt.=2.96 min (method A).

¹H NMR (400 MHz, DMSO/deuterated TFA) δ=7.74-7.69 (m, 1H), 7.56-7.49 (m, 1H), 7.40-7.34 (m, 1H), 6.73 (s, 1H), 3.58 (d, J=12.3, 2H), 3.46-3.37 (m, 2H), 3.22-3.11 (m, 2H), 3.11-2.99 (m, 4H), 2.30-2.17 (m, 2H), 2.03-1.89 (m, 2H), 1.75-1.59 (m, 6H), 1.51-1.40 (m, 2H), 1.39-1.29 (m, 2H), 1.27-1.20 (m, 12H).

Preparation of 1-[3-(5,5,8,8-tetramethyl-5,6,7,8-tetrahydronaphthalen-2-yl)isoxazol-5-yl]piperazine

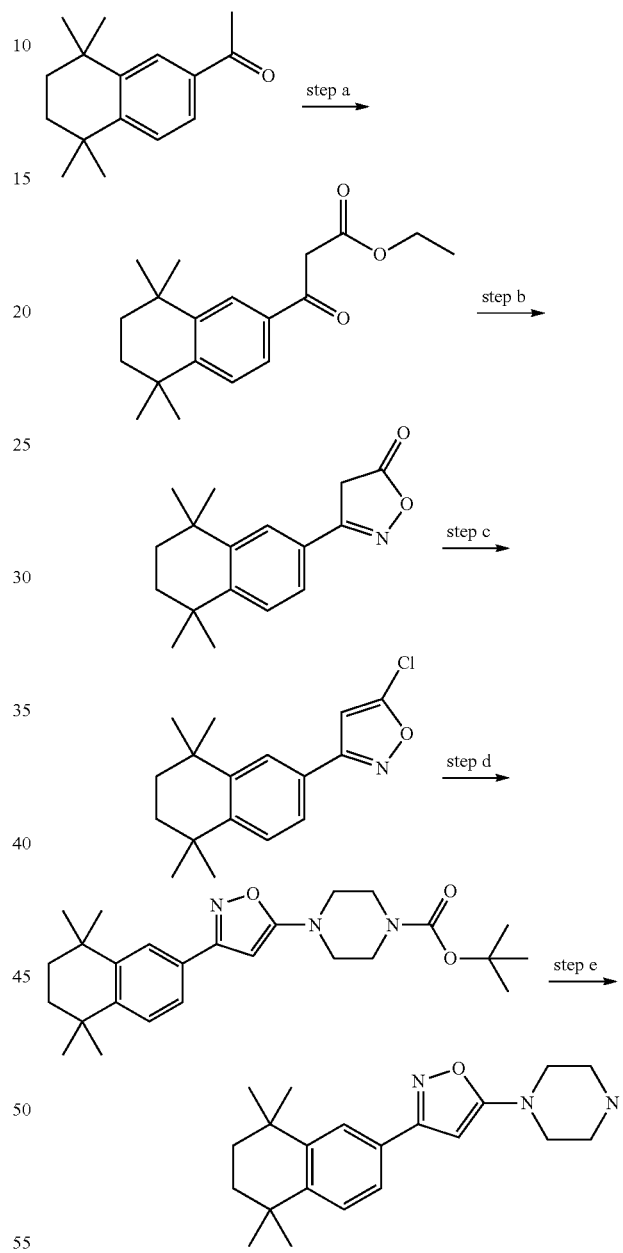

Step a:

1 g (4.21 mmol) of 1-(5,5,8,8-tetramethyl-5,6,7,8-tetrahydronaphthalen-2-yl)ethanone was dissolved in 20 ml of THF, and 1.03 ml (8.422 mmol) of diethyl carbonate were added. 539 mg (13.48 mmol) of sodium hydride were added in portions to the mixture. The mixture was stirred at room temperature over the weekend, diluted with 100 ml of EA, 20 ml of water were added, the mixture was acidified using a 1N HCl solution and extracted with EA. The organic phase was dried, stripped off to dryness and purified by means of flash chromatography on silica gel.

1.51 g, Rt.=3.57 min (method A), LCMS: 303 (M+H).

Step b:

1.51 g (4.62 mmol) of 3-oxo-3-(5,5,8,8-tetramethyl-5,6,7,8-tetrahydronaphthalen-2-yl)propionic acid ethyl ester from step a was dissolved in 20 ml of glacial acetic acid, 327 mg (4.71 mmol) of hydroxylammonium chloride were added, and the mixture was refluxed for 1 h. The reaction mixture was stripped off to dryness and purified by means of flash chromatography on silica gel.

1.15 g, Rt.=3.39 min (method A), LCMS: 272 (M+H).

Step c:

1.22 g (3.60 mmol) of 3-(5,5,8,8-tetramethyl-5,6,7,8-tetrahydronaphthalen-2-yl)-4H-isoxazol-5-one from step b was dissolved in 6 ml (65.35 mmol) of phosphoryl chloride and cooled to 0° C. 399 µl (2.88 mmol) of triethylamine were slowly added dropwise at 0° C. The reaction mixture was refluxed for 2 days, stripped off to dryness, stirred into ice and extracted twice with diethyl ether. The organic phase was dried, stripped off to dryness and purified by means of flash chromatography on silica gel.

441 mg, Rt.=3.92 min (method A), LCMS: 290 (M+H).

Step d:

400 mg (1.38 mmol) of 5-chloro-3-(5,5,8,8-tetramethyl-5,6,7,8-tetrahydronaphthalen-2-yl)isoxazole from step c were weighed out together with 257 mg (1.38 mmol) of tert-butyl 1-piperazinecarboxylate, and 231 µl (1.52 mmol) of 1,8-diazabicyclo[5.4.0]undec-7-ene were added. The mixture was melted at 150° C., stirred at 150° C. for 40 min, diluted with DCM and stripped off to dryness. The residue was purified by flash chromatography on silica gel.

400 mg, Rt.=3.92 min (method A), LCMS: 440 (M+H).

Step e:

The protecting group was cleaved off as already described using TFA in DCM starting from 27 mg (0.06 mmol) of 4-[3-(5,5,8,8-tetramethyl-5,6,7,8-tetrahydronaphthalen-2-yl)isoxazol-5-yl]piperazine-1-carboxylic acid tert-butyl ester from step d. The product is in the form of the TFA salt.

26 mg solid, Rt.=2.84 min (method A), LCMS: 340 (M+H).

Preparation of 5-{4-[3-(5,5,8,8-tetramethyl-5,6,7,8-tetrahydronaphthalen-2-yl)isoxazol-5-yl]piperazin-1-yl}pentan-1-ol

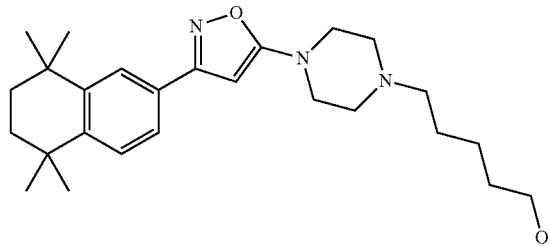 [SMILES: CC1(C)CCC(C)(C)c2cc(-c3cc(N4CCN(CCCCCO)CC4)on3)ccc21]

The preparation was carried out as already described via a reductive amination starting from 26 mg (0.05 mmol) of 1-[3-(5,5,8,8-tetramethyl-5,6,7,8-tetrahydronaphthalen-2-yl)isoxazol-5-yl]piperazine and 5 mg (0.05 mmol) of 5-hydroxypentanal. The product was purified by means of preparative HPLC and converted into the hydrochloride by treatment with methanolic HCl.

4 mg, solid, LCMS: 426 [M+H], HPLC: Rt.=2.88 min (method A).

$^1$H NMR (400 MHz, DMSO/deuterated TFA) δ=7.70 (d, J=1.8, 1H), 7.53 (dd, J=8.2, 1.8, 1H), 7.42 (d, J=8.2, 1H), 4.01-3.93 (m, 2H), 3.64 (d, J=12.7, 2H), 3.50 (t, J=6.3, 2H), 3.47-3.38 (m, 2H), 3.29-3.17 (m, 5H), 1.81-1.73 (m, 2H), 1.71 (s, 4H), 1.58-1.50 (m, 2H), 1.47-1.39 (m, 2H), 1.30 (d, J=10.5, 13H).

Preparation of 4-{2-[(5,5,8,8-tetramethyl-5,6,7,8-tetrahydronaphthalene-2-carbonyl)amino]acetyl}piperidine-1-carboxylic acid tert-butyl ester

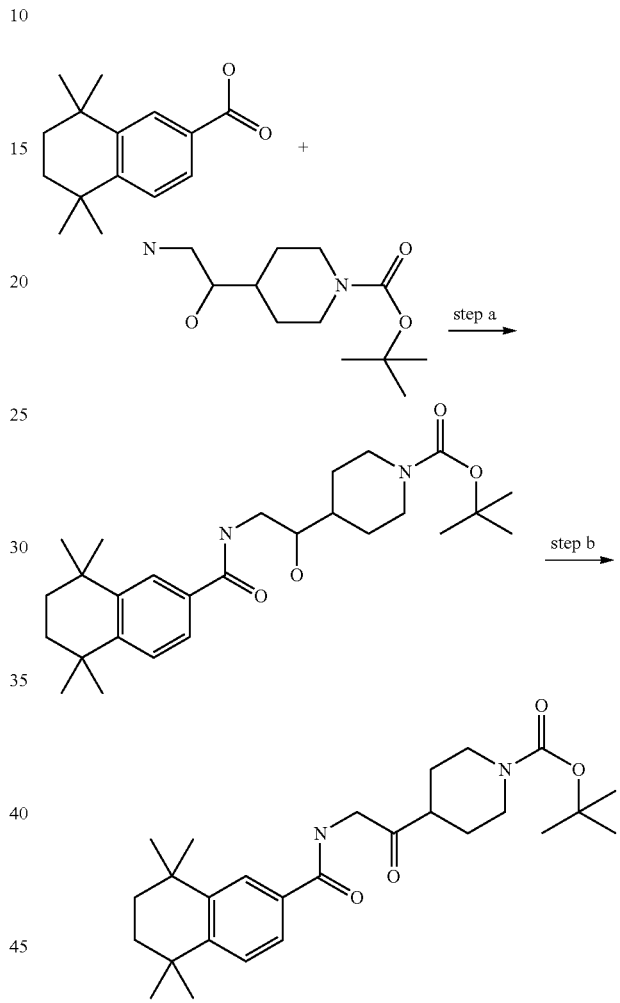

Step a:

1.25 g (5.12 mmol) of 5,5,8,8-tetramethyl-5,6,7,8-tetrahydro-2-naphthalene-carboxylic acid was weighed out together with 2.5 g (10.23 mmol) of 4-(2-amino-1-hydroxyethyl)piperidine-1-carboxylic acid tert-butyl ester (preparation analogous to Bioorganic & Medicinal Chemistry Letters, 2004, vol. 14, #13 p. 3419-3424), 1.96 g (10.23 mmol) of N-(3-dimethylaminopropyl)-N'-ethylcarbodiimide hydrochloride and 783 mg (5.12 mmol) of 1-hydroxybenzotriazole hydrate and suspended in 20 ml of DMF. 844 µl (7.67 mmol) of 4-methylmorpholine were added to the reaction mixture, which was then stirred at room temperature overnight, stirred into 400 ml of water. The mother liquor was decanted off, and the solid formed was washed with water, dissolved in EA, dried over sodium sulfate, filtered, stripped off to dryness and purified by means of flash chromatography on silica gel.

1.15 g, Rt.=3.43 min (method A), LCMS: 403 (M+H-tert-butyl).

Step b:

1.15 g (2.51 mmol) of 4-{1-hydroxy-2-[(5,5,8,8-tetramethyl-5,6,7,8-tetrahydronaphthalene-2-carbonyl)amino]ethyl}piperidine-1-carboxylic acid tert-butyl ester from step a was dissolved in 20 ml of DCM, and 15.61 ml (7.52 mmol) of Dess-Martin periodinane were added. The reaction mixture was stirred at room temperature for 30 min, 20 ml of a saturated sodium hydrogencarbonate solution and 5 ml of a saturated sodium sulfate solution were added, and the mixture was stirred vigorously for 30 min. The organic phase was separated off, and the water phase was extracted again with DCM. The organic phases were combined, dried, stripped off to dryness and purified by means of flash chromatography on silica gel.

800 mg, Rt.=3.55 min (method A), LCMS: 375 (M+H).

Preparation of 4-[2-(5,5,8,8-tetramethyl-5,6,7,8-tetrahydronaphthalen-2-yl)oxazol-5-yl]piperidine

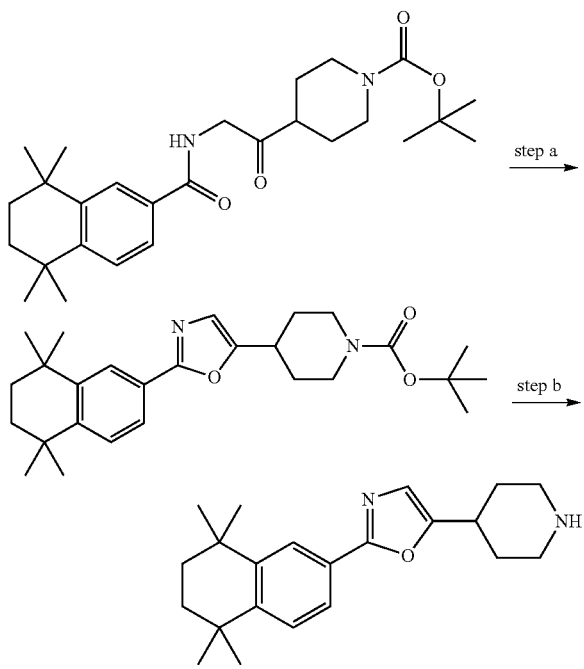

Step a:

400 mg (0.88 mmol) of 4-{2-[(5,5,8,8-tetramethyl-5,6,7,8-tetrahydronaphthalene-2-carbonyl)amino]acetyl}piperidine-1-carboxylic acid tert-butyl ester were dissolved in 20 ml of THF, and 417 mg (1.75 mmol) of Burgess reagent were added. The reaction mixture was stirred at 60° C. overnight stripped off to dryness, dissolved in DCM and washed with a 1N hydrochloric acid solution and a saturated sodium hydrogencarbonate solution. The organic phase was dried and stripped off to dryness.

395 mg, Rt.=4.12 min (method A), LCMS: 439 (M+H).

Step b:

The protecting group was cleaved off as already described using HCl in methanol starting from 395 mg of product from step a.

306 mg oil, Rt.=2.84 min (method A), LCMS: 339 (M+H).

Preparation of 4-{4-[2-(5,5,8,8-tetramethyl-5,6,7,8-tetrahydronaphthalen-2-yl)oxazol-5-yl]piperidin-1-yl}butan-1-ol

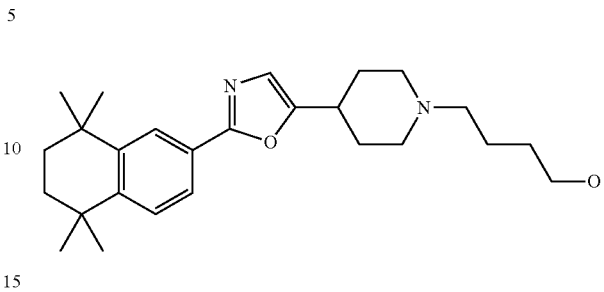

The preparation was carried out as already described starting from 150 mg (0.44 mmol) of 4-[2-(5,5,8,8-tetramethyl-5,6,7,8-tetrahydronaphthalen-2-yl)oxazol-5-yl]piperidine and 96 µl (0.67 mmol) of 4-bromobutyl acetate. The protecting group was cleaved off by means of a 1N NaOH solution in methanol. The product was purified by means of preparative HPLC and converted into the hydrochloride by treatment with methanolic HCl.

57 mg, solid, LCMS: 411 [M+H], HPLC: Rt.=2.82 min (method A).

$^1$H NMR (500 MHz, DMSO/deuterated TFA) δ=7.97-7.87 (m, 1H), 7.65 (d, J=8.2, 1H), 7.40 (d, J=8.3, 1H), 7.31-7.09 (m, 1H), 4.31 (s, 1H), 3.90-3.76 (m, 2H), 3.55 (s, 2H), 3.48-3.26 (m, 2H), 3.06 (s, 5H), 2.20 (d, J=12.1, 2H), 1.98-1.85 (m, 2H), 1.79-1.68 (m, 2H), 1.67-1.55 (m, 4H), 1.50-1.39 (m, 1H), 1.20 (dd, J=18.3, 14.2, 12H).

Preparation of 5-{4-[2-(5,5,8,8-tetramethyl-5,6,7,8-tetrahydronaphthalen-2-yl)oxazol-5-yl]piperidin-1-yl}pentan-1-ol

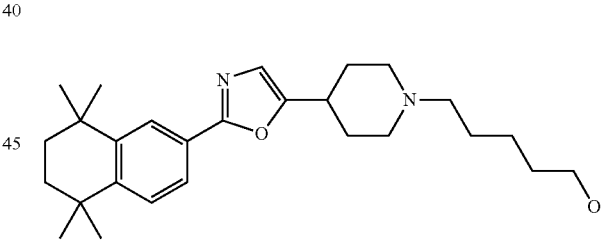

The preparation was carried out as already described via a reductive amination starting from 150 mg (0.44 mmol) of 4-[2-(5,5,8,8-tetramethyl-5,6,7,8-tetrahydronaphthalen-2-yl)oxazol-5-yl]piperidine and 91 mg (0.89 mmol) of 5-hydroxypentanal. The product was purified by means of preparative HPLC and converted into the hydrochloride by treatment with methanolic HCl.

70 mg, solid, LCMS: 425 [M+H], HPLC: Rt.=2.87 min (method A).

$^1$H NMR (500 MHz, DMSO/deuterated TFA) δ=7.97-7.91 (m, 1H), 7.76-7.69 (m, 1H), 7.49 (d, J=8.3, 1H), 7.29-7.11 (m, 1H), 3.67-3.59 (m, 2H), 3.50-3.41 (m, 2H), 3.20-3.06 (m, 5H), 2.33-2.18 (m, 2H), 2.00-1.89 (m, 2H), 1.79-1.65 (m, 6H), 1.56-1.45 (m, 2H), 1.45-1.34 (m, 2H), 1.30 (d, J=13.1, 12H).

Preparation of 4-[2-(5,5,8,8-tetramethyl-5,6,7,8-tetrahydronaphthalen-2-yl)thiazol-5-yl]piperidine

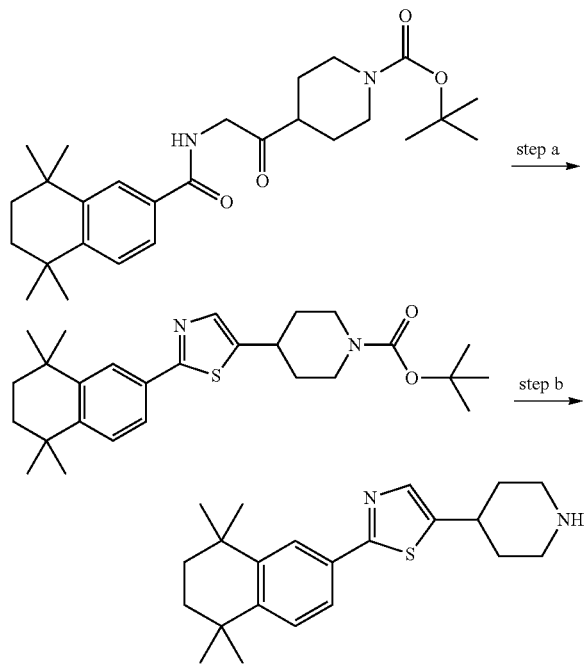

Step a:

233 mg (0.51 mmol) of 4-{2-[(5,5,8,8-tetramethyl-5,6,7,8-tetrahydronaphthalene-2-carbonyl)amino]acetyl}piperidine-1-carboxylic acid tert-butyl ester were dissolved in 5 ml of THF together with 310 mg (0.77 mmol) of 2,4-bis(4-methoxyphenyl)-2,4-dithioxo-1,3,2,4-dithiadiphosphethane and irradiated in the microwave at 100° C. for 10 minutes. The reaction mixture was stripped off to dryness, dissolved in DCM and washed with a 1N HCl solution and a saturated sodium hydrogencarbonate solution. The organic phase was dried, stripped off to dryness.

512 mg.

Step b:

The protecting group was cleaved off as already described using HCl in methanol starting from 512 mg of product from step a.

160 mg oil, Rt.=2.90 min (method A), LCMS: 355 (M+H).

$^1$H NMR (500 MHz, DMSO/deuterated TFA) δ=7.96-7.89 (m, 2H), 7.68 (dd, J=8.3, 2.0, 1H), 7.50 (d, J=8.3, 1H), 3.49-3.41 (m, 2H), 3.40-3.30 (m, 1H), 3.11 (td, J=12.7, 2.5, 2H), 2.24 (d, J=12.5, 2H), 2.00-1.89 (m, 2H), 1.73 (s, 4H), 1.30 (dd, J=19.1, 10.2, 12H).

Preparation of 4-{4-[2-(5,5,8,8-tetramethyl-5,6,7,8-tetrahydronaphthalen-2-yl)thiazol-5-yl]piperidin-1-yl}butan-1-ol

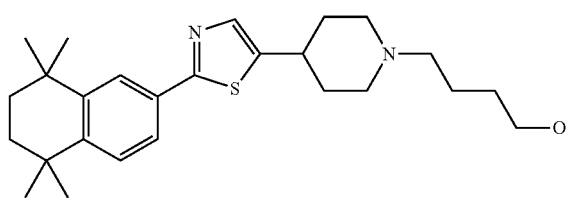 [SMILES: CC1(C)CCC(C)(C)c2cc(-c3ncc(C4CCN(CCCCO)CC4)s3)ccc21]

The preparation was carried out as already described starting from 70 mg (0.20 mmol) of 4-[2-(5,5,8,8-tetramethyl-5,6,7,8-tetrahydronaphthalen-2-yl)thiazol-5-yl]piperidine and 43 μl (0.30 mmol) of 4-bromobutyl acetate. The protecting group was cleaved off by means of a 1N NaOH solution in methanol. The product was purified by means of preparative HPLC and converted into the hydrochloride by treatment with methanolic HCl.

23 mg, solid, LCMS: 427 [M+H], HPLC: Rt.=2.92 min (method A).

$^1$H NMR (500 MHz, DMSO/deuterated TFA) δ=7.97-7.89 (m, 2H), 7.72-7.65 (m, 1H), 7.53-7.48 (m, 1H), 3.67 (d, J=12.4, 2H), 3.60-3.42 (m, 2H), 3.38-3.10 (m, 5H), 2.36-2.23 (m, 2H), 2.09-1.96 (m, 2H), 1.88-1.78 (m, 2H), 1.73 (s, 4H), 1.60-1.52 (m, 2H), 1.32 (d, J=15.9, 12H).

Preparation of 5-{4-[2-(5,5,8,8-tetramethyl-5,6,7,8-tetrahydronaphthalen-2-yl)thiazol-5-yl]piperidin-1-yl}pentan-1-ol

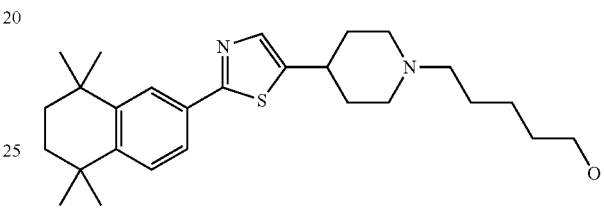

The preparation was carried out as already described via a reductive amination starting from 70 mg (0.20 mmol) of 4-[2-(5,5,8,8-tetramethyl-5,6,7,8-tetrahydronaphthalen-2-yl)thiazol-5-yl]piperidine and 40 mg (0.40 mmol) of 5-hydroxypentanal. The product was purified by means of preparative HPLC and converted into the hydrochloride by treatment with methanolic HCl.

41 mg, solid, LCMS: 441 [M+H], HPLC: Rt.=2.95 min (method A).

$^1$H NMR (500 MHz, DMSO/deuterated TFA) δ=7.89 (d, J=1.9, 1H), 7.81 (s, 1H), 7.69-7.62 (m, 1H), 7.50-7.45 (m, 1H), 3.64 (d, J=12.5, 2H), 3.53-3.39 (m, 2H), 3.34-3.07 (m, 5H), 2.33-2.19 (m, 2H), 2.04-1.91 (m, 2H), 1.78-1.66 (m, 6H), 1.55-1.48 (m, 2H), 1.44-1.36 (m, 2H), 1.31 (d, J=13.7, 12H).

Preparation of 4-[2-(5,5,8,8-tetramethyl-5,6,7,8-tetrahydronaphthalen-2-yl)oxazol-4-yl]piperidine

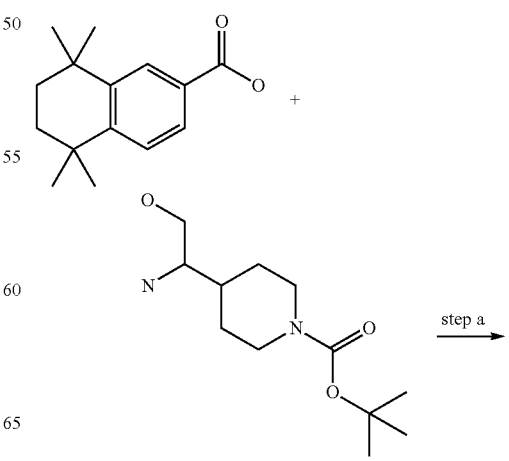

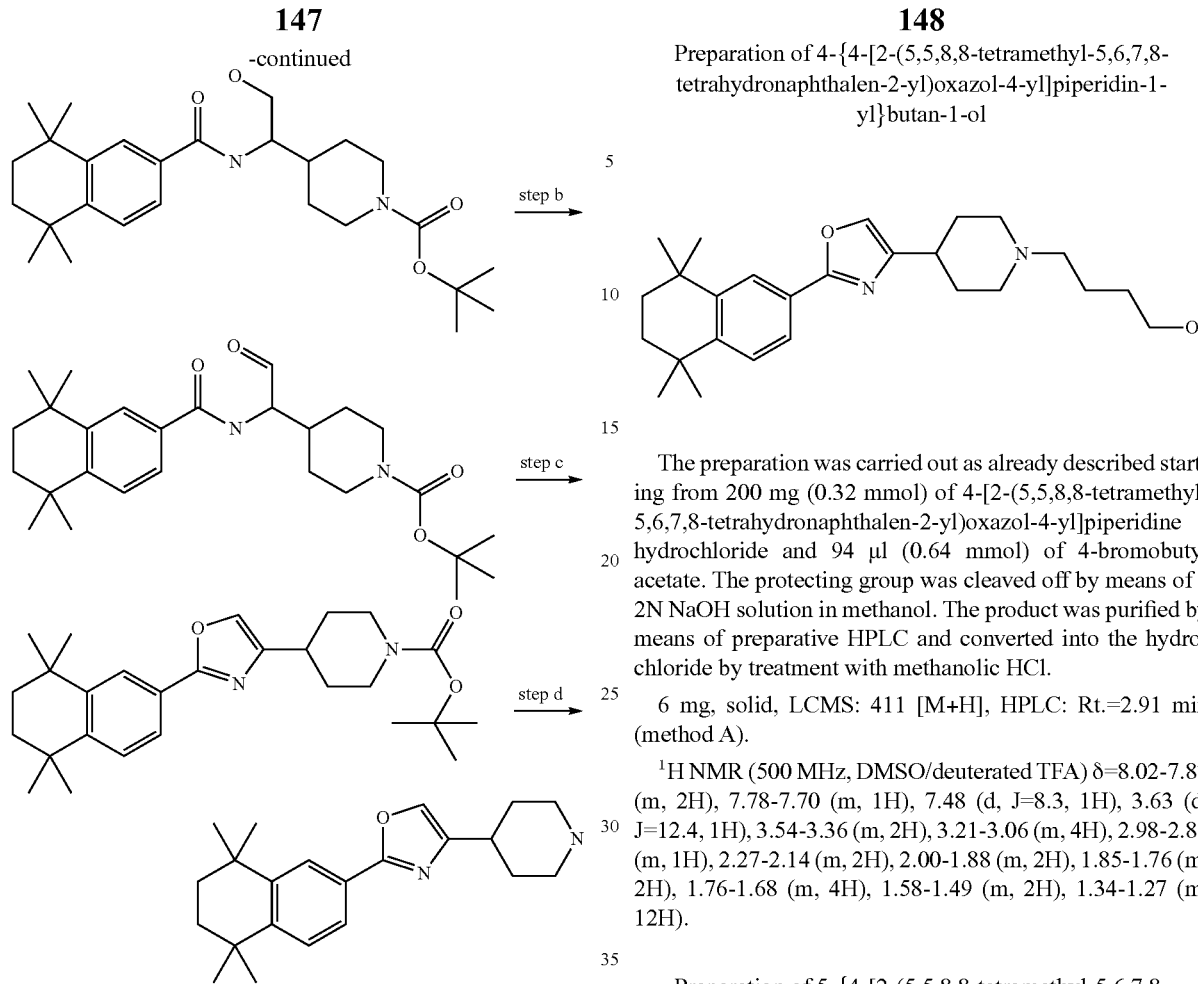

Step a:

The preparation was carried out as already described using EDCI and HOBt in DMF starting from 1 g (4.26 mmol) of 5,5,8,8-tetramethyl-5,6,7,8-tetrahydro-2-naphthalenecarboxylic acid and 1.25 g (5.11 mmol) of 4-(1-amino-2-hydroxyethyl)piperidine-1-carboxylic acid tert-butyl ester (preparation analogous to US2002/183361 A1, 2002).

2.89 g, oil, Rt.=3.40 min (method A), LCMS: 459 (M+H).

Step b:

The preparation was carried out as already described using Dess-Martin periodinane starting from the product from step a.

954 mg, yellow oil, Rt.=3.55 min (method A), LCMS: 357 (M+H-boc).

Step c:

The preparation was carried out as already described using Burgess reagent starting from the product from step b.

1.10 g solid, Rt.=4.17 min (method A), LCMS: 439 (M+H).

Step d:

The protecting group was cleaved off as already described using HCl in dioxane starting from the product from step c. The product is in the form of the hydrochloride.

1.20 g, solid, Rt.=2.93 min (method A), LCMS: 339 (M+H).

Preparation of 4-{4-[2-(5,5,8,8-tetramethyl-5,6,7,8-tetrahydronaphthalen-2-yl)oxazol-4-yl]piperidin-1-yl}butan-1-ol

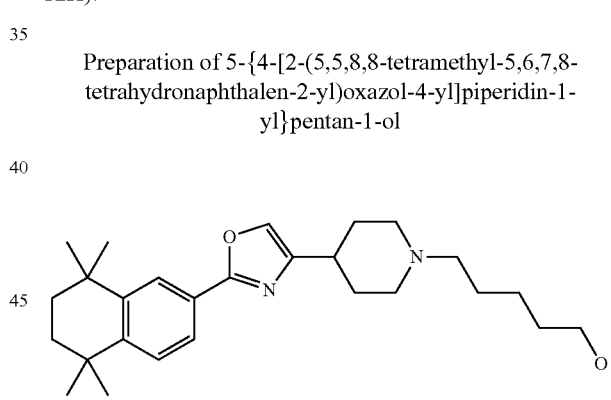

The preparation was carried out as already described starting from 200 mg (0.32 mmol) of 4-[2-(5,5,8,8-tetramethyl-5,6,7,8-tetrahydronaphthalen-2-yl)oxazol-4-yl]piperidine hydrochloride and 94 µl (0.64 mmol) of 4-bromobutyl acetate. The protecting group was cleaved off by means of a 2N NaOH solution in methanol. The product was purified by means of preparative HPLC and converted into the hydrochloride by treatment with methanolic HCl.

6 mg, solid, LCMS: 411 [M+H], HPLC: Rt.=2.91 min (method A).

$^1$H NMR (500 MHz, DMSO/deuterated TFA) δ=8.02-7.87 (m, 2H), 7.78-7.70 (m, 1H), 7.48 (d, J=8.3, 1H), 3.63 (d, J=12.4, 1H), 3.54-3.36 (m, 2H), 3.21-3.06 (m, 4H), 2.98-2.88 (m, 1H), 2.27-2.14 (m, 2H), 2.00-1.88 (m, 2H), 1.85-1.76 (m, 2H), 1.76-1.68 (m, 4H), 1.58-1.49 (m, 2H), 1.34-1.27 (m, 12H).

Preparation of 5-{4-[2-(5,5,8,8-tetramethyl-5,6,7,8-tetrahydronaphthalen-2-yl)oxazol-4-yl]piperidin-1-yl}pentan-1-ol The preparation was carried out as already described via a reductive amination starting from 200 mg (0.32 mmol) of 4-[2-(5,5,8,8-tetramethyl-5,6,7,8-tetrahydronaphthalen-2-yl)oxazol-4-yl]piperidine hydrochloride and 65 mg (0.64 mmol) of 5-hydroxypentanal. The product was purified by means of preparative HPLC and converted into the hydrochloride by treatment with methanolic HCl.

5 mg, solid, LCMS: 425 [M+H], HPLC: Rt.=2.95 min (method A).

$^1$H NMR (500 MHz, DMSO/deuterated TFA) δ=7.98-7.93 (m, 1H), 7.84 (s, 1H), 7.79-7.71 (m, 1H), 7.47 (d, J=8.3, 1H), 3.63 (d, J=12.4, 2H), 3.54-3.38 (m, 2H), 3.23-3.06 (m, 4H), 2.99-2.90 (m, 1H), 2.23 (d, J=12.1, 2H), 2.04-1.92 (m, 2H), 1.81-1.67 (m, 6H), 1.58-1.49 (m, 2H), 1.47-1.38 (m, 2H), 1.31 (d, J=12.8, 12H).

Preparation of 4-[N'-(5,5,8,8-tetramethyl-5,6,7,8-tetrahydronaphthalene-2-carbonyl)hydrazinocarbonyl]piperidine-1-carboxylic acid tert-butyl ester

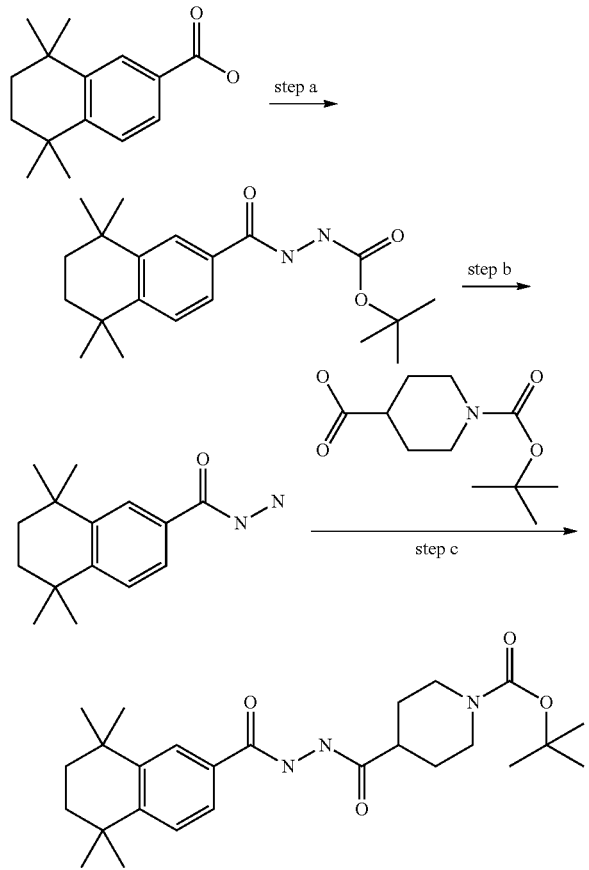

Step a:

2 g (8.18 mmol) of 5,5,8,8-tetramethyl-5,6,7,8-tetrahydronaphthalene-2-carboxylic acid was dissolved in 10 ml of DMF together with 1.08 g (8.18 mmol) of tert-butyl carbazate and 1.88 g (9.81 mmol) of N-(3-dimethylaminopropyl)-N'-ethylcarbodiimide hydrochloride and stirred at room temperature overnight. The reaction mixture was poured into 200 ml of water. The resultant precipitate was filtered off with suction, washed with water, taken up in ether and washed a number of times with water. The organic phase was dried, stripped off to dryness.

2.42 g, Rt.=3.27 min (method A), LCMS: 291 (M+H-tert-butyl).

Step b:

The protecting group was cleaved off as already described starting from the product from step a using a 4N HCl solution in dioxane. The reaction mixture was stripped off to dryness. The product was in the form of the hydrochloride.

2.2 g residue, Rt.=2.56 min (method A), LCMS: 247 (M+H).

Step c:

2.2 g (6.22 mmol) of 5,5,8,8-tetramethyl-5,6,7,8-tetrahydronaphthalene-2-carboxylic acid hydrazide from step b were suspended in 15 ml of DMF together with 1.43 g (6.22 mmol) of 1-Boc-piperazine-4-carboxylic acid (preparation analogous to Bioorganic & Medicinal Chemistry Letters, 2001, vol. 11, #24 p. 3161-3164), 2.41 g (12.45 mmol) of N-(3-dimethylaminopropyl)-N'-ethylcarbodiimide hydrochloride and 867 mg (6.22 mmol) of 1-hydroxybenzotriazole hydrate. 1.40 ml (12.45 mmol) of 4-methylmorpholine were added to the reaction mixture, which was then stirred at room temperature overnight, stirred into 350 ml of water. The resultant precipitate was filtered off with suction, dissolved in DCM, dried, stripped off to dryness and purified by means of flash chromatography on silica gel.

1.23 g, Rt.=3.22 min (method A), LCMS: 402 (M+H-tert-butyl).

Preparation of 4-[5-(5,5,8,8-tetramethyl-5,6,7,8-tetrahydronaphthalen-2-yl)-1,3,4-thiadiazol-2-yl]piperidine

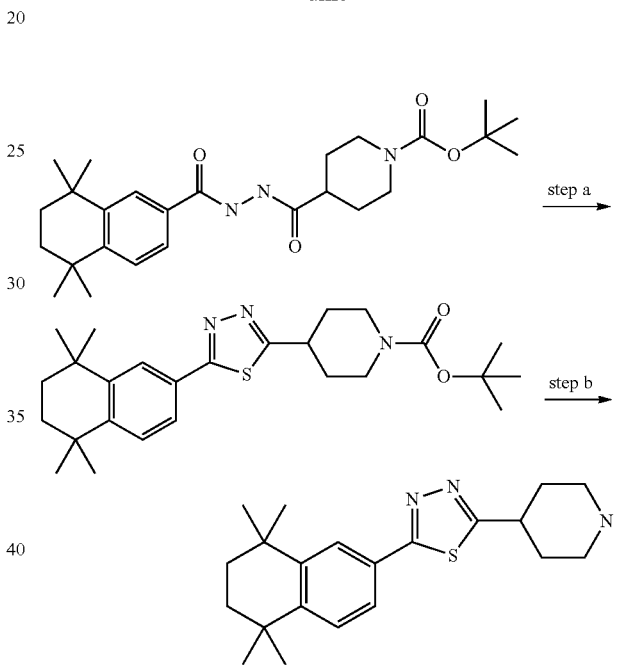

Step a:

The ring closure was carried out as already described starting from 100 mg (0.22 mmol) of 4-[N'-(5,5,8,8-tetramethyl-5,6,7,8-tetrahydronaphthalene-2-carbonyl)hydrazinocarbonyl]piperidine-1-carboxylic acid tert-butyl ester and 133 mg (0.33 mmol) of 2,4-bis(4-methoxyphenyl)-2,4-dithioxo-1,3,2,4-dithiadiphosphethane.

160 mg oil, Rt.=4.03 min (method A), LCMS: 456 (M+H).

Step b:

The protecting group was cleaved off as already described using HCl in methanol starting from 160 mg of product from step a.

20 mg oil, Rt.=2.82 min (method A), LCMS: 356 (M+H).

$^1$H NMR (400 MHz, DMSO/deuterated TFA) δ=7.80 (d, J=1.9, 1H), 7.59 (dd, J=8.2, 1.9, 1H), 7.40 (d, J=8.3, 1H), 3.56-3.46 (m, 1H), 3.41-3.32 (m, 2H), 3.06 (td, J=12.6, 2.9, 2H), 2.24 (dd, J=14.3, 3.1, 2H), 2.08-1.94 (m, 2H), 1.64 (s, 4H), 1.22 (d, J=10.3, 12H).

Preparation of 4-{4-[5-(5,5,8,8-tetramethyl-5,6,7,8-tetrahydronaphthalen-2-yl)-1,3,4-thiadiazol-2-yl]piperidin-1-yl}butan-1-ol

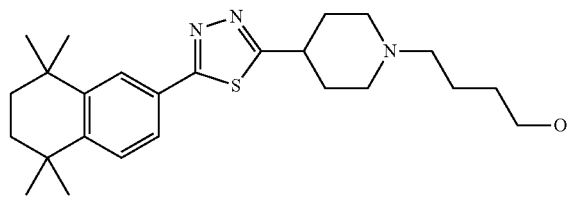 [SMILES: CC1(C)CCC(C)(C)c2cc(-c3nnc(C4CCN(CCCCO)CC4)o3)ccc21]

The preparation was carried out as already described starting from 125 mg (0.35 mmol) of 4-[5-(5,5,8,8-tetramethyl-5,6,7,8-tetrahydronaphthalen-2-yl)-1,3,4-thiadiazol-2-yl]piperidine and 76 µl (0.53 mmol) of 4-bromobutyl acetate. The protecting group was cleaved off by means of a 1N NaOH solution in methanol. The product was purified by means of preparative HPLC and converted into the hydrochloride by treatment with methanolic HCl.

66 mg, solid, LCMS: 428 [M+H], HPLC: Rt.=2.87 min (method A).

$^1$H NMR (500 MHz, DMSO/deuterated TFA) δ=7.90 (d, J=1.9, 1H), 7.72-7.65 (m, 1H), 7.53-7.48 (m, 1H), 4.49-4.41 (m, 1H), 3.80-3.66 (m, 2H), 3.63-3.49 (m, 2H), 3.31-3.14 (m, 4H), 2.41 (d, J=14.0, 2H), 2.24-2.12 (m, 2H), 1.92-1.80 (m, 3H), 1.73 (s, 4H), 1.61-1.52 (m, 1H), 1.32 (d, J=12.9, 12H).

Preparation of 5-{4-[5-(5,5,8,8-tetramethyl-5,6,7,8-tetrahydronaphthalen-2-yl)-1,3,4-thiadiazol-2-yl]piperidin-1-yl}pentan-1-ol

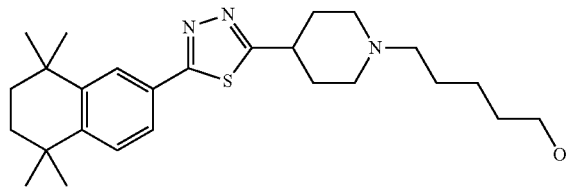

The preparation was carried out as already described via a reductive amination starting from 125 mg (0.35 mmol) of 4-[5-(5,5,8,8-tetramethyl-5,6,7,8-tetrahydronaphthalen-2-yl)-1,3,4-thiadiazol-2-yl]piperidine and 72 mg (0.70 mmol) of 5-hydroxypentanal. The product was purified by means of preparative HPLC and converted into the hydrochloride by treatment with methanolic HCl.

84 mg, solid, LCMS: 442 [M+H], HPLC: Rt.=2.90 min (method A).

$^1$H NMR (500 MHz, DMSO/deuterated TFA) δ=7.90 (d, J=1.9, 1H), 7.72-7.65 (m, 1H), 7.53-7.48 (m, 1H), 4.47-4.39 (m, 1H), 3.69 (d, J=13.6, 2H), 3.62-3.46 (m, 2H), 3.23-3.11 (m, 4H), 2.44-2.36 (m, 2H), 2.21-2.09 (m, 2H), 1.86-1.69 (m, 7H), 1.58-1.37 (m, 3H), 1.32 (d, J=12.7, 12H).

Preparation of 4-[5-(5,5,8,8-tetramethyl-5,6,7,8-tetrahydronaphthalen-2-yl)-1,3,4-oxadiazol-2-yl]piperidine

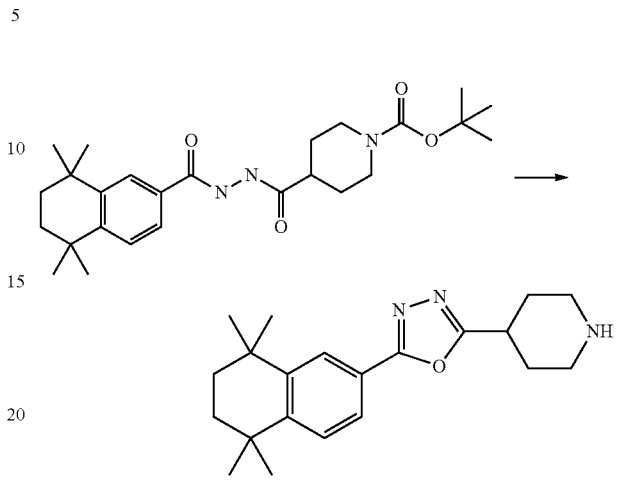

400 mg (0.87 mmol) of 4-[N'-(5,5,8,8-tetramethyl-5,6,7,8-tetrahydronaphthalene-2-carbonyl)hydrazinocarbonyl]piperidine-1-carboxylic acid tert-butyl ester were dissolved in 4 ml of phosphoryl chloride and stirred at 90° C. for 1 h. The reaction mixture was tipped into 120 ml of ice-water, rendered alkaline and extracted 3 times with diethyl ether. The organic phase was dried and stripped off to dryness.

124 mg, Rt.=2.74 min (method A), LCMS: 340 (M+H).

Preparation of 4-{4-[5-(5,5,8,8-tetramethyl-5,6,7,8-tetrahydronaphthalen-2-yl)-1,3,4-oxadiazol-2-yl]piperidin-1-yl}butan-1-ol

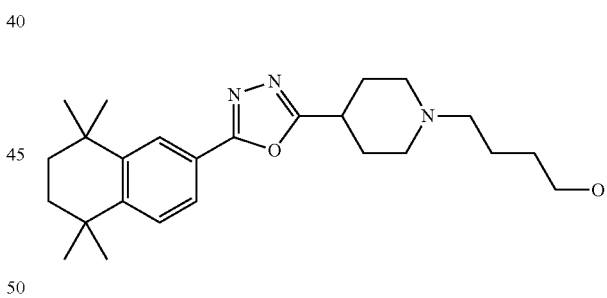

The preparation was carried out as already described starting from 75 mg (0.15 mmol) of 4-[5-(5,5,8,8-tetramethyl-5,6,7,8-tetrahydronaphthalen-2-yl)-1,3,4-oxadiazol-2-yl]piperidine and 33 µl (0.23 mmol) of 4-bromobutyl acetate. The protecting group was cleaved off by means of a 1N NaOH solution in methanol. The product was purified by means of preparative HPLC. The product is in the form of the TFA salt.

21 mg, solid, LCMS: 412 [M+H], HPLC: Rt.=2.76 min (method A).

$^1$H NMR (400 MHz, DMSO/deuterated TFA) δ=7.98-7.92 (m, 1H), 7.79-7.72 (m, 1H), 7.54 (d, J=8.3, 1H), 3.68 (d, J=12.5, 1H), 3.56-3.47 (m, 3H), 3.47-3.36 (m, 1H), 3.22-3.11 (m, 4H), 2.41 (d, J=12.5, 2H), 2.19-2.06 (m, 2H), 1.87-1.69 (m, 6H), 1.60-1.47 (m, 2H), 1.32 (d, J=8.6, 12H).

Preparation of 5-{4-[5-(5,5,8,8-tetramethyl-5,6,7,8-tetrahydronaphthalen-2-yl)-1,3,4-oxadiazol-2-yl]piperidin-1-yl}pentan-1-ol

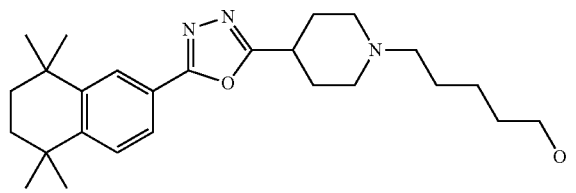 [SMILES: CC1(C)CCC(C)(C)c2cc(-c3nnc(C4CCN(CCCCCO)CC4)o3)ccc21]

The preparation was carried out as already described via a reductive amination starting from 50 mg (0.10 mmol) of 4-[5-(5,5,8,8-tetramethyl-5,6,7,8-tetrahydronaphthalen-2-yl)-1,3,4-oxadiazol-2-yl]piperidine and 21 mg (0.20 mmol) of 5-hydroxypentanal.

13 mg, oil, LCMS: 426 [M+H], HPLC: Rt.=2.78 min (method A).

$^1$H NMR (400 MHz, DMSO/deuterated TFA) δ=7.96 (dd, J=11.5, 1.8, 1H), 7.79-7.73 (m, 1H), 7.53 (d, J=8.3, 1H), 3.73-3.57 (m, 2H), 3.55-3.35 (m, 3H), 3.26-3.08 (m, 4H), 2.41 (d, J=12.9, 2H), 2.35-2.07 (m, 2H), 1.83-1.66 (m, 6H), 1.59-1.49 (m, 2H), 1.48-1.37 (m, 2H), 1.32 (d, J=8.6, 12H).

Preparation of 4-[3-(5,5,8,8-tetramethyl-5,6,7,8-tetrahydronaphthalen-2-yl)-1,2,4-oxadiazol-5-yl]piperidine

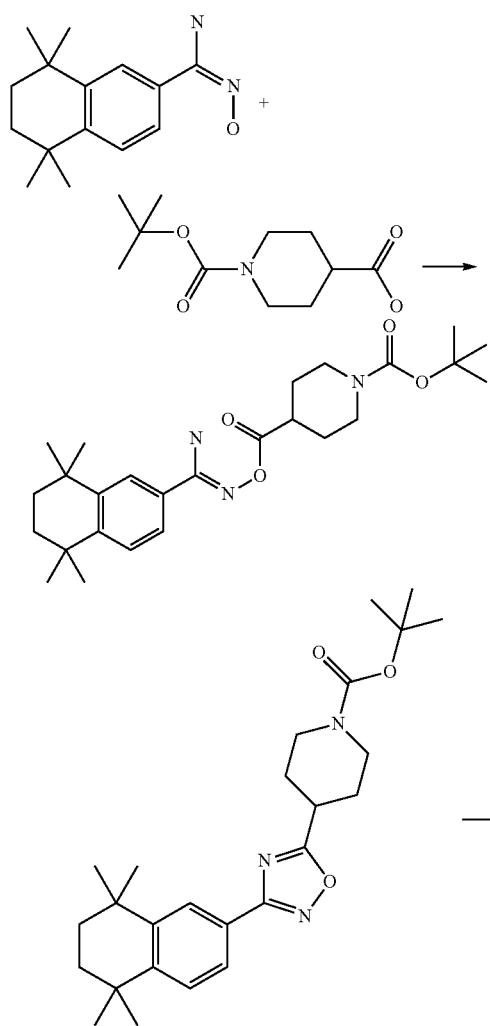

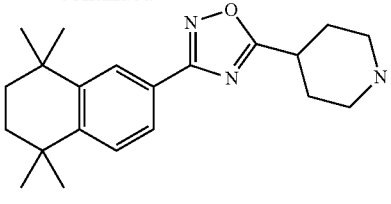

Step a:

The preparation was carried out as already described using EDCI and HOBt in DMF starting from 751 mg (3.05 mmol) of N-hydroxy-5,5,8,8-tetramethyl-5,6,7,8-tetrahydronaphthalene-2-carboxamidine (preparation already described above) and 769 mg (3.35 mmol) of piperidine-1,4-dicarboxylic acid mono-tert-butyl ester.

924 mg, oil, Rt.=3.52 min (method A), LCMS: 458 (M+H).

Step b:

The preparation was carried out as already described using Burgess reagent starting from 100 mg (0.18 mmol) of the product from step b.

37 mg solid, Rt.=4.15 min (method A).

Step c:

The protecting group was cleaved off as already described using HCl in methanol starting from the product from step c. The product is in the form of the hydrochloride.

7 mg, solid, Rt.=2.91 min (method A), LCMS: 340 (M+H).

$^1$H NMR (400 MHz, DMSO/deuterated TFA) δ=8.00 (d, J=1.8, 1H), 7.78 (dd, J=8.2, 1.8, 1H), 7.50 (d, J=8.3, 1H), 3.57-3.47 (m, 3H), 3.44 (dt, J=12.7, 3.6, 2H), 3.16 (td, J=12.7, 3.0, 2H), 2.33 (dd, J=14.4, 3.5, 2H), 2.20-2.05 (m, 2H), 1.73 (s, 4H), 1.31 (d, J=6.8, 12H).

Preparation of 4-{4-[3-(5,5,8,8-tetramethyl-5,6,7,8-tetrahydronaphthalen-2-yl)-1,2,4-oxadiazol-5-yl]piperidin-1-yl}butan-1-ol

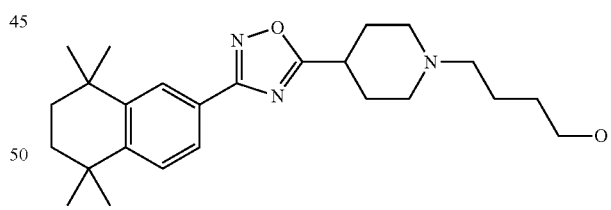

The preparation was carried out as already described starting from 95 mg (0.25 mmol) of 4-[3-(5,5,8,8-tetramethyl-5,6,7,8-tetrahydronaphthalen-2-yl)-1,2,4-oxadiazol-5-yl]piperidine hydrochloride and 55 µl (0.38 mmol) of 4-bromobutyl acetate. The protecting group was cleaved off by means of a 1N NaOH solution in methanol. The product was purified by means of preparative HPLC and is in the form of the hydrochloride.

55 mg, solid, LCMS: 412 [M+H], HPLC: Rt.=2.91 min (method A).

$^1$H NMR (400 MHz, DMSO/deuterated TFA) δ=7.96-7.89 (m, 1H), 7.76-7.67 (m, 1H), 7.49-7.43 (m, 1H), 3.62 (d, J=12.2, 2H), 3.50-3.38 (m, 3H), 3.18-3.05 (m, 5H), 2.35 (d, J=12.5, 2H), 2.13-1.99 (m, 2H), 1.78-1.63 (m, 6H), 1.52-1.38 (m, 2H), 1.25 (d, J=5.1, 12H).

Preparation of 5-{4-[3-(5,5,8,8-tetramethyl-5,6,7,8-tetrahydronaphthalen-2-yl)-1,2,4-oxadiazol-5-yl]piperidin-1-yl}pentan-1-ol

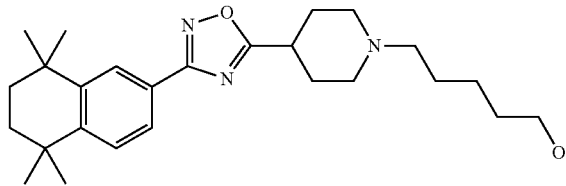 [SMILES: CC1(C)CCC(C)(C)c2cc(-c3noc(C4CCN(CCCCCO)CC4)n3)ccc21]

The preparation was carried out as already described via a reductive amination starting from 95 mg (0.26 mmol) of 4-[3-(5,5,8,8-tetramethyl-5,6,7,8-tetrahydronaphthalen-2-yl)-1,2,4-oxadiazol-5-yl]piperidine hydrochloride and 52 mg (0.51 mmol) of 5-hydroxypentanal.

78 mg, solid, LCMS: 426 [M+H], HPLC: Rt.=2.94 min (method A).

$^1$H NMR (400 MHz, DMSO/deuterated TFA) δ=7.95-7.89 (m, 1H), 7.75-7.66 (m, 1H), 7.46-7.39 (m, 1H), 3.65-3.55 (m, 2H), 3.47-3.35 (m, 3H), 3.17-3.01 (m, 4H), 2.38-2.01 (m, 4H), 1.73-1.59 (m, 6H), 1.51-1.28 (m, 4H), 1.27-1.20 (m, 12H).

Preparation of 4-[4-(5,8-dimethyl-5,6,7,8-tetrahydronaphthalen-2-yl)thiazol-2-yl]piperidine

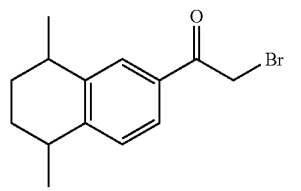

+

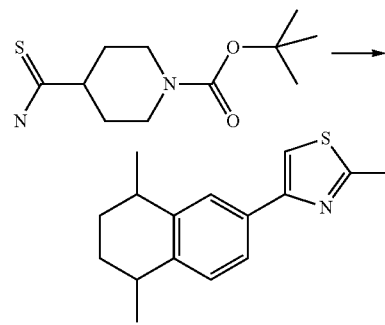

The preparation was carried out as already described starting from 1.09 g (2.05 mmol) of 2-bromo-1-(5,8-dimethyl-5,6,7,8-tetrahydronaphthalen-2-yl)ethanone and 500 mg (2.05 mmol) of 4-thiocarbamoylpiperidine-1-carboxylic acid tert-butyl ester. The product is in the form of the hydrobromide.

514 mg, solid, Rt.=2.55 min (method A), LCMS: 327 (M+H).

$^1$H NMR (400 MHz, DMSO/deuterated TFA) δ=7.92 (s, 1H), 7.77 (d, J=5.2, 1H), 7.74-7.64 (m, 1H), 7.25 (t, J=8.7, 1H), 3.50-3.40 (m, 3H), 3.19-3.04 (m, 2H), 2.99-2.81 (m, 2H), 2.29 (d, J=11.7, 2H), 2.08-1.92 (m, 3H), 1.91-1.79 (m, 1H), 1.67-1.53 (m, 1H), 1.52-1.40 (m, 1H), 1.36-1.22 (m, 6H).

Preparation of 4-{4-[4-(5,8-dimethyl-5,6,7,8-tetrahydronaphthalen-2-yl)thiazol-2-yl]piperidin-1-yl}butan-1-ol

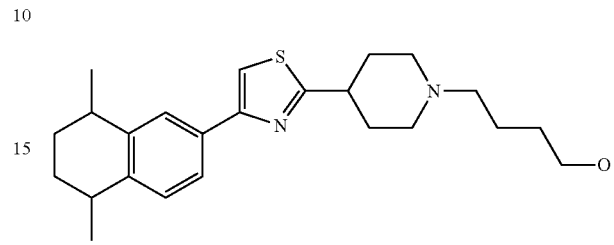

The preparation was carried out as already described starting from 150 mg (0.37 mmol) of 4-[4-(5,8-dimethyl-5,6,7,8-tetrahydronaphthalen-2-yl)thiazol-2-yl]-piperidine hydrobromide and 109 µl (0.74 mmol) of 4-bromobutyl acetate. The protecting group was cleaved off by means of a 1N sodium hydroxide solution in methanol. The product was purified by means of preparative HPLC and is in the form of the hydrochloride.

54 mg, white solid, LCMS: 399 [M+H], HPLC: Rt.=2.86 min (method A).

$^1$H NMR (500 MHz, DMSO/deuterated TFA) δ=7.92-7.83 (m, 1H), 7.79 (d, J=7.6, 1H), 7.75-7.66 (m, 1H), 7.26 (dd, J=11.6, 8.2, 1H), 3.67 (d, J=12.2, 2H), 3.54-3.39 (m, 3H), 3.22-3.11 (m, 4H), 2.99-2.84 (m, 2H), 2.38 (d, J=14.0, 2H), 2.13 (dd, J=23.6, 12.5, 2H), 2.07-1.98 (m, 1H), 1.92-1.72 (m, 3H), 1.66-1.44 (m, 4H), 1.36-1.24 (m, 6H).

Preparation of 5-{4-[4-(5,8-dimethyl-5,6,7,8-tetrahydronaphthalen-2-yl)thiazol-2-yl]piperidin-1-yl}pentan-1-ol

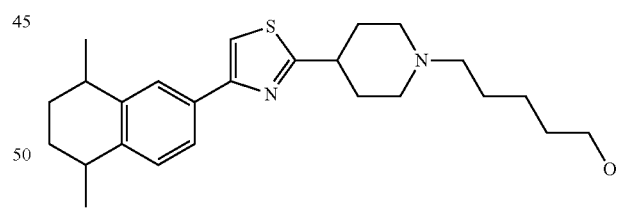

The preparation was carried out as already described via a reductive amination starting from 100 mg (0.25 mmol) of 4-[4-(5,8-dimethyl-5,6,7,8-tetrahydronaphthalen-2-yl)thiazol-2-yl]piperidine hydrobromide and 50 mg (0.49 mmol) of 5-hydroxypentanal. The product is in the form of the hydrochloride.

66 mg, white crystals, LCMS: 413 [M+H], HPLC: Rt.=2.89 min (method A).

$^1$H NMR (500 MHz, DMSO/deuterated TFA) δ=7.89 (dd, J=23.5, 1.2, 1H), 7.79 (d, J=6.6, 1H), 7.75-7.64 (m, 1H), 7.26 (dd, J=11.5, 8.2, 1H), 3.66 (d, J=12.5, 2H), 3.52-3.38 (m, 3H), 3.20-3.08 (m, 4H), 3.00-2.82 (m, 2H), 2.37 (d, J=13.3, 2H), 2.11 (dd, J=23.4, 12.6, 2H), 2.05-1.97 (m, 1H), 1.92-1.82 (m, 1H), 1.81-1.67 (m, 2H), 1.66-1.57 (m, 1H), 1.56-1.45 (m, 3H), 1.45-1.37 (m, 2H), 1.36-1.23 (m, 6H).

Preparation of 2-(4-{1-[4-(5,5-dimethyl-5,6,7,8-tetrahydronaphthalen-2-yl)thiazol-2-yl]piperidin-4-yl}piperazin-1-yl)ethanol

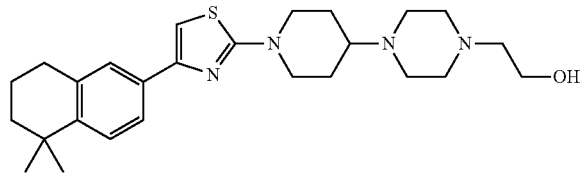 [SMILES: CC1(C)CCCc2cc(-c3csc(N4CCC(N5CCN(CCO)CC5)CC4)n3)ccc21]

The preparation was carried out as already described above in 2 steps starting from 200 mg (0.80 mmol) of 2-(4-piperidin-4-ylpiperazin-1-yl)ethanol hydrochloride. In the 2nd step, the ring closure was carried out starting from the corresponding urea and 103 mg (0.37 mmol) of 2-bromo-1-(5,5-dimethyl-5,6,7,8-tetrahydronaphthalen-2-yl)ethanone. The product was purified by means of preparative HPLC and is in the form of the hydrochloride.

13 mg, solid, Rt.=2.60 min (method A), LCMS: 455 (M+H).

$^1$H NMR (400 MHz, DMSO/deuterated TFA) δ=7.64 (d, J=8.2, 1H), 7.54 (s, 1H), 7.43 (d, J=8.3, 1H), 4.11 (d, J=12.7, 2H), 3.86-3.79 (m, 4H), 3.76-3.65 (m, 3H), 3.44-3.36 (m, 3H), 3.19 (t, J=12.4, 2H), 2.85-2.76 (m, 2H), 2.21 (d, J=10.4, 3H), 1.92-1.75 (m, 5H), 1.72-1.62 (m, 2H), 1.29 (s, 6H).

Preparation of 4-[4-(8-methyl-5,6,7,8-tetrahydronaphthalen-2-yl)thiazol-2-yl]piperidine-1-carboxylic acid tert-butyl ester

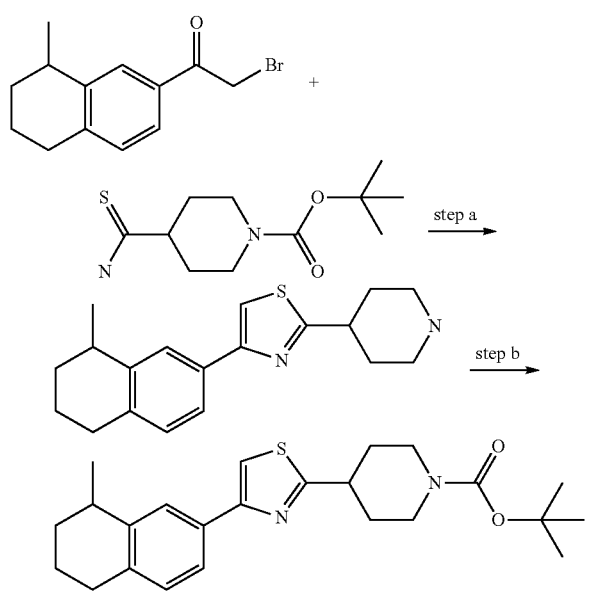

Step a:
The preparation was carried out as already described starting from 500 mg (2.05 mmol) of 2-bromo-1-(8-methyl-5,6,7,8-tetrahydronaphthalen-2-yl)ethanone and 500 mg (2.05 mmol) of 4-thiocarbamoylpiperidine-1-carboxylic acid tert-butyl ester. The product is in the form of the hydrobromide.

Solid, Rt.=2.48 min (method A), LCMS: 313 (M+H).
$^1$H NMR (500 MHz, DMSO/deuterated TFA) δ=7.87 (d, J=12.1, 1H), 7.83-7.61 (m, 2H), 7.19 (dd, J=76.4, 8.0, 1H), 3.50-3.40 (m, 3H), 3.12 (t, J=11.4, 2H), 2.99-2.87 (m, 1H), 2.84-2.70 (m, 2H), 2.29 (d, J=13.7, 2H), 2.08-1.97 (m, 2H), 1.96-1.82 (m, 2H), 1.77-1.66 (m, 1H), 1.59-1.49 (m, 1H), 1.30 (dd, J=18.0, 7.0, 3H).

Step b:
150 mg (0.38 mmol) of 4-[4-(8-methyl-5,6,7,8-tetrahydronaphthalen-2-yl)thiazol-2-yl]piperidine from step a were dissolved in 3 ml of DMF, 64 µl (0.46 mmol) of triethylamine and 98 µl of di-tert-butyl dicarbonate were added, and the mixture was stirred at room temperature for 2 h. The mixture was treated with a 10% citric acid solution and extracted 3 times with DCM. The organic phase was dried, filtered and stripped off to dryness.

200 mg, brown oil, Rt.=4.15 min (method A), LCMS: 413 (M+H).

4 enantiomers were isolated from the racemic mixture by means of chiral chromatography. For each enantiomer, the protecting group was cleaved off as already described using HCl in methanol. The enantiomers are in the form of the hydrochloride.

4-[4-((S)-5-Methyl-5,6,7,8-tetrahydronaphthalen-2-yl)thiazol-2-yl]-piperidine

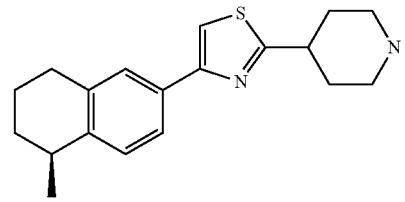 [SMILES: C[C@H]1CCCc2cc(-c3csc(C4CCNCC4)n3)ccc21]

2 mg, solid, Rt.=2.73 min (method A), LCMS: 313 (M+H).

4-[4-((R)-5-Methyl-5,6,7,8-tetrahydronaphthalen-2-yl)thiazol-2-yl]piperidine

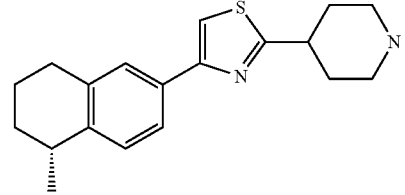 [SMILES: C[C@@H]1CCCc2cc(-c3csc(C4CCNCC4)n3)ccc21]

3 mg, solid, Rt.=2.73 min (method A), LCMS: 313 (M+H).

4-[4-((S)-8-Methyl-5,6,7,8-tetrahydronaphthalen-2-yl)thiazol-2-yl]-piperidine

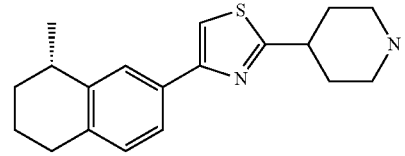 [SMILES: C[C@H]1CCCc2ccc(-c3csc(C4CCNCC4)n3)cc21]

3 mg, solid, Rt.=2.72 min (method A), LCMS: 313 (M+H).

4-[4-((R)-8-Methyl-5,6,7,8-tetrahydronaphthalen-2-yl)thiazol-2-yl]piperidine

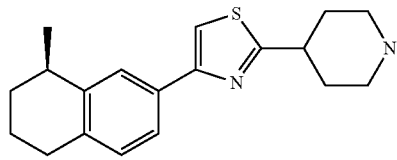 [SMILES: C[C@@H]1CCCc2ccc(-c3csc(C4CCNCC4)n3)cc21]

3 mg, solid, Rt.=2.72 min (method A), LCMS: 313 (M+H).

Preparation of 1-[4-(5,5,8,8-tetramethyl-5,6,7,8-tetrahydronaphthalen-2-yl)thiazol-2-yl]piperidine-4-carboxylic acid

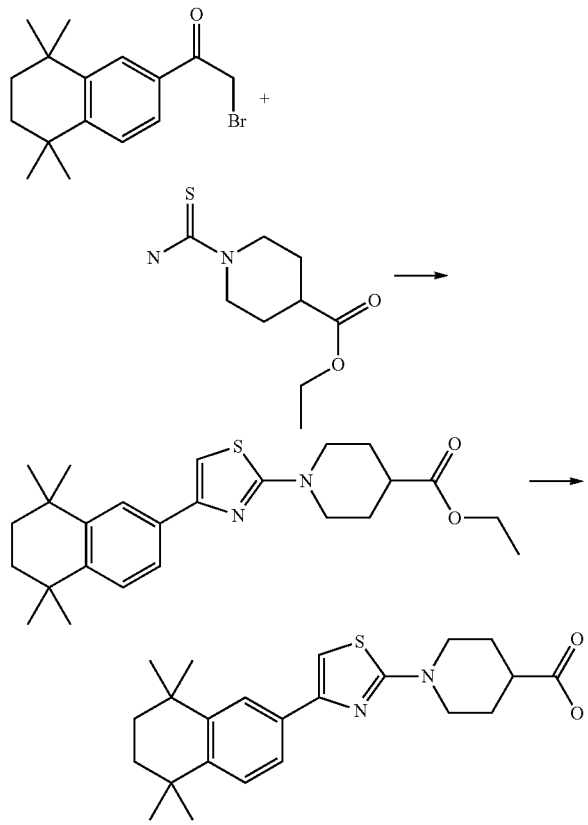

Step a:

The preparation is carried out as already described starting from 4.9 g (11.56 mmol) of 2-bromo-1-(8-methyl-5,6,7,8-tetrahydronaphthalen-2-yl)ethanone and 2.5 g (11.56 mmol) of 1-thiocarbamoylpiperidine-4-carboxylic acid ethyl ester. The product is in the form of the hydrobromide.

4.5 g, green solid, Rt.=3.56 min (method A), LCMS: 427 (M+H).

Step b:

3.5 g (6.90 mmol) of 1-[4-(5,5,8,8-tetramethyl-5,6,7,8-tetrahydronaphthalen-2-yl)thiazol-2-yl]piperidine-4-carboxylic acid ethyl ester hydrobromide from step a were slurried in 25 ml of THF, 21 ml of water and 843 mg (34.48 mmol) of lithium hydroxide were added, and the mixture was stirred at room temperature overnight. The reaction mixture was evaporated in a rotary evaporator, adjusted to pH=1 using a 1N hydrochloric acid solution and then extracted twice with EA. The combined organic phases were dried over sodium sulfate, filtered and evaporated.

2.7 g, green foam, Rt.=3.09 min (method A), LCMS: 399 (M+H).

$^1$H NMR (400 MHz, DMSO/deuterated TFA) δ=7.60 (d, J=1.7, 1H), 7.50-7.41 (m, 2H), 4.05 (d, J=13.3, 2H), 3.60-3.48 (m, 2H), 2.74-2.65 (m, 1H), 2.11 (dd, J=13.7, 3.5, 2H), 1.93-1.80 (m, 2H), 1.72 (s, 4H), 1.31 (d, J=12.7, 14H).

Preparation of 2-({1-[4-(5,5,8,8-tetramethyl-5,6,7,8-tetrahydronaphthalen-2-yl)thiazol-2-yl]piperidin-4-ylmethyl}amino)ethanol

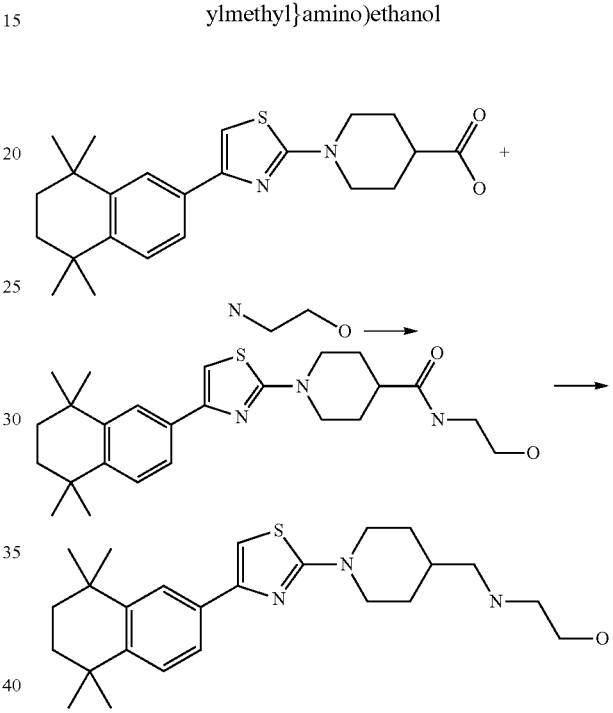

Step a:

200 mg (0.50 mmol) of 1-[4-(5,5,8,8-tetramethyl-5,6,7,8-tetrahydronaphthalen-2-yl)thiazol-2-yl]piperidine-4-carboxylic acid are dissolved in 6 ml of DMF, and 112 µl (1.00 mmol) of N-methylmorpholine, 194 mg (1.00 mmol) of N-(3-dimethylaminopropyl)-N'-ethylcarbodiimide hydrochloride and 140 mg (1.00 mmol) of 1-hydroxybenzotriazole hydrate are added. The solution is stirred at room temperature for 30 min, then 36 µl (0.60 mmol) of ethanolamine are added, and the mixture is stirred further at room temperature overnight. About 10 ml of a 1N hydrochloric acid solution were added to the reaction mixture, which was then extracted with EA. The water phase was subsequently rendered alkaline using a 1 M sodium hydroxyide solution and extracted twice with EA. The last organic phases were combined, dried using sodium sulfate, filtered and evaporated. The product was purified by means of preparative HPLC and is in the form of the TFA salt.

126 mg, solid, LCMS: 442 [M+H], HPLC: Rt.=2.87 min (method A).

Step b:

The preparation was carried out as already described using 350 µl (0.35 mmol) of a 1N lithium aluminium hydride solution in THF starting from 126 mg (0.23 mmol) of 1-[4-(5,5,8,8-tetramethyl-5,6,7,8-tetrahydronaphthalen-2-yl)thiazol-2-yl]-piperidine-4-carboxylic acid (2-hydroxyethyl)amide from step a. The product was purified by means of preparative HPLC and is in the form of the TFA salt.

36 mg, green oil, LCMS: 428 [M+H], HPLC: Rt.=2.73 min (method A).

$^1$H NMR (500 MHz, DMSO/deuterated TFA) δ=7.56 (s, 1H), 7.40 (s, 2H), 4.05 (d, J=13.2, 2H), 3.72-3.62 (m, 2H), 3.35 (t, J=11.5, 2H), 3.05-2.98 (m, 2H), 2.90 (d, J=6.8, 2H), 2.12-2.02 (m, 1H), 1.93 (d, J=11.2, 2H), 1.65 (s, 4H), 1.47-1.36 (m, 2H), 1.24 (d, J=15.2, 12H).

Preparation of 2-(methyl-{1-[4-(5,5,8,8-tetramethyl-5,6,7,8-tetrahydronaphthalen-2-yl)thiazol-2-yl]piperidin-4-ylmethyl}amino)ethanol

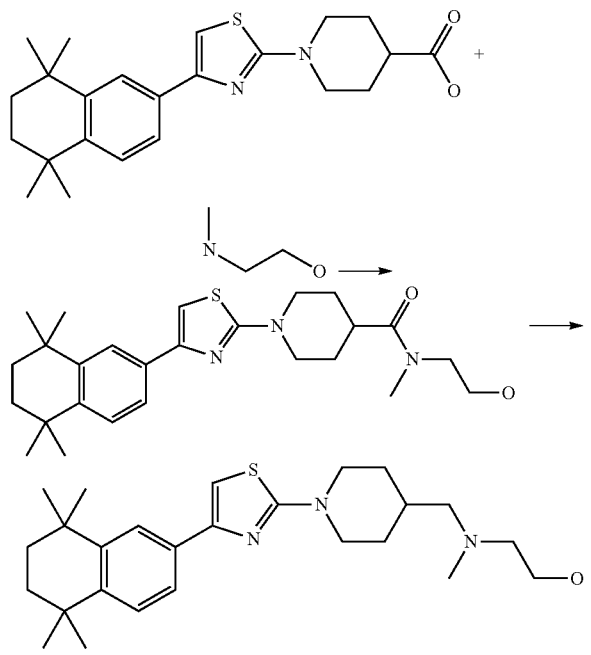

Step a:

The preparation was carried out analogously starting from 80 mg (0.20 mmol) of 1-[4-(5,5,8,8-tetramethyl-5,6,7,8-tetrahydronaphthalen-2-yl)thiazol-2-yl]-piperidine-4-carboxylic acid and 19 µl (0.24 mmol) of 2-methylaminoethanol.

114 mg, yellow oil, LCMS: 456 [M+H], HPLC: Rt.=2.93 min (method A).

Step b:

The reduction was carried out as already described using 375 µl (0.38 mmol) of a 1N lithium aluminium hydride solution in THF starting from 114 mg (0.25 mmol) of 1-[4-(5,5,8,8-tetramethyl-5,6,7,8-tetrahydronaphthalen-2-yl)thiazol-2-yl]piperidine-4-carboxylic acid (2-hydroxyethyl)methylamide from step a. The product was purified by means of preparative HPLC and is in the form of the hydrochloride.

31 mg, grey oil, LCMS: 442 [M+H], HPLC: Rt.=2.77 min (method A).

$^1$H NMR (500 MHz, DMSO/deuterated TFA) δ=7.61 (d, J=1.7, 1H), 7.50-7.42 (m, 2H), 4.14 (d, J=13.0, 2H), 3.87-3.78 (m, 2H), 3.46 (t, J=13.0, 2H), 3.39-3.30 (m, 1H), 3.27-3.18 (m, 2H), 3.10-3.02 (m, 1H), 2.91 (s, 3H), 2.34-2.22 (m, 1H), 2.02 (dd, J=41.6, 12.5, 2H), 1.72 (s, 4H), 1.57-1.44 (m, 2H), 1.31 (d, J=15.1, 13H).

3-({1-[4-(5,5,8,8-Tetramethyl-5,6,7,8-tetrahydronaphthalen-2-yl)thiazol-2-yl]piperidin-4-ylmethyl}amino)propan-1-ol

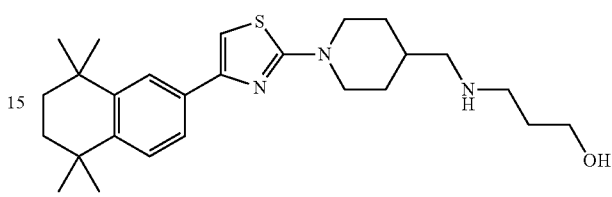

The preparation was carried out analogously to the processes described above.

16 mg, yellow oil, LCMS: 442 [M+H], HPLC: Rt.=2.66 min (method A).

$^1$H NMR (500 MHz, DMSO/deuterated TFA) δ 7.58 (s, 1H), 7.42 (s, 2H), 4.08 (d, J=13.2 Hz, 2H), 3.54 (t, J=5.8 Hz, 2H), 3.40 (dd, J=23.5, 8.6 Hz, 2H), 3.08-2.98 (m, 2H), 2.91 (d, J=6.8 Hz, 2H), 2.07 (s, 1H), 1.95 (d, J=11.7 Hz, 2H), 1.80 (dt, J=12.5, 6.1 Hz, 2H), 1.67 (s, 4H), 1.45 (dd, J=20.8, 11.8 Hz, 2H), 1.27 (d, J=12.1 Hz, 12H).

Preparation of 4-((2-hydroxyethyl)-{1-[4-(5,5,8,8-tetramethyl-5,6,7,8-tetrahydronaphthalen-2-yl)thiazol-2-yl]piperidin-4-yl}amino)butan-1-ol

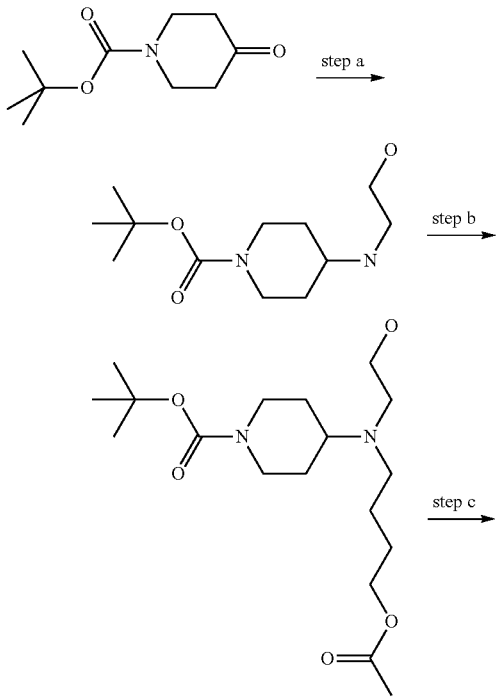

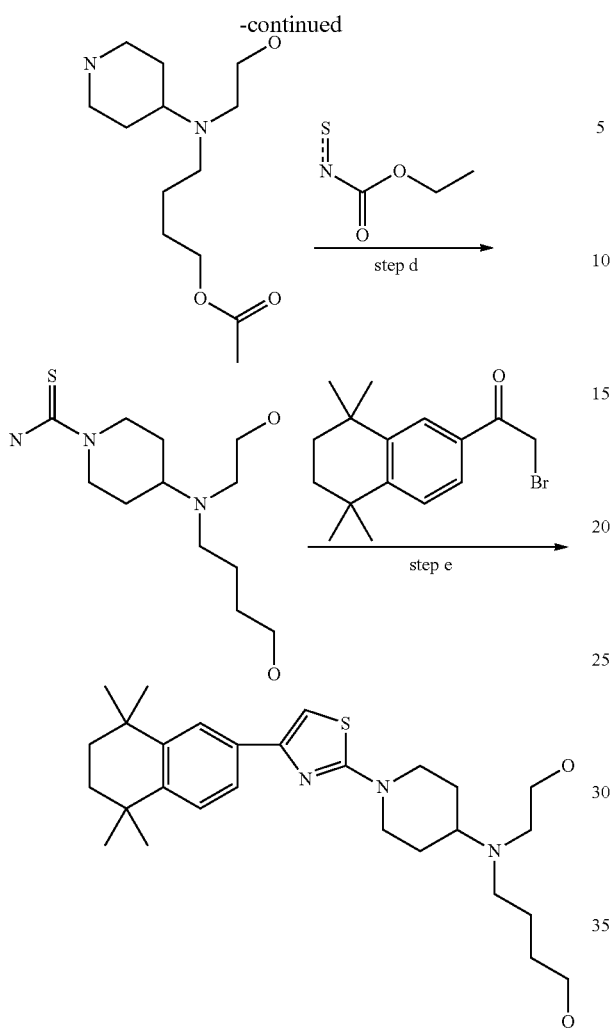

Step a:
The preparation was carried out via a reduction amination (as already described) starting from 5 g (25.1 mmol) of 4-oxopiperidine-1-carboxylic acid tert-butyl ester and 1.50 ml (25.1 mmol) of ethanolamine.

4.15 g, residue, LCMS: 245 (M+H).

Step b:
The preparation was carried out as already described starting from 400 mg (1.64 mmol) of 4-(2-hydroxyethylamino)piperidine-1-carboxylic acid tert-butyl ester from step a and 1.42 ml (9.8 mmol) of 4-bromobutyl acetate.

1.65 g, residue, LCMS: 359 [M+H].

Step c:
The protecting group was cleaved off as already described using HCl in dioxane starting from 758 mg (2.12 mmol) of 4-[(4-acetoxybutyl)-(2-hydroxyethyl)amino]piperidine-1-carboxylic acid tert-butyl ester from step b. The product is in the form of the hydrochloride.

657 mg, residue, LCMS: 259 (M+H).

Step d:
The preparation was carried out as already described starting from 500 mg (1.78 mmol) of acetic acid 4-[(2-hydroxyethyl)piperidin-4-ylamino]butyl ester hydrochloride from step c and 217 µl (1.78 mmol) of ethoxycarbonyl isothiocyanate.

1.08 g, residue.

Step e:
The preparation was carried out as already described starting from 800 mg (1.01 mmol) of 2-bromo-1-(5,5,8,8-tetramethyl-5,6,7,8-tetrahydronaphthalen-2-yl)ethanone and 452 mg (1.01 mmol) of 4-[(4-hydroxybutyl)-(2-hydroxyethyl)amino]-piperidine-1-carbothioic acid amide from step d. The product was purified by means of preparative HPLC and is in the form of the hydrochloride.

6 mg, solid, Rt.=2.89 min (method A), LCMS: 486 (M+H).

$^1$H NMR (400 MHz, DMSO/deuterated TFA) δ=7.63 (s, 1H), 7.50-7.41 (m, 2H), 4.32-4.19 (m, 2H), 3.97 (s, 1H), 3.83 (t, J=5.0, 3H), 3.58-3.36 (m, 5H), 3.29-3.15 (m, 10H), 2.32-2.19 (m, 2H), 2.10-1.96 (m, 2H), 1.94-1.80 (m, 2H), 1.72 (s, 4H), 1.61-1.52 (m, 2H), 1.31 (d, J=12.1, 12H).

Preparation of 4-[{1-[5-bromo-4-(5,5,8,8-tetramethyl-5,6,7,8-tetrahydronaphthalen-2-yl)thiazol-2-yl]piperidin-4-yl}-(2-hydroxyethyl)amino]butan-1-ol

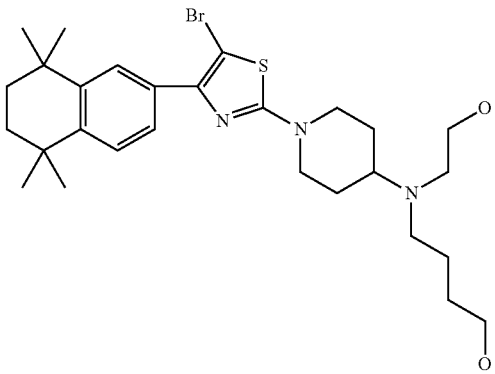 [SMILES: CC1(C)CCC(C)(C)c2cc(-c3nc(N4CCC(N(CCO)CCCCO)CC4)sc3Br)ccc21]

The product is a by-product of the preparation of 4-((2-hydroxyethyl)-{1-[4-(5,5,8,8-tetramethyl-5,6,7,8-tetrahydronaphthalen-2-yl)thiazol-2-yl]piperidin-4-yl}-amino)butan-1-ol. The product was purified by means of preparative HPLC and is in the form of the hydrochloride.

11 mg, solid, Rt.=3.26 min (method A), LCMS: 564 (M+H).

$^1$H NMR (500 MHz, DMSO/deuterated TFA) δ=7.83 (d, J=1.8, 1H), 7.60 (td, J=8.6, 1.8, 1H), 7.40 (d, J=8.3, 1H), 4.07 (d, J=12.7, 2H), 3.80 (t, J=5.1, 2H), 3.75-3.67 (m, 1H), 3.51 (t, J=6.1, 2H), 3.44-3.33 (m, 1H), 3.28-3.13 (m, 5H), 2.24-2.11 (m, 2H), 1.86 (dd, J=26.3, 10.0, 4H), 1.71 (s, 4H), 1.59-1.48 (m, 2H), 1.34-1.27 (m, 12H).

Preparation of 5-((2-hydroxyethyl)-{1-[4-(5,5,8,8-tetramethyl-5,6,7,8-tetrahydronaphthalen-2-yl)thiazol-2-yl]piperidin-4-yl}amino)pentan-1-ol

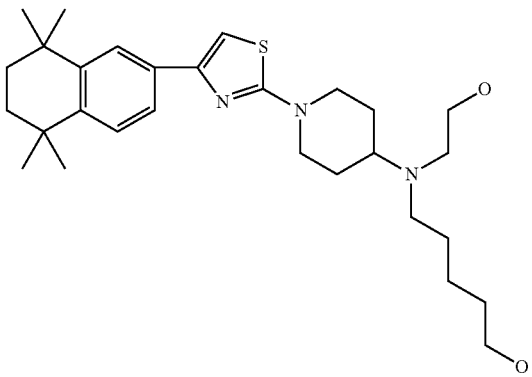 [SMILES: CC1(C)CCC(C)(C)c2cc(-c3csc(N4CCC(N(CCO)CCCCCO)CC4)n3)ccc21]

The preparation was carried out as described above starting from 460 mg (4.50 mmol) of 5-hydroxypentanal in step b. The product was purified by means of preparative HPLC and is in the form of the hydrochloride.

8 mg, solid, Rt.=2.93 min (method A), LCMS: 500 (M+H).

¹H NMR (400 MHz, DMSO/deuterated TFA) δ=7.62 (d, J=1.8, 1H), 7.49 (d, J=8.3, 1H), 7.44 (dd, J=8.2, 1.8, 1H), 4.32-4.22 (m, 2H), 3.84 (t, J=4.9, 3H), 3.59-3.48 (m, 4H), 3.25-3.14 (m, 3H), 2.28 (t, J=13.7, 2H), 2.13-1.96 (m, 2H), 1.86-1.77 (m, 2H), 1.73 (s, 4H), 1.61-1.52 (m, 2H), 1.49-1.39 (m, 2H), 1.32 (d, J=11.8, 13H).

Preparation of 1-[4-(5,5,8,8-tetramethyl-5,6,7,8-tetrahydronaphthalen-2-yl)thiazol-2-yl]piperidin-4-ol

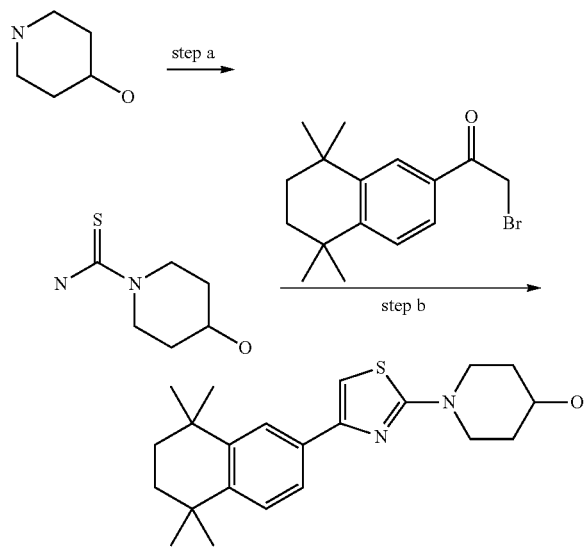

Step a:
The preparation of the thiourea was carried out as already described starting from 1 g (9.69 mmol) of piperidin-4-ol and 2 g (10.66 mmol) of 1,1'-thiocarbonyldiimidazole.
1.4 g, beige solid, Rt.=0.50 min (method A), LCMS: 161 (M+H).

Step b:
The preparation was carried out as already described starting from 397 mg (0.94 mmol) of 2-bromo-1-(5,5,8,8-tetramethyl-5,6,7,8-tetrahydronaphthalen-2-yl)ethanone and 100 mg (0.62 mmol) of 4-hydroxypiperidine-1-carbothioic acid amide from step a. The product was purified by means of preparative HPLC and is in the form of the hydrochloride.
17 mg, beige solid, Rt.=3.01 min (method A), LCMS: 371 (M+H).
¹H NMR (400 MHz, DMSO/deuterated TFA) δ=7.61 (d, J=1.7, 1H), 7.50-7.41 (m, 2H), 3.97-3.88 (m, 3H), 3.68-3.58 (m, 2H), 2.01-1.91 (m, 2H), 1.76-1.63 (m, 7H), 1.31 (d, J=12.8, 12H).

Preparation of 4-[4-(5,5,8,8-tetramethyl-5,6,7,8-tetrahydronaphthalen-2-yl)-1,2,3-triazol-1-yl]piperidine

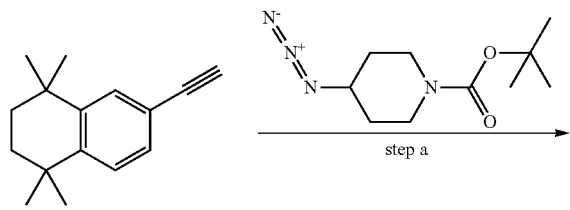

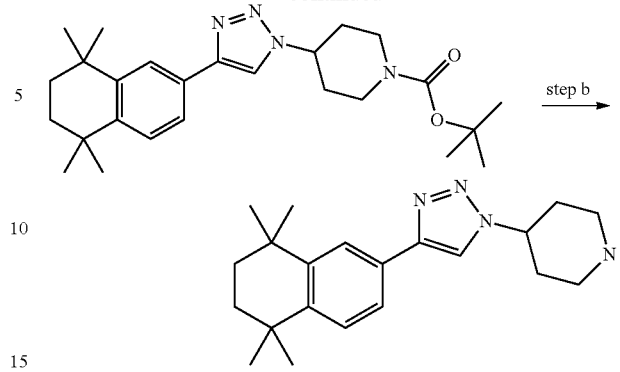

Step a:
100 mg (0.44 mmol) of 6-ethynyl-1,1,4,4-tetramethyl-1,2,3,4-tetrahydronaphthalene (preparation already described above), 94 mg (0.44 mmol) of 4-azidopiperidine-1-carboxylic acid tert-butyl ester (preparation analogous to Bioorganic and Medicinal Chemistry Letters, 2009, vol. 19, #13, p. 3564-3567), 3 mg (0.04 mmol) of copper (finely powdered), 61 mg (0.44 mmol) of triethylammonium chloride were suspended in 300 µl of tert-butanol and 300 µl of water and stirred at room temperature overnight. The reaction mixture was filtered off, and water and DCM were added. The phases were separated. The organic phase was dried over sodium sulfate, filtered and evaporated.
120 mg, brown oil, Rt.=3.82 min (method A), LCMS: 439 (M+H).

Step b:
The protecting group was cleaved off as already described using HCl in dioxane starting from 120 mg (0.27 mmol) of 4-[4-(5,5,8,8-tetramethyl-5,6,7,8-tetrahydronaphthalen-2-yl)-1,2,3-triazol-1-yl]piperidine-1-carboxylic acid tert-butyl ester from step a. The product was purified by means of preparative HPLC and is in the form of the hydrochloride.
11 mg, white solid, Rt.=2.82 min (method A), LCMS: 339 (M+H).
¹H NMR (400 MHz, DMSO/deuterated TFA) δ=8.62 (s, 1H), 7.82 (d, J=1.8, 1H), 7.63 (dd, J=8.2, 1.8, 1H), 7.40 (d, J=8.3, 1H), 4.94-4.82 (m, 1H), 3.50 (d, J=13.4, 2H), 3.21 (t, J=11.0, 2H), 2.45-2.37 (m, 2H), 2.36-2.23 (m, 2H), 1.70 (s, 4H), 1.30 (d, J=16.3, 12H).

Preparation of 4-{4-[4-(5,5,8,8-tetramethyl-5,6,7,8-tetrahydronaphthalen-2-yl)-1,2,3-triazol-1-yl]piperidin-1-yl}butan-1-ol

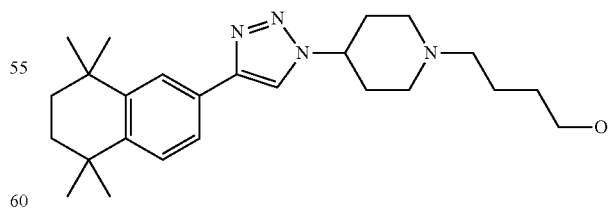

The preparation was carried out as already described starting from 24 mg (0.06 mmol) of 4-[4-(5,5,8,8-tetramethyl-5,6,7,8-tetrahydronaphthalen-2-yl)-1,2,3-triazol-1-yl]piperidine hydrochloride and 13 µl (0.11 mmol) of acetic acid 4-chlorobutyl ester. The protecting group was cleaved off by means of a 1N sodium hydroxide solution in methanol. The product was purified by means of preparative HPLC and is in the form of the hydrochloride.

10 mg, yellow oil, LCMS: 411 [M+H], HPLC: Rt.=2.79 min (method A).

¹H NMR (500 MHz, DMSO) δ=8.73-8.56 (m, 1H), 7.82 (d, J=1.7, 1H), 7.66-7.60 (m, 1H), 7.41 (dd, J=8.2, 4.3, 1H), 5.00-4.82 (m, 1H), 3.73 (d, J=12.3, 1H), 3.57-3.45 (m, 3H), 3.31-3.15 (m, 6H), 2.50 (d, J=13.3, 1H), 2.43-2.31 (m, 2H), 1.85-1.75 (m, 2H), 1.70 (s, 4H), 1.59-1.50 (m, 2H), 1.29 (t, J=14.7, 14H).

Preparation of (2R,3R)-3-amino-4-{1-[4-(5,5,8,8-tetramethyl-5,6,7,8-tetrahydronaphthalen-2-yl)thiazol-2-yl]piperidin-4-ylamino}butan-2-ol

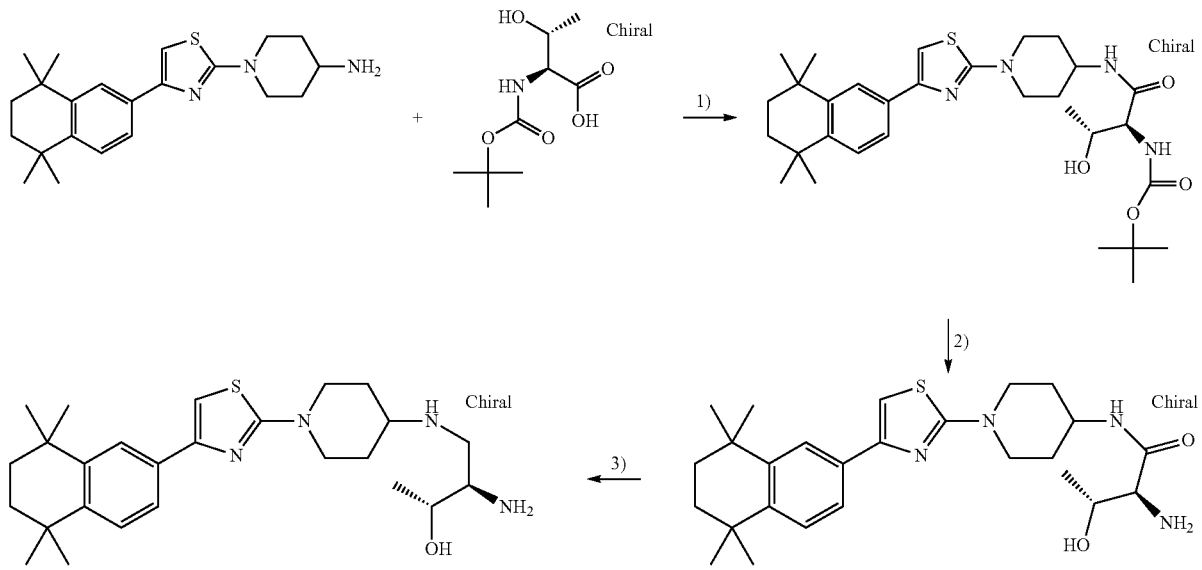

Step 1:

190 mg (0.47 mmol) of 1-[4-(5,5,8,8-tetramethyl-5,6,7,8-tetrahydronaphthalen-2-yl)thiazol-2-yl]piperidin-4-ylamine, 113 mg (0.51 mmol) of N-(tert-butoxycarbonyl)-L-threonine, 86 mg (0.56 mmol) of HOBt, 108 mg (0.56 mmol) of N-(3-dimethylaminopropyl)-N'-ethylcarbodiimide hydrochloride and 240 μl (1.40 mmol) of DIPEA are dissolved in 5 ml of THF and stirred at room temperature for 18 h. Water was added to the crude product, the mixture was extracted with ethyl acetate and purified by column chromatography and silica gel Yield: 280 mg, yellow oil. Rt.=3.22 min (method A), LCMS: 571 (M+H).

Step 2:

281 mg (0.37 mmol) of ((1S,2R)-2-hydroxy-1-{1-[4-(5,5,8,8-tetramethyl-5,6,7,8-tetrahydronaphthalen-2-yl)thiazol-2-yl]piperidin-4-ylcarbamoyl}propyl)carbamic acid tert-butyl ester are dissolved in 2 ml of methanol, and 1 ml of 4N HCl in dioxane is added. The reaction mixture is stirred at room temperature for 12 h, evaporated and purified by means of preparative HPLC. The product is converted into the hydrochloride using methanolic HCl.

Yield: 180 mg, beige solid. Rt.=2.74 min (method A), LCMS: 471 (M+H).

Step 3:

115 mg (0.18 mmol) of (2S,3R)-2-amino-3-hydroxy-N-{1-[4-(5,5,8,8-tetramethyl-5,6,7,8-tetrahydronaphthalen-2-yl)thiazol-2-yl]piperidin-4-yl}butyramide was dissolved in 3 ml of THF, and 272 μl (0.54 mmol) of 2M borane dimethyl sufide solution in THF were added at 70° C. under nitrogen atmosphere, and the mixture was subsequently stirred at 70° C. for 2 hours. In order to decompose the excess borane, 1 ml of MeOH was added dropwise. The reaction mixture was evaporated, and 1 ml of water and 1 ml of conc HCl were added to the oily residue. The mixture was stirred at room temperature for 2 h, rendered alkaline using 2 molar NaOH and extracted with ethyl acetate. The organic phase was dried and purified by column chromatography on silica gel.

Yield: 10 mg, solid. Rt.=2.63 min (method A), LCMS: 457 (M+H).

¹H NMR (500 MHz, DMSO/deuterated TFA) δ 7.64 (d, J=1.9 Hz, 1H), 7.46 (dd, J=8.2, 1.9 Hz, 1H), 7.39 (d, J=8.3 Hz, 1H), 4.16 (d, J=13.4 Hz, 2H), 3.96-3.89 (m, 1H), 3.57-3.47 (m, 1H), 3.41-3.31 (m, 4H), 3.21 (dd, J=13.0, 6.8 Hz, 1H), 2.22 (t, J=12.9 Hz, 2H), 1.86-1.74 (m, 2H), 1.67 (s, 4H), 1.27 (t, J=11.8 Hz, 12H), 1.22 (t, J=8.0 Hz, 3H).

Morpholine-2-carboxylic acid {1-[4-(5,5,8,8-tetramethyl-5,6,7,8-tetrahydronaphthalen-2-yl)thiazol-2-yl]piperidin-4-yl}amide

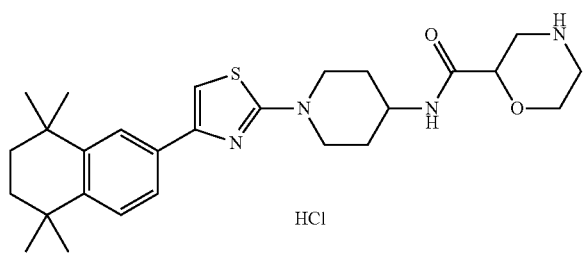 [SMILES: CC1(C)CCC(C)(C)c2cc(-c3csc(N4CCC(NC(=O)C5CNCCO5)CC4)n3)ccc21 ; Cl]

Preparation as described above starting from -[4-(5,5,8,8-tetramethyl-5,6,7,8-tetrahydronaphthalen-2-yl)thiazol-2-yl]piperidin-4-ylamine and morpholine-2,4-dicarboxylic acid 4-tert-butyl ester.

Yield: 110 mg, solid. Rt.=2.73 min (method A), LCMS: 483 (M+H).

$^1$H NMR (500 MHz, DMSO/deuterated TFA) δ 7.60 (s, 1H), 7.45-7.40 (m, 2H), 4.26 (dd, J=10.7, 2.8 Hz, 1H), 4.10-3.98 (m, 4H), 3.86-3.77 (m, 1H), 3.54-3.44 (m, 3H), 3.23 (d, J=12.9 Hz, 1H), 3.11-2.97 (m, 2H), 1.98-1.85 (m, 2H), 1.83-1.70 (m, 2H), 1.67 (s, 4H), 1.33-1.21 (m, 12H).

4-{1-[4-(5,5,8,8-Tetramethyl-5,6,7,8-tetrahydronaphthalen-2-yl)thiazol-2-yl]-piperidin-4-ylamino}butyric acid

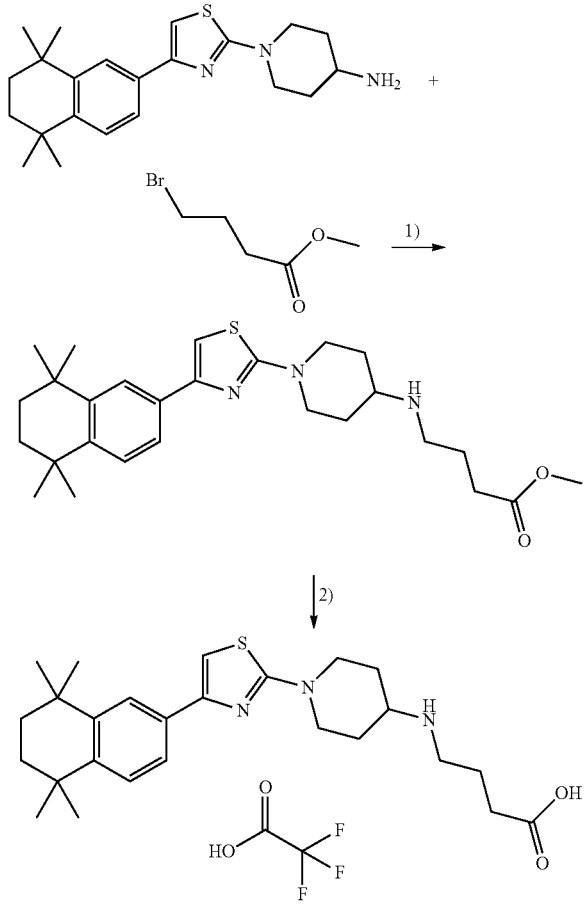

Step 1:

120 mg (0.30 mmol) of 1-[4-(5,5,8,8-tetramethyl-5,6,7,8-tetrahydronaphthalen-2-yl)thiazol-2-yl]piperidin-4-ylamine, 107 mg (0.59 mmol) of methyl 4-bromobutyrate, 481 mg (1.47 mmol) of caesium carbonate and 44 mg (0.30 mmol) of sodium iodide are suspended in 2 ml of NMP and stirred at 110° C. for 18 h. Water is added to the reaction mixture, which is then extracted a number of times with ethyl acetate, dried and evaporated. The product is purified by means of column chromatography on silica gel.

Yield: 45 mg. Rt.=2.89 min (method A), LCMS: 470 (M+H).

Step 2:

45 mg (0.08 mmol) of the ester prepared above are suspended in 2.5 ml of THF and 0.25 ml of water, and 10 mg (0.41 mmol) of lithium hydroxide are added, and the mixture is stirred at room temperature for 24 h. The solution is neutralised, evaporated and purified by means of prep. HPLC. The product is in the form of the trifluoroacetate.

Yield: 5 mg, white solid. Rt.=2.79 min (method A), LCMS: 456 (M+H).

$^1$H NMR (500 MHz, DMSO/deuterated TFA) δ 7.89-7.81 (m, 2H), 7.66 (d, J=8.2 Hz, 1H), 7.45 (d, J=8.3 Hz, 1H), 7.27 (d, J=7.5 Hz, 1H), 7.10 (d, J=8.6 Hz, 1H), 4.51 (d, J=13.9 Hz, 2H), 3.66 (d, J=11.9 Hz, 2H), 3.38 (t, J=12.7 Hz, 2H), 3.25-3.09 (m, 4H), 2.31 (t, J=7.2 Hz, 2H), 1.80-1.70 (m, 2H), 1.69 (s, 4H), 1.63-1.55 (m, 2H), 1.29 (d, J=16.8 Hz, 12H).

The following are prepared analogously:

3-{4-[4-(5,5,8,8-Tetramethyl-5,6,7,8-tetrahydronaphthalen-2-yl)thiazol-2-yl]-piperazin-1-yl}propionic acid

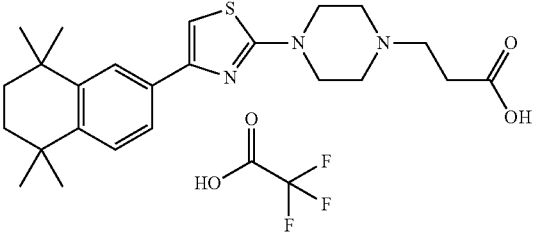

Yield: 37 mg, white solid. The product is in the form of the trifluoroacetate. Rt.=2.91 min (method A), LCMS: 428 (M+H).

$^1$H NMR (500 MHz, DMSO/deuterated TFA) δ 7.73 (d, J=1.8 Hz, 1H), 7.52 (dd, J=8.2, 1.8 Hz, 1H), 7.36-7.31 (m, 1H), 4.30-3.20 (m, 10H), 2.82 (t, J=7.2 Hz, 2H), 1.66 (s, 4H), 1.25 (d, J=17.2 Hz, 12H).

{4-[4-(5,5,8,8-Tetramethyl-5,6,7,8-tetrahydronaphthalen-2-yl)thiazol-2-yl]-piperazin-1-yl}acetic acid

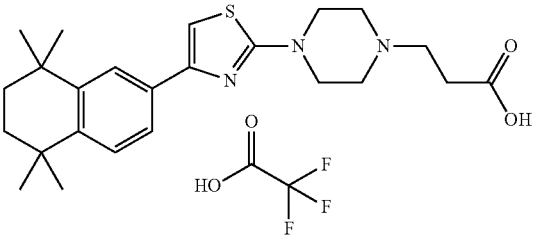

Yield: 53 mg, white solid. The product is in the form of the trifluoroacetate. Rt.=2.94 min (method A), LCMS: 414 (M+H).

$^1$H NMR (500 MHz, DMSO/deuterated TFA) δ 7.71 (d, J=1.8 Hz, 1H), 7.49 (dd, J=8.2, 1.8 Hz, 1H), 7.32 (d, J=8.3 Hz, 1H), 4.21 (s, 2H), 4.03-3.77 (m, 4H), 3.53 (s, 4H), 1.65 (s, 4H), 1.24 (d, J=16.5 Hz, 12H).

{1-[4-(5,5,8,8-Tetramethyl-5,6,7,8-tetrahydronaphthalen-2-yl)thiazol-2-yl]-piperidin-4-ylamino}acetic acid

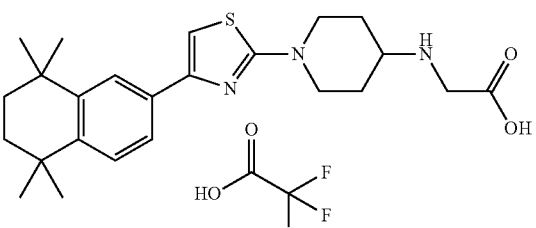

Yield: 22 mg, white solid. The product is in the form of the trifluoroacetate. Rt.=2.78 min (method A), LCMS: 428 (M+H).

$^1$H NMR (400 MHz, DMSO/deuterated TFA) δ 7.60 (d, J=1.7 Hz, 1H), 7.44-7.38 (m, 2H), 6.88 (s, 1H), 4.13 (d, J=13.8 Hz, 2H), 3.97 (s, 2H), 3.47 (t, J=11.4 Hz, 1H), 3.37 (t, J=11.9 Hz, 2H), 2.23 (d, J=10.4 Hz, 2H), 1.76-1.71 (m, 2H), 1.66 (s, 4H), 1.26 (d, J=12.8 Hz, 12H).

3-{1-[4-(5,5,8,8-Tetramethyl-5,6,7,8-tetrahydronaphthalen-2-yl)thiazol-2-yl]piperidin-4-ylamino}propionic acid

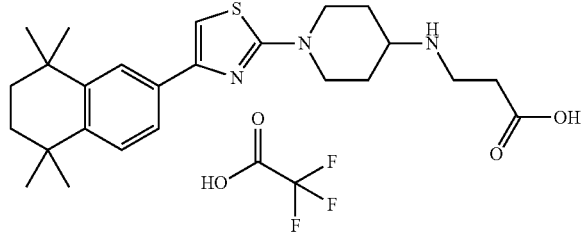

Yield: 32 mg, white solid. The product is in the form of the trifluoroacetate. Rt.=2.76 min (method A), LCMS: 442 (M+H).

$^1$H NMR (400 MHz, DMSO/deuterated TFA) δ 7.54 (d, J=1.3 Hz, 1H), 7.42-7.33 (m, 2H), 6.87 (s, 1H), 4.12 (d, J=13.7 Hz, 2H), 3.49-3.34 (m, 3H), 3.21 (t, J=6.6 Hz, 2H), 2.67 (t, J=6.6 Hz, 2H), 2.21 (d, J=10.4 Hz, 2H), 1.88-1.74 (m, 2H), 1.64 (s, 4H), 1.23 (d, J=12.0 Hz, 12H).

5-{1-[4-(5,5,8,8-Tetramethyl-5,6,7,8-tetrahydronaphthalen-2-yl)thiazol-2-yl]-piperidin-4-ylamino}pentanoic acid

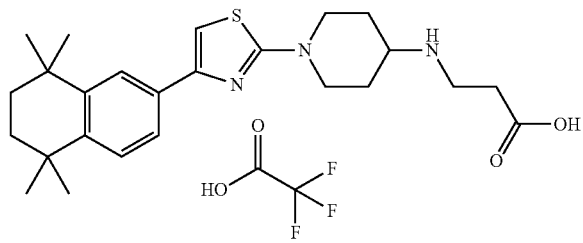

Yield: 46 mg, white solid. The product is in the form of the trifluoroacetate. Rt.=2.81 min (method A), LCMS: 470 (M+H).

$^1$H NMR (500 MHz, DMSO/deuterated TFA) δ 7.63 (d, J=1.8 Hz, 1H), 7.45 (dd, J=8.2, 1.8 Hz, 1H), 7.40 (d, J=8.3 Hz, 1H), 6.88 (s, 1H), 4.13 (d, J=13.3 Hz, 2H), 3.46-3.31 (m, 3H), 3.04-2.93 (m, 2H), 2.29 (t, J=7.0 Hz, 2H), 2.24-2.16 (m, 2H), 1.77-1.72 (m, 4H), 1.67 (s, 4H), 1.64-1.57 (m, 2H), 1.26 (d, J=16.1 Hz, 12H).

(4-Methoxybutyl)-{1-[4-(5,5,8,8-tetramethyl-5,6,7,8-tetrahydronaphthalen-2-yl)thiazol-2-yl]piperidin-4-yl}amine

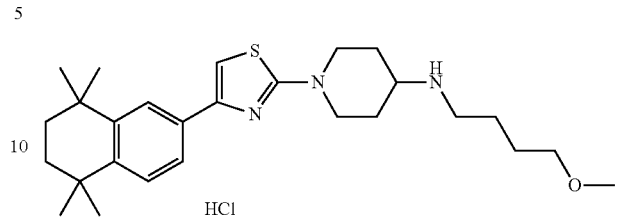

The preparation is carried out as described above starting from 1-[4-(5,5,8,8-tetramethyl-5,6,7,8-tetrahydronaphthalen-2-yl)thiazol-2-yl]piperidin-4-ylamine and 1-bromo-4-methoxybutane in ethanol and triethylamine.

Yield: 17 mg, yellow solid. The product is in the form of the hydrochloride. Rt.=2.91 min (method A), LCMS: 456 (M+H).

$^1$H NMR (500 MHz, DMSO/deuterated TFA) δ 7.55 (s, 1H), 7.38 (s, 2H), 4.13 (d, J=13.6 Hz, 2H), 3.39 (t, J=11.9 Hz, 3H), 3.32 (t, J=6.0 Hz, 2H), 3.21 (s, 3H), 2.95 (dd, J=17.9, 10.0 Hz, 2H), 2.27-2.13 (m, 2H), 2.06-1.66 (m, 4H), 1.65 (s, 4H), 1.57 (dt, J=12.9, 6.3 Hz, 2H), 1.24 (d, J=15.2 Hz, 12H).

(2-Methoxyethyl)-{1-[4-(5,5,8,8-tetramethyl-5,6,7,8-tetrahydronaphthalen-2-yl)thiazol-2-yl]piperidin-4-yl}amine

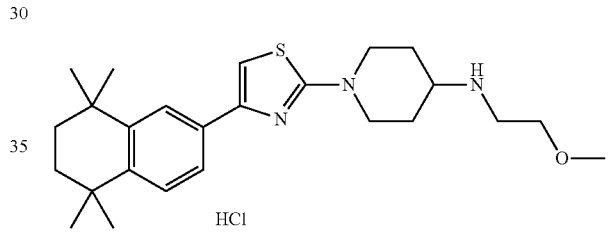

The preparation is carried out as described above starting from 1-[4-(5,5,8,8-tetramethyl-5,6,7,8-tetrahydronaphthalen-2-yl)thiazol-2-yl]piperidin-4-ylamine and 2-bromoethyl methyl ether in ethanol and triethylamine.

Yield: 49 mg, yellow solid. The product is in the form of the hydrochloride. Rt.=2.85 min (method A), LCMS: 428 (M+H).

$^1$H NMR (500 MHz, DMSO) δ 8.73 (s, 2H), 7.76 (d, J=1.8 Hz, 1H), 7.56 (dd, J=8.2, 1.8 Hz, 1H), 7.31 (d, J=8.3 Hz, 1H), 7.21 (s, 1H), 4.04 (d, J=13.2 Hz, 2H), 3.64-3.59 (m, 2H), 3.37-3.27 (m, 4H), 3.21-3.14 (m, 2H), 3.14-3.03 (m, 2H), 2.14 (d, J=10.8 Hz, 2H), 1.72-1.61 (m, 6H), 1.26 (d, J=16.0 Hz, 12H).

4-{4-[5-Hydroxymethyl-4-(5,5,8,8-tetramethyl-5,6,7,8-tetrahydronaphthalen-2-yl)thiazol-2-yl]piperazin-1-yl}butan-1-ol

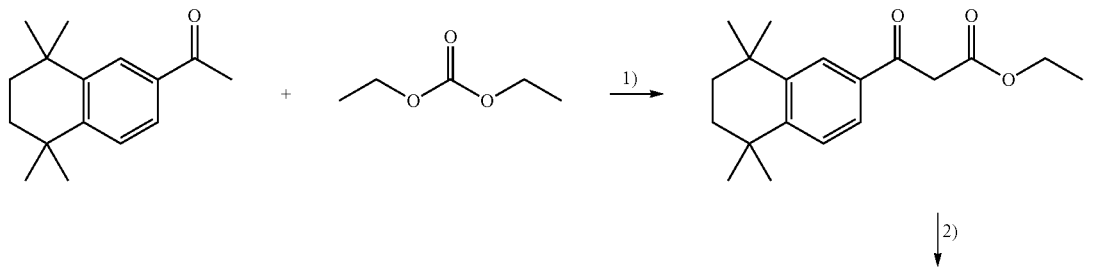

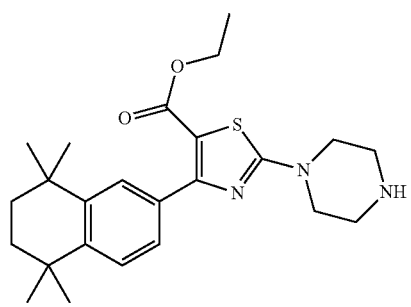
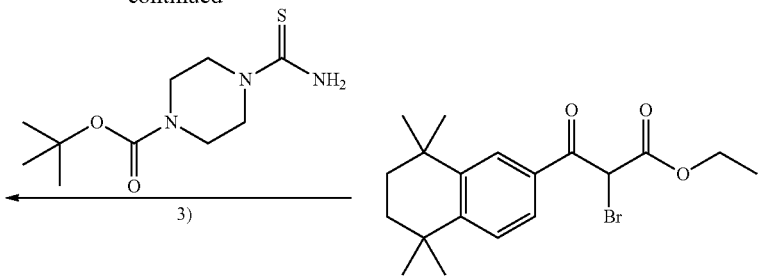
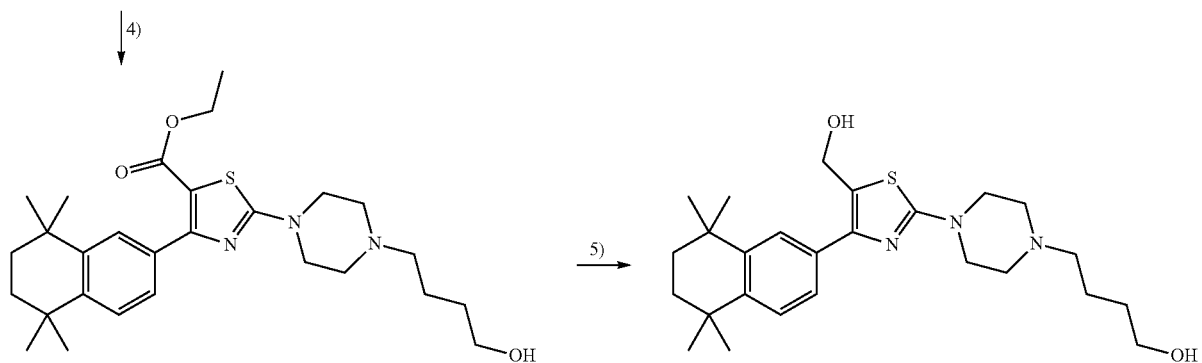

Step 1:

The preparation is carried out analogously to Journal of the Chemical Society, Perkin Transactions 1: Organic and Bio-Organic Chemistry (1972-1999), 1987, p. 317-332 starting from 1-(5,5,8,8-tetramethyl-5,6,7,8-tetrahydronaphthalen-2-yl)ethanone.

Yield: 930 mg, yellow oil. Rt.=3.42 min (method A).

Step 2:

The oxidation of 3-oxo-3-(5,5,8,8-tetramethyl-5,6,7,8-tetrahydronaphthalen-2-yl)propionic acid ethyl ester using PTT is carried out as described above.

Yield: 900 mg, pale-yellow oil. Rt.=3.57 min (method A), LCMS: 381/383 (M+H).

Step 3:

The reaction of 2-bromo-3-oxo-3-(5,5,8,8-tetramethyl-5,6,7,8-tetrahydronaphthalen-2-yl)propionic acid ethyl ester and 2-bromo-1-(5,5,8,8-tetramethyl-5,6,7,8-tetrahydronaphthalen-2-yl)ethanone in ethanol was carried out at 80° C. as described above. The Boc protecting group was cleaved using HCl in dioxane.

Yield: 920 mg, pale-yellow oil. Rt.=2.96 min (method A), LCMS: 428 (M+H).

Step 4:

750 mg (1.75 mmol) of 2-piperazin-1-yl-4-(5,5,8,8-tetramethyl-5,6,7,8-tetrahydronaphthalen-2-yl)thiazole-5-carboxylic acid ethyl ester are dissolved in 8 ml of NMP, are stirred at 60° C. for 5 h with 259 µl (1.75 mmol) of 4-bromobutyl acetate and 1.72 g (5.26 mmol) [lacuna]. The reaction mixture was filtered, 30 ml of THF and 4.5 ml of 2M sodium hydroxide solution were added, and the mixture was stirred at RT overnight Water was added to the reaction mixture, which was then extracted a number of times with ethyl acetate. The organic phase was washed with water, dried and evaporated. The crude product is purified by column chromatography on silica gel Yield: 485 mg, yellow oil. Rt.=2.98 min (method A), LCMS: 500 (M+H).

Step 5

The preparation was carried out as already described starting from 2-[4-(4-hydroxybutyl)piperazin-1-yl]-4-(5,5,8,8-tetramethyl-5,6,7,8-tetrahydronaphthalen-2-yl)thiazole-5-carboxylic acid ethyl ester by reduction using a lithium aluminium hydride solution in THF.

56 mg, LCMS: 458 [M+H], HPLC: Rt.=2.65 min (method A).

$^1$H NMR (400 MHz, DMSO) δ 7.56 (s, 1H), 7.41-7.32 (m, 2H), 5.42 (t, J=5.3 Hz, 1H), 4.57 (d, J=5.3 Hz, 2H), 4.44 (b, 1H), 3.44 (dd, J=11.1, 6.6 Hz, 6H), 2.51 (d, J=5.0 Hz, 4H), 2.37 (t, J=6.9 Hz, 2H), 1.70 (s, 4H), 1.58-1.43 (m, 4H), 1.30 (d, J=3.3 Hz, 12H).

2-[4-(4-Hydroxybutyl)piperazin-1-yl]-4-(5,5,8,8-tetramethyl-5,6,7,8-tetrahydronaphthalen-2-yl)thiazole-5-carboxylic acid dimethylamide

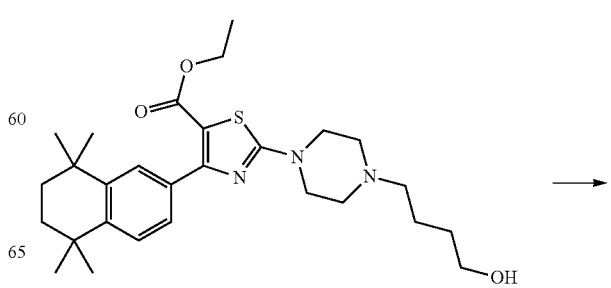

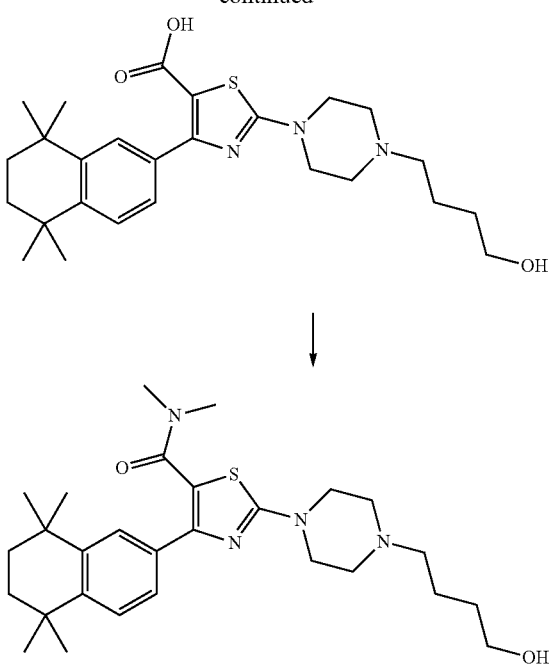

The product is [lacuna] by lithium hydroxide-promoted saponification of the ester in THF at 60° C. and subsequent EDC/HOBt coupling to dimethylamine in THF.

5 mg, LCMS: 499 [M+H].

$^1$H NMR (400 MHz, DMSO/deuterated TFA) δ 7.46-7.37 (m, 3H), 3.47 (dt, J=12.2, 5.2 Hz, 6H), 3.32 (s, 1H), 2.81 (s, 6H), 2.55 (superimposed, 6H), 1.70 (s, 4H), 1.59-1.43 (m, 4H), 1.27 (d, J=18.0 Hz, 12H).

Preparation of 2-{1-[4-(5,8-dimethyl-5,6,7,8-tetrahydronaphthalen-2-yl)thiazol-2-yl]piperidin-4-ylamino}ethanol

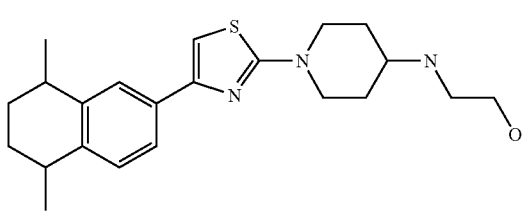 [SMILES: CC1CCC(C)c2cc(-c3csc(N4CCC(NCCO)CC4)n3)ccc21]

The preparation is carried out as described starting from 104 mg (0.26 mmol) of 1-[4-(5,8-dimethyl-5,6,7,8-tetrahydronaphthalen-2-yl)thiazol-2-yl]piperidin-4-ylamine hydrochloride and 55 µl (0.26 mmol) of (tert-butyldimethylsilanyloxy)acetaldehyde. The protecting group is cleaved off using a 4N HCl solution in dioxane. The purification is carried out by means of preparative HPLC. The product is in the form of the hydrochloride.

17 mg, pale solid, LCMS: 386 (M+H), HPLC: Rt.=2.49 min (method B).

$^1$H NMR (400 MHz, DMSO/deuterated TFA) δ=7.58 (d, J=5.8, 1H), 7.54-7.46 (m, 1H), 7.31 (t, J=8.3, 1H), 4.20 (d, J=13.3, 2H), 3.76 (s, 2H), 3.42 (t, J=12.7, 2H), 3.13 (s, 2H), 3.00-2.86 (m, 2H), 2.28 (d, J=11.9, 2H), 2.03 (d, J=7.7, 1H), 1.91-1.82 (m, 2H), 1.67-1.55 (m, 1H), 1.49 (d, J=8.0, 1H), 1.37-1.22 (m, 8H).

Preparation of 4-{1-[4-(5,8-dimethyl-5,6,7,8-tetrahydronaphthalen-2-yl)thiazol-2-yl]piperidin-4-ylamino}butan-1-ol

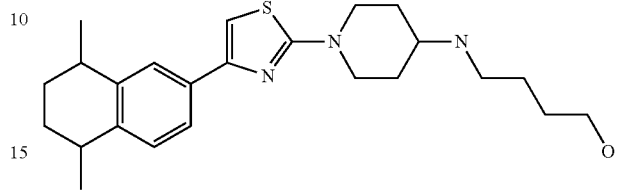

The preparation is carried out as described starting from 218 mg (0.58 mmol) of 1-[4-(5,8-dimethyl-5,6,7,8-tetrahydronaphthalen-2-yl)thiazol-2-yl]piperidin-4-ylamine and 126 µl (0.58 mmol) of 4-bromobutyl acetate. The protecting group is cleaved off by means of a 1N NaOH solution in methanol. The product is in the form of the hydrochloride.

24 mg pale solid, Rt.=2.57 min (method B), LCMS: 414 (M+H).

$^1$H NMR (400 MHz, DMSO/deuterated TFA) δ=7.52-7.46 (m, 1H), 7.45-7.38 (m, 1H), 7.22 (t, J=8.5, 1H), 4.12 (d, J=12.3, 2H), 3.48-3.30 (m, 5H), 3.02-2.92 (m, 2H), 2.91-2.76 (m, 2H), 2.18 (d, J=10.6, 2H), 1.98-1.91 (m, 1H), 1.84-1.62 (m, 5H), 1.59-1.45 (m, 3H), 1.44-1.35 (m, 1H), 1.28-1.15 (m, 6H).

Preparation of 4-{1-[4-(5R,8S)-5,8-dimethyl-5,6,7,8-tetrahydronaphthalen-2-yl)thiazol-2-yl]piperidin-4-ylamino}butan-1-ol

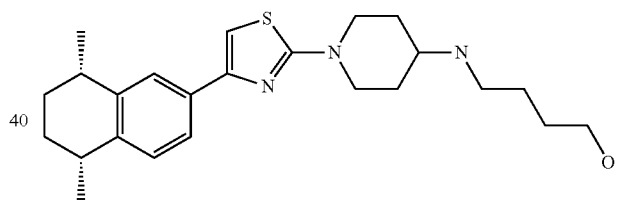

The enantiomer was isolated from the racemic mixture by means of chiral chromatography. The product is in the form of the hydrochloride.

13 mg pale resin, Rt.=2.39 min (method B), LCMS: 414 (M+H).

Preparation of 4-{1-[4-(5S,8S)-5,8-dimethyl-5,6,7,8-tetrahydronaphthalen-2-yl)thiazol-2-yl]piperidin-4-ylamino}butan-1-ol

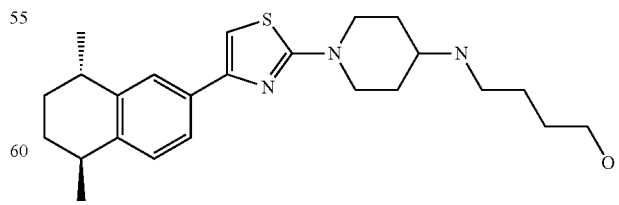

The enantiomer was isolated from the racemic mixture by means of chiral chromatography. The product is in the form of the hydrochloride.

16 mg pale resin, Rt.=2.39 min (method B), LCMS: 414 (M+H).

Preparation of 2-{1-[4-(5,5-dimethyl-5,6,7,8-tetrahydronaphthalen-2-yl)-thiazol-2-yl]piperidin-4-ylamino}ethanol

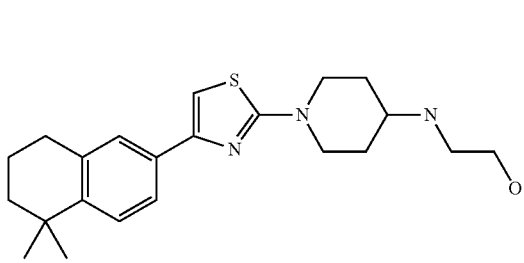 [SMILES: CC1(C)CCCc2cc(-c3csc(N4CCC(NCCO)CC4)n3)ccc21]

The preparation is carried out as described starting from 60 mg (0.16 mmol) of 1-[4-(5,5-dimethyl-5,6,7,8-tetrahydronaphthalen-2-yl)thiazol-2-yl]piperidin-4-ylamine hydrochloride and 34 μl (0.16 mmol) of (tert-butyldimethylsilanyloxy)acetaldehyde. The protecting group is cleaved off using a 4N HCl solution in dioxane. The purification is carried out by means of preparative HPLC. The product is in the form of the formate.

18 mg, white solid, LCMS: 386 (M+H), HPLC: Rt.=2.50 min (method B).

$^1$H NMR (400 MHz, DMSO/deuterated TFA) δ=7.53 (dd, J=8.2, 2.0, 1H), 7.48-7.42 (m, 2H), 4.16 (d, J=13.5, 2H), 3.77-3.69 (m, 2H), 3.52-3.40 (m, 1H), 3.34 (t, J=11.9, 2H), 3.16-3.08 (m, 2H), 2.80 (t, J=6.2, 2H), 2.23 (d, J=11.1, 2H), 1.86-1.73 (m, 4H), 1.70-1.63 (m, 2H), 1.28 (s, 6H).

Preparation of 4-{1-[4-(5,5-dimethyl-5,6,7,8-tetrahydronaphthalen-2-yl)thiazol-2-yl]piperidin-4-ylamino}butan-1-ol

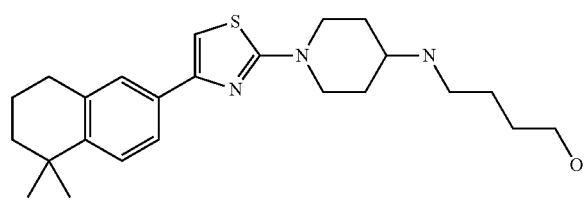 [SMILES: CC1(C)CCCc2cc(-c3csc(N4CCC(NCCCCO)CC4)n3)ccc21]

The preparation is carried out as described starting from 60 mg (0.16 mmol) of 1-[4-(5,5-dimethyl-5,6,7,8-tetrahydronaphthalen-2-yl)thiazol-2-yl]piperidin-4-ylamine hydrochloride and 22 μl (0.16 mmol) of 4-bromobutyl acetate. The protecting group is cleaved off by means of a 2N NaOH solution in methanol. The product is in the form of the formate.

19 mg pale solid, Rt.=2.55 min (method B), LCMS: 414 (M+H).

$^1$H NMR (400 MHz, DMSO/deuterated TFA) δ=7.54-7.41 (m, 3H), 4.19 (d, J=13.5, 2H), 3.52 (t, J=6.0, 2H), 3.48-3.41 (m, 2H), 3.09-2.99 (m, 2H), 2.81 (t, J=6.3, 2H), 2.25 (d, J=10.4, 2H), 1.87-1.66 (m, 9H), 1.61-1.52 (m, 2H), 1.29 (s, 6H).

Preparation of 4-[4-(5,6,7,8-tetrahydronaphthalen-2-yl)thiazol-2-yl]-piperidine

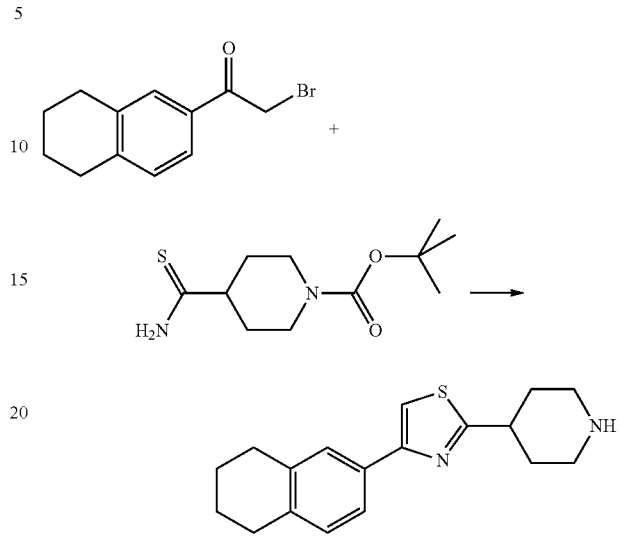

The preparation is carried out as described starting from 8 g (31.6 mmol) of 2-bromo-1-(5,6,7,8-tetrahydronaphthalen-2-yl)ethanone and 8 g (32.7 mmol) of 4-thiocarbamoylpiperidine-1-carboxylic acid tert-butyl ester.

9 g, white crystals.

$^1$H NMR (400 MHz, DMSO/deuterated TFA) δ=7.80 (d, J=1.2, 1H), 7.70-7.63 (m, 2H), 7.13 (d, J=7.8, 1H), 3.50-3.43 (m, 3H), 3.15 (td, J=12.4, 2.6, 2H), 2.79 (d, J=17.3, 4H), 2.32 (dd, J=14.0, 2.8, 2H), 2.15-2.02 (m, 2H), 1.84-1.75 (m, 4H).

Preparation of 4-{4-[4-(5,6,7,8-tetrahydronaphthalen-2-yl)thiazol-2-yl]-piperidin-1-yl}butan-1-ol

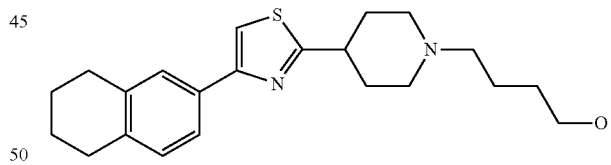

The preparation is carried out as described starting from 39 mg (0.13 mmol) of 4-[4-(5,6,7,8-tetrahydronaphthalen-2-yl)thiazol-2-yl]piperidine and 30 μl (0.20 mmol) of 4-bromobutyl acetate. The protecting group is cleaved off by means of a 2N NaOH solution in methanol. The product is in the form of the hydrochloride.

28 mg white solid, Rt.=2.24 min (method B), LCMS: 371 (M+H).

$^1$H NMR (400 MHz, DMSO/deuterated TFA) δ=7.74 (s, 1H), 7.64-7.56 (m, 2H), 7.05 (d, J=7.8, 1H), 3.60 (d, J=12.6, 2H), 3.48-3.42 (m, 2H), 3.42-3.31 (m, 1H), 3.15-3.03 (m, 4H), 2.79-2.65 (m, 4H), 2.35-2.25 (m, 2H), 2.13-1.99 (m, 2H), 1.81-1.65 (m, 6H), 1.53-1.42 (m, 2H).

Preparation of 4-[4-(5,5,8,8-tetramethyl-5,6,7,8-tetrahydronaphthalen-2-yl)thiazol-2-yl]piperidine

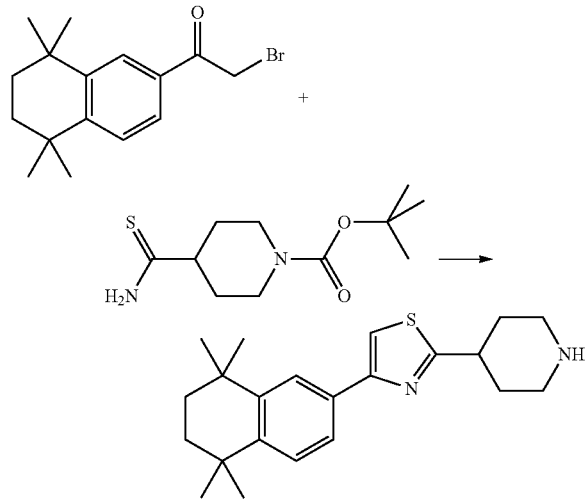

6.12 g (12.28 mmol) of 2-bromo-1-(5,5,8,8-tetramethyl-5,6,7,8-tetrahydronaphthalen-2-yl)ethanone and 3 g (12.28 mmol) of 4-thiocarbamoylpiperidine-1-carboxylic acid tert-butyl ester were suspended in 50 ml of ethanol and refluxed overnight. The reaction mixture was cooled and evaporated. The residue was slurried using a little EA and PE, digested and filtered off with suction. The solid was suspended in 180 ml of EA, washed with 60 ml of a saturated sodium hydrogencarbonate solution. The organic phase was dried over sodium sulfate, filtered and evaporated.

3.70 g, brown oil. LCMS: 355 (M+H), HPLC: Rt.=2.65 min (method B).

$^1$H NMR (400 MHz, DMSO/deuterated TFA) δ=7.95-7.88 (m, 2H), 7.69 (dd, J=8.2, 1.8, 1H), 7.39 (d, J=8.3, 1H), 3.51-3.40 (m, 3H), 3.19-3.05 (m, 2H), 2.36-2.24 (m, 2H), 2.10-1.95 (m, 2H), 1.70 (s, 4H), 1.30 (d, J=15.7, 12H).

Preparation of the Racemates (SR)-2,2-dimethyl-4-((RS)-4-oxo-1-triethylsilanyloxybutyl)oxazolidine-3-carboxylic acid tert-butyl ester and (SR)-2,2-dimethyl-4-((SR)-4-oxo-1-triethylsilanyloxybutyl)oxazolidine-3-carboxylic acid tert-butyl ester

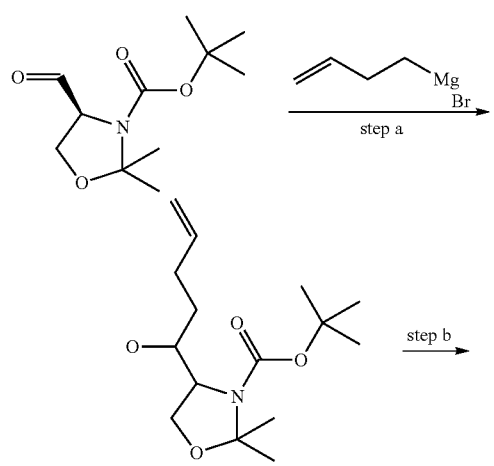

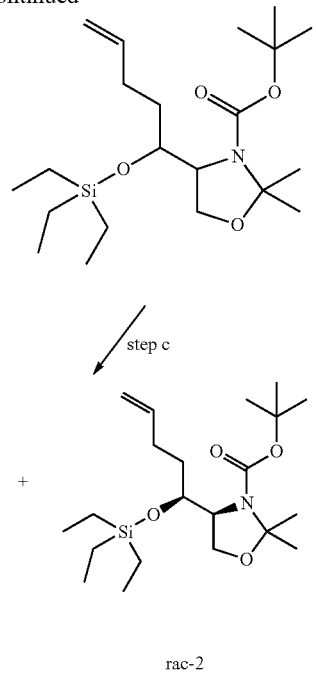

rac-1    rac-2

Step a 4-(1-Hydroxypent-4-enyl)-2,2-dimethyloxazolidine-3-carboxylic acid tert-butyl ester 5 g (21.81 mmol) of racemate (SR)-4-formyl-2,2-dimethyloxazolidine-3-carboxylic acid tert-butyl ester are dissolved in 33 ml of THF, placed under argon and cooled to −78° C. 43.62 ml (21.81 mmol) of a 0.5 M 3-butenylmagnesium bromide solution in THF are added dropwise. The mixture is stirred further at room temperature overnight. After a TLC check, about 90 ml of a saturated NH$_4$Cl solution are added to the mixture with cooling, the mixture is stirred further overnight and diluted with about 50 ml of water. The phases are separated, and the aqueous phase is extracted a further twice with EA. The combined organic phases are dried over sodium sulfate, filtered and evaporated. The oily residue is subjected to flash chromatography on silica gel.

4.89 g, colourless oil.

Step b 2,2-Dimethyl-4-(1-triethylsilanyloxypent-4-enyl)oxazolidine-3-carboxylic acid tert-butyl ester 4.89 g (17.14 mmol) of product from step a are dissolved in 200 ml of DCM, placed under nitrogen and cooled to 0° C. 2.58 g (17.14 mmol) of chlorotriethylsilane and 209 mg (1.71 mmol) of 4-(dimethylamino)pyridine are added. The reaction solution is stirred further at 0° C. for 15 min. 4.75 ml (34.27 mmol) of triethylamine are subsequently added. The mixture is allowed to come back to room temperature and is left to stir further overnight. After a TLC check, about 200 ml of a saturated NH$_4$Cl solution are added to the reaction mixture. The phases are separated, and the aqueous phase is extracted a further twice with EA. The combined organic phases are dried over sodium sulfate, filtered and evaporated. The residue is subjected to flash chromatography on silica gel.

Clear colourless oil, 5.02 g.

Step c

(SR)-2,2-Dimethyl-4-((RS)-4-oxo-1-triethylsilanyloxybutyl)oxazolidine-3-carboxylic acid tert-butyl ester and (SR)-2,2-dimethyl-4-((SR)-4-oxo-1-triethylsilanyloxybutyl)oxazolidine-3-carboxylic acid tert-butyl ester 5.02 g (12.56 mmol) of product from step b are dissolved in 140 ml of DCM and cooled to −78° C. At this temperature, 2.11 g (25.12 mmol) of sodium hydrogencarbonate are added, and ozone is passed through the mixture for 2.5 h with stirring until the solution has a blue coloration. After a TLC check, oxygen is then passed through the mixture for 1.5 h until complete decoloration. Triphenylphsophine (3.30 g, 12.56 mmol) is subsequently added. The mixture is stirred at room temperature overnight and then filtered off. The filtrate is evaporated to dryness in a rotary evaporator. The 2 products are separated by means of flash chromatography on silica gel.

Racemate 1: clear colourless oil, 1.21 g.
Racemate 2: clear colourless oil, 1.83 g.

Preparation of the Racemates (SR)-2,2-dimethyl-4-((RS)-3-oxo-1-triethylsilanyloxypropyl)oxazolidine-3-carboxylic acid tert-butyl ester and (SR)-2,2-dimethyl-4-((SR)-3-oxo-1-triethylsilanyloxypropyl)oxazolidine-3-carboxylic acid tert-butyl ester

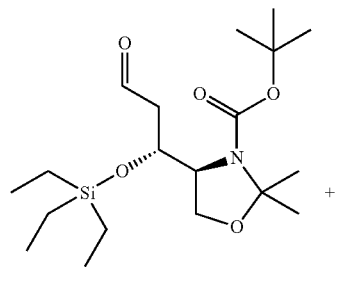

rac-3

+

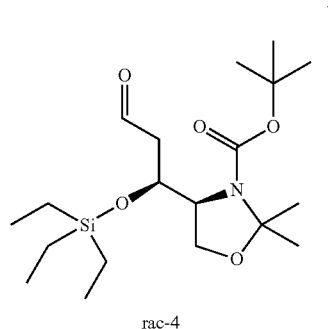

rac-4

The preparation is carried out as described above starting from 5 g of racemate (21.81 mmol) (SR)-4-formyl-2,2-dimethyloxazolidine-3-carboxylic acid tert-butyl ester and 21.81 ml (21.81 mmol) of a 1 M allylmagnesium bromide solution in diethyl ether.

Racemate 3: clear colourless oil, 323 mg.
Racemate 4: clear colourless oil, 329 mg.

Preparation of the Racemates (SR)-2,2-dimethyl-4-((SR)-2-oxo-1-triethylsilanyloxyethyl)oxazolidine-3-carboxylic acid tert-butyl ester and (SR)-2,2-dimethyl-4-((RS)-2-oxo-1-triethylsilanyloxyethyl)oxazolidine-3-carboxylic acid tert-butyl ester

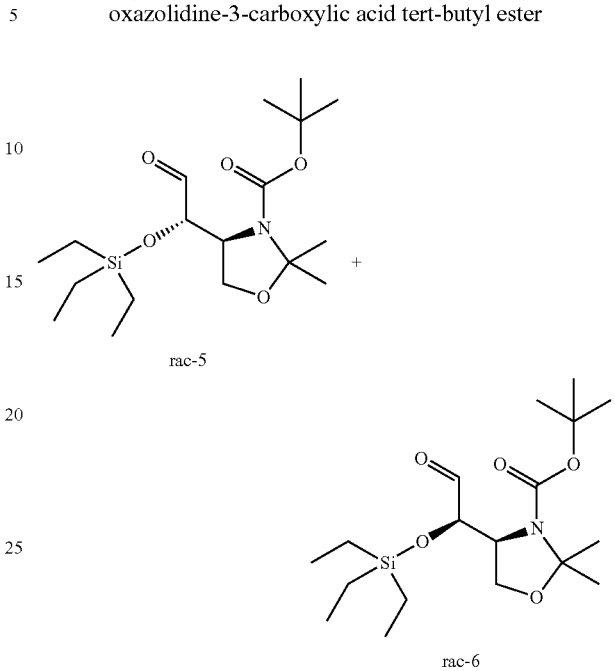

rac-5 rac-6

The preparation is carried out as described above starting from 5.01 g of racemate (21.85 mmol) (SR)-4-formyl-2,2-dimethyloxazolidine-3-carboxylic acid tert-butyl ester and 24.0 ml (24.0 mmol) of a 1 M vinylmagnesium bromide solution in THF.

Racemate 5: clear colourless oil, 1.92 g.
Racemate 6: clear colourless oil, 0.81 g.

Preparation of the Racemate (2SR,3RS)-2-amino-6-{4-[4-(5,5,8,8-tetramethyl-5,6,7,8-tetrahydronaphthalen-2-yl)thiazol-2-yl]piperidin-1-yl}hexane-1,3-diol

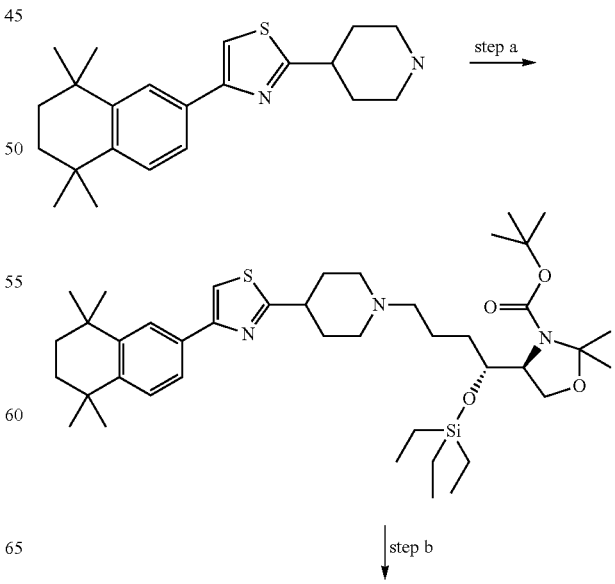

step a step b

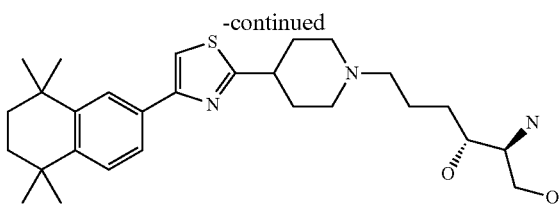

Step a (SR)-2,2-Dimethyl-4-((RS)-4-{4-[4-(5,5,8,8-tetramethyl-5,6,7,8-tetrahydronaohthalen-2-yl)thiazol-2-yl]piperidin-1-yl}-1-triethylsilanyloxybutyl)oxazolidine-3-carboxylic acid tert-butyl ester 97 mg (0.249 mmol) of 4-[4-(5,5,8,8-tetramethyl-5,6,7,8-tetrahydronaphthalen-2-yl)thiazol-2-yl]piperidine hydrochloride and 100 mg (0.249 mmol) of racemate 1 were suspended with 4.3 ml of THF, and 175 µl of glacial acetic acid were added. The reaction mixture was stirred at room temperature for 30 min. 106 mg (0.50 mmol) of sodium triacetoxyborohydride were subsequently added. The reaction mixture was stirred at room temperature overnight, stripped off to dryness, suspended with EA, washed with a saturated sodium hydrogencarbonate solution and a saturated sodium chloride solution. The organic phase was dried over sodium sulfate, filtered, evaporated to dryness and purified by means of flash chromatography on silica gel.

21 mg, clear oil, Rt.=3.93 min (method B), LCMS: 741 (M+H).

Step b

Preparation of the Racemate (2SR,3RS)-2-amino-6-{4-[4-(5,5,8,8-tetramethyl-5,6,7,8-tetrahydronaphthalen-2-yl)thiazol-2-yl]piperidin-1-yl}hexane-1,3-diol 1 ml of a 4N HCl solution in dioxane was added to the intermediate from step a, and the mixture was stirred at room temperature overnight. The reaction mixture is evaporated and separated by means of flash chromatography on C18 silica gel. The product is in the form of the hydrochloride.

10 mg pale solid, Rt.=2.34 min (method B), LCMS: 486 (M+H).
$^1$H NMR (500 MHz, DMSO/deuterated TFA) δ=7.83 (d, J=1.8, 1H), 7.74 (s, 1H), 7.66-7.56 (m, 1H), 7.31 (d, J=8.3, 1H), 3.66-3.57 (m, 4H), 3.56-3.50 (m, 1H), 3.47-3.34 (m, 1H), 3.14-3.04 (m, 4H), 2.96-2.87 (m, 1H), 2.31 (d, J=15.2, 2H), 2.09 (q, J=12.3, 2H), 1.91-1.69 (m, 2H), 1.63 (s, 4H), 1.59-1.49 (m, 1H), 1.48-1.38 (m, 1H), 1.22 (d, J=20.0, 12H).

Preparation of the Racemate (2SR,3SR)-2-amino-6-{4-[4-(5,5,8,8-tetramethyl-5,6,7,8-tetrahydronaphthalen-2-yl)thiazol-2-yl]piperidin-1-yl}hexane-1,3-diol

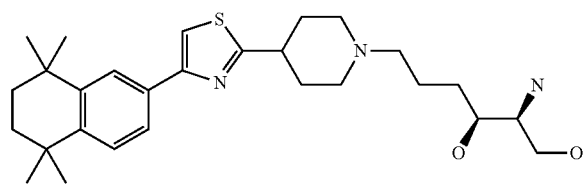

The preparation is carried out analogously starting from 97 mg (0.249 mmol) of 4-[4-(5,5,8,8-tetramethyl-5,6,7,8-tetrahydronaphthalen-2-yl)thiazol-2-yl]piperidine hydrochloride and 100 mg (0.249 mmol) of racemate 2. The product is in the form of the hydrochloride.

50 mg pale solid, Rt.=2.28 min (method B), LCMS: 486 (M+H).
$^1$H NMR (400 MHz, DMSO/deuterated TFA) δ=7.93-7.87 (m, 2H), 7.74-7.65 (m, 1H), 7.40 (d, J=8.3, 1H), 3.82-3.73 (m, 2H), 3.72-3.60 (m, 3H), 3.52-3.43 (m, 1H), 3.20-3.10 (m, 4H), 2.43-2.33 (m, 3H), 2.20-2.07 (m, 2H), 1.98-1.87 (m, 1H), 1.85-1.76 (m, 1H), 1.70 (s, 4H), 1.60-1.44 (m, 2H), 1.30 (d, J=15.5, 12H).

Preparation of the Enantiomer Pair (2R,3S)-2-amino-5-{4-[4-(5,5,8,8-tetramethyl-5,6,7,8-tetrahydronaphthalen-2-yl)thiazol-2-yl]piperidin-1-yl}pentane-1,3-diol and (2S,3R)-2-amino-5-{4-[4-(5,5,8,8-tetramethyl-5,6,7,8-tetrahydronaphthalen-2-yl)thiazol-2-yl]piperidin-1-yl}pentane-1,3-diol

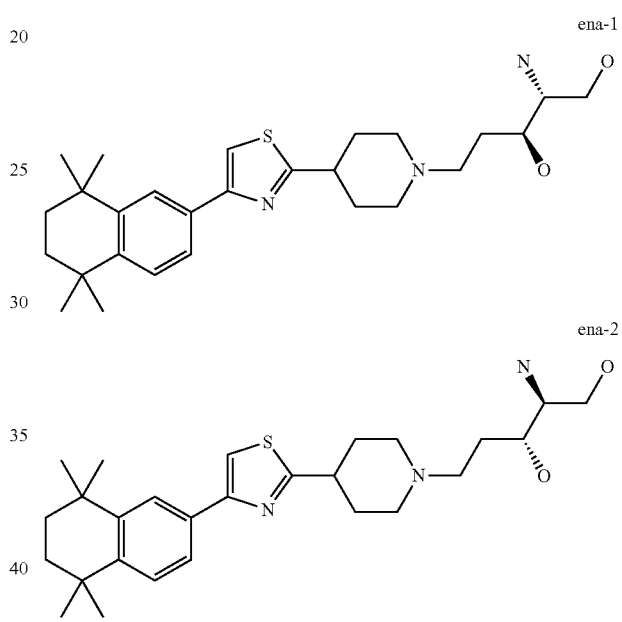

The preparation is carried out analogously starting from 357 mg (0.914 mmol) of 4-[4-(5,5,8,8-tetramethyl-5,6,7,8-tetrahydronaphthalen-2-yl)thiazol-2-yl]piperidine hydrochloride and 322 mg (0.831 mmol) of racemate 3. The 2 enantiomers were subsequently separated from the racemic mixture by means of chiral chromatography. The products are in the form of the hydrochloride.

Enantiomer 1: 47 mg pale resin, Rt.=2.28 min (method B), LCMS: 472 (M+H).
$^1$H NMR (500 MHz, DMSO/deuterated TFA) δ=7.83 (d, J=1.8, 1H), 7.76 (s, 1H), 7.66-7.56 (m, 1H), 7.31 (d, J=8.3, 1H), 3.76-3.70 (m, 1H), 3.65-3.55 (m, 3H), 3.48-3.34 (m, 2H), 3.29-3.22 (m, 1H), 3.21-3.17 (m, 1H), 3.15-3.07 (m, 2H), 3.02-2.96 (m, 1H), 2.32 (d, J=15.0, 2H), 2.14-2.03 (m, 2H), 2.02-1.93 (m, 1H), 1.88-1.77 (m, 1H), 1.63 (s, 4H), 1.23 (d, J=19.9, 12H).

Enantiomer 2: 50 mg pale resin, Rt.=2.29 min (method B), LCMS: 472 (M+H).
$^1$H NMR (500 MHz, DMSO/deuterated TFA) δ=7.84 (d, J=1.8, 1H), 7.78 (s, 1H), 7.68-7.57 (m, 1H), 7.31 (d, J=8.3, 1H), 3.76-3.70 (m, 1H), 3.66-3.54 (m, 3H), 3.43-3.35 (m, 1H), 3.30-3.15 (m, 3H), 3.15-3.07 (m, 2H), 3.02-2.96 (m, 1H), 2.32 (d, J=15.0, 2H), 2.15-2.03 (m, 2H), 2.01-1.93 (m, 1H), 1.89-1.79 (m, 1H), 1.63 (s, 4H), 1.23 (d, J=19.9, 12H).

Preparation of the Enantiomer Pair (2S,3S)-2-amino-5-{4-[4-(5,5,8,8-tetramethyl-5,6,7,8-tetrahydronaphthalen-2-yl)thiazol-2-yl]piperidin-1-yl}pentane-1,3-diol and (2R,3R)-2-amino-5-{4-[4-(5,5,8,8-tetramethyl-5,6,7,8-tetrahydronaphthalen-2-yl)thiazol-2-yl]piperidin-1-yl}pentane-1,3-diol

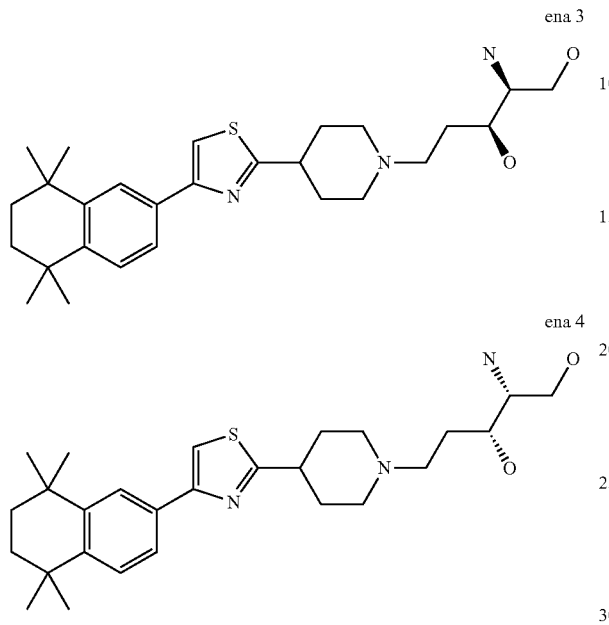

The preparation is carried out analogously starting from 360 mg (0.923 mmol) of 4-[4-(5,5,8,8-tetramethyl-5,6,7,8-tetrahydronaphthalen-2-yl)thiazol-2-yl]piperidine hydrochloride and 325 mg (0.839 mmol) of racemate 4. The 2 enantiomers were subsequently separated from the racemic mixture by means of chiral chromatography. The products are in the form of the hydrochloride.

Enantiomer 3: 44 mg pale solid, Rt.=2.30 min (method B), LCMS: 472 (M+H).

$^1$H NMR (500 MHz, DMSO/deuterated TFA) δ=7.83 (d, J=1.6, 1H), 7.76 (s, 1H), 7.67-7.56 (m, 1H), 7.31 (d, J=8.3, 1H), 3.85-3.77 (m, 1H), 3.75-3.67 (m, 1H), 3.65-3.52 (m, 3H), 3.45-3.34 (m, 1H), 3.30-3.22 (m, 1H), 3.19-3.06 (m, 4H), 2.32 (d, J=14.9, 2H), 2.09 (q, J=13.5, 2H), 1.99-1.90 (m, 1H), 1.89-1.78 (m, 1H), 1.63 (s, 4H), 1.22 (d, J=20.0, 12H).

Enantiomer 4: 50 mg pale solid, Rt.=2.27 min (method B), LCMS: 472 (M+H).

$^1$H NMR (500 MHz, DMSO/deuterated TFA) δ=7.84 (d, J=1.8, 1H), 7.78 (s, 1H), 7.67-7.57 (m, 1H), 7.32 (dd, J=8.2, 3.2, 1H), 3.84-3.77 (m, 1H), 3.75-3.68 (m, 1H), 3.58 (ddd, J=18.3, 13.2, 6.0, 3H), 3.45-3.35 (m, 1H), 3.29-3.21 (m, 1H), 3.20-3.07 (m, 4H), 2.32 (d, J=14.5, 2H), 2.15-2.03 (m, 2H), 2.00-1.90 (m, 1H), 1.88-1.76 (m, 1H), 1.63 (s, 4H), 1.23 (d, J=19.9, 12H).

Preparation of the Racemate (2SR,3SR)-2-amino-4-{4-[4-(5,5,8,8-tetramethyl-5,6,7,8-tetrahydronaphthalen-2-yl)thiazol-2-yl]piperidin-1-yl}butane-1,3-diol

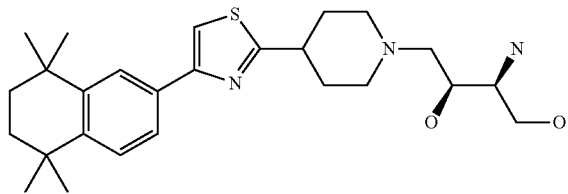 [SMILES: CC1(C)CCC(C)(C)c2cc(-c3csc(C4CCN(C[C@H](O)[C@@H](N)CO)CC4)n3)ccc21]

The preparation is carried out analogously starting from 100 mg (0.256 mmol) of 4-[4-(5,5,8,8-tetramethyl-5,6,7,8-tetrahydronaphthalen-2-yl)thiazol-2-yl]piperidine hydrochloride and 144 mg (0.385 mmol) of racemate 6. The product is in the form of the formate.

4 mg pale solid, LCMS: 456 (M+H).

Preparation of the Racemate (2SR,3RS)-2-amino-6-{4-[4-(5,5,8,8-tetramethyl-5,6,7,8-tetrahydronaphthalen-2-yl)thiazol-2-yl]piperazin-1-yl}hexane-1,3-diol

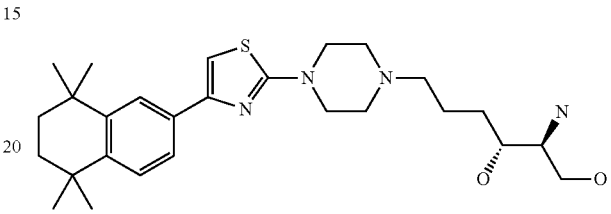

The preparation is carried out analogously starting from 160 mg (0.450 mmol) of 1-[4-(5,5,8,8-tetramethyl-5,6,7,8-tetrahydronaphthalen-2-yl)thiazol-2-yl]piperazine and 204 mg (0.249 mmol) of racemate 1. The product is in the form of the formate.

29 mg pale solid, Rt.=2.33 min (method B), LCMS: 487 (M+H).

$^1$H NMR (400 MHz, DMSO/deuterated TFA) δ=8.13 (s, 1H), 7.79 (d, J=1.8, 1H), 7.58 (dd, J=8.2, 1.8, 1H), 7.33 (d, J=8.3, 1H), 4.21-4.08 (m, 2H), 3.68-3.59 (m, 4H), 3.50-3.40 (m, 2H), 3.31-3.15 (m, 4H), 3.01-2.93 (m, 1H), 1.92-1.71 (m, 2H), 1.67 (s, 4H), 1.61-1.38 (m, 3H), 1.27 (d, J=13.4, 13H).

Preparation of the Racemate (2SR,3SR)-2-amino-6-{4-[4-(5,5,8,8-tetramethyl-5,6,7,8-tetrahydronaphthalen-2-yl)thiazol-2-yl]piperazin-1-yl}hexane-1,3-diol

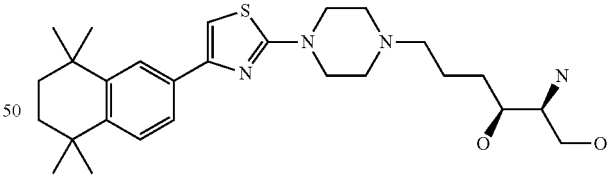

The preparation is carried out analogously starting from 140 mg (0.394 mmol) of 4-[4-(5,5,8,8-tetramethyl-5,6,7,8-tetrahydronaphthalen-2-yl)thiazol-2-yl]piperidine hydrochloride and 190 mg (0.473 mmol) of racemate 2. The product is in the form of the formate.

59 mg pale solid, Rt.=2.33 min (method B), LCMS: 487 (M+H).

$^1$H NMR (400 MHz, DMSO/deuterated TFA) δ=7.73 (s, 1H), 7.51 (d, J=8.0, 1H), 7.30 (d, J=8.3, 1H), 4.12 (s, 1H), 3.74-3.39 (m, 7H), 3.32-3.12 (m, 4H), 3.11-3.03 (m, 1H), 1.94-1.81 (m, 1H), 1.79-1.67 (m, 1H), 1.63 (s, 4H), 1.56-1.33 (m, 2H), 1.23 (d, J=13.8, 13H).

Preparation of 1-[4-(5,5,8,8-tetramethyl-5,6,7,8-tetrahydronaphthalen-2-yl)thiazol-2-yl]-1,4-diazepane

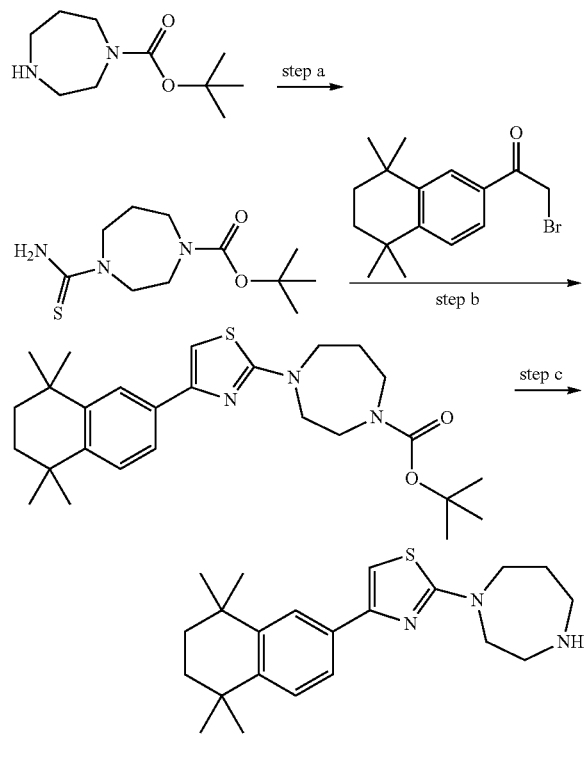

Step a

Preparation of 4-thiocarbamoyl-1,4-diazepane-1-carboxylic acid tert-butyl ester 1.37 g (6.85 mmol) of 1,4-diazepane-1-carboxylic acid tert-butyl ester and 1.12 g (6.85 mmol) of benzoyl isothiocyanate were dissolved in 13 ml of THF and stirred at 50° C. for 2 h. The solvent was subsequently distilled off, and the residue was taken up in 34 ml of methanol and 3.4 ml of water, and 1.89 g of potassium carbonate were added. The mixture was boiled under reflux overnight and then filtered off. The filtrate was evaporated, slurried in 80 ml of water and extracted 3 times with 20 ml of EA each time. The organic phase was dried over sodium sulfate, filtered, evaporated, digested using a little PE and EA and filtered off with suction.

1.12 g white crystals, Rt.=1.92 min (method B), LCMS: 260 (M+H).

Step b and c

Preparation of 1-[4-(5,5,8,8-tetramethyl-5,6,7,8-tetrahydronaphthalen-2-yl)thiazol-2-yl]-1,4-diazepane The preparation is carried out as already described starting from 1.12 g (4.55 mmol) of 4-thiocarbamoyl-1,4-diazepane-1-carboxylic acid tert-butyl ester from step a and 1.93 g (6.25 mmol) of 2-bromo-1-(5,5,8,8-tetramethyl-5,6,7,8-tetrahydronaphthalen-2-yl)ethanone.

888 mg yellow solid, Rt.=2.63 min (method B), LCMS: 370 (M+H).

$^1$H NMR (500 MHz, DMSO/deuterated TFA) δ=7.50 (d, J=1.7, 1H), 7.38 (d, J=8.2, 1H), 7.33 (dd, J=8.2, 1.8, 1H), 4.03-3.98 (m, 2H), 3.71 (t, J=5.7, 2H), 3.43-3.38 (m, 2H), 3.30-3.24 (m, 2H), 2.21-2.13 (m, 2H), 1.62 (s, 4H), 1.23-1.19 (m, 12H).

Preparation of 4-{4-[4-(5,5,8,8-tetramethyl-5,6,7,8-tetrahydronaphthalen-2-yl)thiazol-2-yl]-1,4-diazepan-1-yl}butan-1-ol

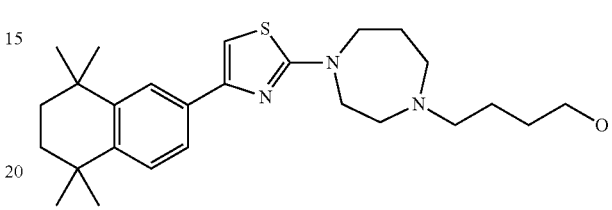

The preparation is carried out as already described starting from 79 mg (0.214 mmol) of 1-[4-(5,5,8,8-tetramethyl-5,6,7,8-tetrahydronaphthalen-2-yl)thiazol-2-yl]-1,4-diazepane and 47 μl (0.321 mmol) of 4-bromobutyl acetate. The protecting group is cleaved off by means of a 1N NaOH solution in methanol. The product is in the form of the hydrochloride.

45 mg pale solid, Rt.=2.69 min (method B), LCMS: 442 (M+H).

$^1$H NMR (500 MHz, DMSO/deuterated TFA) δ=7.66 (d, J=1.7, 1H), 7.52-7.43 (m, 2H), 4.33-4.22 (m, 1H), 4.12-4.02 (m, 1H), 3.82-3.62 (m, 4H), 3.53-3.47 (m, 3H), 3.35 (t, J=11.6, 1H), 2.46-2.26 (m, 2H), 1.80 (dt, J=15.9, 7.9, 2H), 1.71 (s, 4H), 1.56-1.48 (m, 2H), 1.37-1.25 (m, 14H).

Preparation of 3-{4-[4-(5,5,8,8-tetramethyl-5,6,7,8-tetrahydronaphthalen-2-yl)thiazol-2-yl]-1,4-diazepan-1-yl}propan-1-ol

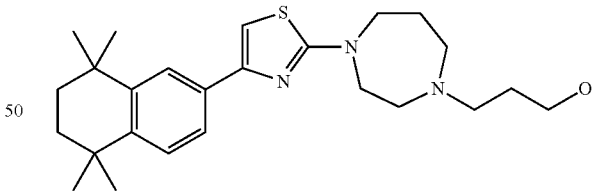

The preparation is carried out as already described starting from 95 mg (0.244 mmol) of 1-[4-(5,5,8,8-tetramethyl-5,6,7,8-tetrahydronaphthalen-2-yl)thiazol-2-yl]-1,4-diazepane and 30 μl (0.321 mmol) of 3-chloropropan-1-ol. The product is in the form of the hydrochloride.

85 mg pale solid, Rt.=2.69 min (method B), LCMS: 428 (M+H).

$^1$H NMR (400 MHz, DMSO/deuterated TFA) δ=7.64 (s, 1H), 7.51-7.43 (m, 2H), 4.34-4.21 (m, 1H), 4.19-4.06 (m, 1H), 3.87-3.65 (m, 4H), 3.62-3.48 (m, 3H), 3.44-3.26 (m, 3H), 2.45-2.22 (m, 2H), 1.97-1.88 (m, 2H), 1.72 (s, 4H), 1.32 (d, J=11.3, 12H).

Preparation of 1-[4-(5,5,8,8-tetramethyl-5,6,7,8-tetrahydronaphthalen-2-yl)thiazol-2-yl]piperidin-3-ylamine

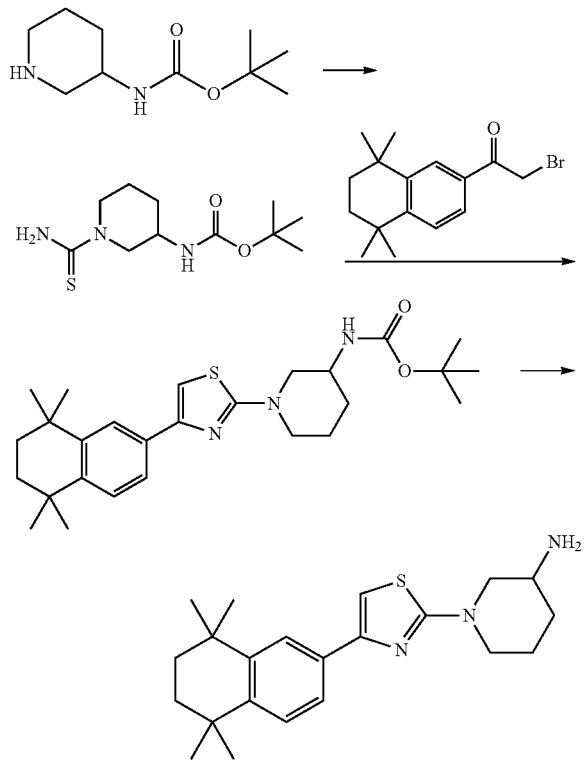

The preparation is carried out analogously to the above-mentioned procedure starting from 877 mg (4.38 mmol) of piperidin-3-ylcarbamic acid tert-butyl ester.

579 mg, yellow solid, Rt.=2.65 min (method B), LCMS: 370 (M+H).

$^1$H NMR (400 MHz, DMSO/deuterated TFA) δ=7.69 (d, J=1.8, 1H), 7.51 (dd, J=8.2, 1.9, 1H), 7.43 (d, J=8.3, 1H), 4.06 (dd, J=12.7, 3.2, 1H), 3.84-3.76 (m, 1H), 3.62-3.47 (m, 3H), 2.14-2.03 (m, 1H), 2.01-1.90 (m, 1H), 1.83-1.74 (m, 2H), 1.71 (s, 4H), 1.31 (d, J=14.2, 12H).

Preparation of 4-{1-[4-(5,5,8,8-tetramethyl-5,6,7,8-tetrahydronaphthalen-2-yl)thiazol-2-yl]piperidin-3-ylamino}butan-1-ol

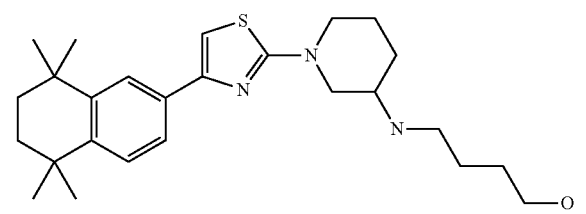 [SMILES: CC1(C)CCC(C)(C)c2cc(-c3csc(N4CCCC(NCCCCO)C4)n3)ccc21]

The preparation is carried out as described starting from 75 mg (0.20 mmol) of 1-[4(5,5,8,8-tetramethyl-5,6,7,8-tetrahydronaphthalen-2-yl)thiazol-2-yl]piperidin-3-ylamine and 45 μl (0.31 mmol) of 4-bromobutyl acetate. The protecting group is cleaved off by means of a 1N NaOH solution in methanol. The product is in the form of the hydrochloride.

12 mg pale solid, Rt.=2.71 min (method B), LCMS: 442 (M+H).

$^1$H NMR (500 MHz, DMSO/deuterated TFA) δ=7.70 (s, 1H), 7.51 (d, J=8.2, 1H), 7.42 (d, J=8.3, 1H), 4.18 (dd, J=13.2, 3.2, 1H), 3.83-3.75 (m, 1H), 3.70-3.61 (m, 1H), 3.54-3.44 (m, 4H), 3.09 (dd, J=8.7, 6.0, 2H), 2.21-2.13 (m, 1H), 2.00-1.92 (m, 1H), 1.86-1.73 (m, 4H), 1.70 (s, 4H), 1.61-1.54 (m, 2H), 1.30 (d, J=17.8, 12H).

Preparation of 3-{1-[4-(5,5,8,8-tetramethyl-5,6,7,8-tetrahydronaphthalen-2-yl)thiazol-2-yl]piperidin-3-ylamino}propan-1-ol

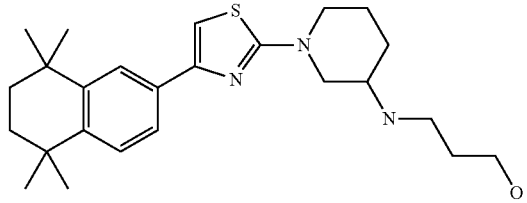 [SMILES: CC1(C)CCC(C)(C)c2cc(-c3csc(N4CCCC(NCCCO)C4)n3)ccc21]

The preparation is carried out as described starting from 50 mg (0.11 mmol) of 1-[4-(5,5,8,8-tetramethyl-5,6,7,8-tetrahydronaphthalen-2-yl)thiazol-2-yl]piperidin-3-ylamine and 14 μl (0.16 mmol) of 3-chloropropan-1-ol. The product is in the form of the hydrochloride.

13 mg pale solid, Rt.=2.67 min (method B), LCMS: 428 (M+H).

$^1$H NMR (400 MHz, DMSO/deuterated TFA) δ=7.70-7.66 (m, 1H), 7.52-7.42 (m, 2H), 4.27-4.19 (m, 1H), 3.88-3.80 (m, 1H), 3.75-3.66 (m, 1H), 3.66-3.59 (m, 2H), 3.58-3.48 (m, 2H), 3.19 (t, J=7.5, 1H), 2.24-2.15 (m, 1H), 2.04-1.94 (m, 2H), 1.93-1.85 (m, 2H), 1.84-1.75 (m, 2H), 1.72 (s, 4H), 1.31 (d, J=13.7, 12H).

Preparation of 4-{1-[4-(5,5,8,8-tetramethyl-5,6,7,8-tetrahydronaphthalen-2-yl)thiazol-2-yl]azepan-4-ylamino}butan-1-ol

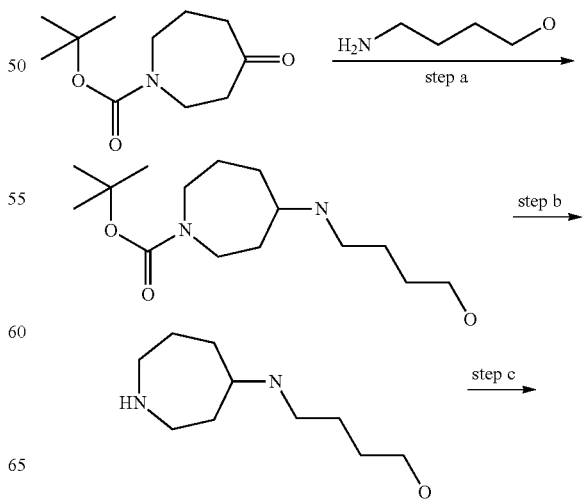

-continued

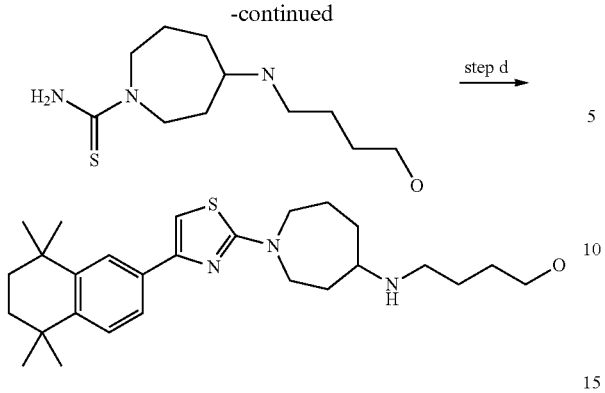

Step a

Preparation of 4-(4-hydroxybutylamino)azepane-1-carboxylic acid tert-butyl ester 1.09 g (4.65 mmol) of 4-oxoazepane-1-carboxylic acid tert-butyl ester and 864 µl (9.30 mmol) of 4-aminobutan-1-ol were suspended in 40 ml of ethanol, stirred at room temperature for 40 minutes, 532 µl (9.30 mmol) of glacial acetic acid were added, and the mixture was stirred for a further 10 min. Sodium triacetoxyborohydride (1.97 g, 9.30 mmol) was added, and the mixture was stirred at room temperature overnight and evaporated to dryness in vacuo. The residue was taken up in water and extracted 4 times with EA. The organic phase was dried over sodium sulfate, filtered and evaporated.

1.39 g clear oil, LCMS: 287 (M+H).

Step b

Preparation of 4-(azepan-4-ylamino)butan-1-ol

The Boc protecting group is cleaved off as described using 4 N HCl in dioxane.

1.09 g, yellow oil, LCMS: 187 (M+H).

Step c

Preparation of 4-(4-hydroxybutylamino)azepane-1-carbothioic acid amide

The preparation is carried out as already described starting from 419 mg (2.25 mmol) of product from step b and 401 mg (2.25 mmol) of thiocarbonylimidazole.

LCMS: 246 (M+H).

Step d

Preparation of 4-{1-[4-(5,5,8,8-tetramethyl-5,6,7,8-tetrahydronaphthalen-2-yl)thiazol-2-yl]azepan-4-ylamino}butan-1-ol The preparation is carried out as already described starting from 508 mg (1.15 mmol) of 2-bromo-1-(5,5,8,8-tetramethyl-5,6,7,8-tetrahydronaphthalen-2-yl)ethanone and the product from step c. The purification was carried out by means of preparative HPLC. The product is in the form of the hydrochloride.

31 mg pale solid, Rt.=2.53 min (method B), LCMS: 456 (M+H).

$^1$H NMR (500 MHz, DMSO/deuterated TFA) δ=7.53 (s, 1H), 7.42-7.35 (m, 2H), 3.93-3.85 (m, 1H), 3.77-3.57 (m, 3H), 3.43 (t, J=6.1, 2H), 3.32-3.25 (m, 1H), 2.97-2.89 (m, 2H), 2.34-2.26 (m, 1H), 2.18-2.10 (m, 1H), 2.09-2.01 (m, 1H), 1.97-1.88 (m, 1H), 1.87-1.79 (m, 1H), 1.70-1.57 (m, 7H), 1.51-1.44 (m, 2H), 1.27-1.21 (m, 12H).

Preparation of 3-{1-[4-(5,5,8,8-tetramethyl-5,6,7,8-tetrahydronaphthalen-2-yl)thiazol-2-yl]azepan-4-ylamino}propan-1-ol

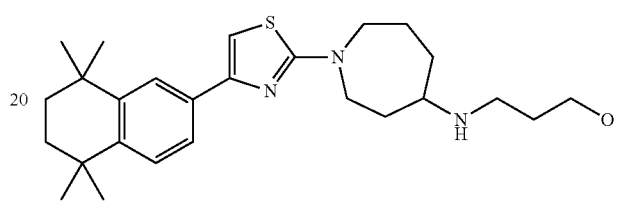

The preparation is carried out in 4 steps as described above starting from 3-aminopropan-1-ol. The product is in the form of the hydrochloride.

75 mg pale solid, Rt.=2.57 min (method B), LCMS: 442 (M+H).

$^1$H NMR (500 MHz, DMSO/deuterated TFA) δ=8.75 (s, 2H), 7.74 (d, J=1.7, 1H), 7.55 (dd, J=8.2, 1.7, 1H), 7.32 (d, J=8.3, 1H), 7.10 (s, 1H), 3.93-3.86 (m, 1H), 3.67-3.60 (m, 1H), 3.58-3.50 (m, 2H), 3.48 (t, J=6.0, 2H), 3.25-3.18 (m, 1H), 3.02-2.92 (m, 2H), 2.35-2.26 (m, 1H), 2.19-2.10 (m, 1H), 2.08-1.99 (m, 1H), 1.91-1.82 (m, 1H), 1.82-1.73 (m, 3H), 1.68-1.62 (m, 4H), 1.61-1.51 (m, 1H), 1.30-1.22 (m, 14H).

Preparation of 2-{1-[4-(5,5,8,8-tetramethyl-5,6,7,8-tetrahydronaphthalen-2-yl)thiazol-2-yl]azepan-4-ylamino}ethanol

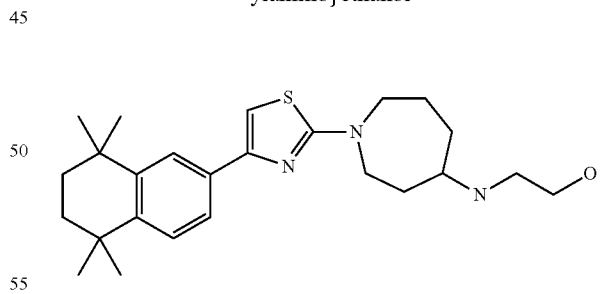

The preparation is carried out in 4 steps as described above starting from 2-aminoethanol. The product is in the form of the hydrochloride.

29 mg pale solid, Rt.=2.59 min (method B), LCMS: 428 (M+H).

$^1$H NMR (400 MHz, DMSO/deuterated TFA) δ=8.86 (s, 2H), 7.74 (d, J=1.8, 1H), 7.55 (dd, J=8.2, 1.8, 1H), 7.33 (d, J=8.3, 1H), 7.11 (s, 1H), 3.94-3.85 (m, 1H), 3.72-3.61 (m, 3H), 3.60-3.46 (m, 2H), 3.28-3.18 (m, 1H), 3.05-2.96 (m, 2H), 2.39-2.28 (m, 1H), 2.22-2.12 (m, 1H), 2.09-1.98 (m, 1H), 1.94-1.81 (m, 1H), 1.81-1.69 (m, 1H), 1.69-1.63 (m, 4H), 1.63-1.52 (m, 1H), 1.31-1.22 (m, 13H).

Preparation of 2-(3,3-dimethylindan-5-yl)-4,4,5,5-tetramethyl-1,3,2-dioxaborolane

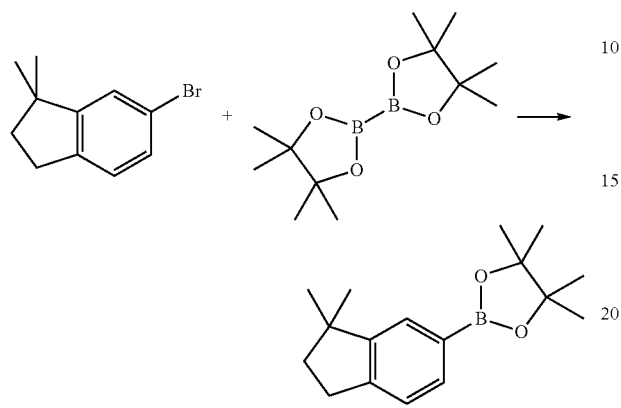

500 mg (8.36 mmol) of 6-bromo-1,1-dimethylindane (preparation see WO 2005/66115A2) are dissolved in 5 ml of THF, and 733 mg (2.89 mmol) of bis(pinacolato)diboron and 654 mg (6.66 mmol) of potassium acetate are added. The reaction mixture is degassed a number of times, 78 mg (0.11 mmol) of bis(triphenylphosphine)palladium(II) dichloride are added under nitrogen atmosphere, and the mixture is stirred at 70° C. overnight. The reaction mixture is filtered and rinsed with 75 ml of EA. The filtrate is washed with 50 ml of water, dried over sodium sulfate, filtered and evaporated. The crude product is purified by means of flash chromatography on silica gel.

140 mg white solid, Rt.=3.83 min (method B), LCMS: 273 (M+H).

Preparation of 2-(8,8-dimethyl-5,6,7,8-tetrahydronaphthalen-2-yl)-4,4,5,5-tetramethyl-1,3,2-dioxaborolane

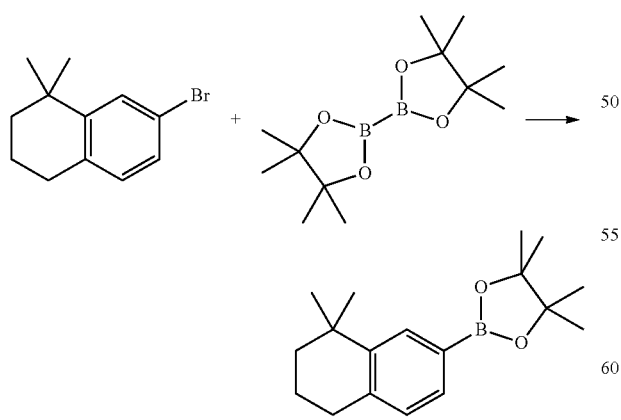

The preparation is carried out analogously starting from 1 g (4.18 mmol) of 7-bromo-1,1-dimethyl-1,2,3,4-tetrahydronaphthalene (preparation see WO2005/66115) and 1.38 g (5.44 mmol) of bis(pinacolato)diboron.

844 mg, yellow oil, Rt.=3.91 min (method B), LCMS: 287 (M+H).

Preparation of 4,4,5,5-tetramethyl-2-(1,1,3,3-tetramethylindan-5-yl)-1,3,2-dioxaborolane

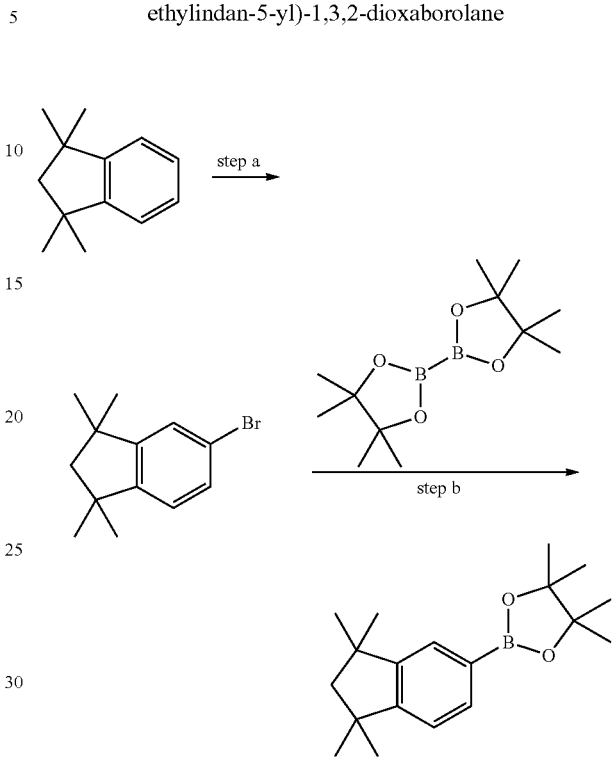

Step a:
The bromination of 500 mg (2.87 mmol) of 1,1,3,3-tetramethylindane (see US 2005/148590) is carried out analogously to the procedure in Organic Synthesis, Collective Vol. 3, p. 138 (1995).

732 mg, yellow oil, Rt.=3.97 min (method B).

Step b:
The preparation is carried out analogously starting from 360 mg (1.42 mmol) of 5-bromo-1,1,3,3-tetramethylindane from step a and 469 mg (1.85 mmol) of bis(pinacolato)diboron.

365 mg, yellow oil, Rt.=4.07 min (method B).
$^1$H NMR (400 MHz, DMSO/deuterated TFA) δ 7.57 (dd, J=7.5, 1.0, 1H), 7.50 (s, 1H), 7.17 (d, J=7.2, 1H), 1.90 (s, 2H), 1.31 (s, 12H), 1.30 (s, 6H), 1.28 (s, 6H).

Preparation of 2-{1-[4-(3,3-dimethylindan-5-yl)thiazol-2-yl]piperidin-4-ylamino}ethanol

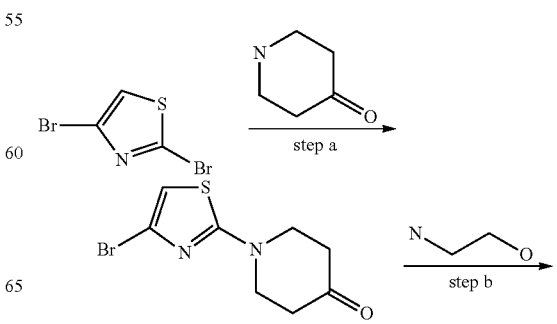

-continued

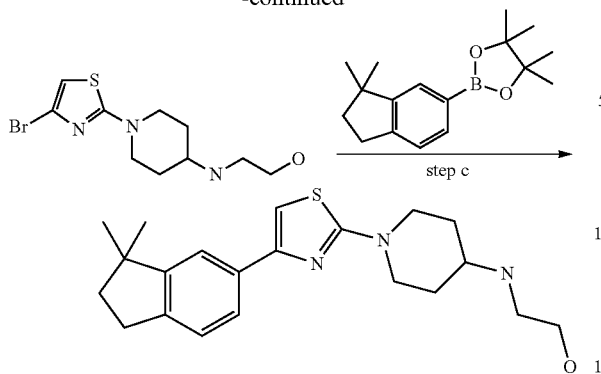

Step a

Preparation of 1-(4-bromothiazol-2-yl)piperidin-4-one 1 g (4.12 mmol) of 2,4-dibromothiazole was dissolved in 10 ml of DMF, 1.06 g (7.82 mmol) of piperidin-4-one hydrochloride and 2.3 ml (16.47 mmol) of triethylamine were added, and the mixture was stirred at 80° C. for 3 days. The reaction mixture was stirred into 300 ml of water and extracted by shaking with EA. The organic phase was dried over sodium sulfate, filtered and evaporated. The purification was carried out by means of flash chromatography on silica gel.

500 mg, yellow oil, Rt.=2.23 min (method A), LCMS: 262 (M+H).

Step b

Preparation of 2-[1-(4-bromothiazol-2-yl)piperidin-4-ylamino]ethanol 100 mg (0.37 mmol) of 1-(4-bromothiazol-2-yl)piperidin-4-one from step a and 22 µl (0.37 mmol) of 2-aminoethanol were suspended in 7 ml of THF, stirred at room temperature for 1 h, 21 µl (0.37 mmol) of glacial acetic acid and 164 mg (0.74 mmol) of sodium triacetoxyborohydride were added. The mixture was stirred at room temperature overnight, water and EA were added, the mixture was adjusted to pH 12 using a concentrated NaOH solution and extracted by shaking with EA. The organic phase was dried over sodium sulfate, filtered and evaporated.

122 mg brown residue, LCMS: 307 (M+H), Rt.=1.78 min (method A).

Step c

Preparation of 2-{1-[4-(3,3-dimethylindan-5-yl)thiazol-2-yl]piperidin-4-ylamino}-ethanol 130 mg (0.30 mmol) of 2-[1-(4-bromothiazol-2-yl]piperidin-4-ylamino]ethanol from step b, 92 mg (0.29 mmol) of 2-(3,3-dimethylindan-5-yl)-4,4,5,5-tetramethyl-1,3,2-dioxaborolane, 92 mg (0.03 mmol) of tetrakis(triphenlyphosphine)palladium(0) and 125 mg (1.18 mmol) of sodium carbonate were weighed out, placed under nitrogen. 2.5 ml of dioxane and 0.5 ml of water were added with stirring. The mixture was degassed, homogenised in an ultrasound bath and heated at 120° C. in the microwave for 30 min, diluted with about 20 ml of EA and 20 ml of water and filtered off. The phases were separated, and the water phase was extracted a further once with EA. The organic phases were combined, dried over sodium sulfate, filtered and evaporated. The oily residue was purified by means of preparative HPLC. The product is in the form of the hydrochloride.

19 mg, pale solid, LCMS: 372 (M+H), Rt.=2.47 min (method B).

¹H NMR (500 MHz, DMSO/deuterated TFA) δ=7.45-7.41 (m, 2H), 7.22 (d, J=8.4, 1H), 4.13 (d, J=13.6, 2H), 3.70-3.65 (m, 2H), 3.45-3.31 (m, 3H), 3.06-3.02 (m, 2H), 2.83 (t, J=7.2, 2H), 2.20 (d, J=10.7, 2H), 1.90-1.83 (m, 2H), 1.82-1.73 (m, 2H), 1.20 (s, 6H).

Preparation of 2-{1-[4-(1,1,3,3-tetramethylindan-5-yl)thiazol-2-yl]-piperidin-4-ylamino}ethanol

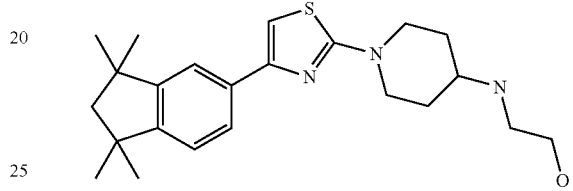

The preparation is carried out as described above starting from 110 mg (0.29 mmol) of 2-[1-(4-bromothiazol-2-yl)piperidin-4-ylamino]ethanol and 98 mg (0.29 mmol) of 4,4,5,5-tetramethyl-2-(1,1,3,3-tetramethylindan-5-yl)-1,3,2-dioxaborolane. The product is in the form of the formate.

13 mg, white solid, LCMS: 400 (M+H), Rt.=2.74 min (method B).

¹H NMR (400 MHz, DMSO/deuterated TFA) δ=7.56 (dd, J=7.9, 1.7, 1H), 7.49 (d, J=1.5, 1H), 7.28 (d, J=7.9, 1H), 4.22 (d, J=13.5, 2H), 3.81-3.75 (m, 2H), 3.56-3.41 (m, 3H), 3.17-3.10 (m, 2H), 2.34-2.25 (m, 2H), 1.97 (s, 2H), 1.88 (qd, J=12.6, 4.3, 2H), 1.34 (d, J=10.6, 12H).

Preparation of 2-{1-[4-(8,8-dimethyl-5,6,7,8-tetrahydronaphthalen-2-yl)thiazol-2-yl]piperidin-4-ylamino}ethanol

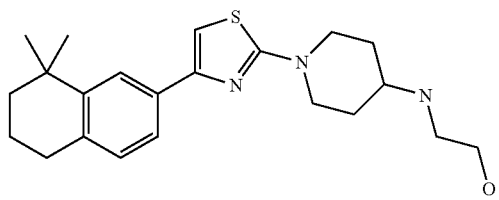 [SMILES: CC1(C)CCCc2ccc(-c3csc(N4CCC(NCCO)CC4)n3)cc21]

The preparation is carried out as described above starting from 100 mg (0.27 mmol) of 2-[1-(4-bromothiazol-2-yl)piperidin-4-ylamino]ethanol and 98 mg (0.30 mmol) of 2-(8,8-dimethyl-5,6,7,8-tetrahydronaphthalen-2-yl)-4,4,5,5-tetramethyl-1,3,2-dioxaborolane. The product is in the form of the hydrochloride.

16 mg, pale solid, LCMS: 386 (M+H), Rt.=2.62 min (method B).

¹H NMR (500 MHz, DMSO/deuterated TFA) δ=7.77 (d, J=1.7, 1H), 7.50 (dd, J=7.9, 1.8, 1H), 7.12 (d, J=8.0, 1H), 4.18 (d, J=13.4, 2H), 3.76-3.70 (m, 2H), 3.50-3.40 (m, 1H), 3.38-3.27 (m, 2H), 3.14-3.07 (m, 2H), 2.76 (t, J=6.2, 2H), 2.24 (d, J=10.3, 2H), 1.85-1.74 (m, 4H), 1.70-1.64 (m, 2H), 1.33-1.29 (m, 6H).

Preparation of 1-[4-(5,5,8,8-tetramethyl-5,6,7,8-tetrahydronaphthalen-2-yl)thiazol-2-yl]piperidin-4-one

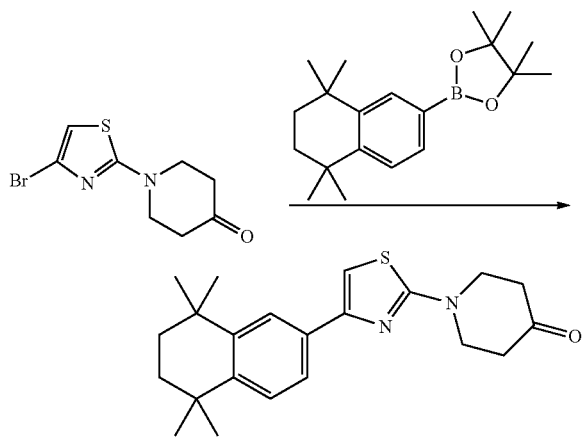

The preparation is carried out as already described via a Suzuki reaction starting from 339 mg (1.18 mmol) of 1-(4-bromothiazol-2-yl)piperidin-4-one (preparation already described above) and 449 mg (1.30 mmol) of 4,4,5,5-tetramethyl-2-(5,5,8,8-tetramethyl-5,6,7,8-tetrahydronaphthalen-2-yl)-1,3,2-dioxaborolane.

208 mg, pale solid, Rt.=3.55 min (method B), LCMS: 369 (M+H).

$^1$H NMR (500 MHz, DMSO/deuterated TFA) δ=7.68 (d, J=1.9, 1H), 7.51 (dd, J=8.2, 1.9, 1H), 7.44 (d, J=8.3, 1H), 4.01 (t, J=6.3, 4H), 2.71-2.68 (m, 4H), 1.70 (s, 4H), 1.30 (d, J=16.7, 12H).

Preparation of (1R,2S,3R)-3-{1-[4-(5,5,8,8-tetramethyl-5,6,7,8-tetrahydronaphthalen-2-yl)thiazol-2-yl]piperidin-4-ylamino}cyclopentane-1,2-diol

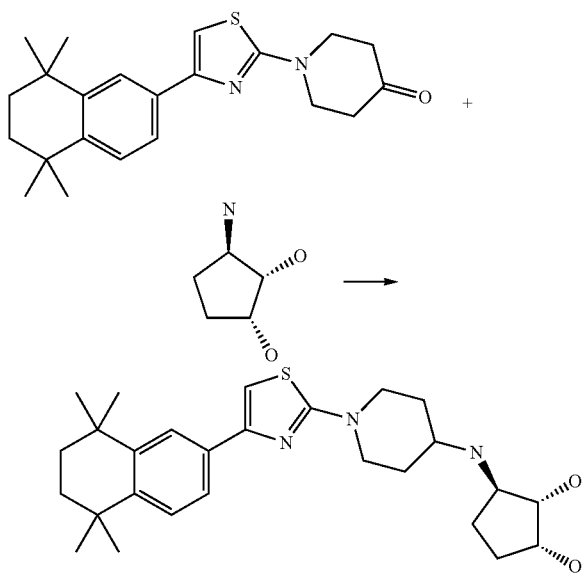

24 mg (0.16 mmol) of (1R,2S,3R)-3-aminocyclopentane-1,2-diol hydrochloride are dissolved in 1 ml of THF and 2 ml of DMF, and 27 μl (0.16 mmol) of DIPEA are added. 60 mg (0.16 mmol) of 1-[4-(5,5,8,8-tetramethyl-5,6,7,8-tetrahydronaphthalen-2-yl)thiazol-2-yl]piperidin-4-one are added. The mixture is stirred at room temperature for 30 min, 18 μl (0.32 mmol) of glacial acetic acid are added, and the mixture is stirred for a further 10 min. 70 mg (0.32 mmol) of sodium triacetoxyborohydride are subsequently added. The reaction mixture is stirred at room temperature overnight, a concentrated sodium hydrogencarbonate solution is added, and the mixture is extracted twice with EA. The organic phase is dried over sodium sulfate, filtered and evaporated. The residue is purified by means of preparative HPLC. The product is in the form of the hydrochloride.

46 mg, pale solid, Rt.=2.52 min (method B), LCMS: 470 (M+H).

$^1$H NMR (400 MHz, DMSO/deuterated TFA) δ=7.63 (s, 1H), 7.50-7.43 (m, 2H), 4.28-4.18 (m, 2H), 4.13-4.06 (m, 1H), 4.05-4.00 (m, 1H), 3.69-3.58 (m, 2H), 3.57-3.43 (m, 3H), 2.42-2.21 (m, 3H), 2.08-1.80 (m, 5H), 1.75-1.64 (m, 5H), 1.32 (d, J=12.5, 13H).

Preparation of (1S,2R,3R)-3-{1-[4-(5,5,8,8-tetramethyl-5,6,7,8-tetrahydronaphthalen-2-yl)thiazol-2-yl]piperidin-4-ylamino}cyclopentane-1,2-diol

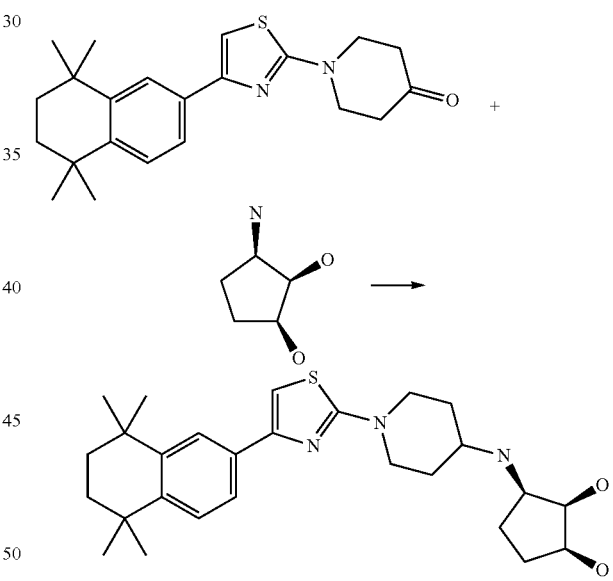

The preparation is carried out analogously starting from 24 mg (0.16 mmol) of (1S,2R,3R)-3-aminocyclopentane-1,2-diol hydrochloride and 60 mg (0.16 mmol) of 1-[4-(5,5,8,8-tetramethyl-5,6,7,8-tetrahydronaphthalen-2-yl)thiazol-2-yl]-piperidin-4-one. The product is in the form of the hydrochloride.

33 mg, pale solid, Rt.=2.50 min (method B), LCMS: 470 (M+H).

$^1$H NMR (500 MHz, DMSO/deuterated TFA) δ=7.44 (d, J=1.5, 1H), 7.33 (d, J=8.3, 1H), 7.26 (dd, J=8.2, 1.6, 1H), 4.07 (d, J=13.5, 2H), 4.01-3.93 (m, 2H), 3.50-3.43 (m, 1H), 3.42-3.31 (m, 3H), 2.21 (dd, J=27.2, 12.1, 2H), 1.94-1.85 (m, 1H), 1.85-1.75 (m, 3H), 1.74-1.65 (m, 2H), 1.59 (s, 4H), 1.17 (d, J=13.3, 12H).

Preparation of (R)-4-{1-[4-(5,5,8,8-tetramethyl-5,6,7,8-tetrahydronaphthalen-2-yl)thiazol-2-yl]piperidin-4-ylamino}butane-1,2-diol

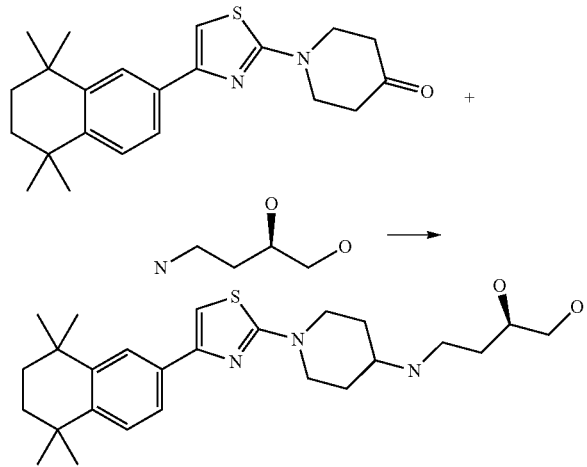

The preparation is carried out analogously starting from 22 mg (0.21 mmol) of (R)-4-aminobutane-1,2-diol and 80 mg (0.21 mmol) of 1-[4-(5,5,8,8-tetramethyl-5,6,7,8-tetrahydronaphthalen-2-yl)thiazol-2-yl]piperidin-4-one. The product is in the form of the hydrochloride.

52 mg, pale resin, Rt.=2.44 min (method B), LCMS: 458 (M+H).

$^1$H NMR (500 MHz, DMSO/deuterated TFA) δ=7.45 (d, J=1.7, 1H), 7.34 (d, J=8.3, 1H), 7.27 (dd, J=8.2, 1.7, 1H), 4.09 (d, J=13.6, 2H), 3.65-3.57 (m, 1H), 3.43-3.31 (m, 5H), 3.12-3.00 (m, 2H), 2.17 (d, J=10.8, 2H), 1.83-1.72 (m, 3H), 1.71-1.62 (m, 1H), 1.59 (s, 4H), 1.17 (d, J=13.7, 12H).

Preparation of (S)-4-{1-[4-(5,5,8,8-tetramethyl-5,6,7,8-tetrahydronaphthalen-2-yl)thiazol-2-yl]piperidin-4-ylamino}butane-1,2-diol

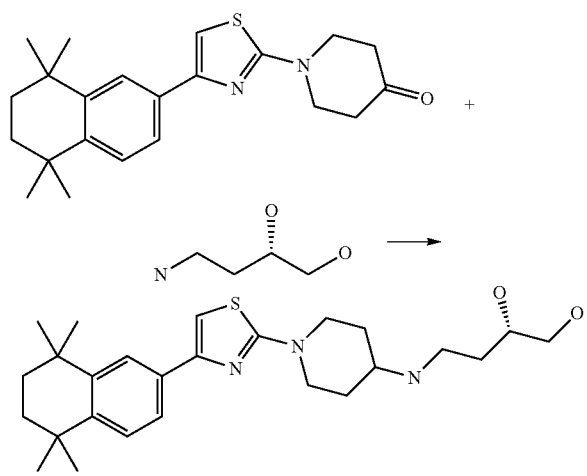

The preparation is carried out analogously starting from 22 mg (0.21 mmol) of (S)-4-aminobutane-1,2-diol and 80 mg (0.21 mmol) of 1-[4-(5,5,8,8-tetramethyl-5,6,7,8-tetrahydronaphthalen-2-yl)thiazol-2-yl]piperidin-4-one. The product is in the form of the hydrochloride.

72 mg, pale resin, Rt.=2.49 min (method B), LCMS: 458 (M+H).

$^1$H NMR (500 MHz, DMSO/deuterated TFA) δ=7.69 (s, 1H), 7.50 (d, J=8.2, 1H), 7.44 (d, J=8.3, 1H), 4.20 (d, J=13.4, 2H), 3.68-3.61 (m, 1H), 3.53-3.33 (m, 5H), 3.19-3.09 (m, 2H), 2.26 (d, J=11.0, 2H), 1.96-1.78 (m, 3H), 1.76-1.66 (m, 5H), 1.31 (d, J=17.3, 12H).

Preparation of ((3aS,4R,7aR)-2,2-dimethylhexahydrobenzo-1,3-dioxol-4-yl)-{1-[4-(5,5,8,8-tetramethyl-5,6,7,8-tetrahydronaphthalen-2-yl)thiazol-2-yl]-piperidin-4-yl}amine

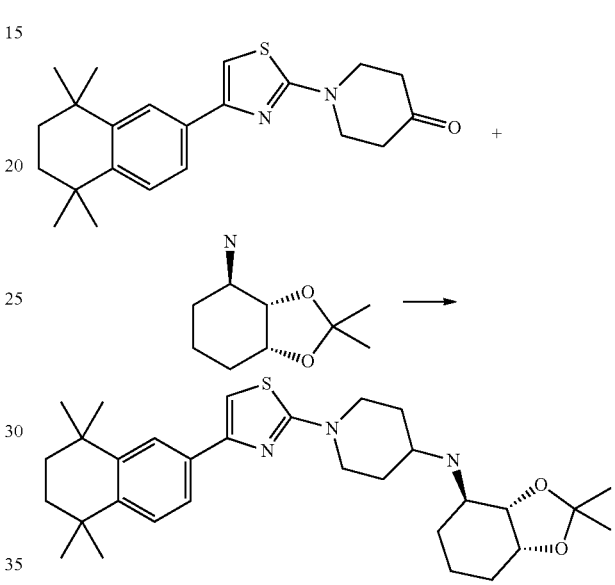

The preparation is carried out analogously in THF starting from 27 mg (0.16 mmol) of (3aS,4R,7aR)-2,2-dimethylhexahydrobenzo-1,3-dioxol-4-ylamine and 60 mg (0.16 mmol) of 1-[4-(5,5,8,8-tetramethyl-5,6,7,8-tetrahydronaphthalen-2-yl)thiazol-2-yl]piperidin-4-one. The purification is carried out by means of flash chromatography on silica gel.

45 mg, yellow resin, Rt.=3.02 min (method B), LCMS: 524 (M+H).

Preparation of (1R,2S,3R)-3-{1-[4-(5,5,8,8-tetramethyl-5,6,7,8-tetrahydronaphthalen-2-yl)thiazol-2-yl]piperidin-4-ylamino}cyclohexane-1,2-diol

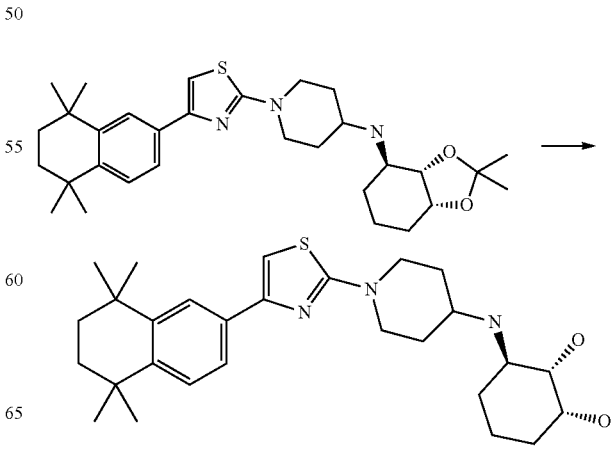

3 ml of 1.25 N HCl in methanol are added to 45 mg of ((3aS,4R,7aR)-2,2-dimethylhexahydrobenzo-1,3-dioxol-4-yl)-{1-[4-(5,5,8,8-tetramethyl-5,6,7,8-tetrahydronaphthalen-2-yl)thiazol-2-yl]piperidin-4-yl}amine, and the mixture is stirred at room temperature overnight. The reaction mixture is evaporated and dried under high vacuum. The product is in the form of the hydrochloride.

45 mg, pale solid, Rt.=2.55 min (method B), LCMS: 484 (M+H).

¹H NMR (500 MHz, DMSO/deuterated TFA) δ=7.61 (s, 1H), 7.43 (d, J=8.2, 1H), 7.37 (d, J=8.3, 1H), 4.16-4.08 (m, 2H), 3.92 (d, J=2.5, 1H), 3.64-3.55 (m, 1H), 3.44 (dd, J=10.1, 2.7, 1H), 3.34 (t, J=12.8, 2H), 3.25 (td, J=12.0, 4.0, 1H), 2.19-2.03 (m, 3H), 2.02-1.92 (m, 1H), 1.84-1.68 (m, 2H), 1.68-1.60 (m, 5H), 1.46 (d, J=13.5, 1H), 1.42-1.29 (m, 2H), 1.24 (d, J=16.6, 12H).

Preparation of (S)-2-amino-3-hydroxy-N-{2-[4-(5,5,8,8-tetramethyl-5,6,7,8-tetrahydronaphthalen-2-yl]thiazol-2-yl]ethyl}propionamide

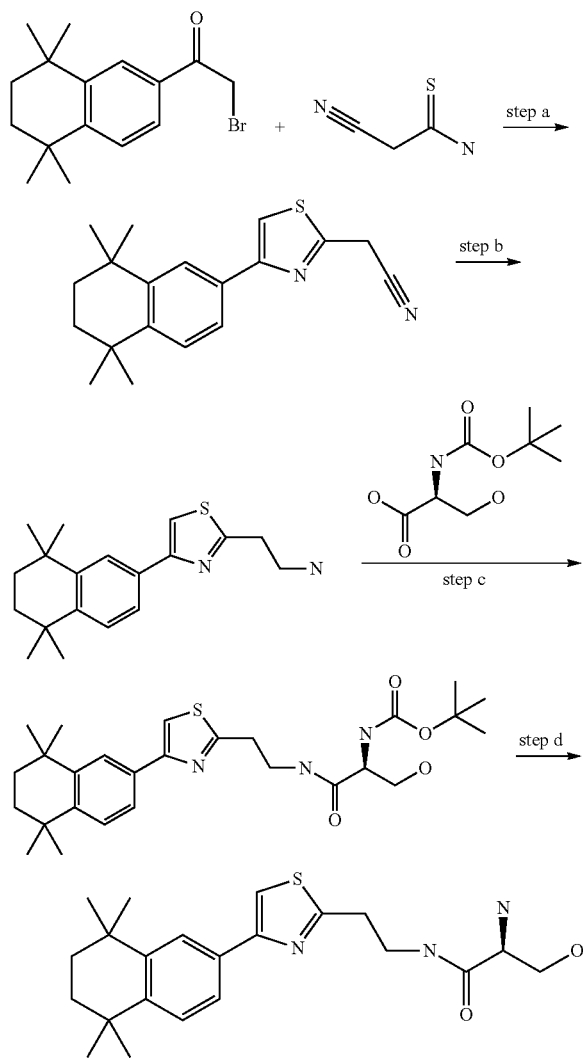

Step a

Preparation of [4-(5,5,8,8-tetramethyl-5,6,7,8-tetrahydronaphthalen-2-yl)thiazol-2-yl]acetonitrile The preparation is carried out as already described starting from 576 mg (5.75 mmol) of 2-cyanothioacetamide and 2 g (4.72 mmol) of 2-bromo-1-(5,5,8,8-tetramethyl-5,6,7,8-tetrahydronaphthalen-2-yl)ethanone.

680 mg, brown oil, Rt.=3.45 min (method B), LCMS: 311 (M+H).

¹H NMR (500 MHz, DMSO/deuterated TFA) δ=8.03-8.00 (m, 1H), 7.91 (d, J=1.8, 1H), 7.70 (dd, J=8.2, 1.8, 1H), 7.40 (d, J=8.2, 1H), 1.73-1.67 (m, 4H), 1.34-1.27 (m, 12H).

Step b

Preparation of 2-[4-(5,5,8,8-tetramethyl-5,6,7,8-tetrahydronaphthalen-2-yl)thiazol-2-yl]ethylamine 680 mg (2.19 mmol) of [4-(5,5,8,8-tetramethyl-5,6,7,8-tetrahydronaphthalen-2-yl)thiazol-2-yl]acetonitrile from step a are dissolved in 10 ml of THF, placed under nitrogen, boiled to reflux, and 1.21 ml (2.41 mmol) of a 2M borane dimethyl sulfide complex solution in THF are added. The mixture is refluxed for a further 40 min, cooled, a 1.25 M HCl solution in methanol is slowly added, the mixture is evaporated in a rotary evaporator. The residue is taken up in DCM, washed with a saturated sodium hydrogencarbonate solution. The organic phase is dried, filtered and evaporated. The brown oily residue is digested using a little ACN and filtered off with suction.

375 mg, beige crystals, Rt.=2.48 min (method B), LCMS: 315 (M+H).

Step c

Preparation of ((S)-2-hydroxy-1-{2-[4-(5,5,8,8-tetramethyl-5,6,7,8-tetrahydronaphthalen-2-yl)thiazol-2-yl]ethylcarbamoyl}ethyl)carbamic acid tert-butyl ester The preparation is carried out as already described starting from 186 mg (0.59 mmol) of 2-[4-(5,5,8,8-tetramethyl-5,6,7,8-tetrahydronaphthalen-2-yl)thiazol-2-yl]ethylamine from step b and 133 mg (0.65 mmol) of (S)-2-tert-butoxycarbonylamino-3-hydroxypropionic acid.

82 mg, brown oil, Rt.=3.15 min (method B), LCMS: 502 (M+H).

Step d

Preparation of (S)-2-amino-3-hydroxy-N-{2-[4-(5,5,8,8-tetramethyl-5,6,7,8-tetrahydronaphthalen-2-yl)thiazol-2-yl]ethyl}propionamide The protecting group is cleaved off as already described using HCl in dioxane starting from 82 mg (0.16 mmol) of ((S)-2-hydroxy-1-{2-[4-(5,5,8,8-tetramethyl-5,6,7,8-tetrahydronaphthalen-2-yl)thiazol-2-yl]ethylcarbamoyl}ethyl)carbamic acid tert-butyl ester from step c. The product is purified by means of preparative HPLC and is in the form of the formate.

10 mg, solid, Rt.=2.36 min (method B), LCMS: 402 (M+H).

¹H NMR (400 MHz, DMSO/deuterated TFA) δ=8.12 (s, 1H), 7.94-7.88 (m, 2H), 7.69 (dd, J=8.2, 1.9, 1H), 7.40 (dd, J=8.2, 4.7, 1H), 3.87-3.75 (m, 2H), 3.75-3.67 (m, 2H), 3.65-3.55 (m, 1H), 3.30 (t, J=6.8, 2H), 1.71 (s, 4H), 1.31 (d, J=17.5, 12H).

Preparation of morpholine-2-carboxylic acid [6-(5,5,8,8-tetramethyl-5,6,7,8-tetrahydronaphthalen-2-yl)pyridin-2-yl]amide

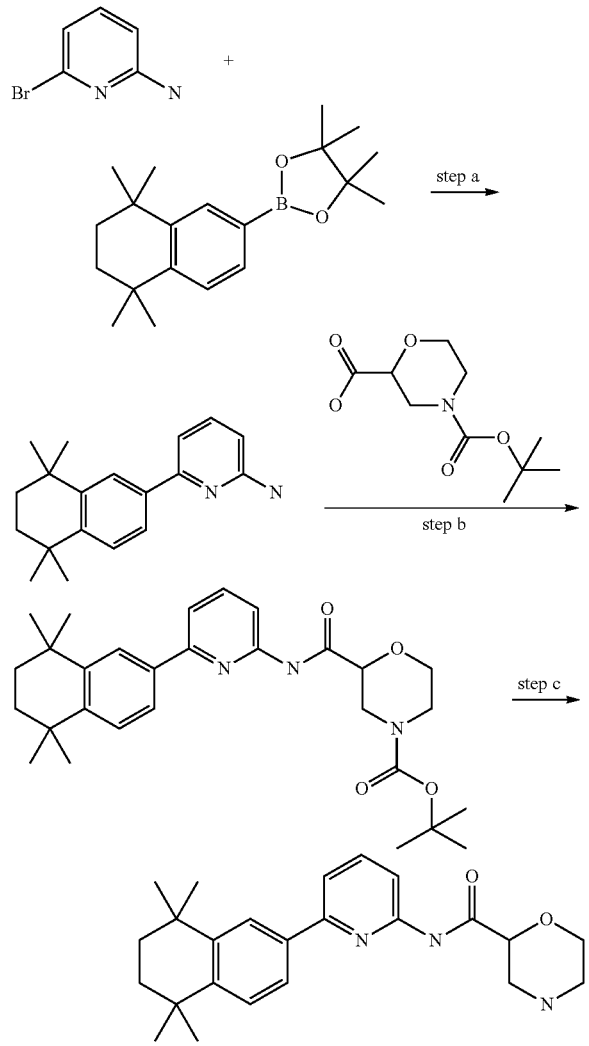

Step a

Preparation of 6-(5,5,8,8-tetramethyl-5,6,7,8-tetrahydronaphthalen-2-yl)pyridin-2-ylamine The preparation is carried out as already described starting from 2.30 g (13.0 mmol) of 6-bromopyridin-2-ylamine and 5.22 g (13.7 mmol) of 4,4,5,5-tetramethyl-2-(5,5,8,8-tetramethyl-5,6,7,8-tetrahydronaphthalen-2-yl)-1,3,2-dioxaborolane.

4.49 g, pale solid, Rt.=2.43 min (method B), LCMS: 281 (M+H).

$^1$H NMR (500 MHz, DMSO/deuterated TFA) δ=7.83 (dd, J=8.8, 7.5, 1H), 7.63 (d, J=1.8, 1H), 7.50-7.41 (m, 2H), 7.02 (d, J=7.1, 1H), 6.91 (d, J=8.8, 1H), 1.63 (s, 4H), 1.23 (d, J=19.6, 12H).

Step b

Preparation of 2-[6-(5,5,8,8-tetramethyl-5,6,7,8-tetrahydronaphthalen-2-yl)pyridin-2-ylcarbamoyl]morpholine-4-carboxylic acid tert-butyl ester 82 mg (0.36 mmol) of morpholine-2,4-dicarboxylic acid 4-tert-butyl ester and 97 mg (0.39 mmol) of ethyl 2-ethoxy-1,2-dihydroquinoline-1-carboxylate (EEDQ) are suspended in 2 ml of THF and stirred at room temperature for 20 min. 100 mg (0.36 mmol) of 6-(5,5,8,8-tetramethyl-5,6,7,8-tetrahydronaphthalen-2-yl)pyridin-2-ylamine from step a are added to the mixture. The mixture is stirred further overnight, water is added, the mixture is adjusted to pH 9-10 using a 2N NaOH solution and extracted twice with EA. The combined organic phases are dried, filtered and evaporated (191 mg). The residue is purified by means of flash chromatography on silica gel.

92 mg, white solid, Rt.=3.97 min (method B), LCMS: 494 (M+H).

Step c

Preparation of morpholine-2-carboxylic acid [6-(5,5,8,8-tetramethyl-5,6,7,8-tetrahydronaphthalen-2-yl)pyridin-2-yl]amide The protecting group is cleaved off as already described using TFA in DCM starting from 92 mg (0.19 mmol) of 2-[6-(5,5,8,8-tetramethyl-5,6,7,8-tetrahydronaphthalen-2-yl)pyridin-2-ylcarbamoyl]morpholine-4-carboxylic acid tert-butyl ester from step b. The product is purified by means of preparative HPLC and is in the form of the TFA salt.

23 mg, solid, Rt.=2.63 min (method B), LCMS: 394 (M+H).

$^1$H NMR (400 MHz, DMSO/deuterated TFA) δ=8.22-8.09 (m, 2H), 7.96 (d, J=2.0, 1H), 7.85-7.72 (m, 2H), 7.59-7.51 (m, 1H), 4.68 (dd, J=10.7, 2.8, 1H), 4.25 (d, J=13.0, 1H), 4.11-3.98 (m, 1H), 3.71-3.64 (m, 1H), 3.40-3.16 (m, 3H), 1.75 (s, 4H), 1.34 (d, J=17.6, 12H).

II. Biological Assays

The compounds of the formula (I) described in the examples can be tested for a kinase inhibiting activity in by the assays described below. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

Tests for the Inhibition of the SphK1 Activity

Test Description

Biochemical Assay

The kinase assay is carried out as a 384-well flashplate assay.

5 nM modified SphK1, 800 nM omega-biotinyl-D-erythro-sphingosine and 1 μM ATP (with 0.3 μCi of $^{33}$P-ATP/well) are incubated in a total volume of 50 μl (25 mM HEPES, 5 mM MgCl$_2$, 1 mM dithiothreitol, 0.01% of Brij35, 0.1% of BSA (fatty acid-free), pH 7.4) without or with test substance (5-10 concentrations) at 30° C. for 120 min. The reaction is terminated using 25 μl of 200 mM EDTA solution, filtered off with suction at room temperature after 30 min, and the cavities are washed 3 times with 100 μl of 0.9% NaCl solution. The non-specific proportion of the kinase reaction (blank) is determined using 0.5 mM NaCl. Radioactivity is measured in topcount. $IC_{50}$ values are calculated using RS1.

Besides checking the activity of the substance for the purified SphK1 enzyme, it is necessary to investigate in the next step whether the substances also inhibit SphK1 in its physiological environment, i.e. in the cytoplasm of the cell.

For this purpose, the formation of S1P in U2OS osteosarcoma cells which have overproduced the enzyme through the introduction of modified SphK1-cDNA is measured using two different methods:
1. The cells are incubated for 1 hour with substances and subsequently for 15 min with tritium-labelled sphingosine. The radioactively labelled sphingosine is taken up by the cells in this time and converted into S1P by SphK1. The cells are then washed and lysed using ammonia solution. In order to separate S1P from unreacted sphingosine, an extraction is carried out by addition of a chloroform/methanol mixture. Whereas the majority of the sphingosine is transferred into the organic phase, S1P accumulates in the aqueous phase and is quantified with the aid of a scintillation counter.
2. The cells are incubated for 1 hour with substances and subsequently for 15 min with sphingosine. The sphingosine is taken up by the cells in this time and converted into S1P by SphK1. The cells are then washed and lysed using methanol. The methanol solution is then evaporated, and the S1P is taken up in lipid-free serum. The quantification of the S1P is carried out using an S1P-specific antibody with the aid of a competitive ELISA assay. The biotin-linked S1P antibody is incubated with the sample solution, and this mixture is transferred into a well whose base has been coated with S1P. Only the antibodies which have not yet bound any S1P from the sample solution bind to the S1P immobilised on the plate and can be quantified, after a washing step, by addition of horseradish peroxidase-coupled streptavidin. To this end, the substrate is added to TMB, which, after conversion by the peroxidase, absorbs at a wavelength of 450 nm and can be measured. A high signal consequently corresponds to a low S1P concentration in the sample solution and a low signal correspondingly to a high S1P concentration.

Pharmacological Data
SphK1 Inhibition
($IC_{50}$ ranges: A: <100 nM, B: 100 nM-1000 nM, C: >1000 nM)

TABLE 2

| Compound according to the invention | $IC_{50}$ |
|---|---|
| 1-[4-(5,5,8,8-Tetramethyl-5,6,7,8-tetrahydronaphthalen-2-yl)thiazol-2-yl]piperidin-4-ylamine | B |
| 1-[4-(5,5,8,8-Tetramethyl-5,6,7,8-tetrahydronaphthalen-2-yl)thiazol-2-yl]piperazine | B |
| 2-{4-[4-(5,5,8,8-Tetramethyl-5,6,7,8-tetrahydronaphthalen-2-yl)-thiazol-2-yl]piperazin-1-yl}ethanol | B |
| 3-{4-[4-(5,5,8,8-Tetramethyl-5,6,7,8-tetrahydronaphthalen-2-yl)-thiazol-2-yl]piperazin-1-yl}propan-1-ol | B |
| 5-{4-[4-(5,5,8,8-Tetramethyl-5,6,7,8-tetrahydronaphthalen-2-yl)-thiazol-2-yl]piperazin-1-yl}pentan-1-ol | B |
| (1H-Imidazol-4-ylmethyl)-{1-[4-(5,5,8,8-tetramethyl-5,6,7,8-tetrahydronaphthalen-2-yl)thiazol-2-yl]piperidin-4-yl}amine | A |
| 4-(2-Pyrrolidin-1-ylethyl)-1-[4-(5,5,8,8-tetramethyl-5,6,7,8-tetrahydronaphthalen-2-yl)thiazol-2-yl]piperidine | B |
| 1-[4-(5,5,8,8-Tetramethyl-5,6,7,8-tetrahydronaphthalen-2-yl)thiazol-2-yl]-4,4'-bipiperidinyl | B |
| 1-[4-(5,5,8,8-Tetramethyl-5,6,7,8-tetrahydronaphthalen-2-yl)thiazol-2-yl]piperidine-4-carboxylic acid ethyl ester | C |
| 1-{1-[4-(5,5,8,8-Tetramethyl-5,6,7,8-tetrahydronaphthalen-2-yl)-thiazol-2-yl]piperidin-4-yl}pyrrolidin-3-ylamine | B |
| C-{1-[4-(5,5,8,8-Tetramethyl-5,6,7,8-tetrahydronaphthalen-2-yl)-thiazol-2-yl]piperidin-4-yl}methylamine | B |
| 1-[4-(5,5,8,8-Tetramethyl-5,6,7,8-tetrahydronaphthalen-2-yl)thiazol-2-yl]pyrrolidin-3-ylamine | B |
| 2-{1-[4-(5,5,8,8-Tetramethyl-5,6,7,8-tetrahydronaphthalen-2-yl)-thiazol-2-yl]piperidin-4-yl}ethylamine | B |
| 4-{1-[4-(5,5,8,8-Tetramethyl-5,6,7,8-tetrahydronaphthalen-2-yl)-thiazol-2-yl]piperidin-4-yl}morpholine | C |
| 1-Methyl-4-{1-[4-(5,5,8,8-tetramethyl-5,6,7,8-tetrahydronaphthalen-2-yl)thiazol-2-yl]piperidin-4-yl}piperazine | B |
| 3-{1-[4-(5,5,8,8-Tetramethyl-5,6,7,8-tetrahydronaphthalen-2-yl)-thiazol-2-yl]piperidin-4-ylamino}propane-1,2-diol | A |
| 3-[4-(5,5,8,8-Tetramethyl-5,6,7,8-tetrahydronaphthalen-2-yl)thiazol-2-yl]-3,9-diazaspiro[5.5]undecane | B |
| (3-Methyl-3H-imidazol-4-ylmethyl)-{1-[4-(5,5,8,8-tetramethyl-5,6,7,8-tetrahydronaphthalen-2-yl)thiazol-2-yl]piperidin-4-yl}amine | B |
| 3-[4-(5,5,8,8-Tetramethyl-5,6,7,8-tetrahydronaphthalen-2-yl)thiazol-2-yl]piperidine | B |
| 1-[4-(5,5,8,8-Tetramethyl-5,6,7,8-tetrahydronaphthalen-2-yl)thiazol-2-yl]piperidine-4-carboxylic acid (2-hydroxyethyl)amide | C |
| 3-{4-[4-(5,5,8,8-Tetramethyl-5,6,7,8-tetrahydronaphthalen-2-yl)-thiazol-2-yl]piperazin-1-yl}propane-1,2-diol | B |
| Bis-(1H-pyrazol-3-ylmethyl)-{1-[4-(5,5,8,8-tetramethyl-5,6,7,8-tetrahydronaphthalen-2-yl)thiazol-2-yl]piperidin-4-yl}amine | B |
| 2-{1-[4-(5,5,8,8-Tetramethyl-5,6,7,8-tetrahydronaphthalen-2-yl)-thiazol-2-yl]piperidin-4-ylamino}ethanol | A |
| 1'-[4-(5,5,8,8-Tetramethyl-5,6,7,8-tetrahydronaphthalen-2-yl)thiazol-2-yl]-1,4'-bipiperidinyl-3-ol | B |
| 3-{1-[4-(5,5,8,8-Tetramethyl-5,6,7,8-tetrahydronaphthalen-2-yl)-thiazol-2-yl]piperidin-4-yl}propan-1-ol | C |
| 2-{1-[4-(5,5,8,8-Tetramethyl-5,6,7,8-tetrahydronaphthalen-2-yl)-thiazol-2-yl]piperidin-3-yl}ethanol | B |
| 1-[4-(5,5,8,8-Tetramethyl-5,6,7,8-tetrahydronaphthalen-2-yl)thiazol-2-yl]piperidine-3-carboxylic acid (2-hydroxyethyl)amide | B |
| 1-[4-(5,5,8,8-Tetramethyl-5,6,7,8-tetrahydronaphthalen-2-yl)thiazol-2-yl]piperidine-3-carboxylic acid (3-hydroxypropyl)amide | C |
| 3-{1-[4-(5,5,8,8-Tetramethyl-5,6,7,8-tetrahydronaphthalen-2-yl)-thiazol-2-yl]piperidin-3-yl}propan-1-ol | C |
| (R)-1-[4-(5,5,8,8-Tetramethyl-5,6,7,8-tetrahydronaphthalen-2-yl)-thiazol-2-yl]pyrrolidin-3-ylamine | B |
| (S)-1-[4-(5,5,8,8-Tetramethyl-5,6,7,8-tetrahydronaphthalen-2-yl)-thiazol-2-yl]pyrrolidin-3-ylamine | B |
| Dimethyl-{1-[4-(5,5,8,8-tetramethyl-5,6,7,8-tetrahydronaphthalen-2-yl)thiazol-2-yl]piperidin-4-yl}amine | A |
| 4-[4-(5,5,8,8-Tetramethyl-5,6,7,8-tetrahydronaphthalen-2-yl)thiazol-2-yl]cyclohexylamine | B |
| N-(1-{1-[4-(5,5,8,8-Tetramethyl-5,6,7,8-tetrahydronaphthalen-2-yl)-thiazol-2-yl]piperidin-4-yl}pyrrolidin-3-yl)acetamide | A |
| 2-{4-[4-(5,5,8,8-Tetramethyl-5,6,7,8-tetrahydronaphthalen-2-yl)-thiazol-2-yl]piperazin-1-yl}cyclohexanol | B |
| 2-Pyrrolidin-3-yl-4-(5,5,8,8-tetramethyl-5,6,7,8-tetrahydronaphthalen-2-yl)thiazole | B |
| 1-[4-(5,5-Dimethyl-5,6,7,8-tetrahydronaphthalen-2-yl)thiazol-2-yl]-piperazine | B |
| 4-{4-[4-(5,5,8,8-Tetramethyl-5,6,7,8-tetrahydronaphthalen-2-yl)-thiazol-2-yl]piperazin-1-yl}butan-1-ol | B |
| 1-[4-(5,5-Dimethyl-5,6,7,8-tetrahydronaphthalen-2-yl)thiazol-2-yl]-piperidin-4-ylamine | B |
| 1-{4-[2-(5,5,8,8-Tetramethyl-5,6,7,8-tetrahydronaphthalen-2-yl)-thiazol-4-yl]piperidin-1-yl}ethanone | B |
| 2-(4-{1-[4-(5,5,8,8-Tetramethyl-5,6,7,8-tetrahydronaphthalen-2-yl)-thiazol-2-yl]piperidin-4-yl}piperazin-1-yl)ethanol | B |
| 4-[2-(5,5,8,8-Tetramethyl-5,6,7,8-tetrahydronaphthalen-2-yl)thiazol-4-yl]piperidine | B |
| 3-[1-[4-(5,5,8,8-Tetramethyl-5,6,7,8-tetrahydronaphthalen-2-yl)-thiazol-2-yl]piperidin-4-ylamino}propan-1-ol | A |
| 4-{4-[4-(5,5-Dimethyl-5,6,7,8-tetrahydronaphthalen-2-yl)thiazol-2-yl]-piperazin-1-yl}butan-1-ol | B |
| 5-{4-[4-(5,5-Dimethyl-5,6,7,8-tetrahydronaphthalen-2-yl)thiazol-2-yl]-piperazin-1-yl}pentan-1-ol | C |
| (R)-2-Amino-3-{1-[4-(5,5,8,8-tetramethyl-5,6,7,8-tetrahydronaphthalen-2-yl)thiazol-2-yl]piperidin-4-ylamino}propan-1-ol | B |
| 2-{(R)-1-[4-(5,5,8,8-Tetramethyl-5,6,7,8-tetrahydronaphthalen-2-yl)-thiazol-2-yl]pyrrolidin-3-ylamino}ethanol | C |
| 3-{(S)-1-[4-(5,5,8,8-Tetramethyl-5,6,7,8-tetrahydronaphthalen-2-yl)-thiazol-2-yl]pyrrolidin-3-ylamino}propan-1-ol | C |

TABLE 2-continued

| Compound according to the invention | IC$_{50}$ |
|---|---|
| 2-{3-[4-(5,5,8,8-Tetramethyl-5,6,7,8-tetrahydronaphthalen-2-yl)-thiazol-2-yl]piperidin-1-yl}ethanol | B |
| 3-{3-[4-(5,5,8,8-Tetramethyl-5,6,7,8-tetrahydronaphthalen-2-yl)-thiazol-2-yl]piperidin-1-yl}propan-1-ol | C |
| 4-(5,5-Dimethyl-5,6,7,8-tetrahydronaphthalen-2-yl)-2-pyrrolidin-3-yl-thiazole | B |
| 4-[2-(5,5,8,8-Tetramethyl-5,6,7,8-tetrahydronaphthalen-2-yl)oxazol-5-yl]piperidine | C |
| 4-{3-[4-(5,5,8,8-Tetramethyl-5,6,7,8-tetrahydronaphthalen-2-yl)-thiazol-2-yl]piperidin-1-yl}butan-1-ol | C |
| 5-{3-[4-(5,5,8,8-Tetramethyl-5,6,7,8-tetrahydronaphthalen-2-yl)-thiazol-2-yl]piperidin-1-yl}pentan-1-ol | C |
| 4-{3-[4-(5,5-Dimethyl-5,6,7,8-tetrahydronaphthalen-2-yl)thiazol-2-yl]-pyrrolidin-1-yl}butan-1-ol | B |
| 5-{3-[4-(5,5-Dimethyl-5,6,7,8-tetrahydronaphthalen-2-yl)thiazol-2-yl]-pyrrolidin-1-yl}pentan-1-ol | B |
| (R)-3-{1-[4-(5,5,8,8-Tetramethyl-5,6,7,8-tetrahydronaphthalen-2-yl)-thiazol-2-yl]piperidin-4-ylamino}propane-1,2-diol | B |
| (S)-3-{1-[4-(5,5,8,8-Tetramethyl-5,6,7,8-tetrahydronaphthalen-2-yl)-thiazol-2-yl]piperidin-4-ylamino}propane-1,2-diol | A |
| 2-[{1-[4-(5,5-Dimethyl-5,6,7,8-tetrahydronaphthalen-2-yl)thiazol-2-yl]piperidin-4-yl}-(2-hydroxyethyl)amino]ethanol | B |
| 2-((2-Hydroxyethyl)-{1-[4-(5,5,8,8-tetramethyl-5,6,7,8-tetrahydronaphthalen-2-yl)thiazol-2-yl]piperidin-4-yl}amino)ethanol | B |
| 1-[4-(1,1-Dimethylindan-5-yl)thiazol-2-yl]piperidin-4-ylamine | B |
| 2-{1-[4-(1,1-Dimethylindan-5-yl)thiazol-2-yl]piperidin-4-ylamino}-ethanol | B |
| 3-{1-[4-(1,1-Dimethylindan-5-yl)thiazol-2-yl]piperidin-4-ylamino}-propan-1-ol | B |
| (S)-2-Amino-3-{1-[4-(5,5,8,8-tetramethyl-5,6,7,8-tetrahydro-naphthalen-2-yl)thiazol-2-yl]piperidin-4-ylamino}propan-1-ol | |

The invention claimed is:

1. A compound selected from:

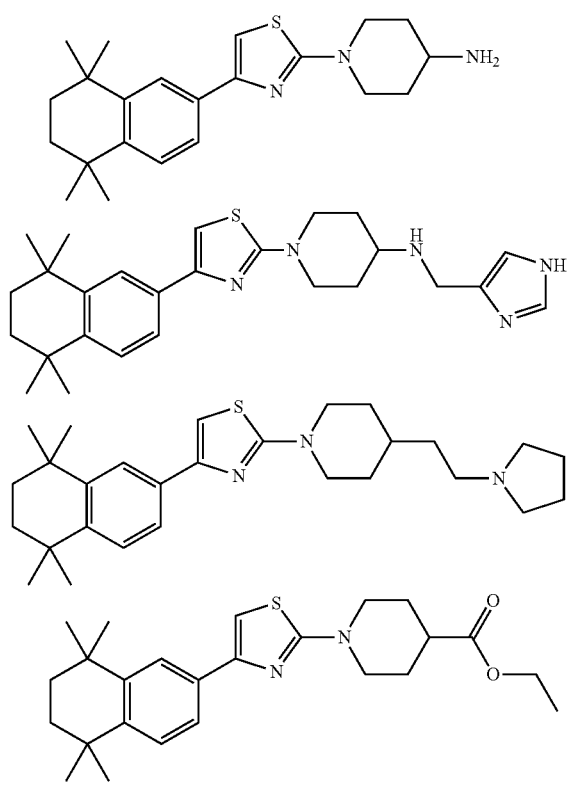

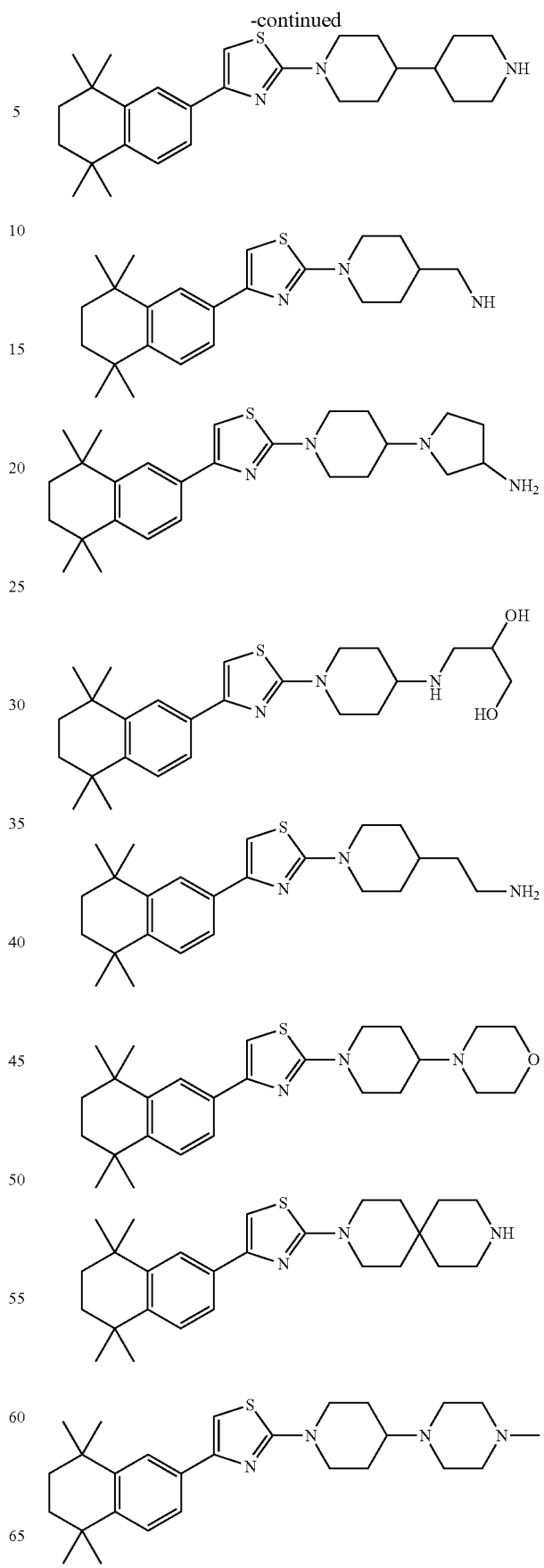

209
-continued
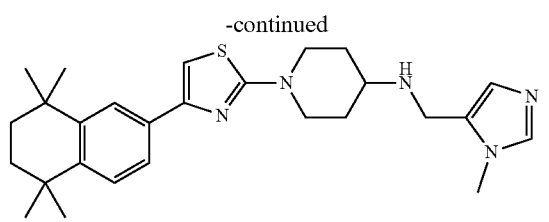
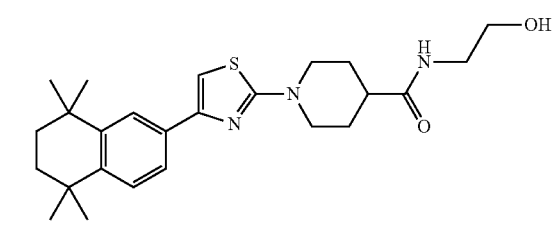
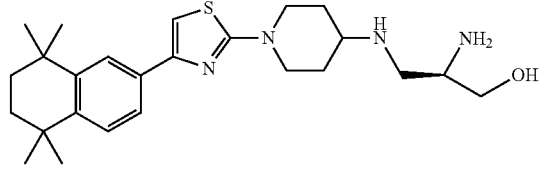
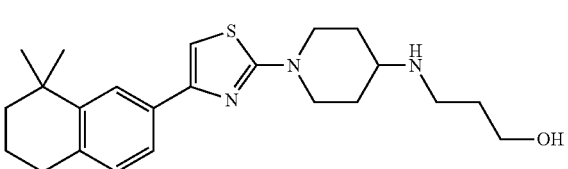
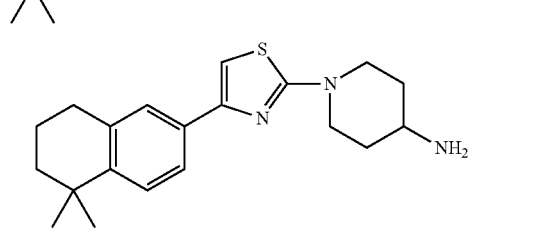
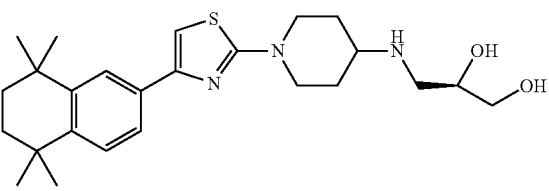
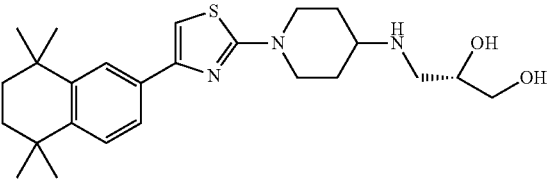
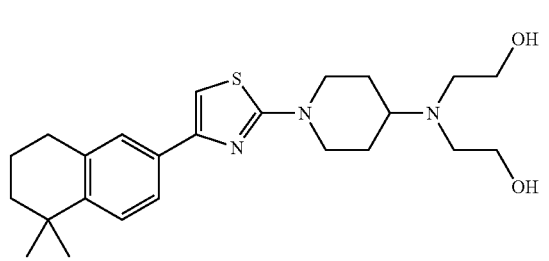
210
-continued
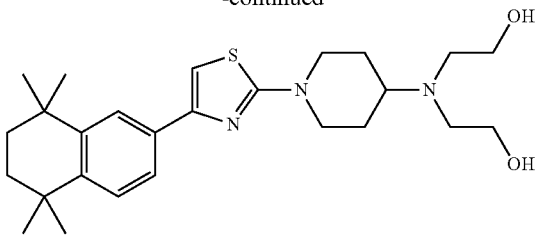
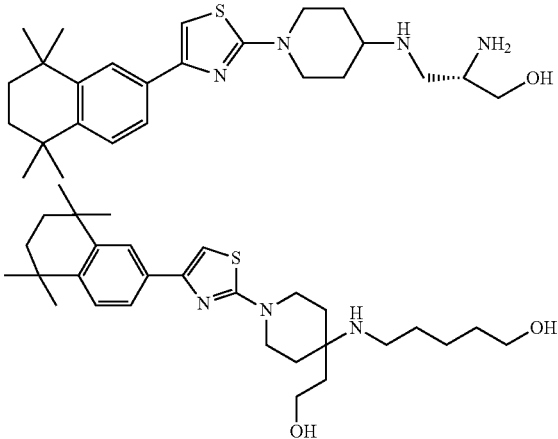
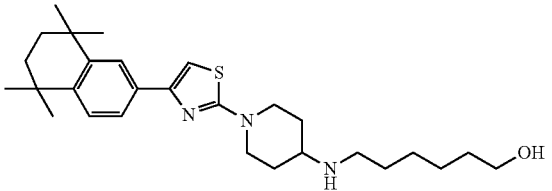
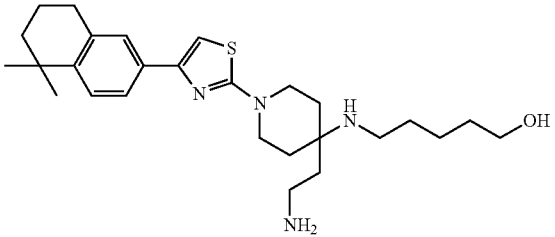
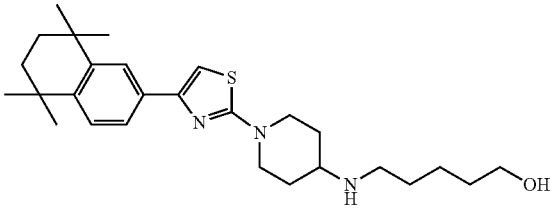
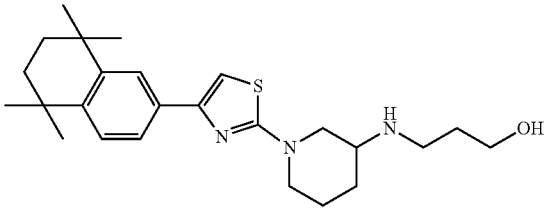
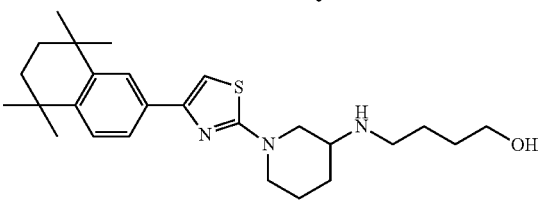

211
-continued
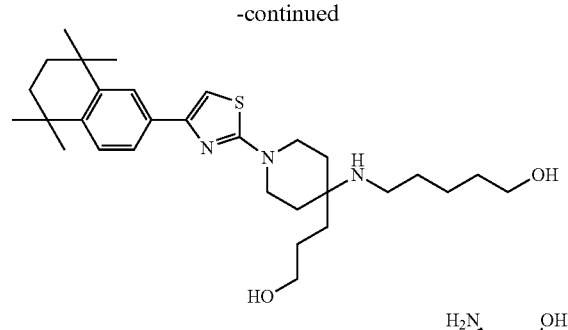
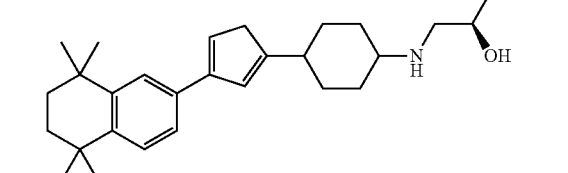
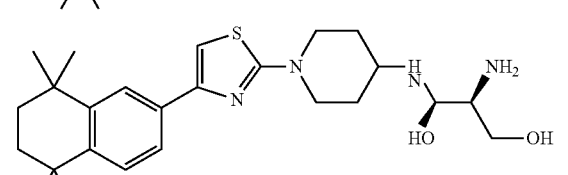
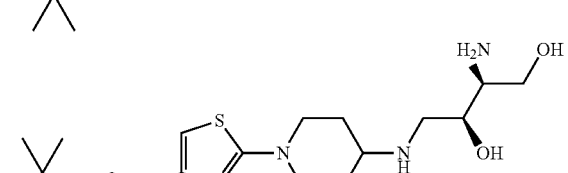
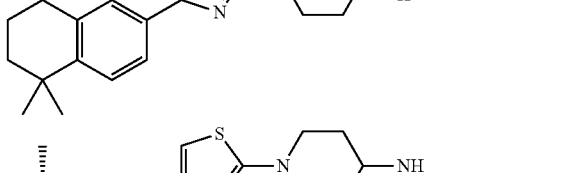
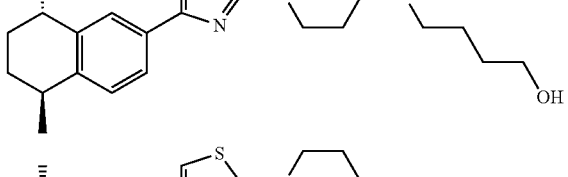
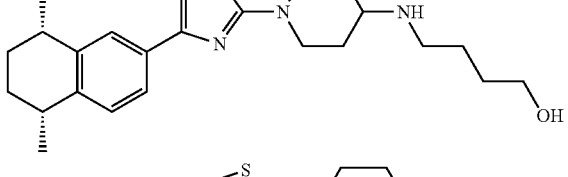
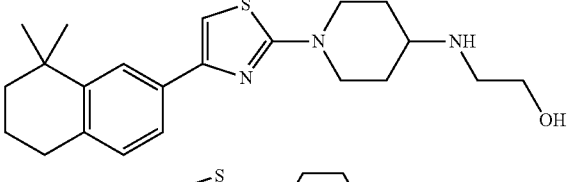
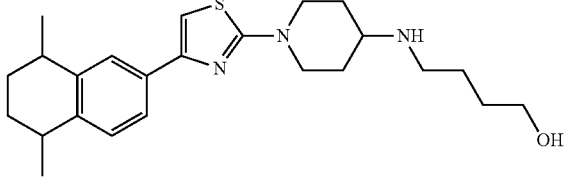
212
-continued
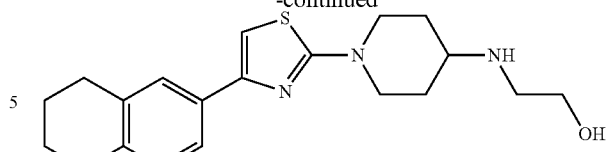
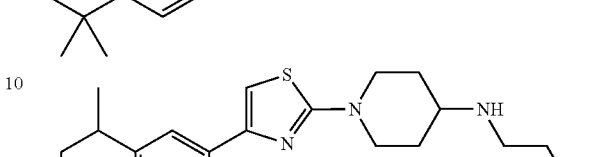
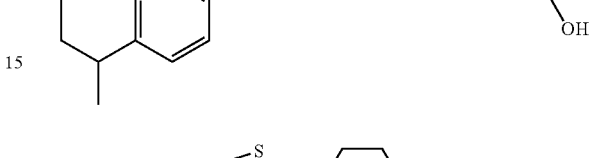
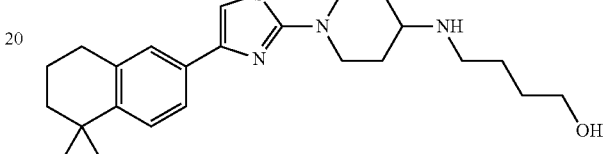
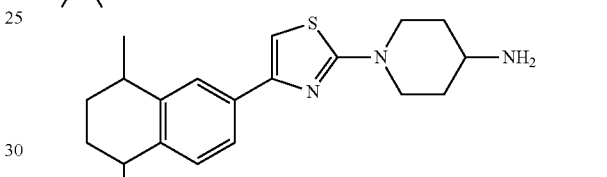
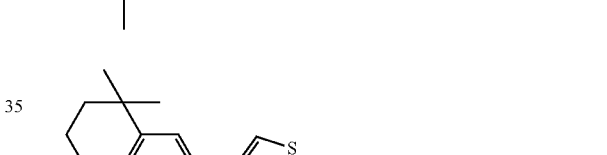
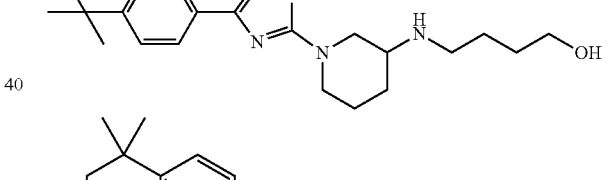
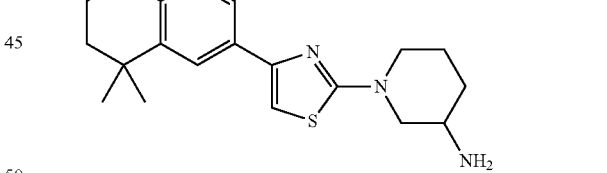
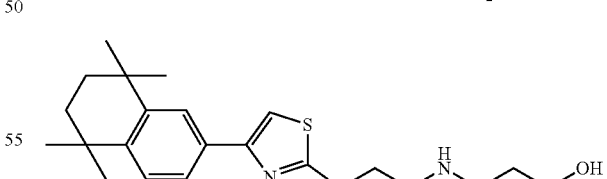
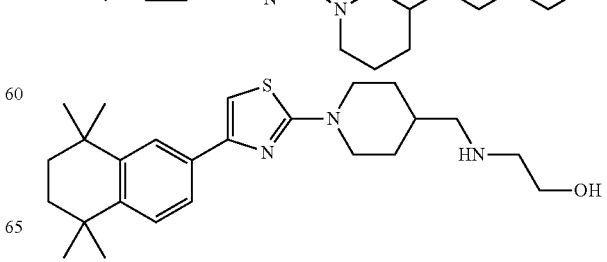

213
-continued
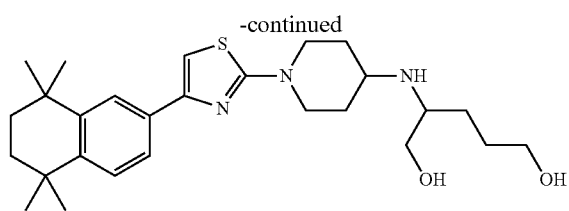
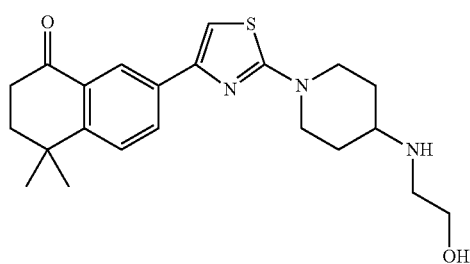
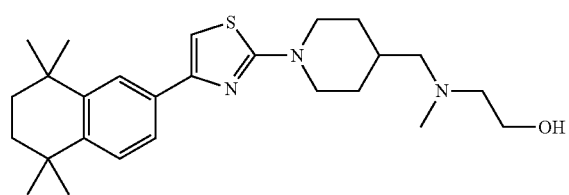
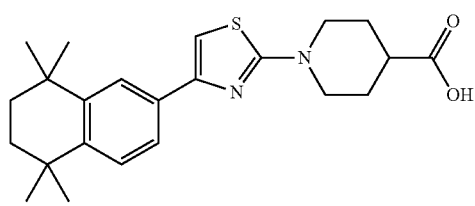
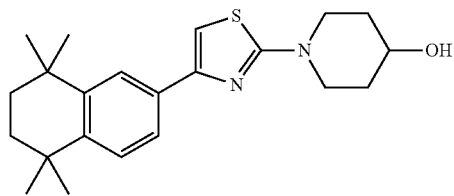
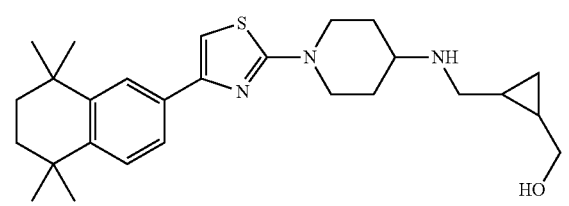
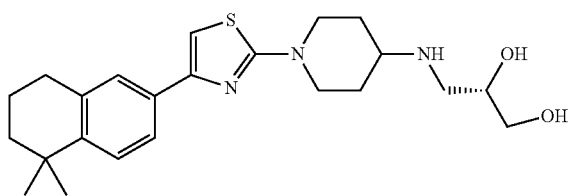
214
-continued
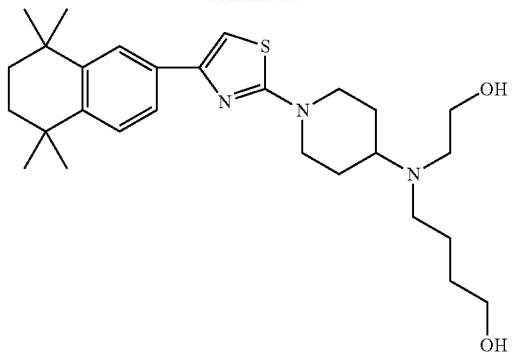
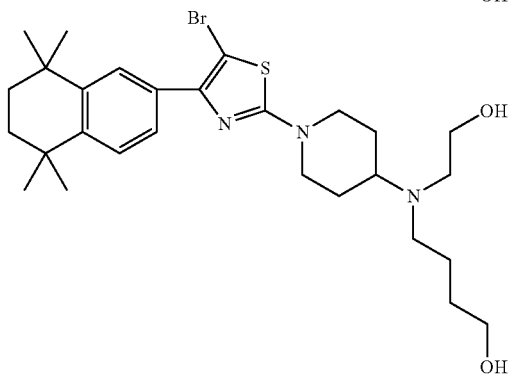
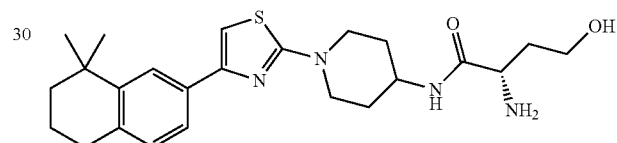
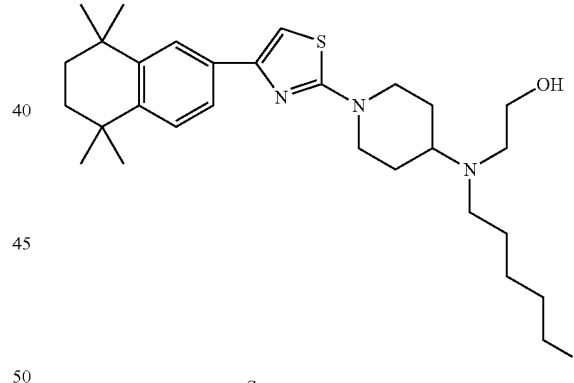
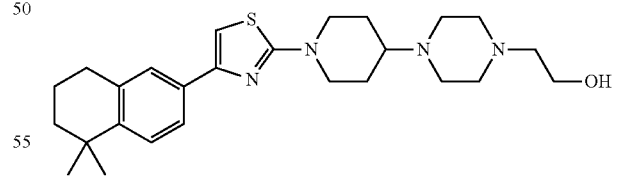
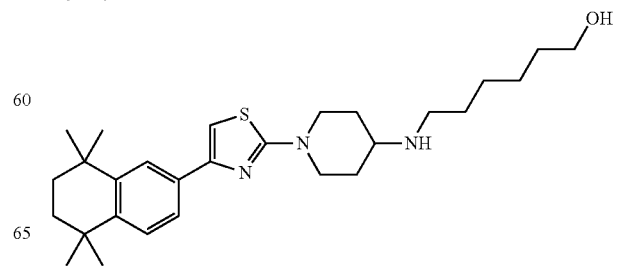

215
-continued
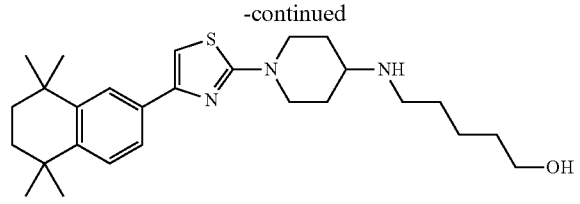
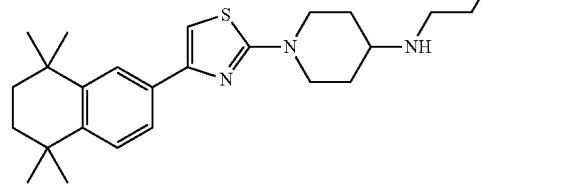
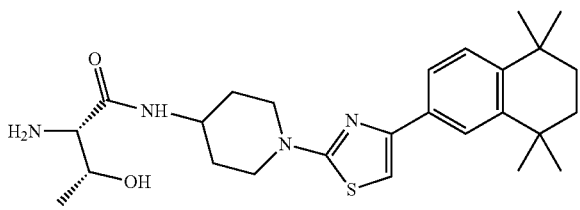
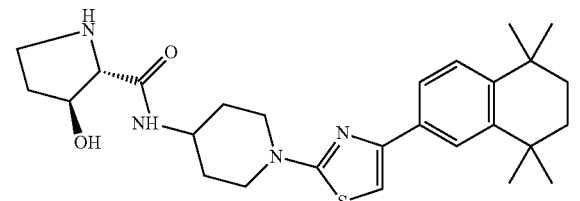
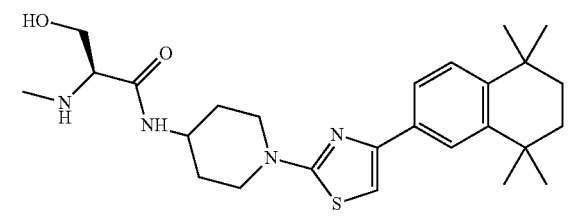
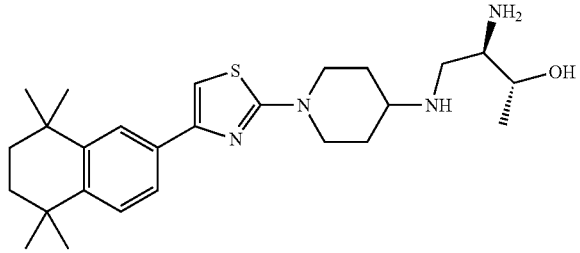
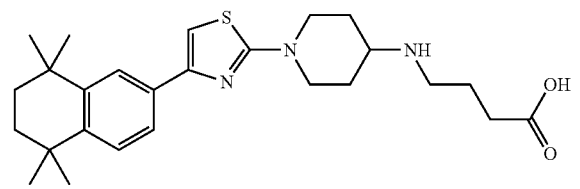
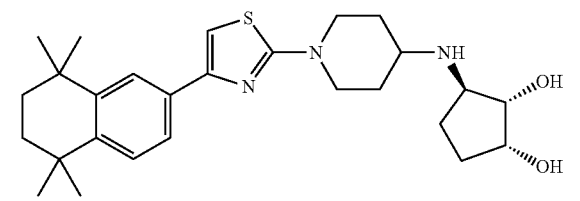
216
-continued
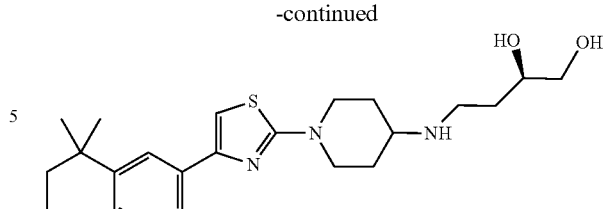
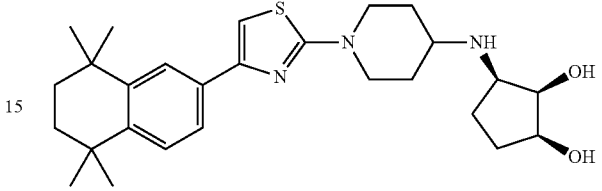
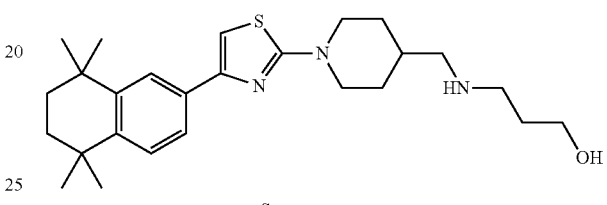
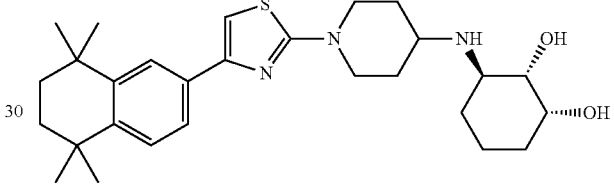
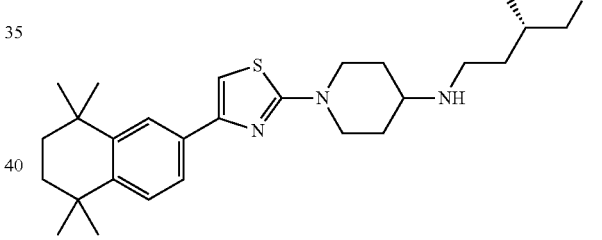
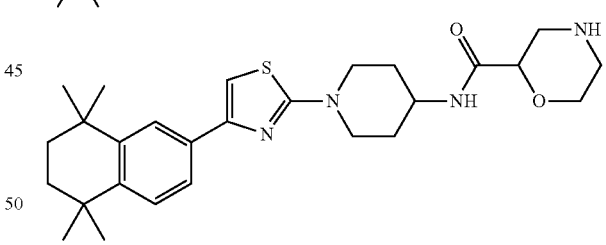
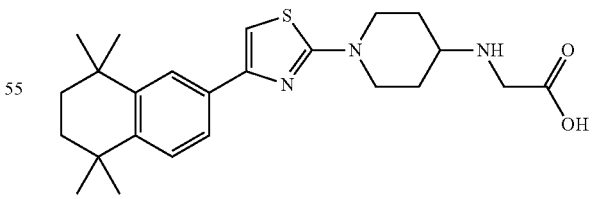
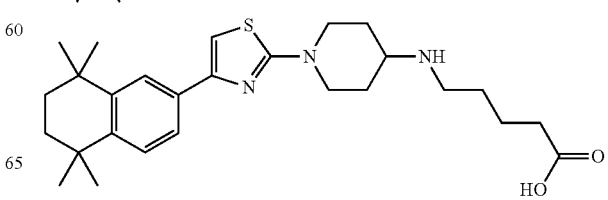

217
-continued
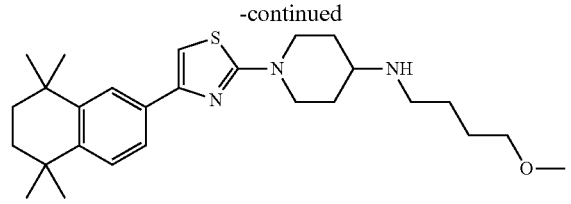
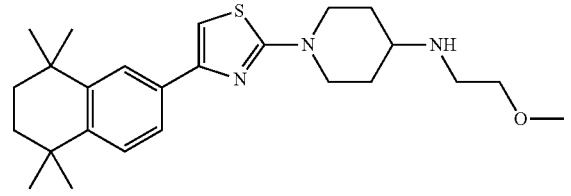
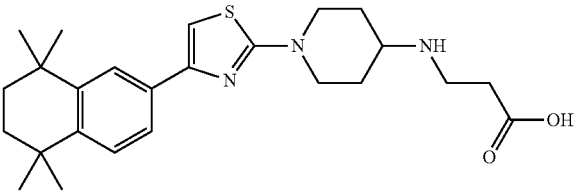
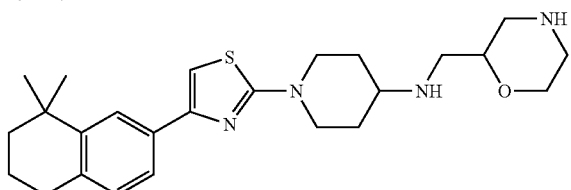
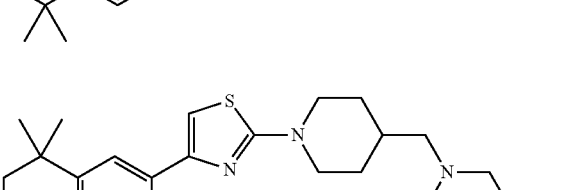
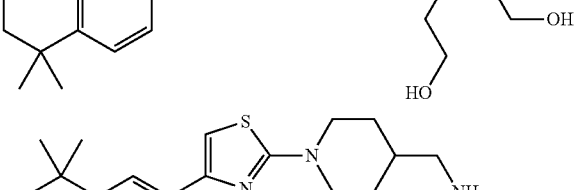
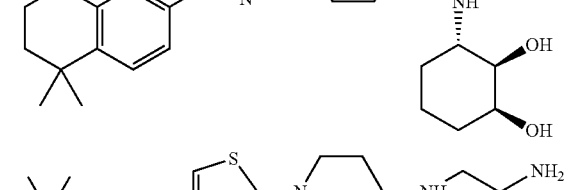
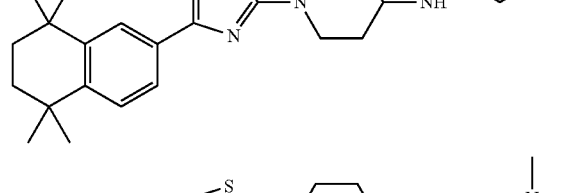
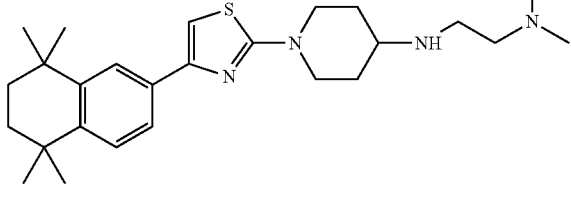
218
-continued
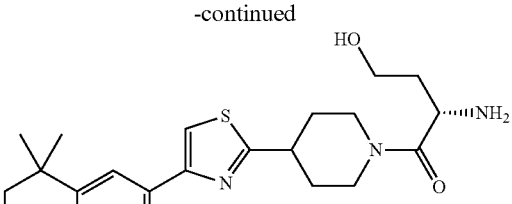
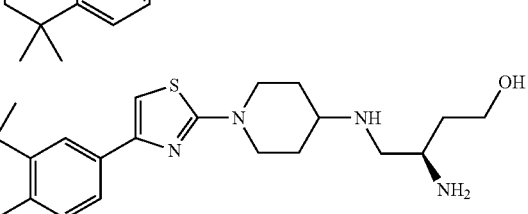
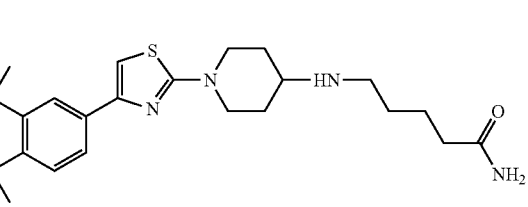
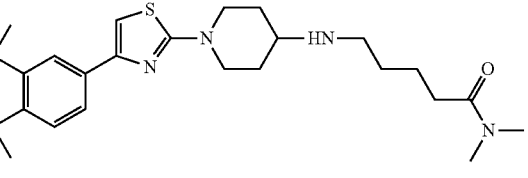
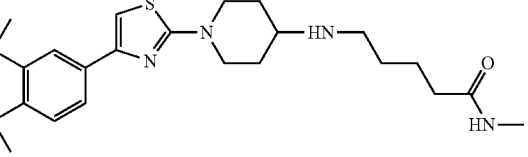
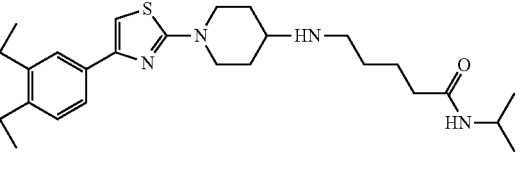
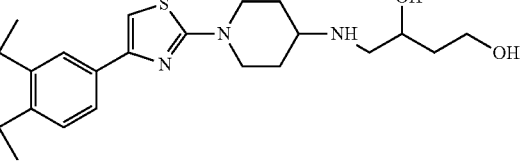
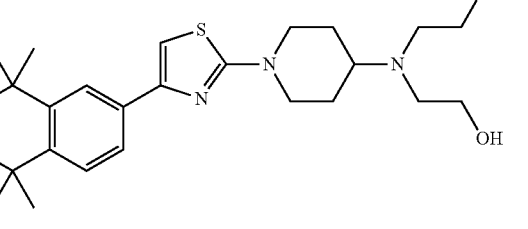

-continued

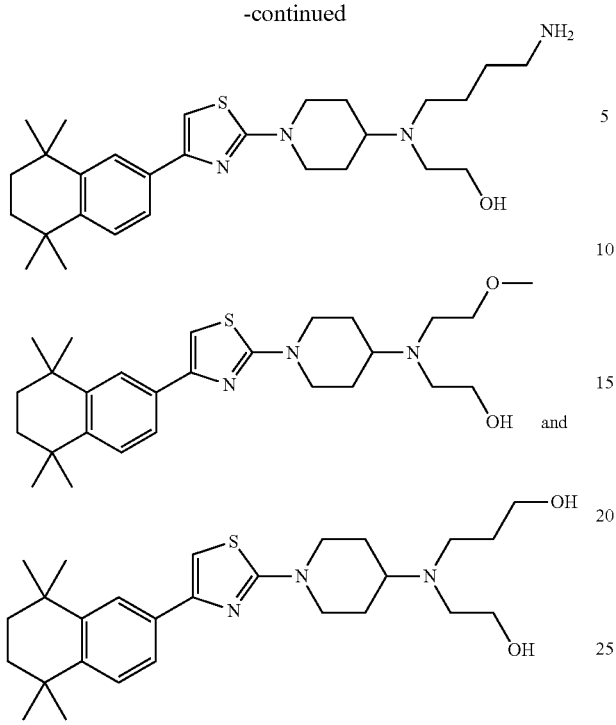

and physiologically acceptable salts, prodrugs, solvates, tautomers and stereoisomers thereof, including mixtures thereof in all ratios.

2. A compound selected from:

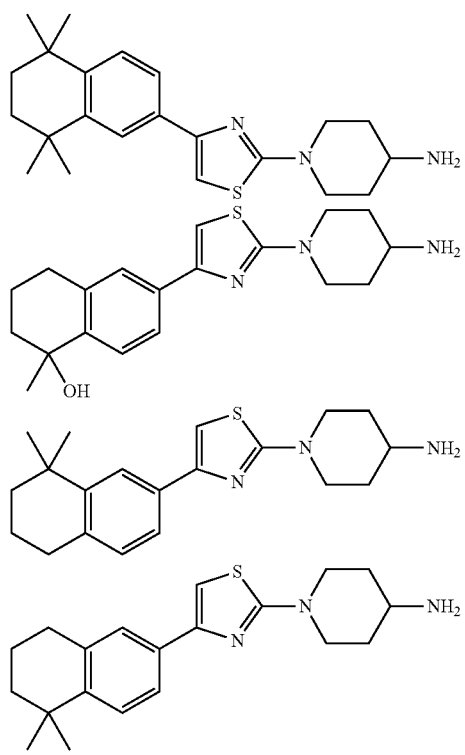

-continued

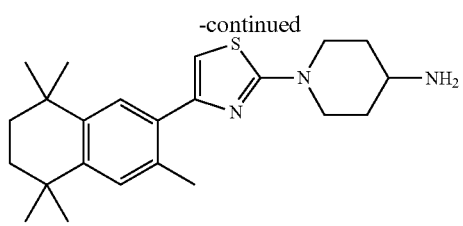

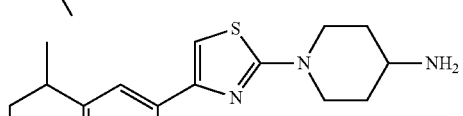

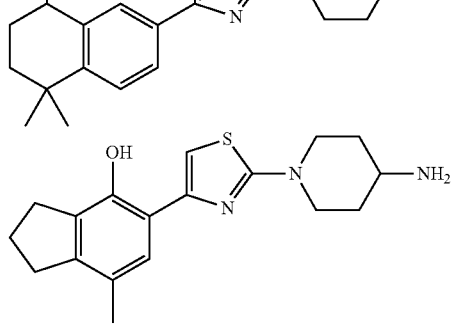

and physiologically acceptable salts, prodrugs, solvates, tautomers and stereoisomers thereof, including mixtures thereof in all ratios.

3. A medicament comprising one or more compounds according to claim 1.

4. A medicament according to claim 3, in which medicament comprises at least one pharmacologically active substance in addition to said one or more compounds.

5. A pharmaceutical composition comprising a therapeutically effective amount of at least one compound according to claim 1.

6. A pharmaceutical composition according to claim 5, further comprising at least one additional compound selected from physiologically acceptable extenders, adjuvants, additives, diluents, excipients and/or additional pharmaceutically active substances.

7. A kit comprising a therapeutically effective amount of at least one compound according to claim 1 and a therapeutically effective amount of at least one further pharmacologically active substance apart from said at least one compound.

8. A medicament according to claim 3, further comprising at least one additional compound selected from physiologically acceptable extenders, adjuvants, additives, diluents, and excipients.

* * * * *